United States Patent [19]
Bakshi et al.

[11] Patent Number: 5,710,275
[45] Date of Patent: *Jan. 20, 1998

[54] 7β-SUBSTITUTED-4-AZA-5α-ANDROSTAN-3-ONES AS 5α-REDUCTASE INHIBITORS

[75] Inventors: Raman K. Bakshi, Edison; Gary H. Rasmusson, Watchung; Richard L. Tolman, Warren; Gool F. Patel, Califon; Georgianna S. Harris, Tinton Falls; Donald W. Graham, Mountainside; Bruce E. Witzel, Westfield, all of N.J.

[73] Assignee: Merck & Co., Inc., Rahway, N.J.

[*] Notice: The term of this patent shall not extend beyond the expiration date of Pat. No. 5,536,727.

[21] Appl. No.: 341,602

[22] PCT Filed: May 14, 1993

[86] PCT No.: PCT/US93/04643

§ 371 Date: Apr. 3, 1995

§ 102(e) Date: Apr. 3, 1995

[87] PCT Pub. No.: WO93/23420

PCT Pub. Date: Nov. 25, 1993

Related U.S. Application Data

[63] Continuation-in-part of Ser. No. 886,572, May 20, 1992, abandoned.

[51] Int. Cl.$^6$ ............................................. A61K 31/47
[52] U.S. Cl. ............................... 546/78; 546/77; 514/284
[58] Field of Search ........................ 546/77, 78; 514/284

[56] References Cited

U.S. PATENT DOCUMENTS

| | | | |
|---|---|---|---|
| 4,220,775 | 9/1980 | Rasmusson et al. | 546/77 |
| 4,377,584 | 3/1983 | Johnston et al. | |
| 4,760,071 | 7/1988 | Rasmusson et al. | 514/284 |
| 4,859,681 | 8/1989 | Rasmusson et al. | 514/284 |
| 5,049,562 | 9/1991 | Rasmusson et al. | 514/284 |
| 5,138,063 | 8/1992 | Rasmusson et al. | 546/77 |
| 5,215,894 | 6/1993 | Arison et al. | 546/77 |
| 5,237,064 | 8/1993 | Bakshi et al. | 546/14 |
| 5,278,159 | 1/1994 | Bakshi et al. | 546/77 |
| 5,300,294 | 4/1994 | Johnson | 514/178 |
| 5,302,621 | 4/1994 | Kojima et al. | 514/284 |
| 5,494,914 | 2/1996 | Labrie | 514/284 |
| 5,510,351 | 4/1996 | Graham et al. | 514/284 |
| 5,510,485 | 4/1996 | Graham et al. | 514/284 |
| 5,527,807 | 6/1996 | Bakshi et al. | 514/284 |
| 5,536,727 | 7/1996 | Witzel et al. | 514/284 |
| 5,543,417 | 8/1996 | Waldstreicher | 514/284 |

FOREIGN PATENT DOCUMENTS

| | | |
|---|---|---|
| 0 004 949 | 10/1979 | European Pat. Off. |
| 0 155 096 | 9/1985 | European Pat. Off. |
| 0 277 002 | 8/1988 | European Pat. Off. |
| 0 314 199 | 5/1989 | European Pat. Off. |
| 0 375 349 | 6/1990 | European Pat. Off. |
| 0 414 529 | 2/1991 | European Pat. Off. |
| 0 547 691 | 6/1993 | European Pat. Off. |
| 93/13124 | 7/1993 | WIPO. |
| 93-23420 | 11/1993 | WIPO. |

OTHER PUBLICATIONS

The Daily (Tuesday, May 7, 1996), "New Data on Proscar, Abbott's Hytrin Show Conflicting Results".
Winslow Wall Street Journal (Tuesday, May 7, 1996), "Study Finds Abbott's Prostate Drug is Much More Effective than Merck's", p. B4.
US NEWS & WORLD REPORT, May 20, 1996, "Zapping a problem prostate".
Rasmusson et al., J. Med Chem., vol. 29, No. 11, pp. 2298–2315(1986), "Azasteroids: Structure–activity relationships for inhibition of 5alpha–reductase and of androgen receptor binding".
Mellin et al., J. Steroid Biochem. Mol. Biol., vol. 44, No. 2, pp.121–131(1993), "Azasteroids as inhibitors of testosterone 5alpha–reductase in mammalian skin".
Geldof et. al., "Enzyme Inhibitors in Hormone Dependent Prostate Cancer Treatment"Abstract 90–28432, Abstracted from Eur. J. Cancer 26(2): 188 (1990).
Geldof, "Consideration of the Use of 17 beta–N, N–diethylcarbamoyl–4–methyl–4–aza–5–alpha–androstan–3–one(HMA), a 5 alpha–reductase inhibitor, in prostate cancer therapy"J. Cancer Res. Oncol. 118: 50–55 (1992).
Diani, et al. "Hair Growth Effects of Oral Administration of Finasteride, A steroid 5 alpha–reductase inhibitor, alone and in combination with Topical Minoxidil in the Balding Stumptail Macaque", J. Clin. Endo. & Metab. 74(2):345–350 (1992).
Rasmusson et al., "Azasteroids" Structure Activity Relationships for Inhibition of 5 alpha–reductase and of androgen receptor binding, J. Med. Chem. 29(11): 2298–2315 (1986).
Brooks, et al., "5 Alpha–reductase Inhibitory and Anti–Androgenic Activities of Some 4–Aza–steroids in the rat" Steroids: Structure Function and Regulation vol. 47(1). . . 1–19(1986).
Burger, Medicinal Chemistry, 2nd Ed. New York, Interscience p. 42 (1960).
Helliker, "Alopecia Sufferers Seek to Suffer Less, and Not In Silence" Wall Street Jour. pp. A1 and A7, Jun. 7, 1991.
Back "Oxidation of Azasteroid Lactams and Alcohols with Benzeneseleninic Anhydride". J. Org. Chem. 46(7); 1442–1446 (1981).
Back et al., "N–Chloroazasteroids: A Novel Class of Reactive Steroid Analogues Preparation, Reaction with Thiols and Photochemical Conversion to Electrophilic N–acylamines", J. Org. Chem. 54(8):1904–1910 (1989).
Stinson, "Prostate Drug Proscar cleared for Marketing", Chem. Eng. News pp. 7–8, 29 Jun. 1992.
Gormley, "Preparation of 17–Beta carbamoyl–4–aza–5 alpha–androstan–1–en–3–ones as testosterone 5 alpha reductase inhibitors for the prevention of prostatic carcinoma", Chem. Abstrs. vol. 119, Entry 160644S, Abstracting EP 547691 (1993).

(List continued on next page.)

Primary Examiner—Donald G. Daus
Attorney, Agent, or Firm—Catherine D. Fitch; William H. Nicholson; Melvin Winokur

[57] ABSTRACT

Described are new 7β-substituted 4-aza-5α-androstan-3-ones and related compounds as 5α-reductase inhibitors.

2 Claims, No Drawings

OTHER PUBLICATIONS

Li et al., J. Med. Chem. 1995, 38, pp.1158–1173, "Synthesis and in Vitro Activity Of 17Beta–(N–alkyl/arylform amido)–and 17Beta–[N–alkyl/aryl)alky/arylamido] –4–methyl–4–aza–3–oxo–5alpha–androstan–3–ones as Inhibitors of Human 5alpha–Reductases and Antagonists of the Androgen Receptor".

7β-SUBSTITUTED-4-AZA-5α-ANDROSTAN-3-ONES AS 5α-REDUCTASE INHIBITORS

CROSS REFERENCE TO RELATED APPLICATIONS

This application is a national phase application under 35 U.S.C. §371 of PCT application Ser. No. PCT/US93/04643, filed May 14, 1993, which, in turn is a continuation in part of application Ser. No. 07/886,572 filed May 20, 1992, now abandoned.

BACKGROUND OF THE INVENTION

The present invention is directed to new 7β-substituted-4-aza-5α-androstan-3-ones and related compounds and the use of such compounds as 5α-reductase inhibitors.

DESCRIPTION OF THE PRIOR ART

The art reveals that certain undesirable physiological manifestations, such as acne vulgaris, seborrhea, female hirsutism, male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs is 5α-dihydrotestosterone, and that it is formed locally in the target organ by the action of testosterone-5α-reductase. It is also known that inhibitors of testosterone-5α-reductase will serve to prevent or lessen symptoms of hyperandrogenic stimulation.

A number of 4-aza steroid compounds are known in the art as 5α-reductase inhibitors. For example, See U.S. Pat. Nos. 4,377,584, 4,220,775, 4,859,681, 4,760,071 and the articles J. Med. Chem. 27, p. 1690–1701 (1984) and J. Med. Chem. 29, 2998–2315 (1986) of Rasmusson, et al., U.S. Pat. No. 4,845,104 to Carlin, et al., and U.S. Pat. No. 4,732,897 to Cainelli, et al. describe 4-aza-17β-substituted-5α-androstan-3-ones which are said to be useful in the treatment of DHT-related hyperandrogenic conditions.

However, despite the suggestion in the prior art that hyperandrogeneic diseases are the result of a single 5α-reductase, there are reports regarding the presence of other 5α-reductase isozymes in both rats and humans. For example, in human prostate, Bruchovsky, et al. (See J. Clin. Endocrinol. Metab. 67, 806–816, 1988) and Hudson (see J. Steroid Biochem. 26, p 349–353, 1987) found different 5α-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases of rats. The sequence of this rat gene was later used to select a human prostatic cDNA encoding a 5α-reductase termed "5α-reductase 1". (See Proc. Nat'l. Acad. Sci. 87, p. 3640–3644, 1990.)

More recently, a second, human prostatic reductase (5α-reductase 2) has been cloned with properties identified with the more abundant form found in crude human prostatic extracts. (See Nature, 354, p. 159–161, 1991.)

Further, "Syndromes of Androgen Resistance"—The Biology of Reproduction, Vol. 46, p. 168–173 (1992) by Jean O. Wilson indicates that the 5α-reductase 1 enzyme may be associated with hair follicles.

Thus, the art supports the existence of at least two genes for 5α-reductase and two distinct isozymes of 5α-reductase in humans. Both forms are present in prostatic tissue although reductase 2 is the more abundant. The other isozyme, 5α-reductase 1, is believed to be more abundant in scalp tissue.

In the treatment of hyperandrogenic disease conditions, e.g. benign prostatic hyperplasia (BPH) it would be desirable to have one drug entity which is active against both isozymes 1 and 2 in the prostate to substantially inhibit dihydrotesterone (DHT) production. Alternatively, it would be desirable to have a drug entity which is highly selective for inhibiting the scalp-associated enzyme 5α-reductase 1, for use in treating diseases of the skin and scalp, e.g. acne and alopecia. This latter drug could also be used in combination with PROSCAR® (finasteride) which is highly selective for the prostatic enzyme 5α-reductase 2 for combination therapy in the treatment of BPH.

SUMMARY OF THE INVENTION

The present invention discloses novel 7β-substituted-4-aza-5α-androstan-3-one compounds which are useful for inhibiting the 5α-reductase isozymes 1 and/or 2 and are particularly effective in selectively inhibiting the 5α-reductase 1 associated with the scalp and individually inhibiting both isozymes 1 and 2 in the treatment of benign prostatic hyperplasia, acne, female hirsutism, male pattern baldness, androgenic alopecia, prostatitis, and the [prevention and] treatment of prostatic carcinoma.

In accordance with the present invention there is provided novel 7β-substituted-4-aza-5α-androstan-3-one compounds of the formula:

General Formula I

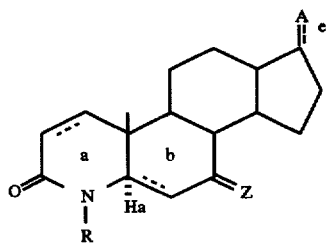

wherein
R is selected from hydrogen, methyl or ethyl; the dashed lines -a, b, e indicate double bonds which can be present, providing that if double bond b is present, then the 5α hydrogen, Ha, is not present;
Z can be:
1) oxo, 2) α-hydrogen and a β-substituent selected from $C_1$-$C_4$ alkyl, $C_2$-$C_4$ alkenyl, —$CH_2COOH$, hydroxy, carboxy, $COOC_1$-$C_4$ alkyl esters; $OCONR^1R^2$, where $R^1$ and $R^2$ are independently H, $C_1$-$C_4$ alkyl, phenyl, benzyl, and where $R^1$ and $R^2$ together with the nitrogen can form a 5–6 membered saturated heterocyclic ring, optionally with one other heteroatom; $OC_1$-$C_4$ alkyl, $OC_3$-$C_6$ cycloalkyl, —$OCOCH_3$, halo, halo $C_1$-$C_2$ alkyl, or trifluoromethyl, $C_3$-$C_6$ cycloalkyl;

3) =CH—$R^1$ where $R^1$ is H, $C_1$-$C_4$ alkyl;

4) Spiro

where
$R^1$ is H, $C_1$-$C_4$ alkyl; and
A can be:

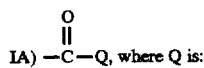

IA) —C—Q, where Q is:

(1) $NR^2R^3$, where $R^3$ is independently hydrogen, methyl or ethyl; and $R^2$ is a hydrocarbon radical, selected from substituted or unsubstituted straight or branched chain alkyl, cycloalkyl, or aralkyl of from 1–12 carbons or monocyclic aryl optionally containing 1 or more lower alkyl substituents of from 1–2 carbon atoms and/or 1 or more halogen substituents, with the proviso that Z is not beta-methyl where $R^2$ is $C_1$-$C_8$ alkyl;

(2) a hydrocarbon radical being:
(a) a monovalent aliphatic radical selected from straight or branched chain alkyl, or cycloalkyl, of from 1–12 carbons, which can be substituted by one or more of $C_1$-$C_2$ alkyl or halo, excluding $C_1$-$C_4$ alkyl when Z is beta-methyl;
(b) an aralkyl radical selected from benzyl or phenethyl;
(c) a polycyclic aromatic radical which can be substituted with one or more of: —OH, organosilyl protected —OH, —$OC_1$-$C_4$ alkyl, $C_1$-$C_4$ alkyl, halo or nitro;
(d) a monocyclic aromatic radical which can be substituted with one or more of:
(i) —OH, —$OC_1$-$C_4$ alkyl, $C_1$-$C_4$ alkyl, —$(CH_2)_m$OH, —$(CH_2)_n$COOH, including organosilyl protected hydroxy, where m is 1–4, n is 1–3, providing $C_1$-$C_4$ alkyl is only present when one of the above oxygen-containing radicals is present;
(ii) —SH, —$SC_1$-$C_4$ alkyl, —$SOC_1$-$C_4$ alkyl, —$SO_2C_1$-$C_4$ alkyl, —$SO_2NH(C_1$-$C_4$-alkyl$)_2$, —$SO_2NH(C_1$-$C_4$alkyl), —$(CH_2)_m$SH, —S—$(CH_2)_n$—O—$COCH_3$, where m is 1–4 n is 1–3, providing $C_1$-$C_4$ alkyl is only present when one of the above sulfur containing radicals is present;
(iii) $N(R^3)_2$, which can be protected, where $R^3$ is independently H or $C_1$-$C_4$ alkyl, where the monoaryl ring can also be further substituted with $C_1$-$C_4$ alkyl; and
(iv) heterocyclic selected from 2-, 3-, or 4-pyridyl, 2-pyrrolyl, 2-furyl or thiophenyl; and (IIA), where:
A is —$XR^4$, or —$(CHR^1)_n$—$XR^4$;
n is 1–10;
X is —O— or —$S(O)_p$—,
 wherein p is zero, 1 or 2; and
$R^1$ can be the same or different when n is greater than 1 and is —H, aryl, or —$C_{1-3}$alkyl unsubstituted or substituted with $C_6$-$C_{10}$ aryl;
R is —H, methyl or ethyl;
$R^4$ is
1) hydrogen or —$C_{1-20}$ alkyl, unsubstituted or substituted with one or more of:
a) —OH,
b) halo,
c) —$C_{1-8}$ alkoxy,
d) —$C_{1-6}$ alkenyl,
e) —$CONR^5R^5$, wherein $R^5$ is independently
 i) —H,
 ii) —$C_{1-8}$ alkyl unsubstituted or substituted with one or more of $R^7$, aryl or heterocyclic, defined below, the aryl being unsubstituted or substituted with one or more of $R^7$ or $R^9$,
 iii) aryl unsubstituted or substituted with one or more of $R^7$ or $R^9$, or
 iv) heterocyclic, defined below, unsubstituted or substituted with one or more of $R^7$ or $R^9$,
f) —$COOR^6$, wherein $R^6$ is
 i) —H,
 ii) —$C_{1-8}$ alkyl unsubstituted or substituted with one or more of $R^7$ or aryl, the aryl being unsubstituted or substituted with one or more of $R^7$ or $R^9$, or
 iii) aryl, unsubstituted or substituted with one or more of $R^7$ or $R^9$,
g) —$S(O)_p$—$R^5$, wherein p is defined above,
h) —$N(R^5)_2$,
i) aryl, unsubstituted or substituted with one or more of aryl, $R^7$ or $R^9$,
j) heterocyclic, unsubstituted or substituted with one or more of $R^7$ or $R^9$,
k) —$C_{3-10}$ cycloalkyl, unsubstituted or substituted with one or more of $R^7$ or $R^9$, or
l) —$CONR^8$—CO—$NHR^8$, wherein $R^8$ is —H, —$C_{1-8}$ alkyl, benzyl or cyclohexyl; or
2) aryl, unsubstituted or substituted with one or more of aryl, $R^7$ or $R^9$, or
3) heterocycle or —$C_{3-10}$ cycloalkyl, either of which is unsubstituted or substituted with one or more of $R^7$ or $R^9$;

$R^7$ is
1) —OH,
2) —$C_{1-3}$ alkoxy,
3) —CN,
4) —$COOR^6$
5) —$C_{1-8}$alkyl-$COOR^6$
6) —$NO_2$, or
7) -halo; and
8) amino, mono $C_1$-$C_4$ alkylamino, di $C_1$-$C_4$ alkylamino;

$R^9$ is
1) —$C_{1-8}$ alkyl, unsubstituted or substituted with one or more of aryl or $R^7$,
2) —CO—A, —$C_{1-8}$ alkyl-CO—A, —NHCO—A, or —$S(O)_p$—A, wherein p is defined above and A is
a) —H,
b) —$C_{1-8}$ alkyl, unsubstituted or substituted with one or more of i) —$R^7$, or
ii) aryl, unsubstituted or substituted with one or more of $R^7$, or
c) aryl, unsubstituted or substituted with one or more of $R^7$,
3) —NHCO-heterocyclic,
4) —N($R^{10}$)$_2$ or —CON($R^{10}$)$_2$ wherein $R^{10}$ is independently —H, heterocyclic, or —A,
5) —NHCO—(CH$_2$)$_q$—CO—Q, wherein q is 1–4, and Q is —N($R^{10}$)$_2$ or —OR$^{10}$;

(IIIA), where:

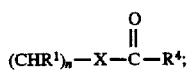

$R^1$ can be the same or different when n is greater than 1 and is —H, aryl, or —C$_{1-3}$alkyl unsubstituted or substituted with aryl;
R is —H, methyl or ethyl;
n is zero through 10;
X is —O— or —S—; and
$R^4$ is
1) hydrogen or —C$_{1-20}$ alkyl, unsubstituted or substituted with one or more of:
   a) —OH,
   b) halo,
   c) —C$_{1-8}$ alkoxy,
   d) —C$_{1-6}$ alkenyl,
   e) —CONR$^5$R$^5$, wherein $R^5$ is independently
      i) —H,
      ii) —C$_{1-8}$ alkyl unsubstituted or substituted with one or more of $R^7$, aryl or heterocycle, the aryl being unsubstituted or substituted with one or more of $R^7$ or $R^9$,
      iii) aryl unsubstituted or substituted with one or more of $R^7$ or $R^9$, or
      iv) heterocyclic, unsubstituted or substituted with one or more of $R^7$ or $R^9$,
   f) —COOR$^6$, wherein $R^6$ is
      i) —H,
      ii) -C$_{1-8}$ alkyl unsubstituted or substituted with one or more of $R^7$ or aryl, the aryl being unsubstituted or substituted with one or more of $R^7$ or $R^9$, or
      iii) aryl, unsubstituted or substituted with one or more of $R^7$ or $R^9$,
   g) —S(O)$_p$—R$^5$, wherein p is zero, 1 or 2;
   h) —N(R$^5$)$_2$,
   i) aryl, unsubstituted or substituted with one or more of aryl, $R^7$ or $R^9$,
   j) heterocycle, unsubstituted or substituted with one or more of $R^7$ or $R^9$,
   k) —C$_{3-10}$ cycloalkyl, such as cyclohexyl, norbornyl, or adamantyl, unsubstituted or substituted with one or more of $R^7$ or $R^9$, or
      1) —CONR$^8$—CO—NHR$^8$, wherein $R^8$ is —H, —C$_{1-8}$ alkyl, benzyl or cyclohexyl,
      2) aryl, unsubstituted or substituted with one or more of aryl, $R^7$ or $R^9$,
      3) heterocycle or —C$_{3-10}$ cycloalkyl, either of which is unsubstituted or substituted with one or more of $R^7$ or $R^9$,
      4) —NR$^5$R$^5$, or
      5) —OR$^5$;
$R^7$ is
   1) —OH,
   2) —C$_{1-3}$ alkoxy,
   3) —CN,
   4) —COOR$^6$,
   5) —C$_{1-8}$alkyl-COOR$^6$,
   6) —NO$_2$, or
   7) halo; and
   8) amino, mono C$_1$–C$_4$ alkylamino, di C$_1$–C$_4$ alkylamino;
$R^9$ is
   1) —C$_{1-8}$ alkyl, unsubstituted or substituted with one or more of aryl or $R^7$,
   2) —CO—A, —C$_{1-8}$ alkyl-CO—A, —NHCO—A, or —S(O)$_p$—A, wherein p is defined above and A is
      a) —H,
      b) —C$_{1-8}$ alkyl, unsubstituted or substituted with one or more of
         i) —R$^7$, or
         ii) aryl, unsubstituted or substituted with one or more of $R^7$, or
      c) aryl, unsubstituted or substituted with one or more of $R^7$,
   3) —NHCO-heterocycle,
   4) —N(R$^{10}$)$_2$ or —CON(R$^{10}$)$_2$ wherein $R^{10}$ is independently, heterocycle or —A,
   5) —NHCO—(CH$_2$)$_q$—CO—Q, wherein q is 1–4, and Q is —N(R$^{10}$)$_2$ or —OR$^{10}$;

with the provisos that when Z is beta-methyl, the following are excluded:

when n is 1–12, $R^1$ is —H at each occurrence, X is —O—, and $R^4$ is —C$_{1-6}$alkyl, $R^4$ is not substituted with an unsubstituted phenyl ring;

when n is 1–12, $R^1$ is —H at each occurrence, and X is —O—, $R^4$ is not unsubstituted C$_{5-10}$cycloalkyl, unsubstituted phenyl, amino, —C$_{1-8}$alkyl substituted amino, or —C$_{1-8}$alkoxy; and when n is zero, $R^4$ is not —CH$_3$; and (IVA), where A is:

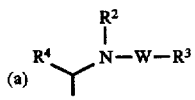

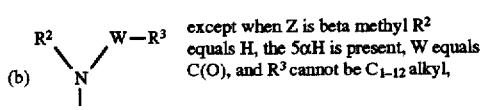

except when Z is beta methyl $R^2$ equals H, the 5αH is present, W equals C(O), and $R^3$ cannot be C$_{1-12}$ alkyl,

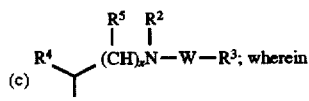

wherein $R^2$ is:
H, methyl or ethyl;
$R^3$ is:
H,
mono C$_1$–C$_4$ alkylaminoaryl,
di C$_1$–C$_4$ alkylaminoaryl,
C$_{1-20}$ alkyl,
C$_6$–C$_{14}$ aryl,
heteroaryl, as defined below,
C$_6$–C$_{14}$ arylC$_{1-20}$alkyl,
heteroarylC$_{1-20}$alkyl,
C$_{1-20}$alkylthioC$_{1-20}$alkyl,
C$_{1-20}$alkylsulfinylC$_{1-20}$alkyl,
C$_{1-20}$alkylsulfonylC$_{1-20}$alkyl,
C$_{1-20}$alkyloxycarbonylC$_{1-20}$alkyl, carboxylC$_{1-20}$alkyl,
C$_{1-20}$ alkylcarbonylC$_{1-20}$alkyl,
C$_{3-20}$cycloalkyl,
C$_{3-20}$cycloalkylC$_{1-20}$alkyl,
C$_6$–C$_{14}$ arylC$_{1-20}$alkyloxycarbonylC$_{1-20}$alkyl,
heteroaryl C$_{1-20}$alkyloxycarbonylC$_{1-20}$alkyl,
haloC$_{1-20}$alkyl,
hydroxylC$_{1-20}$alkyl,
thiosulfatoC$_{1-20}$alkyl,
C$_6$–C$_{14}$ arylC$_{1-20}$alkyloxyC$_{1-20}$alkyl,
C$_{1-20}$alkyloxyC$_{1-20}$alkyl,
arylcarbonylarylC$_{1-20}$alkyl,
diarylC$_{1-20}$alkyl,
triarylC$_{1-20}$alkyl,
C$_{2-20}$ alkenyl,
C$_{2-20}$ alkenylC$_{1-20}$alkyl,
heteroarylC$_{2-20}$alkenyl,
arylC$_{2-20}$alkenyl,
C$_{2-20}$alkynylC$_{1-20}$alkyl,
arylC$_{2-20}$alkynylC$_{1-20}$alkyl, or
heteroarylC$_{2-20}$alkynylC$_{1-20}$alkyl;

R$^4$ is:
H,
C$_{1-20}$ alkyl,
C$_6$–C$_{14}$ aryl or
heteroaryl;

R$^5$ can be the same or different when X is greater than 1 and is:
H, or
C$_{1-20}$ alkyl;

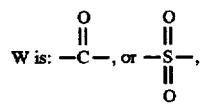

x is an integer from 1–25;
(VA), where:
A is:

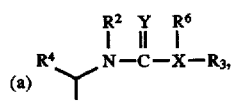

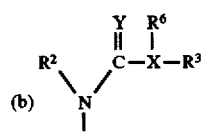

except when Z is beta methyl, R$^2$ equals H, Y equals O, X equals N and the 5αH is present, R$^6$ and R$^3$ can not be independently selected from H, C$_{1-8}$ alkyl, C$_{3-6}$ cycloalkyl, phenyl and R$^6$ and R$^3$ cannot be taken together with the adjacent N to form a 5–6 membered ring comprising up to one other heteroatom selected from O or N, or

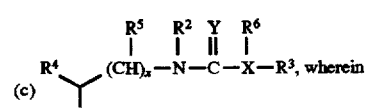

R$^2$ is:
H, or
C$_{1-20}$ alkyl;

R$^3$ is:
H
amino,
mono C$_1$–C$_4$ alkylamino,
di C$_1$–C$_4$ alkylamino,
mono C$_1$–C$_4$ alkylaminoaryl,
di C$_1$–C$_4$ alkylaminoaryl,
C$_{1-20}$ alkyl,
C$_6$–C$_{14}$ aryl,
heteroaryl,
C$_6$–C$_{14}$ arylC$_{0-20}$alkyl,
C$_{3-20}$ cycloalkyl,
C$_{3-20}$ cycloalkylC$_{1-20}$alkyl,
heteroarylC$_{1-20}$alkyl,
C$_{2-20}$ alkenylC$_{1-20}$alkyl,
haloC$_{1-20}$alkyl,
C$_{1-20}$alkyloxycarbonyl,
C$_{1-20}$alkyl,
C$_{1-20}$ alkyloxyC$_{1-20}$alkyl,
carboxyC$_{1-20}$alkyl,
C$_6$–C$_{14}$arylcarbonylarylC$_{1-20}$alkyl,
C$_{1-20}$ alkylcarbonylC$_{1-20}$alkyl,
C$_6$–C$_{14}$arylC$_{1-20}$alkyloxycarbonylC$_{1-20}$alkyl,
heteroarylC$_{1-20}$alkyloxycarbonylC$_{1-20}$alkyl,
hydroxylC$_{1-20}$alkyl,
halohydroxylC$_{1-20}$alkyl,
arylC$_{1-20}$alkyloxyC$_{1-20}$alkyl,
heteroarylC$_{1-20}$alkyloxyC$_{1-20}$alkyl,
diarylC$_{1-20}$alkyl,
triarylC$_{1-20}$alkyl,
C$_{2-20}$ alkenyl,
C$_{2-20}$ alkenylC$_{1-20}$alkyl,
C$_{2-20}$ alkynylC$_{1-20}$alkyl,
arylC$_{2-20}$alkynylC$_{1-20}$alkyl,
heteroarylC$_{2-20}$alkynylC$_{1-20}$alkyl,
C$_{1-20}$ alkylthioC$_{1-20}$alkyl,
C$_{1-20}$ alkylsulfonylC$_{1-20}$alkyl, or
C$_{1-20}$ alkylsulfinyl C$_{1-20}$alkyl;

R$^4$ is:
H
C$_{1-20}$ alkyl,
heteroaryl, or
C$_6$–C$_{14}$ aryl;

R$^5$ can be the same or different when X is greater than 1 and is:
H,
C$_{1-20}$ alkyl,
heteroaryl, or
C$_6$–C$_{14}$ aryl;

R$^6$ is present when X equals N and is independently
H,
or C$_1$–C$_{20}$ alkyl and can be taken together with R$^3$ and the N to which they are attached to form a heteroaryl ring system; as defined below, and
(VIA), where:
A is
(a)

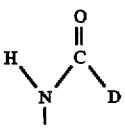

D is R$^1$ or OR$^1$,
where R$^1$ is: C$_1$–C$_{10}$alkyl, $C_3-C_{12}$cycloalkyl,
$C_6-C_{10}$aryl, or
$C_7-C_{11}$ aralkyl with the proviso that when D is $R^1$ and Z is beta-methyl, the value of $C_1-C_{10}$ alkyl is excluded; and (b)

$$(b) -C-OC_1-C_{12}\text{alkyl},$$
$$\phantom{(b) -}\|$$
$$\phantom{(b) -}O$$

alkyl, providing Z is not methyl;

(VIIA), where A is of the formula:

$$\begin{array}{c} Alk = R^2 \\ e \| f \end{array}$$

wherein:
Alk is $C_1-C_4$ straight or branched chain alkyl or alkenyl; dashed lines e and f each can independently represent a double bond when present, with the proviso that double bonds formed by e and f are not both present concurrently; and $R^2$ is
  (a) $C_6-C_{10}$ aryl, or 5–6 membered heteroaryl radical which can contain 1–4 nitrogen atoms, one oxygen or sulfur atoms or combinations thereof with 1–2 nitrogen atoms;
  (b) $COR_1$, where $R^1$ is $C_6-C_{10}$ aryl, substituted $C_6-C_{10}$ aryl, and heteroaryl;
  (c) $CONHR_2$, where $R_2$ is substituted phenyl, heteroaryl, substituted heteroaryl, or $C_7$ to $C_{12}$ cycloalkyl;
  (d) $CO_2R_3$, where $R_3$ is $C_1-C_{18}$ linear or branched alkyl, $C_6-C_{10}$ aryl, substituted $C_6-C_{10}$ aryl, or $C_7-C_{12}$ cycloalkyl; providing that in (b), (c) or (d), Alk is only alkenyl;

(VIIIA), where A is of the structure:

$$R^{20}\diagdown\diagup(CH_2)_n-R^4$$

where:
$R^{20}$ is H, methyl;
n is 0–10
$R^4$ is selected from:
  (a) —$COR^1$, where $R^1$ is phenyl or substituted phenyl;
  (b) —$CONHR^2$, where $R^2$ is substituted phenyl, heteroaryl, substituted heteroaryl;
  (c) —$COOR^3$, where $R^3$ is phenyl, substituted phenyl, heteroaryl, substituted heteroaryl; wherein said heteroaryl radical is a 5–6 membered ring which can contain 1–4 nitrogen atoms, one oxygen or sulfur atom, or combinations thereof with 1–2 nitrogen atoms, and wherein phenyl and heteroaryl can be substituted; wherein the above aryl or heteroaryl radicals can also be fused with a benzo or another heteroraryl ring and can further be substituted with one or more substitutents; and stereoisomers and pharmaceutically acceptable salts and esters thereof.

Also disclosed are processes for their preparation, pharmaceutical formulations comprising the novel compounds as active ingredients and methods of inhibiting prostatic and scalp 5α-reductases in diseases which occur under hyperandrogenic conditions, e.g. benign prostatic hyperplasia, with the novel compounds and their pharmaceutical formulations.

DETAILED DESCRIPTION OF THE INVENTION AND PREFERRED EMBODIMENTS

The description of the novel 7-substituted compounds disclosed and encompassed by this invention is conveniently discussed in terms of the 17-A substituent categories IA–VIIIA. It is to be noted that there may be some duplication of symbols of radicals which have slightly different meanings, e.g., where A is IA, the $R^3$ radical represents H, methyl or ethyl; however, where A is IVA, $R^3$ represents a long list of possible radicals. However, within a given 17-A substituent category, the nomenclature is consistent. Therefore, the discussion of the synthesis, properties and description of the compounds herein must first refer to the specific 17-A structure IA–VIIIA being discussed.

The following is a detailed description of the 7-position radical Z as used herein.

By the term "$C_1-C_4$ alkyl" as used herein, is meant to include: e.g. methyl, ethyl, propyl, isopropyl, n-butyl, sec-butyl, isobutyl and t-butyl.

By the term "$C_2-C_4$ alkenyl" as used herein is meant to include: vinyl, allyl, 1-propen-1-yl, 1-propen-2-yl, 1-buten-1-yl, 1-buten-2-yl, and the like.

By the term "$C_3-C_6$ cycloalkyl" as used herein is meant to include: cyclopropyl, cyclobutyl, cyclopentyl, cyclohexyl.

By the term "halo" as used herein is meant to include: fluoro, chloro, bromo, iodo.

By the term "$OC_1-C_4$ alkyl" as used herein is meant to include: methoxy, ethoxy, propoxy, isopropoxy, n-butoxy, isobutoxy, sec-butoxy, t-butoxy.

By the term "$OC_3-C_6$ cycloalkyl" as used herein is meant to include: cyclopropyloxy, cyclobutyloxy, cyclopentyloxy, cyclohexyloxy.

Representative examples of Z are where a-substituent (dashed lines) is hydrogen and the beta substituent (wedge) is e.g. methyl, ethyl, propyl, allyl, carboxymethyl, hydroxy, methoxy, ethoxy, cyclopropyloxy, cyclopentyloxy, acetoxy, fluoro, chloro, bromo, trifluoromethyl, trichloromethyl, fluoromethyl, chloromethyl, carboxy, N,N-dimethylcarbamoyl, hydroxymethyl, methoxymethyl, and the like.

Representative examples where Z is an alkenyl substituent, =CH—R', includes, e.g. =$CH_2$, =CH—$CH_3$, =CH—$CH_2CH_3$, and the like.

Representative examples where $R^1$, $R^2$ and the N can form a heterocyclic ring include: N-morpholinyl, N-(4-methyl)piperazinyl, N-piperidinyl, and the like.

Representative examples where Z is the spiro substituent:

$$\begin{array}{c}\diagup\diagdown R^1, \text{ includes: } \diagup\diagdown H,\\ \diagup\diagdown CH_3, \quad \diagup\diagdown CH_2CH_3,\end{array}$$

stereoisomers thereof and the like.

Unless otherwise indicated the 17-position substituent is assumed to be in the beta configuration.

Representative compounds included in the invention wherein all of the 7- and 17-substituents are in the beta configuration are:
4,7β-Dimethyl-4-aza-Androst-5-en-3-one-17β-ol, t-butyldimethylsilyl ether,
4,7β-Dimethyl-4-aza-Androst-5-en-3-one-17β-ol, 4,7β-Dimethyl-4-aza-androstan-3-one-17β-ol, 17β-Pivaloyloxy-4,7β-Dimethyl-4-Aza-Androstan-3-one, 17β-(t-Butylaminocarbonyloxy)-4,7β-dimethyl-5α-4-Aza-Androstan-3-one, 17β-Methoxycarbonyl-4-methyl-4-aza-androst-5-en-3,7-dione, 17β-t-Butylcarbonylamino-4,7β-dimethyl-4-aza-5α-androstane-3-one, 17β-Amino-4,7β-dimethyl-4-aza-5α-androstan-3-one, 17β-(1-Adamantyloxy)carbonylamino-4,7β-dimethyl-4-aza-5α-androstane-3-one, 17β-Benzoylamino-4,7β-dimethyl-4-aza-5α-androstane-3-one, 17-Oximino-4,7β-Dimethyl-4-aza-5α-androstan-3-one, 7β-Acetoxy-17β-carbomethoxy-4-methyl-4-aza-5α-androstan-3-one.

17β-(1-adamantyl)carbonylamino-4,7β-dimethyl-4-aza-5α-androstane-3-one, 4,7β-dimethyl-4-aza-5α-androstan-3,17-dione, 17β(N,N-diisopropyl)carboxamido-4-methyl-4-aza-5α-androstan-3,7-dione 17β-Benzylcarbonylamino-4,7β-dimethyl-4-aza-5α-androstan-3-one.

The first group of preferred compounds of this invention can be made by procedures outlined in the following Flowsheets:

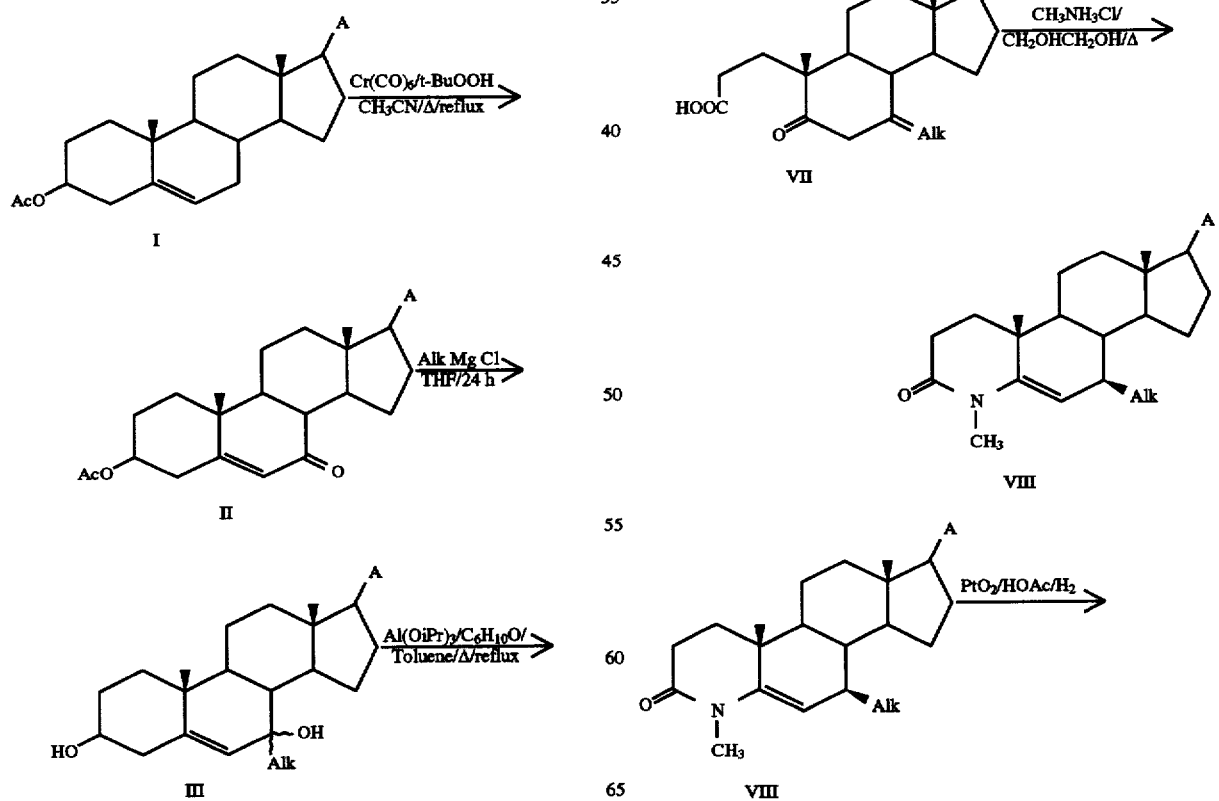

-continued
GENERAL FLOWSHEET I

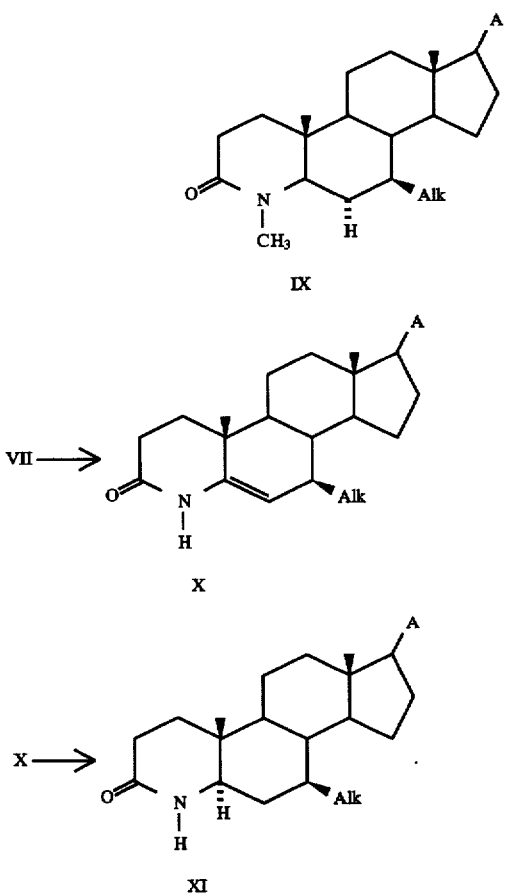

7-Beta Alkyl-17-A Series

The compounds of the instant invention comprising Z as a 7β alkyl group, e.g. methyl, ethyl, isopropyl, where A is defined above, can be prepared by the procedure outlined in The General Flowsheet.

As seen in the Flowsheet, the 3-acetoxy-androst-5-en-17-A I is oxidized to the corresponding 5-en-7-one II by treatment with hydrogen t-butyl peroxide and chromium hexacarbonyl in e.g. acetonitrile, at reflux. The $C_1$–$C_4$ alkyl group, designated Alk, e.g. methyl, can be introduced at this point by a Grignard reaction using e.g., alkyl magnesium chloride in e.g., anhydrous THF at 0°–10° C. to produce the 7-alkyl-7-hydroxy adduct III. This is then oxidized with e.g. aluminum isopropoxide and cyclohexanone (Oppenauer oxidation conditions) in refluxing toluene solvent to produce the 7-alkyl-4,6-dien-3-one IV. This in turn is reduced via a e.g., metal-ammonia reduction, using e.g., lithium, liquid ammonia, THF and toluene at −78° C. to selectively yield the 7-beta-alkyl-5-en-3-one V. In the next step the delta-5 double bond is isomerized to the 4-ene by use of DBU (1,8-diazabicyclo[5.4.0]undec-7-ene) in, e.g. refluxing tetrahydrofuran (THF) to produce the 7-alkyl 4-en-3-one, VI. The A Ring is next cleaved by treatment with e.g. potassium permanganate, sodium periodate in t-butyl alcohol at 80° C. to produce the corresponding seco-acid VII. Treatment of the seco-acid with an appropriate amine e.g., methylamine hydrochloride and sodium acetate in ethylene glycol at 180° C., yields e.g., the 4-methyl-4-aza-androst-5-en-3-one VIII. This in turn is selectively reduced with e.g., $PtO_2$, to remove the 5- double bond to produce the 5α-hydrogen compound IX. The seco-acid VII can be similarly treated with ammonia to produce the corresponding N—H compound, X, which can then be analogously treated with $PtO_2$ to produce the corresponding 5α-4N—H compound XI.

Throughout this series of reactions, the 17-A group should be inert to the individual reaction conditions and can be practiced with all of the herein disclosed 17-A side chains. There is now presented a sub-series of flowsheets denoted letter A through letter I.

FLOWSHEET A

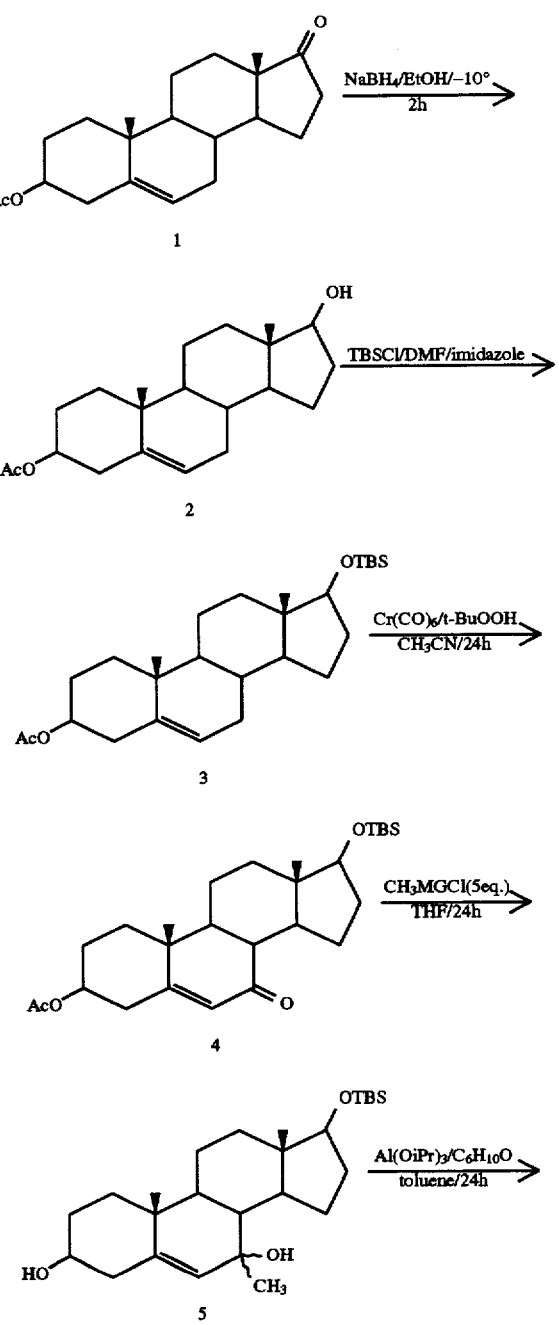

FLOWSHEET A
-continued
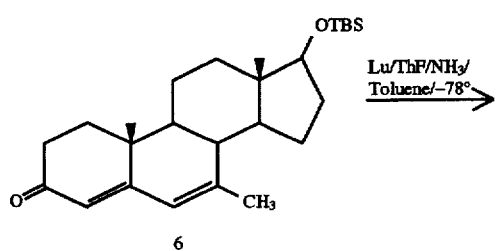
6
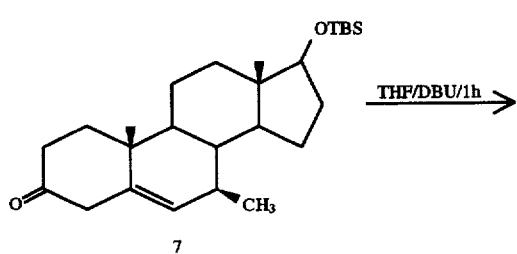
7
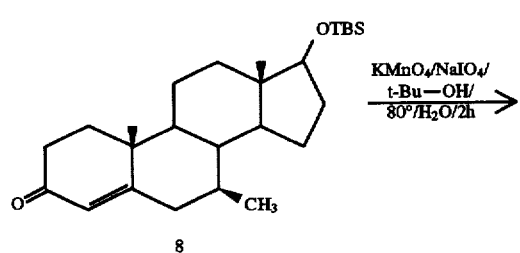
8
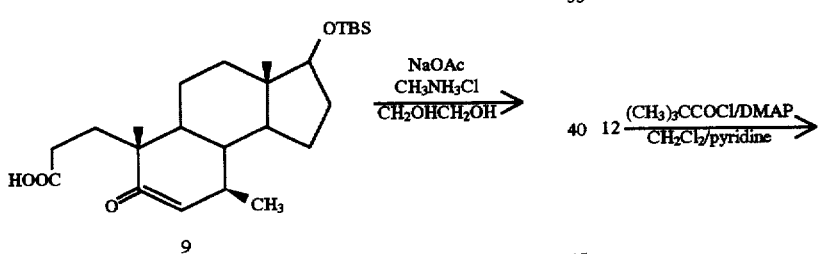
9
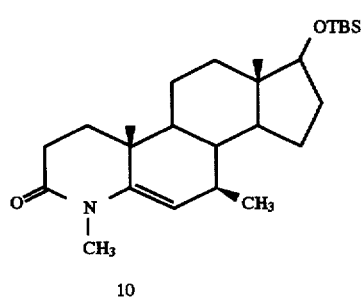
10
FLOWSHEET B
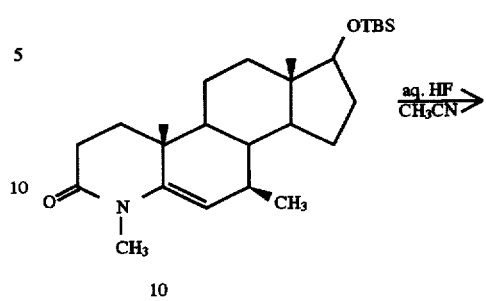
10
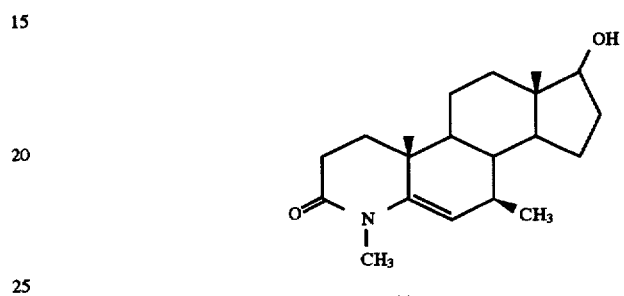
11
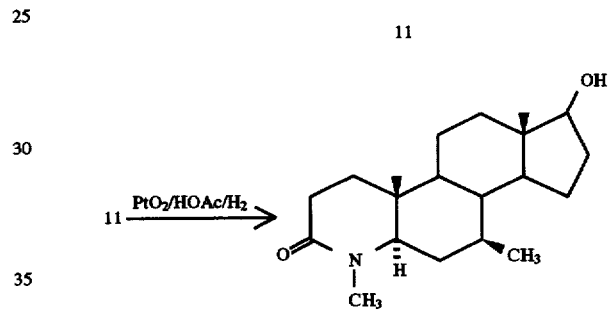
12
12 →((CH₃)₃CCOCl/DMAP)/(CH₂Cl₂/pyridine)→
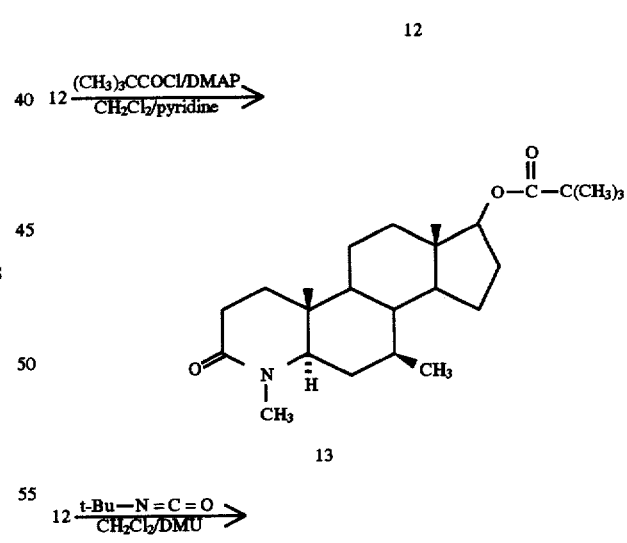
13
12 →(t-Bu—N=C=O)/(CH₂Cl₂/DMU)→

-continued
FLOWSHEET B

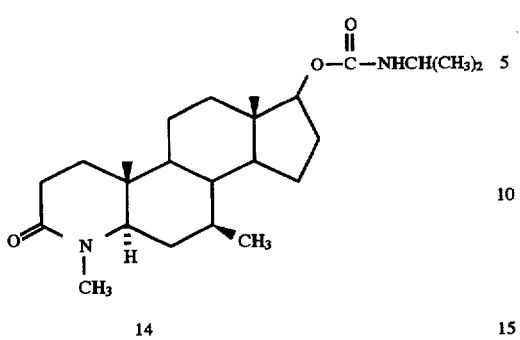

7-Beta Alkyl-17-Oxy-Androstanes

The compounds of the instant invention where A is hydroxy or derivatived hydroxy and Z is an 7β alkyl group, e.g. methyl, ethyl, propyl, isopropyl, allyl, can be prepared by the procedure outlined in Flowsheets A and B.

As seen in Flowsheet A, the 3-acetoxy-androst-5-en-17-one 1 is reacted with sodium borohydride in a suitable solvent, e.g. ethanol, at −10° C. to stereospecifically reduce the 17-ketone to the 17β-ol 2. The 17-hydroxy group is protected with the TBS group (t-butyldimethyl-silyl) by reacting TBS chloride with 2 in a suitable solvent, e.g. DMF in the presence of the proton acceptor, e.g. imidazole, at room temperature, to form 3.

Following the hydroxy protection, this compound is oxidized in the seven position to the corresponding 5-en-7-one 4 by treatment of 3 with hydrogen t-butyl peroxide and chromium hexacarbonyl in e.g. acetonitrile, at reflux. The alkyl group, e.g. methyl, can be introduced at this point by a Grignard reaction using e.g., methyl magnesium chloride in anhydrous THF at 0°–10° C. to produce the 7-methyl-7-hydroxy adduct 5. This Grignard product is then oxidized with aluminum isopropoxide and cyclohexanone (Oppenauer oxidation conditions) in refluxing toluene solvent to produce the 7-methyl-4,6-dien-3-one 6. This in turn is reduced via a metal-ammonia reduction using lithium in liquid ammonia, THF and toluene at −78° C. to selectively yield the 7-beta-methyl-5-en-3-one 7. In the next step the 5-double bond is isomerized to the 4-ene by use of DBU (1,8-diazabicyclo[5.4.0]undec-7-ene) in refluxing tetrahydrofuran (THF) to produce the 4-en-3-one, 8. The A Ring is next cleaved by treatment with potassium permanganate, sodium periodate in t-butyl alcohol at 80° C. to produce the corresponding seco-acid 9. Treatment of the seco-acid 9 with an appropriate amine e.g., methylamine hydrochloride and sodium acetate in ethylene glycol at 180° C., yields the 4-aza-androst-5-en-3-one 10. The TBS protecting group is then removed e.g., by aqueous HF in acetonitrile at 0° C., to yield the 17β alcohol 11. This in turn is selectively reduced to remove the 5-double bond to produce the 5α-hydrogen compound 12. At this point, the 17β hydroxy group can be derivatized with a variety of reagents. For example, it can be esterified with an acid moiety, e.g. t-butyl acid chloride in a solvent, e.g., pyridine, to produce the t-pentanoic acid ester 13.

Further, 12 can be reacted with an isocyanate, e.g. t-butyl-isocyanate in a solvent and in the presence of DBU to yield the urethane ester 14.

Similarily, other acylating agents obvious to one skilled in the art can be used to derivatize the 17-beta-ol grouping.

Carrying out the above series of reactions but using, e.g. ethyl magnesium chloride as the Grignard reagent, leads to the corresponding 7-beta ethyl analogs.

FLOWSHEET C

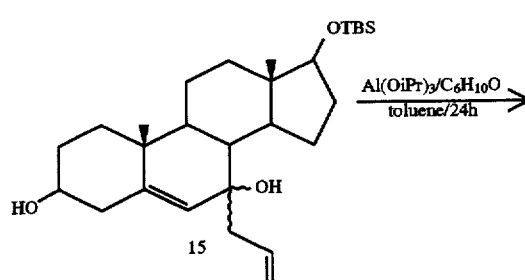

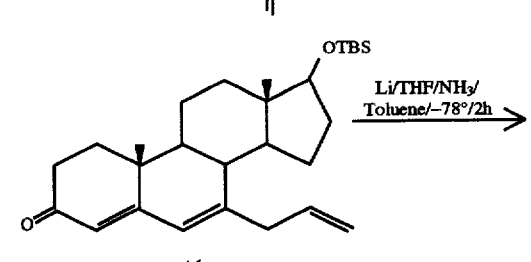

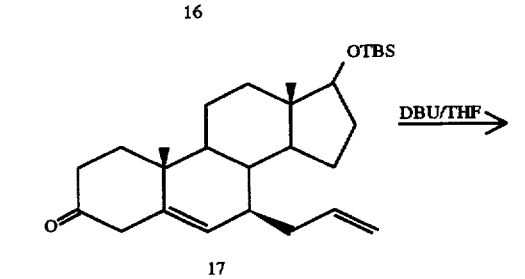

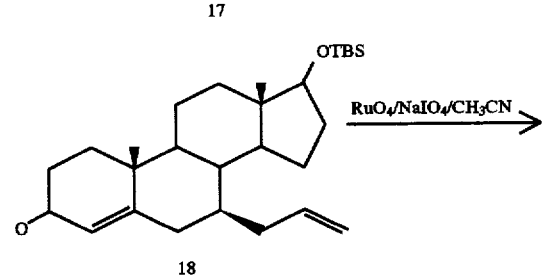

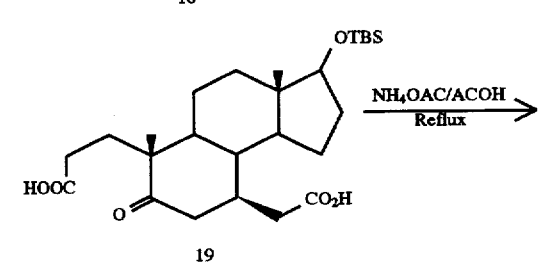

FLOWSHEET C

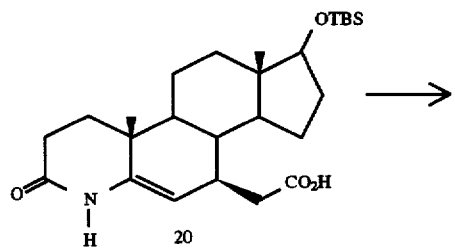

20

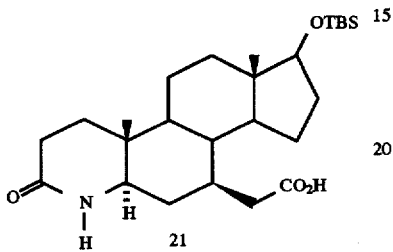

21

7-Carboxymethyl-17-OTBS Series

The 7-carboxy substituent is formed through the corresponding 7-allyl group. As seen in Flowsheet C, acetate 4 is reacted with allyl Grignard reagent to form the adduct 15 which is oxidized to the dienone 16 by Oppenauer oxidation conditions. Metal-ammonia reduction affords the 5-ene analog 17, followed by DBU-catalyzed double bond isomerization to 18. This in turn is oxidized in a key step with potassium permanganate, sodium periodate in t-butanol to form the 7-carboxymethyl seco-acid 19. Treatment with amines, e.g. ammonium salts, forms the 4-aza derivative, 20 which is then reduced to the 5-alpha 21. Use of methylamine in place of ammonia yields the corresponding 4-methyl analogs of 20 and 21.

FLOWSHEET D

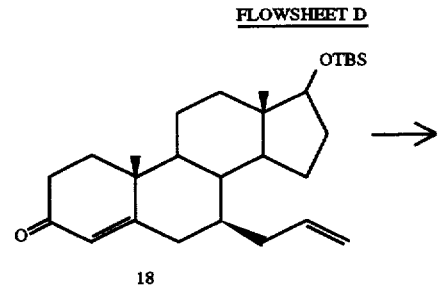

18

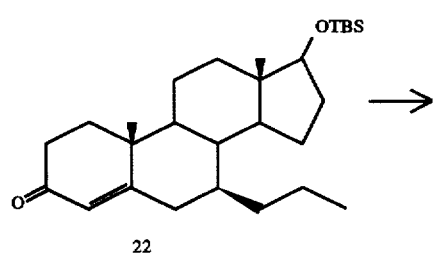

22

FLOWSHEET D (continued)

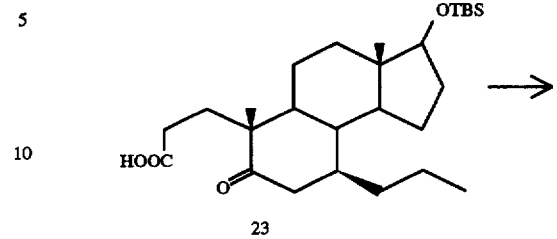

23

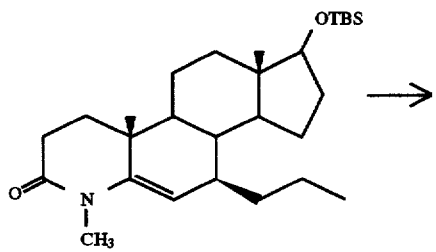

24

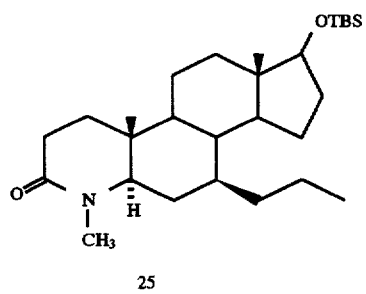

25

FLOWSHEET E

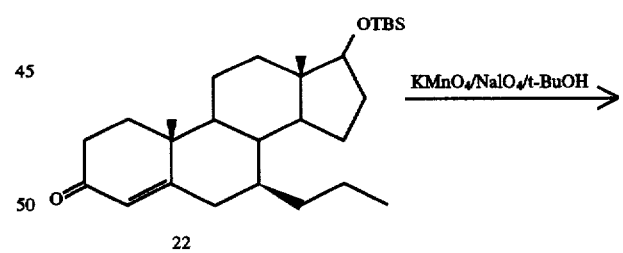

22

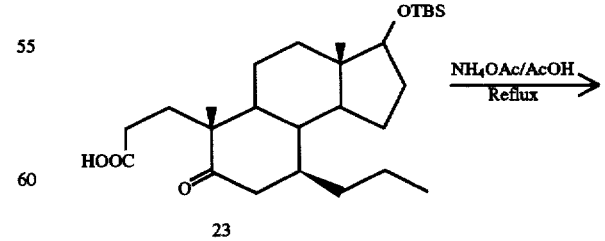

23

-continued
FLOWSHEET E

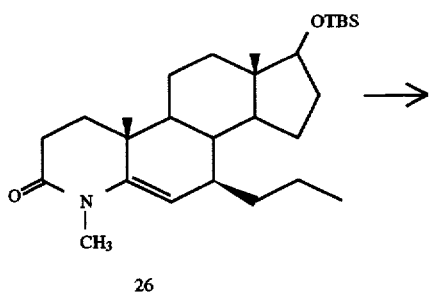

26

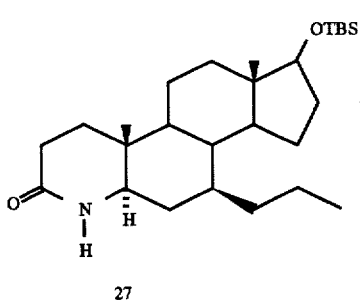

27

7-Propyl-17-OTBS Series

The 7-propyl analogs are made as illustrated in Flowsheet D starting with the 7-allyl-4-en-3-one 18, which is reduced by Wilkinson's catalyst to the propyl derivative 22, oxidized to the seco-acid 23, then condensed with amines, e.g. methylamine, to form the 4-methyl analog 24 and then reduced to the 5-alpha 25. Corresponding treatment with ammonia is shown in Flowsheet E shows the corresponding unsubstituted 4-aza 26 and 5-alpha 27 analogs.

FLOWSHEET F

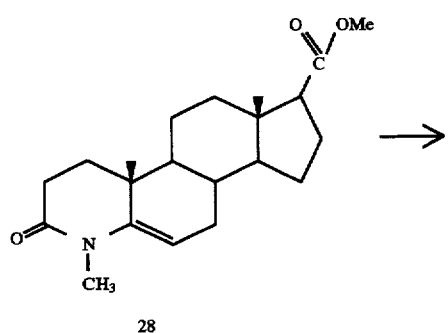

28

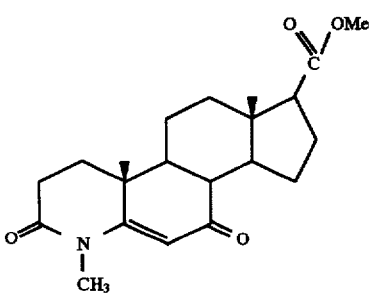

29

-continued
FLOWSHEET F

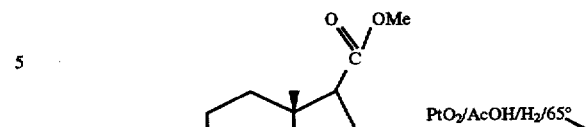

30

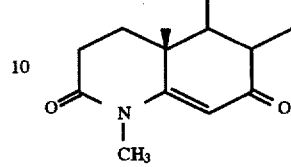

+ 32

31

FLOWSHEET G

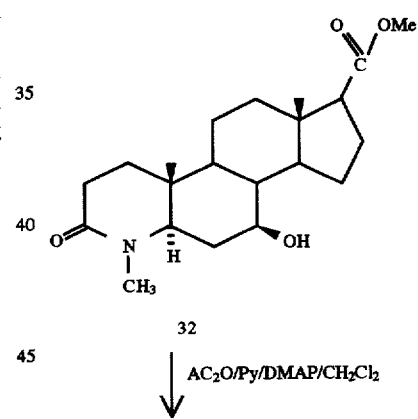

32

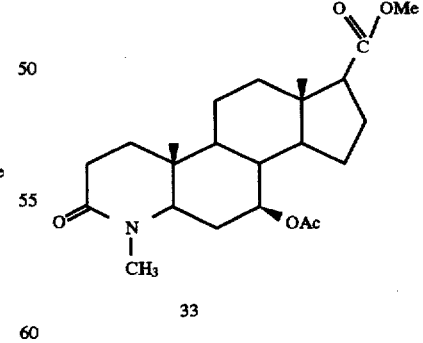

33

7-Beta Acetoxy 17-carboxyester Series

The 7-beta acetoxy series is prepared as illustrated in Flowsheets F and G by the oxidation of starting ester 28 to the 5-en-7-one 29 by the chromiumhexacarbonyl/t-butylhydroperoxide/acetonitrile procedure described above. Platinum catalyzed hydrogenation of 29 yields two products, the fully reduced 7-H compound 31, and 7-beta hydroxy compound 32. Acylation of 32 with acetic anhydride yields the 7-beta acetoxy compound 33.
FLOWSHEET H
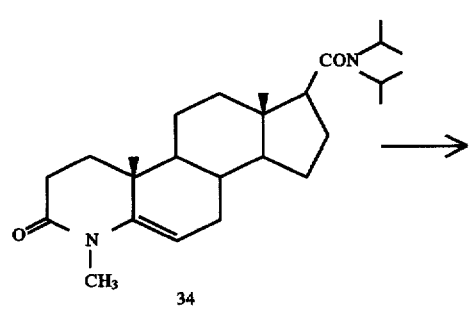
34
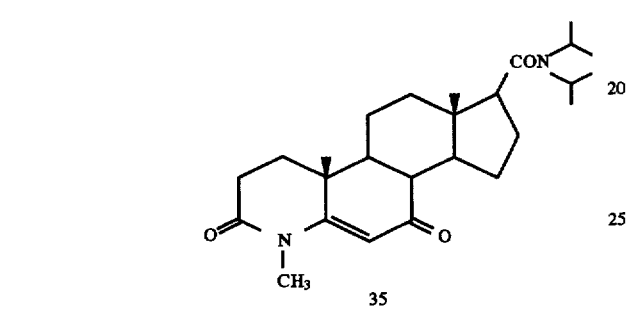
35
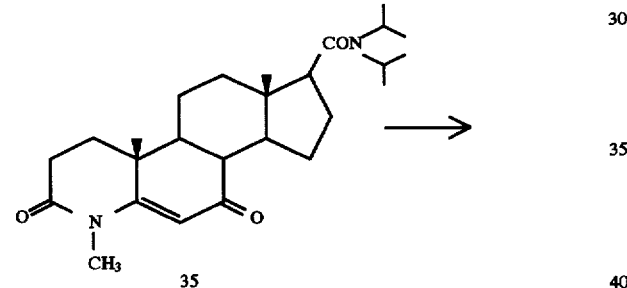
35
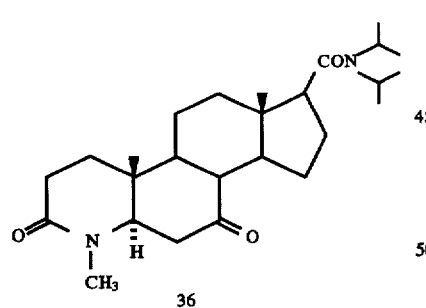
36
7-Keto-17-Carboxamide Series
The compound 34 is known in the art. This in can be oxidized with the chromium carbonyl reagent to yield the 5-en-7-one 35. The 5-double bond is catalytically reduced to yield the 7-one 36.
FLOWSHEET I
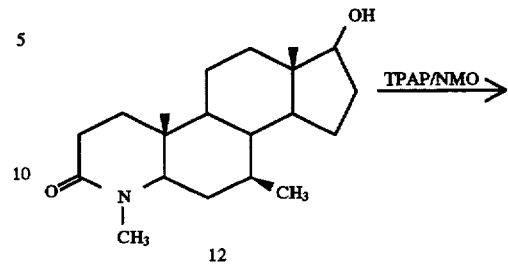
12
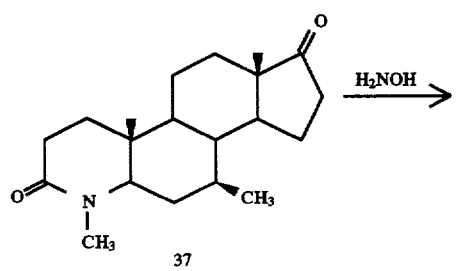
37
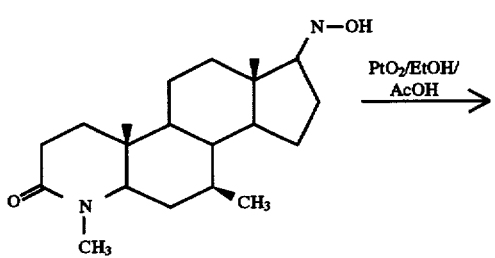
38
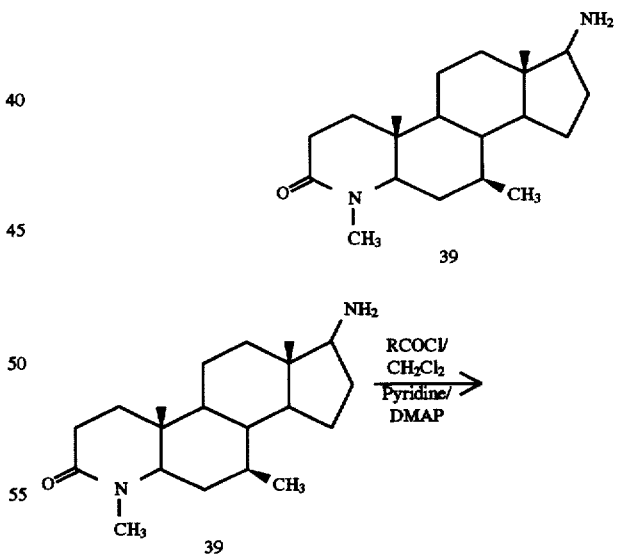
39

-continued
FLOWSHEET I

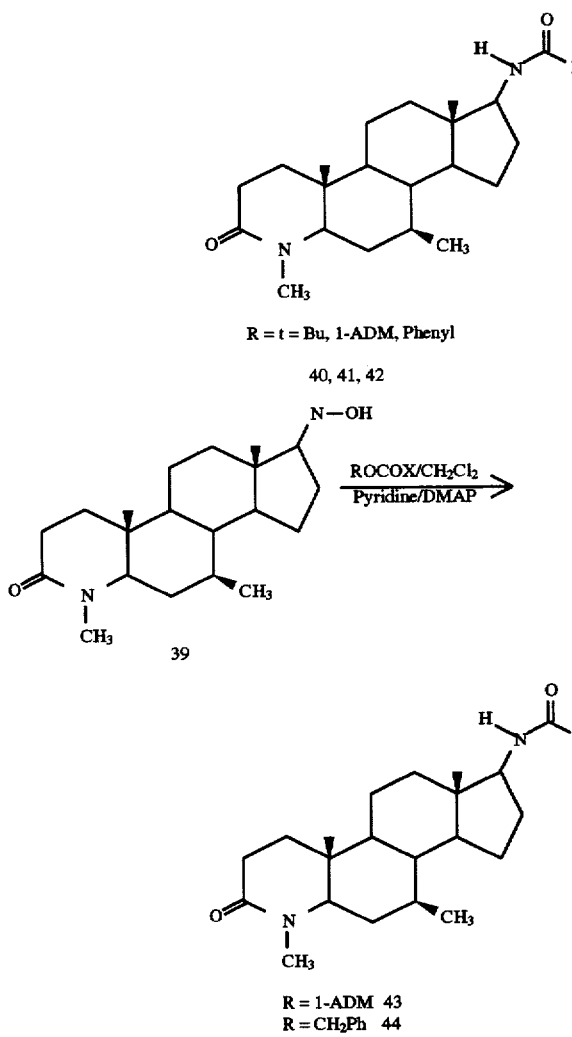

R = t = Bu, 1-ADM, Phenyl 40, 41, 42

R = 1-ADM 43
R = CH₂Ph 44

7-Beta Methyl-17-Aza Series

This series can be prepared as illustrated in Flowsheet I starting with the 7-beta methyl-4-N-methyl-17-ol 12. This is oxidized to the 17-keto compound 37, by the use of tetrapropylammonium perruthenate (TPAP) and N-methylmorphiline-N-oxide (NMO) at room temperature. This is reacted in turn with hydroxylamine in ethanol, pyridine at 100° C. to form the oxime 38, which is catalytically hydrogenated with platinum oxide in ethanol/acetic acid at room temperature to form the 17-amino 39.

The amine 39 can be reacted with a variety of acylating agents. Reaction with pivaloyl chloride in methylene chloride, pyridine, 4-dimethylamino pyridine (DMAP), yields 40, the "reverse finasteride"; reaction with 1-adamantane carbonyl chloride yields the 1-ADM 41; and reaction with benzyl chloride yields the benzoyl derivative 42.

Reaction of the amine 39 with different chloroformates yields the corresponding urethanes. Reaction of 39 with 1-adamantyl fluoroformate in DMAP, pyridine and methylene chloride yields the urethane 43: reaction with e.g. benzyl chloroformate correspondingly yields 44.

Other acylating agents and chloroformates known in the art can be used to produce the corresponding acyl and urethane compounds.

The above 7-substituents can be introduced into all of the compounds defined for the 17-A group herein by appropriate analogous procedures.

Accordingly, the present invention is particularly concerned with providing a method of treating the hyperandrogenic conditions of androgenic alopecia, acne vulgaris, seborrhea, and female hirsutism, benign prostatic hyperplasia, prostatitis, the [prevention and/or] treatment of prostatic carcinoma, by oral, topical, or parenteral administration, of the novel compounds of the present invention.

The following examples are illustrative of representative preferred embodiments of this invention and should not be construed to be limits on the scope or spirit of the instant invention.

EXAMPLES FOR THE CASE WHEN SUBSTITUENT "A" OF GENERAL FORMULA "T" IS AS DEFINED IN GROUP "VI(A)"

EXAMPLE 1

Synthesis of 3-Acetoxy-Androst-5-en-17-ol (2)

To a solution of 100 mg. (0.303 mmol) of 3-acetoxy-androst-5-en-17-one, 1, in 3 ml EtOH at −10° C., was added 22.9 mg (0.606 mmol) of sodium borohydride with stirring. After the reaction mixture was stirred for one and ½ hours, the mixture was diluted with 10 ml water, the ethanol solvent removed under vacuum, and the residue extracted with ethyl acetate. The organic layer was washed with aqueous Na₂CO₃, brine, dried over sodium sulfate and concentrated to leave a residue of crude title compound 2. Proton NMR confirmed the assigned structure.

EXAMPLE 2

Synthesis of 3-Acetoxy-Androst-5-en-17-ol, 17-t-butyl-dimethyl-silyl ether (3)

To a solution of the androstan-17-ol, 2, from Example 1, being 4.5 g (13.55 mmol) in 50 ml. dimethylformamide at 23° C. was added 2.76 g (40–65 mmol) imidazole followed by 3.063 g (20.32 mmol) of t-butyldimethylsilyl chloride. The reaction mixture was stirred and a solid began to precipitate. Twenty additional ml of DMF were added was and the mixture further stirred overnight. The mixture was poured into 1 liter water, the solid filtered and washed with water. The solid was dissolved in ethylacetate, the organic layer washed with brine and dried over sodium sulfate, concentrated to yield the silyl protected 17-ol title compound 3. The proton NMR confirmed the assigned structure.

EXAMPLE 3

Synthesis of 3-Acetoxy-Androst-5-ene-7-one-17β-ol, 17-t-butyldimethylsilyl ether (4)

To a solution of the TBMS protected 17-ol 3 from Example 2, being 5.6 g (12.55 mmol) in 100 ml acetonitrile at 23° C. was added 90% t-butyl hydrogen peroxide, 3.958 g (43.92 mol), and 138 mg chromium hexacarbonyl. After refluxing the mixture under nitrogen for 24 hours, the reaction mixture was poured into one liter water, solid was filtered, the residue washed with 500 ml water and the residue dissolved in 350 ml methylene chloride. The organic layer was washed with brine, dried over sodium sulfate and concentrated to yield crude material. Thin layer chromatography (3:1 hexane/ethyl acetate on silica gel) showed the presence of starting material. The solid was purified by column chromatography over silica gel by elution with 7% ethyl acetate/hexane to yield the title compound 4. Proton NMR confirmed the assigned structure.

EXAMPLE 4

Synthesis of 3,7-Dihydroxy-7-methyl-Androst-5-en-17β-ol, 17-TBMS ether (5)

To a solution of the product 4 from Example 3, being 440 mg. (0.956 mmol) in dry tetrahydrofuran at 0° C. was added dropwise methyl magnesium chloride over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield crude product. Proton NMR confirmed the assigned structure of the title compound 5 which was used in the next step without further purification.

EXAMPLE 5

Synthesis of 7-methyl-Androst-4,6-dien-3-one-17β-ol, 17-t-butyldimethylsilyl ether (6)

The above Grignard product 5, 3.5 g. (7.142 mmol) was dissolved in 50 ml toluene/50 ml. cyclohexanone and 20 ml of solvent distilled off under vacuum. To this was added 4.54 g. aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, washed with brine, dried and purified by column chromatography on silica gel, eluting with 5% EtOAc/hexane to yield the title compound 6.

EXAMPLE 6

Synthesis of 7β-Methyl-Androst-5-en-3-one-17β-ol, t-Butyldimethylsilyl ether, (7)

To a solution of 370 mg of 6, from Example 5, in 5.5 ml ammonia, 1 ml THF, 1 ml. toluene, was added 50 mg. of metallic lithium in small pieces. After stirring the blue solution for 2 hours, a solution of 1,2-dibromethane in 2 ml THF was added. After stirring the solution at −78° C. for 10 minutes, 250 mg of ammonium chloride was added and the mixture stirred for 10 minutes. The excess ammonia was removed by evaporation under a nitrogen stream. The reaction mixture was diluted with brine, extracted with ethyl acetate. The organic layer was washed with brine, dried and concentrated to yield crude material 7 which was used as such in Example 7.

EXAMPLE 7

Synthesis of 7β-Methyl-Androst-4-en-3-on-17β-ol, t-Butyldimethylsilyl ether, (8)

To a solution of 7, from Example 6, being 432 mg in 4 ml THF was added 150 microliters DBU (1,8-diaza-bicyclo [5.4.0]undec-7-ene under nitrogen with stirring. The mixture was refluxed for 1.5 hours, then cooled, diluted with NH₄Cl solution. The solvent THF was removed under vacuum and the residue extracted with ethyl acetate. The organic layer was washed with brine, dried and concentrated under reduced pressure to yield crude material. The titled product 8 was purified by chromatography on silica gel using 10% EtOAc/hexane as eluant.

EXAMPLE 8

Synthesis of 17β-(t-butyldimethylsilyloxy)-7β-methyl-5-oxo-A-nor-3,5-secoandrostan-3-oic acid, (9)

To a solution of 884 mg of 8 in 15 ml. t-butyl alcohol at 80° C. was added 248 mg sodium carbonate in 1.5 ml water followed by a dropwise addition over 15–20 minutes of a mixture of 2.273 g sodium periodate with 16.8 mg potassium permanganate in 8 ml. water. The reaction mixture was heated at 80° C. for 2 hours, cooled, filtered, the residue washed with water, and then the extract L-concentrated under vaccum. The extract was acidified with aqueous HCl, extracted with ethyl acetate and the organic layer washed with aqueous NaHSO₃, brine, dried and concentrated to yield crude 9. The proton NMR confirmed the assigned structure.

Following are descriptions and methods of synthesis of the other various 17-A radical compounds of structures IA–VIIIA, in this invention which can be used as starting materials to which the methods described herein can be applied to introduce the 16-substituent to yield the corresponding 16-substituted 17-A and 7,16-disubstituted 17-A derivatives.

EXAMPLES FOR THE CASE WHEN SUBSTITUENT "A" OF GENERAL FORMULA "I" IS AS DEFINED IN GROUP "I(A)(1)"

A preferred embodiment of the compound of general formula I is where A is structure IA (1) is represented by the general structural formula II:

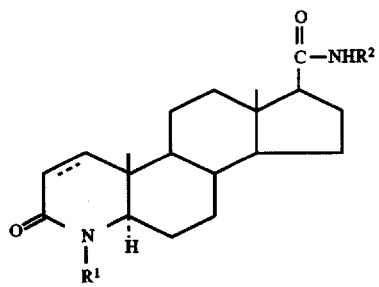

wherein

R¹ is hydrogen, methyl or ethyl, and

R² is branched chain alkyl cycloalkyl, aralkyl of from 4–12 carbons, phenyl, optionally substituted by methyl, chloro or fluoro, substituted or unsubstituted 1-, 2-adamantyl, 1-, 2-adamantylmethyl, 1-, 2- or 7-norbornanyl, 1-, 2- or 7-norbornanymethyl.

Representative compounds to which the 17 substituent may be introduced include the following:

17β-(N-tert-amylcarbamoyl)-4-aza-5α-androst-1-en-3-one,
17β-(N-tert-hexylcarbamoyl)-4-aza-5α-androst-1-en-3-one,
17β-(N-tert-butylcarbamoyl)-4-aza-4-methyl-5α-androst-1-en-3-one,
17β-(N-isobutylcarbamoyl)-4-aza-5α-androst-1-en-3-one,
17β-(N-tert-octylcarbamoyl)-4-aza-5 α-androst-1-en-3-one,
17β-(N-octylcarbamoyl)-4-aza-5β-androst-1-en-3-one,
17β-(N-t-butylcarbamoyl)-4-aza-5α-androst-1-en-3-one,
17β-(N-neopentylcarbamoyl)-4-aza-5α-androst-1-en-3-one,
17β-(N-2-adamantylcarbamoyl)-4-aza-5α-androst-1-en-3-one,
17β-(N-1-adamantylcarbamoyl)-4-aza-5α-androst-1-en-3-one,
17β-(N-2-norbornylcarbamoyl)-4-aza-5α-androst-1-en-3-one,
17α-(N-1-norbornylcarbamoyl)-4-aza-5α-androst-1-en-3-one,
17β-(N-phenylcarbamoyl)-4-aza-4-methyl-5α-androst-1-en-3-one,
17β-(N-benzylcarbamoyl)-4-aza-4-methyl-5α-androst-1-en-3-one, 17β-(N-tert-amylcarbamoyl)-4-aza-4-methyl-5α-androst-1-en-3-one, 17β-(N-tert-hexylcarbamoyl)-4-aza-4-methyl-5α-androst-1-en-3-one, 17β-(N-tert-butylcarbamoyl)-4-aza-4-methyl-5α-androst-1-en-3-one, 17β-(N-isobutylcarbamoyl)-4-aza-4-methyl-5α-androst-1-en-3-one, 17β-(N-tert-octylcarbamoyl)-4-aza-4-methyl-5α-androst-1-en-3-one, 17β-(N-1,1,3,3-tetramethylbutylcarbamoyl)-4-aza-5α-androst-1-en-3-one, 17β-(N-octylcarbamoyl)-4-aza-4-methyl-5α-androst-1-en-3-one, 17β-(N-1,1-diethylbutylcarbamoyl)-4-aza-4-methyl-5α-androst-1-en-3-one, 17β-(N-neopentylcarbamoyl)-4-aza-4-methyl-5α-androst-1-en-3-one, 17β(N-1-adamantylcarbamoyl)-4-aza-5α-androstan-3-one;

17β(N-1-adamantylcarbamoyl)-4-methyl-4-aza-5α-androst-1-en-3-one;

17β(N-1-adamantylcarbamoyl)-4-methyl-4-aza-5α-androstan-3-one;

17β-(N-1-adamantylmethylcarbamoyl)-4-aza-5α-androst-1-en-3-one;

17β-(N-2-adamantylcarbamoyl)-4-aza-5α-androstan-3-one;

17β-(N-methyl-N-2-adamantylcarbamoyl)-4-methyl-4-azaandrostan-3-one;

17β-(N-2-adamantylcarbamoyl)-4-methyl-4-aza-5α-androstane-3-one;

17β-(N-2-adamantylcarbamoyl)-4-methyl-4-aza-5α-androst-1-en-3-one;

17β-(N-methyl-N-2-adamantyl)carbamoyl-4-methyl-4-aza-androst-1-en-3-one;

17β-(N-(3-methyl)-1-adamantyl-carbamoyl)-4-aza-4-methyl-5α-androstan-3-one;

17β-(N-exo-2-norbornanylcarbamoyl)-4-aza-4-methyl-5α-androst-1-en-3-one;

17β-(N-exo-2-norbornanylcarbamoyl)-4-aza-5α-androst-1-en-3-one;

17β-(N-2-adamantylcarbamoyl)-4-aza-5α-androst-en-3-one;

17β-(N-methyl-N-2-adamantylcarbamoyl)-4-aza-4-methyl-androstan-3-one;

17β-(N-2-adamantylcarbamoyl)-4-methyl-4-aza-5α-androstan-3-one; and

17β-(N-methyl-N-2-adamantyl)carbamoyl-4-methyl-4-aza-androst-1-en-3-one.

The corresponding compounds of those above wherein the 4-aza substituent is substituted in each of the above named compounds with a hydrogen, methyl or an ethyl radical, to form a different N-substituent, and wherein a double bond can be optionally present as indicated by the dotted line in position 1.

The alkyl, cycloalkyl, aralkyl, monocyclic aryl, 1-, 2-adamantyl or 1-, 2-norbornanyl moieties can be substituted with one or more substituents of the following: $C_1$–$C_4$ linear/branched alkyl, including methyl, ethyl, isopropyl, n-butyl; nitro; oxo; $C_7$–$C_9$ aralkyl, including benzyl; $(CH_2)_n$COOR where n is 0–2 and R is H or $C_1$–$C_4$ linear/branched alkyl including methyl, ethyl; $CH_2OH$; OH; OR where R is $C_1$–$C_4$ linear/branched alkyl including methyl, ethyl; halo, including fluoro, bromo, iodo; COOH; COOR, where R is linear/branched $C_1$–$C_4$ alkyl; —$CONH_2$; $CH_2NH_2$; $CH_2NHCOR$ where R is $C_1$–$C_4$ linear/branched alkyl including methyl, ethyl; phenyl; o, m, p-substituted phenyl including p-nitro, p-amino and p-sulfo; or cyano. The amino group of the adamantyl or norbornanyl moiety can also be substituted as $R^1$ with methyl and ethyl, as well as hydrogen.

Also included within the scope of this invention are pharmaceutically acceptable salts or esters, where a basic or acidic group is present on the substituted alkyl, cycloalkyl, aralkyl, adamantyl or norbornanyl moiety. When an acidic substituent is present, i.e. —COOH, there can be formed the ammonia, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present; pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Representative examples include for $R^2$ (where AD is adamantyl):

3, 5, 7-trinitro-1-AD;
4-oxo-1-AD;
1-benzyl-1-AD; 4,4-dimethyl-1-Ad; 3,7-dimethyl-5-carboxymethyl-1-AD; 3-carboxymethyl-1-AD;
3-chloro-1-AD;
1,3-dihydroxy-6,6-dimethyl-2-AD;
3-chloro-1-AD;
4-carbethoxy-2-AD;
4-carboxy-2-AD;
3-isopropyl-1-AD;
3-n-butyl-1-AD;
3-propyl-1-AD;
3-,5-diethyl-1-AD;
3-hydroxymethyl-1-AD;
2-carboxy-1-AD;
3-methyl-1-AD;
5-hydroxy-2-AD;
2-hydroxy-1-AD;
1-aminomethyl-1-hydroxy-2-AD;
2-oxo-1-AD;
2-phenyl-2-AD;
1-amino-methyl-2-AD;
1-carboxy-2-AD;
1-aminocarbonyl-2-AD;
3-hydroxy-5,7-dimethyl-1-AD;
4-fluoro-1-AD;
3-fluoro-1-AD;
4-hydroxy-2-AD;
3-phenyl-1-AD;
3-(p-aminophenyl)-1-AD;
3-(p-nitrophenyl)-1-AD;
3-methyl-5- hydroxymethyl-1-AD;
3,5-dimethyl-4-hydroxy-1-AD;
2-hydroxymethyl-2-AD;
3-(p-sulfophenyl)-1-AD;
3-methyl-5-ethyl-1-AD;
2-carboxy-2-AD;
3,5-7-trimethyl-1-AD;
4-iodo-2-AD;
4-bromo-2-AD;
4-chloro-2-AD;
1 -acetylaminomethyl-2-AD;
1-carboxymethyl-2-AD;
1-methyl-2-AD;
1-aminocarboxylmethyl-2-AD;
1-aminocarboxyl-1-AD;
2-cyano-2-AD;

3,5-dimethyl-7-ethyl-1-AD;
4-hydroxy-1-AD;
1-hydroxy-2-AD;
5-carboxy-3-methyl-1-AD;
3,5-dimethyl-7-carboxy-1-AD;
3-carboxy-1-AD;
3-hydroxy-1-AD; and the like.

Representative examples include for $R^2$ as substituted norbornanyl moieties are (where NB is norborn-anyl):
2-NB;
1,7,7-trimethyl-4-phenyl-2-NB;
3-carboxy-2-NB;
3-phenyl-2-carboxy-2-NB;
2-cyano-3-phenyl-2-NB;
3-hydroxy-4,7,7-trimethyl-2-NB; 6-hydroxymethyl-2-NB;
5-cyano-2-NB;
3-allyl-2-NB;
1-NB
7,7-dimethyl-1-hydroxymethyl-2-NB;
3-methoxy-4,7,7-trimethyl-2-NB;
3-aminocarbonyl-2-NB;
3-ethoxycarbonyl-2-NB;
3,3-dimethyl-2-NB;
7-oxo-1-NB;
3-phenyl-2-NB;
1-carboxy-methyl-7,7-dimethyl-2-NB;
1-ethyl-2-NB;
1-methyl-2-NB;
2,2,3,3,5,5,6,6,7,7-decafluoro-1-NB;
3-hydroxy-2-NB;
3-chloro-2-NB;
3-(p-methoxyphenyl)-2-NB;
2,2-dimethyl-3-methylene-7-NB;
3-oxo-2-NB;
1-methoxy-2-NB;
7-NB;
3-isopropyl-2-NB;
2-bromo-1-NB;
3-chloro-1-NB and the like.

Procedures for preparing the starting compounds of structure IA for introducing the 16-substituent including the above, are well known in the art.

The novel compounds of formula I of the present invention can be prepared by a method starting with the known steroid esters (III) of the formula:

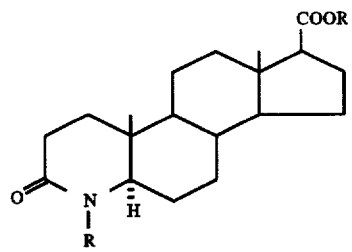

III

17β-(carbomethoxy)-4-aza-5-α-androstan-3-ones which includes the stages of optionally 1) dehydrogenating said starting material to produce the corresponding compound containing a double-bond in the 1,2-position of the A-ring, 2) converting the 17-carbomethoxy substituent into an N-substituted alkyl, cycloalkyl, aralkyl, monocylic acyl, or adamantylcarbamoyl substituent and, if desired, 3) alkylating the A-ring nitrogen to introduce a N-methyl or N-ethyl substituent into the A ring 4-position. For the dehydrogenation step, it is preferable that the 4-aza nitrogen be unsubstituted. The alternate pathways can consist of one or more discrete chemical steps and if desired can take place before step (1) or following step (1) or step (3).

In accordance with the present invention (see general flow sheet II, below at page 57), the starting materials are formed by optionally: (1) heating a 17β-alkoxycarbonyl-4-aza-5α-androstan-3-ones, compound III, (prepared in the literature as described in the reference U.S. Pat. No. 4,377,584) with a dehydrogenating agent such as benzeneseleninic anhydride in a refluxing inert solvent, e.g. chlorobenzene, to form a 17β-alkoxycarbonyl-4-aza-5α-androst-1-ene- 3-one IV (alternately, the dichlorodicyanobenzoquinone process of Dolling, et al., JACS 1988, Vol. 110, pp. 3318–3319, can be used); (2) the formed 5α-androst-1-en-3-one compound from Step 1 can be reacted with, e.g. sodium hydride under anhydrous conditions in a neutral solvent such as dimethylformamide; (3) contacting the resulting reaction mixture with an alkyl (methyl or ethyl) iodide to form the corresponding 17-β-alkoxy-adamantyl-carbamoyl-4-alkyl-4-aza-5α-androst-1-en-3-one V; (4) subsequently hydrolyzing said 17β-alkoxycarbonyl-4-alkyl-4-aza-5α-androst-1-en-3-one with a strong base, such as aqueous methanolic potassium hydroxide at the reflux temperature, followed by acidification and isolation of the resulting steroidal acid to yield 17β-carboxy 4-alkyl-4-aza-5α-androst-1-en-3-one VI; (5) said steroidal acid can be then converted to its corresponding 2-pyridylthio ester by refluxing with triphenyl phosphine and 2,2'-dipyridyl disulfide in an inert solvent such as toluene and the resulting product 17β-(2-pyridylthiocarbonyl)-4-alkyl-4-aza-5α-androst-1-en-3-one VII can be isolated by chromatography on e.g. silica gel; and (6) said pyridylthio ester can be then reacted with 1-adamantyl-, 2-adamantylamine or norbornanylamine in an inert solvent e.g. tetrahydro-furan, to form the desired product 17β-N-adamantyl-carbamoyl-4-alkyl-4-aza-5α-androst-1-en-3-one VIII which can be isolated by chromatography e.g. on silica gel. When the previous reaction is carried out in the absence of first forming the double bond at position 1, the corresponding 17β-(N-adamantyl-carbamoyl)-4-alkyl-4-aza-5α-androstan-3-one (or N-norbornanyl carbamoyl compound) is prepared.

In accordance with an alternate process of our invention the corresponding N-unsubstituted-17β(N-adamantyl-carbamoyl)-4-aza-5α-androst-1-en-3-one XIV is readily prepared from the 17β (alkoxycarbonyl)-4-aza-5α-androstone-3-one IV by repeating the above series of reaction steps but omitting the alkylation Step 2 herein above, i.e. treatment of the 4-aza-5α-androst-1-en-3-one with e.g. sodium amide followed by methyl or ethyl iodide via intermediates XII and XIII.

In accordance with a further alternate process of preparing the compounds of our invention having only hydrogen as the sole substituent on the ring A—nitrogen, the double bond in the A ring is introduced as the last step of the process. Thus, a 17β-alkoxycarbonyl 4-aza-5α-androstan-3-one III is hydrolyzed to the corresponding steroidal acid IX 17β-carboxy-4-aza-5α-androstan-3-one which in turn is converted to the corresponding pyridylthio ester, 17β (2-pyridylthiocarbonyl)-4-aza-5α-androstan-3-one, X followed by treatment of the ester with an amine of formula $R^2$—$NH_2$ wherein $R^2$ is as defined hereinabove as 1- or 2-adamantyl or 1-, 2-, or 7-norbornanyl to form a 17β (N-adamantyl-carbamoyl)-4-aza-5α-androstone-3-one XI which is dehydrogenated as previously described to produce compound XIV, 17β-(N-adamantyl-carbamoyl)-4-aza-androst-1-en-3-one or corresponding norbornanyl derivative.

In another alternate method of introducing the 17β-(N-adamantyl-carbamoyl)substituent into a 17β-carboxy androstane compound of formula VI, XII or IX, each is treated in a manner similar to the procedure described in Steroids, Vol. 35 #3, March 1980, p. 1–7 with dicyclohexylcarbodiimide and 1-hydroxybenzotriazole to form the 17β-(1-benzo-triazoloxycarbonyl)-4-aza-5α-androst-1-en-3-one, VII, XIII or compound X, wherein the substituent X is benzotriazoloxy group.

The above reactions are schematically represented in the following general flowsheet II.

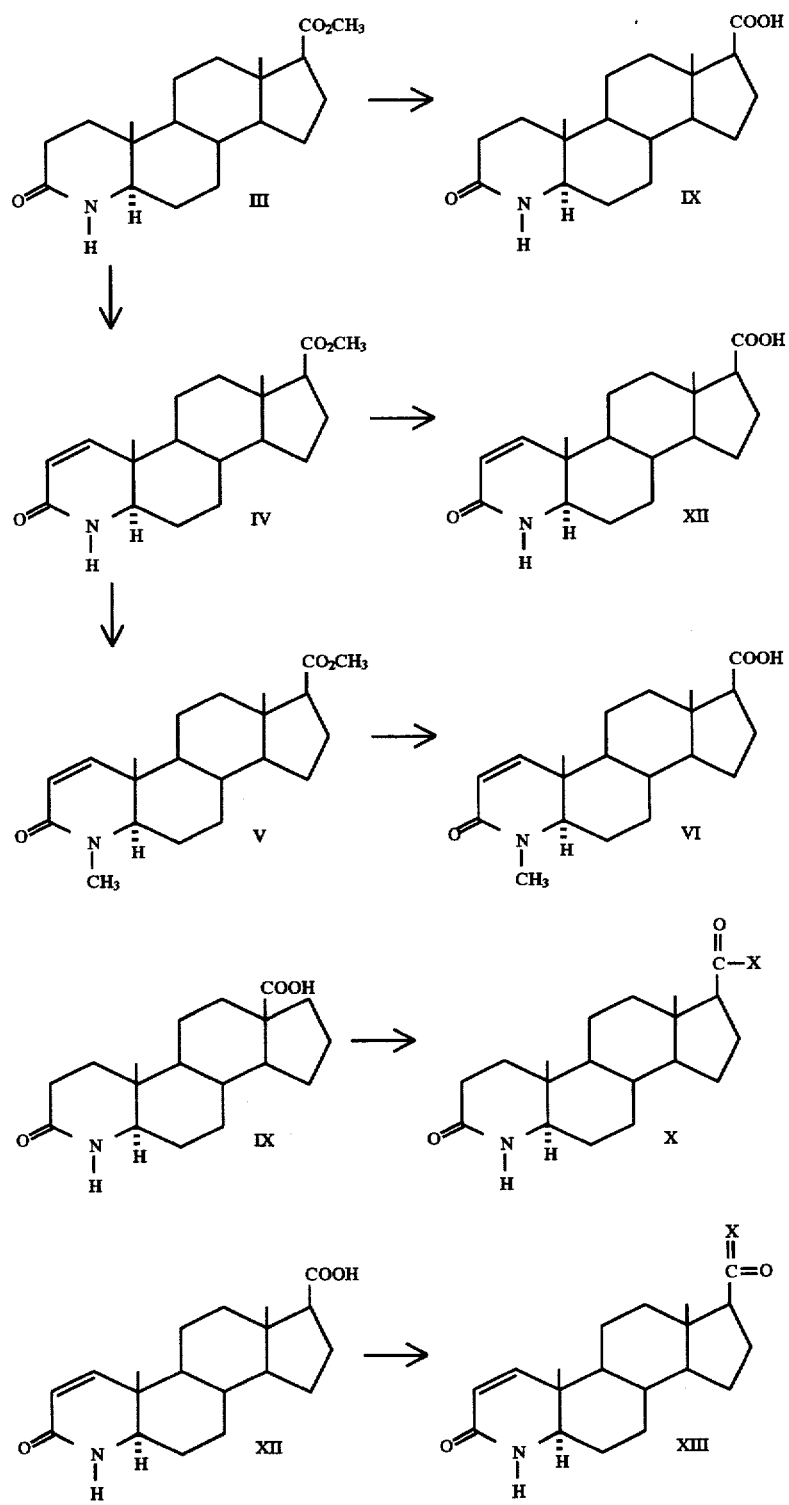

-continued
GENERAL FLOWSHEET II

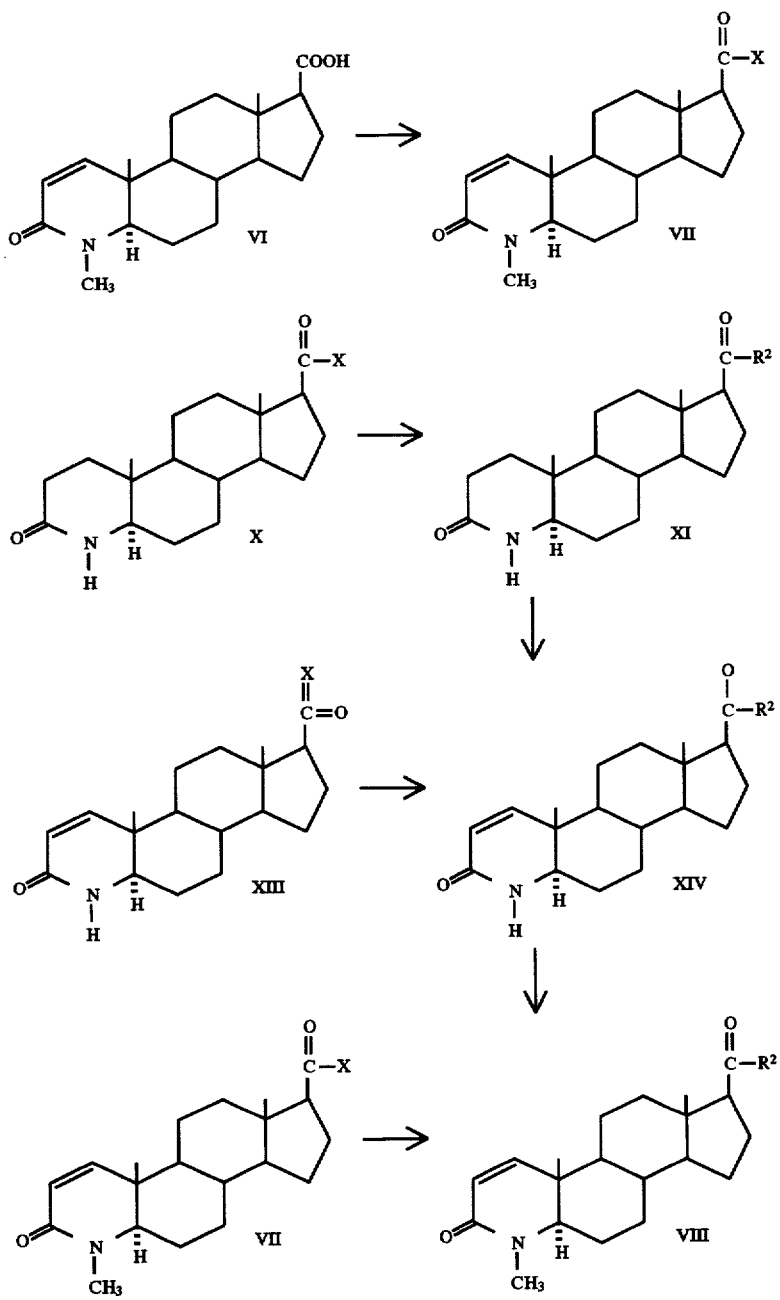

X is 2-pyridylthio or 1-benzotriazoloxy.
R² is 1- or 2-adamantyl or norbornanyl.

EXAMPLES FOR THE CASE WHEN SUBSTITUENT "A" OF GENERAL FORMULA "I" IS AS DEFINED IN GROUP "I(A)(2)"

Another preferred embodiment of the compounds of our invention is the compound of above general structure I, wherein the dotted line between the A ring positions 1 and 2 is a double bond, R is hydrogen or methyl, and "A" is COQ where "Q" is branched chain alkyl, or cycloalkyl of from 4–10 carbons.

Another embodiment of the invention is the compounds of above Structure I where "Q" is phenyl, or phenyl substituted by substituents described above, including where Q is phenyl, 2-, 3-, or 4-tolyl, xylyl, 2-bromophenyl, 2-chlorophenyl, 2,6-dichlorophenyl, 2,6-dibromophenyl, aminophenyl, N-alkylaminophenyl, N-N-dialkyl-aminophenyl, 4-biphenyl, 3-biphenyl, naphthyl, anthracyl, phenanthryl, thiophenyl, methylthiophenyl, methylsulfinyl, phenyl, methylsulfophenyl, aminosulfophenyl, thioethylphenyl, acetoxymethylthiophenyl, 17β-(4-hydroxyphenyl), 17β-(3-hydroxyphenyl), 17β-(3,4-dihydroxyphenyl), or 17β-(3,5-dimethyl-4-hydroxyphenyl).

Representative compounds of the invention are:
17β-(phenylcarbonyl)-4-aza-4-methyl-5α-androst-1-ene-3-one;
17β-(2-tolylcarbonyl)-4-aza-4-methyl-5α-androst-1-ene-3-one;.
17β-(3-tolylcarbonyl)-4-aza-4-methyl-5α-androst-1-ene-3-one;
17β-(4-tolylcarbonyl)-4-aza-4-methyl-5α-androst-1-ene-3-one;
17β-(2-bromophenylcarbonyl)-4-aza-4-methyl-5α-androst-1-ene-3-one;
17β-(2-chlorophenylcarbonyl)-4-aza-4-methyl-5α-androst-1-ene-3-one;
17β-(2,6-dichlorophenylcarbonyl)-4-aza-4-methyl-5α-androst-1-ene-3-one;
17β-(2,6-dibromophenylcarbonyl)-4-aza-4-methyl-5α-androst-1-ene-3-one;
17β-(xylylcarbonyl)-4-aza-4-methyl-5α-androst-1-ene-3-one;
17β-(t-butylcarbonyl)-4-aza-5α-androst-1-ene-3-one;
17β-(isobutylcarbonyl)-4-aza-5α-androst-1-ene-3-one;
17β-(isooctylcarbonyl)-4-aza-5α-androst-1-ene-3-one;
17β-(n-octylcarbonyl)-4-aza-5α-androst-1-ene-3-one;
17β-(1,1-diethylbutylcarbonyl)-4-aza-5α-androst-1-ene-3-one;
17β-(neopentylcarbonyl)-4-aza-5α-androst-1-ene-3-one;
17β-(tert-amylcarbonyl)-4-aza-4-5α-androst-1-ene-3-one;
17β-(tert-hexylcarbonyl)-4-aza-4-5α-androst-1-ene-3-one;
17β-(cyclohexylcarbonyl)-4-aza-5α-androst- 1-ene-3-one;
17β-(cyclopentylcarbonyl)-4-aza-5α-androst-1-ene-3-one;
17β-(benzylcarbonyl)-4-aza-5α-androst-1-ene-3-one;
17β-(2-pyridylcarbonyl)-4-aza-5α-androst-1-ene-3-one;
17β-(4-pyridylcarbonyl)-4-aza-5α-androst-1-ene-3-one;
17β-(2-pyrrolylcarbonyl)-4-aza-5α-androst-1-ene-3-one;
17β-(2-furylcarbonyl)-4-aza-5α-androst-1-ene-3-one;
17β-(2-thiophenylcarbonyl)-4-aza-5α-androst-1-ene-3-one;
17β-(2-adamantylcarbonyl)-4-aza-5α-androst-1-ene-3-one;
17β-(phenylcarbonyl)-4-aza-5α-androst-1-ene-3-one;
17β-(2-tolylcarbonyl)-4-aza-5α-androst-1-ene-3-one;
17β-(3-tolylcarbonyl)-4-aza-5α-androst-1-ene-3-one;
17β-(4-tolylcarbonyl)-4-aza-5α-androst-1-ene-3-one;
17β-(2-bromophenylcarbonyl)-4-aza-5α-androst-1-ene-3-one;
17β-(2-chlorophenylcarbonyl)-4-aza-5α-androst-1-ene-3-one;
17β-(2,6-dichlorophenylcarbonyl)-4-aza-5α-androst-1-ene-3-one;
17β-(2,6-dibromophenylcarbonyl)-4-aza-5α-androst-1-ene-3-one;
17β-(xylylcarbonyl)-4-aza-5α-androst-1-ene-3-one;
17β-(phenylethyl)carbonyl-4-aza-5α-androst-1-ene-3-one;
17β-(4-dimethylaminophenylcarbonyl)-4-aza-5α-androst-1-en-3-one;
17β-(3-dimethylaminophenylcarbonyl)-4-aza-5α-androst-1-en-3-one.
17β-(3,4-diethylaminophenylcarbonyl)-4-aza-androst-1-en-3-one.
17β-(3,5-dimethyl-4-diethylaminophenylcarbonyl)-4-aza-5α-androst-1-en-3-one;
17β-(4-N-methylaminomethylphenylcarbonyl)-4-aza-5α-androst-1-en-3-one; or
17β-(2-N-ethylamino-4-ethylphenylcarbonyl)-4-aza-5α-androst-1-en-3-one;
17β-(4-phenylbenzoyl)-4-aza-5α-androst-1-en-3-one;
17β-(3-phenylbenzoyl)-4-aza-5α-androst-1-en-3-one;
17β-(4-biphenyl)-4-aza-5α-androst-1-en-3-one; 17β-(3-biphenyl)-4-aza-5α-androst-1-en-3-one;
17β-(1-naphthyl)-4-aza-5α-androst-1-en-3-one;
17β-(2-naphthyl)-4-aza-5α-androst-1-en-3-one;
17β-(1-phenanthryl)-4-aza-5α-androst-1-en-3-one;
17β-(2-phenanthryl)-4-aza-5α-androst-1-en-3-one;
17β-(1-biphenyl)-4-aza-5α-androst-1-en-3-one;
17β-(9-anthracyl)-4-aza-5α-androst-1-en-3-one;
17β-(4-thiophenylcarbonyl)-4-aza-5α-androst-1-en-3-one;
17β-(3-thiophenylcarbonyl)-4-aza-5α-androst-1-en-3-one;
17β-(4-methylthiophenylcarbonyl)-4-aza-5α-androst-1-en-3-one;
17β-(4-methylsulfinylphenylcarbonyl)-4-aza-5α-androst-1-en-3-one;
17β-(4-methylsulfophenylcarbonyl)-4-aza-5α-androst-1-en-3-one;
17β-(3-methylsulfinylphenylcarbonyl )-4-aza-5α-androst-1-en-3-one;
17β-(4-N,N-dimethylaminosulfophenylcarbonyl)-4-aza-5α-androst-1-en-3-one;
17β-(2-ethyl-4-methylthiophenylcarbonyl)-4-aza-5α-androst-1-en-3-one;
17β-(4-thioethylphenylcarbonyl)-4-aza-4-methyl-5α-androst-1-en-3-one;
17β-(4-acetoxymethylthiophenylcarbonyl)-4-aza-4-methyl-5α-androst-1-en-3-one;
17β-(2-methyl-4-methylthiophenylcarbonyl)-4-aza-4-methyl-5α-androst-1-en-3-one;
17β-(2-methyl-4-methylsulfinylphenylcarbonyl)-4-aza-4-methyl-5α-androst-1-en-3-one;
17β-(2-isopropyl-4-methylsulfophenylcarbonyl)-4-aza-4-methyl-5α-androst-1-en-3-one;
17β-(4-methylthiophenylcarbonyl)-4-aza-4-methyl-5α-androstan-3-one;
17β-(4-methylsulfinylphenylcarbonyl)-4-aza-4-methyl-5α-androstan-3-one;
17β-(4-methylsulfophenylcarbonyl)-4-aza-4-methyl-5α-androstan-3-one;
17β-(4-hydroxyphenyl)-4-aza-5α-androst-1-en-3-one;
17β-(3-hydroxyphenyl)-4-aza-5α-androst-1-en-3-one;
17β-(3,4-dihydroxyphenyl)-4-aza-5α-androst-1-en-3-one;
17β-(3,5-dimethyl-4-hydroxyphenyl)-4-aza-5α-androst-1-en-3-one;
17β-(4-hydroxymethylphenyl)-4-aza-5α-androst-1-en-3-one;
17β-(2-hydroxyethylphenylcarbonyl)-4-aza-5α-androst-1-en-3-one;
17β-(4-methoxyphenyl)-4-aza-5α-androst-1-en-3-one;
17β-(4-carboxymethylphenyl)-4-aza-5α-androst-1-en-3-one;
17β-(4-hydroxyphenyl)-4-aza-4-methyl-5α-androst-1-en-3-one;
17β-(3-hydroxyphenyl)-4-aza-4-methyl-5α-androst-1-en-3-one;
17β-(3,4-dihydroxyphenyl)-4-aza-4-methyl-5α-androst-1-en-3-one;
17β-(3,5-dimethyl-4-hydroxyphenyl)-4-aza-4-methyl-5α-androst-1-en-3-one;
17β-(4-hydroxymethylphenyl)-4-aza-4-methyl-5α-androst-1-en-3-one;
17β-(2-hydroxyethylphenylcarbonyl)-4-aza-4-methyl-5β-androst-1-en-3-one;
17β-(4-methoxyphenyl)-4-aza-4-methyl-5α-androst-1-en-3-one;
17β-(4-carboxymethylphenyl)-4-aza-4-methyl-5α-androst-1-en-3-one; and
17β-(4-carboxyphenyl)-4-aza-5α-androst-1-en-3-one;
and the corresponding compounds wherein the 4-hydrogen substituent is replaced in each of the above named compounds by a methyl or an ethyl radical.

The compounds of formula I of the present invention can be prepared by a method starting with the known steroid ester of the formula:

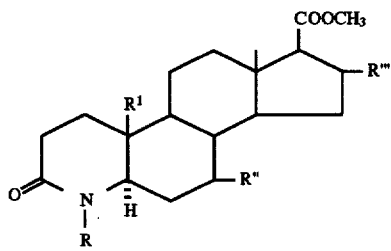

named 17β-(carbomethoxy)-4-aza-5α-androstan-3-one, which includes the stages of (1) dehydrogenating said staffing material to produce the corresponding compound containing a double bond in the 1,2-position of the A-ring, (2) converting the 17-carbomethoxy substituent into a 17β-acyl substituent and, if desired (3) alkylating the A-ring nitrogen to introduce 4-methyl or 4-ethyl substituents into the A-ring. For the dehydrogenation step, it is preferable that the 4-aza nitrogen be unsubstituted. The dehydrogenation step can be carried out, e.g. according to the procedure of Dolling, et al. involving dichlorodicyanobenzo-quinone, JACS (1988) Vol. 110, pp. 3318–3319. Stage (2) may consist of one or more chemical steps and if desired may take place before stage (1) or following stage (1) or stage (3).

In accordance with a further alternate process of preparing the compounds of our invention, having only hydrogen as the sole substituent on the ring A-nitrogen, the 1,2-double bond in the A-ring is introduced as the last step of the process. Thus, with reference to the flow sheet below on page 66, a 17β-alkoxycarbonyl- 4-aza-5α-androstan-3-one (III) is hydrolyzed to the corresponding steroidal acid, 17β-carboxy-4-aza-5α-androstan-3-one, (IX) which, in turn, is converted to the corresponding thiopyridyl ester, 17β-(2-pyridylthiocarbonyl)-4-aza-5α-androstan-1-one (X) followed by treatment of the ester with an $R^2MgX$ or $R^2Li$ compound wherein $R^2$ is as defined hereinabove to form a 17β-(acyl)-4-aza-5α-androstan-3-one (XI) which is dehydrogenated as previously described to produce compound XIV, 17β-(acyl)-4-aza-5α-androst-1-en-3-one.

In an additional alternative process for making the compounds of formula I when the starting material is an ester, particularly methyl ester as shown in formula III-V in the schematic, reaction with a Grignard reagent $R^2MgX$, gives the ketone, 17β-$R^2$CO—, corresponding to the $R^2$ moiety associated with the Grignard reagent.

The above reactions are schematically represented in the following general flowsheet III:

Flow Sheet III

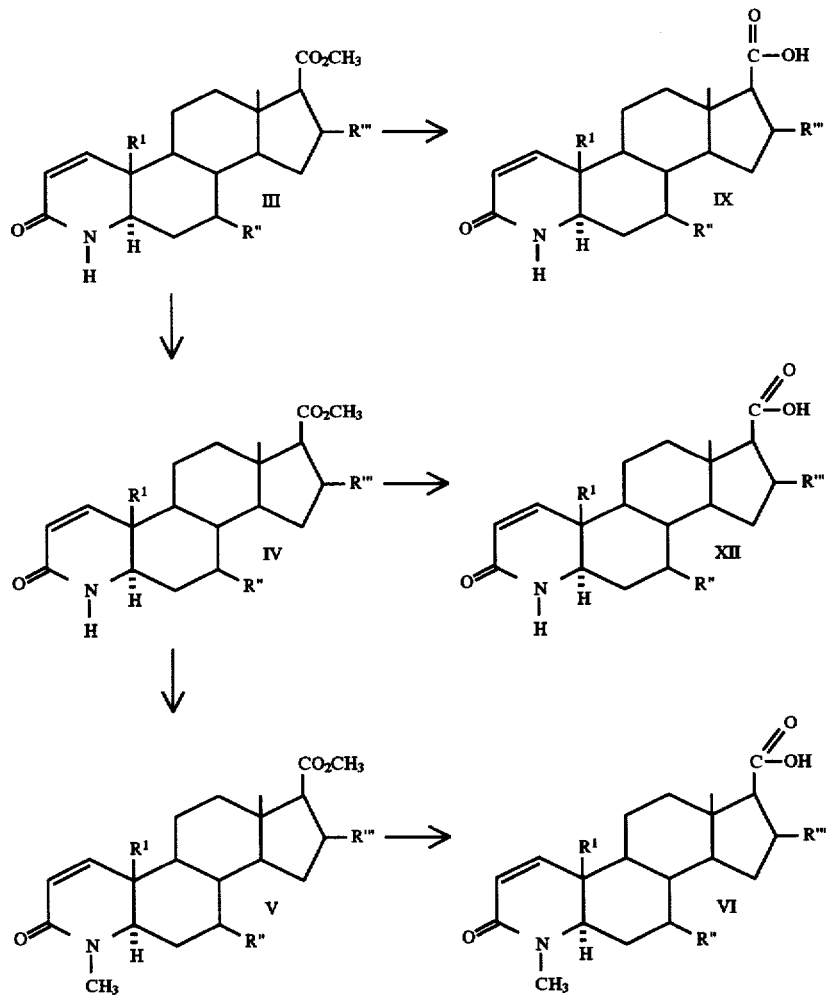

-continued
Flow Sheet III
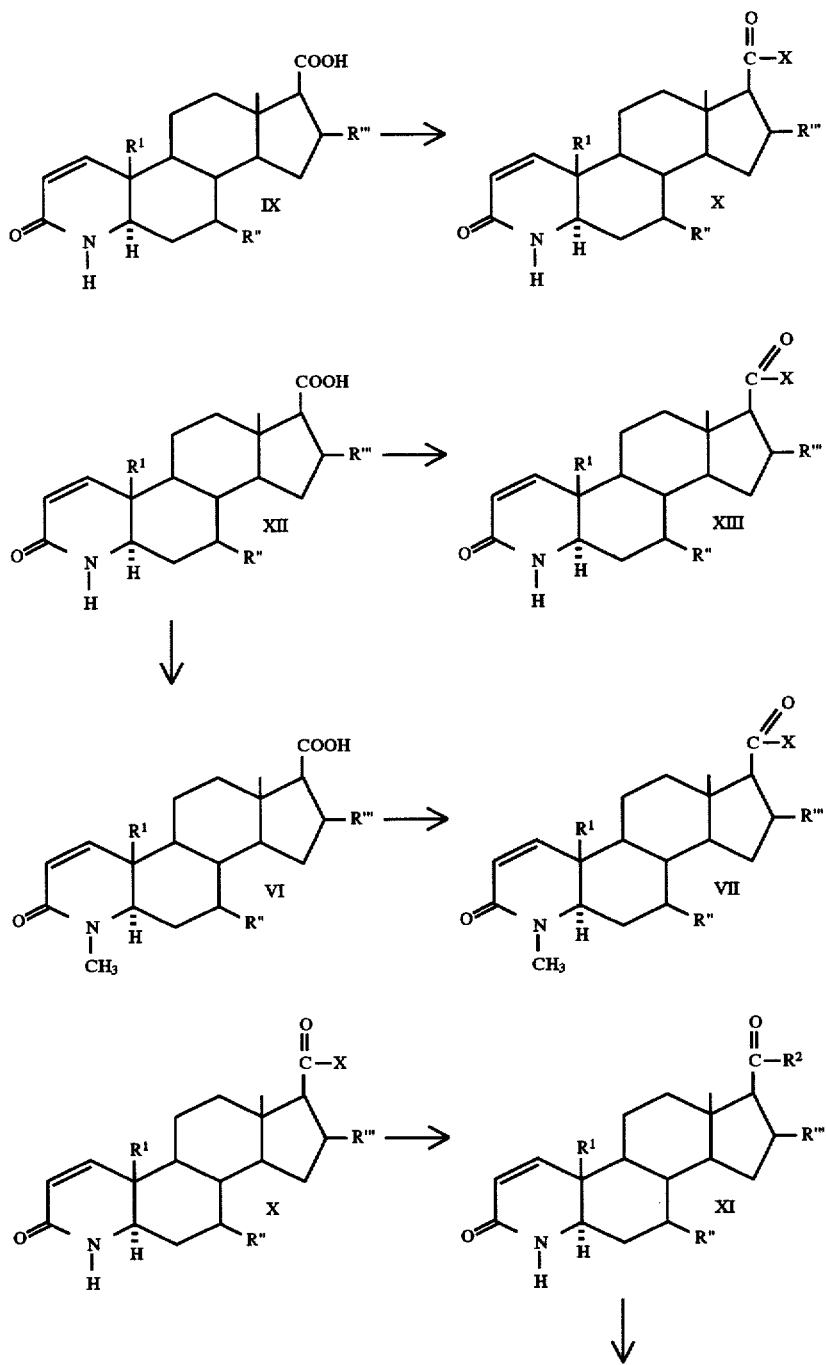

-continued
Flow Sheet III

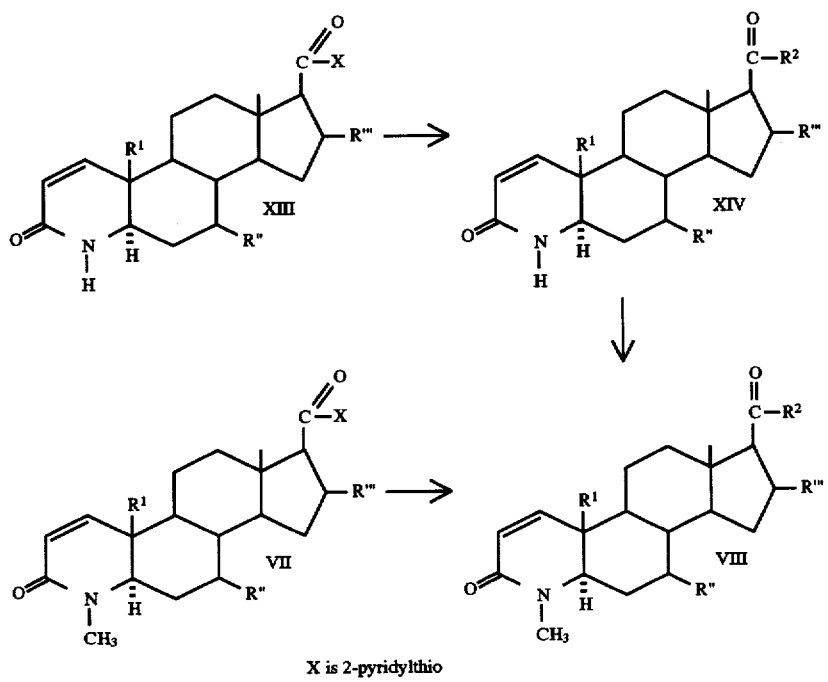

X is 2-pyridylthio wherein X is a 2-pyridylthio substituent and $R^2$ is defined as hereinabove.

In the above described flowsheet, where $R^2$ is p-hydroxybiphenyl, this can be derived by starting with an appropriate bromobiphenylylphenol, e.g. p-bromobiphenylphenol, protecting the phenolic —OH with a conventional blocking group, e.g. trioganosilyl, i.e. t-butyldimethylsilyl, carrying out the Grignard reaction and then deblocking the silyl group by the use of, e.g. refluxing aqueous tetrabutylammonium fluoride.

Other halo substituted benzenes to form the appropriate Grignard reagent useful in the instant invention will be obvious to one skilled in the art from this disclosure.

By the term "protected hydroxy" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Preferred are the trioganosilyl groups, e.g. t-butyldimethylsilyl, phenyldimethylsilyl, diphenylmethylsilyl, and the like.

By the term "$C_1$-$C_4$ alkyl" is used herein, is meant linear or branched alkyl, including methyl, ethyl, propyl, isopropyl, n-butyl, isobutyl, sec-butyl and t-butyl.

When this reaction scheme is carried out using an $R^2MgX$ or $R^2$-Li compound containing an thiophenyl substituted $R^2$, e.g. p-methylthiophenyl magnesium chloride, the corresponding 17β-(substituted thio-benzoyl)-4-alkyl-4-aza-5α-androst-1-en-3-one is prepared wherein phenyl is $R^2$.

The Grignard reagent, $R^2MgX$, for all the species included within the scope of this invention, are available or can readily be made by one skilled in the art. For example, where $R^2$ is $C_1$-$C_4$ alkyl thiophenyl, can be formed from the appropriate $C_1$-$C_4$ alkyl thiobromobenzene, e.g. p-methylthiobromobenzene.

The formed $C_1$-$C_4$ alkyl thiobenzene can be used to further prepare $C_1$-$C_4$ alkyl sulfoxides by oxidation with e.g. m-chloroperbenzoic acid. The resulting sulfoxide can be further oxidized by the use of the m-chloroperbenzoic acid reaction to proceed for a longer period of time to form the $C_1$-$C_4$ alkyl sulfone.

Further, the sulfoxide can be used in the Pummerer rearrangement to form the corresponding thiol.

The —$SO_2N(C_1$-$C_4$ alkyl$)_2$ substituted phenyl ($R^2$) is formed from the appropriate bromobenzene, e.g. p-N,N-dimethylaminosulfobromobenzene which is used directly in the Grignard reaction to form the final product.

The thioalkyl groups on the phenyl ring, i.e. —$(CH_2)_mSH$, where m is 1–4, are readily formed via a four step procedure from an alkoxy alkyl phenyl bromide, Br—$C_6H_4$—$(CH_2)_mOCH_3$. Direct addition of the Grignard reagent prepared from above-bromoalkyl phenyl derivative to the thiopyridyl ester results in the keto derivative, i.e. 17β(4-methoxyalkyl-benzoyl)-4-aza-5α-androst-1-ene-3-one. This can be readily converted into thio analogue via $BBr_3$ at $-70°$ C. to form the hydroxyalkyl derivative, followed by displacement by halogen, e.g. bromo and then converting the halogenated compound through NaSH displacement to give the final mercapto compound. Where in the Reaction Scheme said pyridylthio ester is reacted with an aminophenyl containing $R^2$—Li or an $R^2MgX$ (X=Cl, Br) compound, such as p-dimethyl-aminophenyl magnesium chloride, this is carried out in tetrahydrofuran to form the desired product 17β-(p-dimethylaminophenylcarbonyl)-4-alkyl-4-aza-5α-androst-1-en-3-one (VIII) which is isolated by chromatography on silica gel.

The Grignard reagent, $R^2MgX$, for all of the aminophenyl species included within the scope of this invention, are available and can be made readily by one skilled in the art.

Where in the process said Grignard reagent contains a phenolic type $R^2$ moiety, then said pyridylthio ester is then reacted with an $R^2$—Li or an $R^2MgX$ (X=Cl, Br) Grignard reagent, such as p-methoxyphenyl-magnesium chloride in tetrahydrofuran to form the desired product, e.g. 17β-(p- methoxy-phenylcarbonyl)-4-alkyl-4-aza-5α-androst-1-en-3-one (VIII) which is isolated by chromatography on silica gel. When this reaction is carried out using another $R^2MgX$ or, an $R^2$—Li compound in place of p-methoxyphenylmagnesium chloride, the corresponding 17β-(substituted benzoyl)-4-alkyl-4-aza-5α-androst-1-en-3-one is prepared wherein phenyl is $R^2$.

The Grignard reagent, $R^2MgX$, for all of the species included within the scope of this invention, are available and can be made readily by one skilled in the art.

For example, where $R^2$ is hydroxyphenyl, this can be derived by starting with an appropriate bromophenol, e.g. p-bromophenol, protecting the phenolic —OH with a conventional blocking group, e.g. trioganosilyl, i.e. t-butyldimethylsilyl, carrying out the Grignard reaction and then deblocking the silyl group by the use of, e.g. refluxing aqueous tetrabutylammonium fluoride.

For $R^2$ being hydroxyethylphenyl, the same blocking procedure can be analogously conducted starting with the appropriate hydroxyalkyl bromophenol, e.g. p-hydroxymethylbromobenzene, or p-hydroxyethylbromobenzene.

Where $R^2$ is carboxyphenyl, this can be obtained by the chromic acid oxidation of the appropriate hydroxymethylbenzene, e.g. p-bromo-hydroxymethylbenzene, formed as described above.

Where $R^2$ is —O—$C_1$-$C_4$ alkyl, the appropriate bromo-O—$C_1$-$C_4$ alkyl benzene, e.g. p-methoxybromobenzene, is utilized for the Grignard reaction.

Other halo substituted benzenes to form the appropriate Grignard reagent useful in the instant invention will be obvious to one skilled in the art from this disclosure.

By the term "protected hydroxy" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like.

Also within the scope of the present invention is the use of ketone reduction products of I, in combination with minoxidil for treatment of patterned alopecia, being secondary alcohols of the formula:

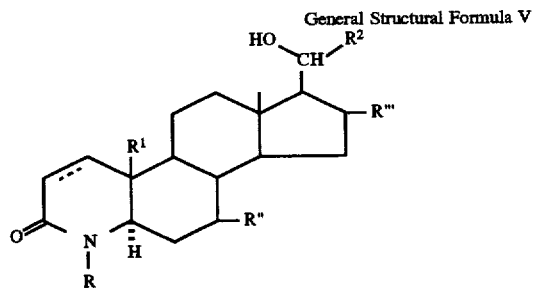

General Structural Formula V wherein

R is selected from hydrogen, methyl and ethyl;

$R^2$ is (a) a monovalent radical selected from straight or branched chain alkyl, or cycloalkyl, of from 1–12 carbons, which can be substituted by one or more of $C_1$-$C_2$ alkyl or halo;

(b) an aralkyl radical selected from benzyl or phenethyl;

(c) a polycyclic aromatic radical which can be substituted with one or more of: —OH, protected —OH, —$OC_1$-$C_4$ alkyl, $C_1$-$C_4$ alkyl, halo or nitro;

(d) a monocyclic aromatic radical which can be substituted with one or more of:

(1) —OH, —$OC_1$-$C_4$ alkyl, $C_1$-$C_4$ alkyl, —$(CH_2)_m$OH, —$(CH_2)_n$COOH, including protecting hydroxy, where m is 1–4, n is 1–3, providing $C_1$-$C_4$ alkyl is only present when one of the above oxygen-containing radicals is present;

(2) —SH, —$SC_1$-$C_4$ alkyl, —$SOC_1$-$C_4$ alkyl, —$SO_2C_1$-$C_4$ alkyl, —$SO_2N(C_1$-$C_4$-alkyl$)_2$, $C_1$-$C_4$ alkyl —$(CH_2)_m$SH, —S—$(CH_2)_n$—O—$COCH_3$, where m is 1–4 n is 1–3, providing $C_1$-$C_4$ alkyl is only present when one of the above sulfur containing radicals is present;

(3) $N(R^3)_2$, which can be protected, where $R^3$ is independently H or $C_1$-$C_4$ alkyl, where the monoaryl ring can also be further substituted with $C_1$-$C_4$ alkyl; and (4) heterocyclic radical selected from 2- or 4-pyridyl, 2-pyrrolyl, 2-furyl or thiophenyl;

R', R" and R'" are hydrogen or methyl, wherein the dotted line represents a double bond which can be present, and pharmaceutically acceptable salts and esters thereof.

These compounds can be made by conventional sodium borohydride reduction of the carbonyl attached to $R^2$ without reducing the amide carbonyl in Ring A or the 1,2-double bond, if present. If the $R^2$ phenyl contains a carbonyl function, it can be selectively blocked and then regenerated after the borohydride reduction by conventional methods.

The borohydride reduction can be carried out in, e.g. water or aqueous methanol, at a temperature of room temperature to 50° C. and the product then isolated and purified by conventional means. The compounds are also active as 5-alpha reductase inhibitors in the treatment of patterned alopecia.

EXAMPLES FOR THE CASE WHEN SUBSTITUENT "A" OF GENERAL FORMULA "I" IS AS DEFINED IN GROUP "II(A)"

Description Where A is IIA

Another preferred embodiment of the invention is where;

Z is —$XR^4$, or —$(CHR^1)_n$—$XR^4$;

n is 1–10;

X is —O— or —$S(O)_p$—, wherein p is zero, 1 or 2; and $R^1$ can be the same or different when n is greater than 1 and is —H, aryl, or —$C_{1-3}$alkyl unsubstituted or substituted with aryl;

R is —H, methyl or ethyl;

$R^4$ is

1) —$C_{1-20}$ alkyl, unsubstituted or substituted with one or more of:

a) —OH, b) halo, c) —$C_{1-8}$ alkoxy, d) —$C_{1-6}$ alkenyl, e) —$CONR^5R^5$, wherein $R^5$ is independently i) —H, ii) —$C_{1-8}$ alkyl unsubstituted or substituted with one or more of $R^7$, aryl or heterocycle, the aryl being unsubstituted or substituted with one or more of $R^7$ or $R^9$, iii) aryl unsubstituted or substituted with one or more of $R^7$ or $R^9$, or iv) heterocycle, unsubstituted or substituted with one or more of $R^7$ or $R^9$, f) —$COOR^6$, wherein $R^6$ is i) —H, ii) —$C_{1-8}$ alkyl unsubstituted or substituted with one or more of $R^7$ or aryl, the aryl being unsubstituted or substituted with one or more of $R^7$ or $R^9$, or iii) aryl, unsubstituted or substituted with one or more of $R^7$ or $R^9$, g) —$S(O)_p$—$R^5$, wherein p is defined above, h) —$N(R^5)_2$, i) aryl, unsubstituted or substituted with one or more of aryl, $R^7$ or $R^9$, j) heterocycle, unsubstituted or substituted with one or more of $R^7$ or $R^9$, k) —$C_{3-10}$ cycloalkyl, such as cyclohexyl, norbornyl, or adamantyl, unsubstituted or substituted with one or more of $R^7$ or $R^9$, or l) —$CONR^8$—CO—$NHR^8$, wherein $R^8$ is —H, —$C_{1-8}$ alkyl, benzyl or cyclohexyl; or 2) aryl, unsubstituted or substituted with one or more of aryl, $R^7$ or $R^9$, or 3) heterocycle or —$C_{3-10}$ cycloalkyl, either of which is unsubstituted or substituted with one or more of $R^7$ or $R^9$;

$R^7$ is

1) —OH,

2) —$C_{1-3}$ alkoxy,

3) —CN,

4) —$COOR^6$

5) —$C_{1-8}$alkyl-$COOR^6$

6) —$NO_2$, or

7) -halo; and 8) amino, mono $C_1$-$C_4$ alkylamino, di $C_1$-$C_4$ alkylamino;

$R^9$ is

1) —$C_{1-8}$ alkyl, unsubstituted or substituted with one or more of aryl or $R^7$, 2) —CO—A, —$C_{1-8}$ alkyl-CO—A, —NHCO—A, or —$S(O)_p$—A, wherein p is defined above and A is a) —H, b) —$C_{1-8}$ alkyl, unsubstituted or substituted with one or more of i) —$R^7$, or ii) aryl, unsubstituted or substituted with one or more of $R^7$, or c) aryl, unsubstituted or substituted with one or more of $R^7$, 3) —NHCO-heterocycle, 4) —$N(R^{10})_2$ or —$CON(R^{10})_2$ wherein $R^{10}$ is independently —H, heterocycle, or —A, 5) —NHCO—$(CH_2)_q$—CO—Q, wherein q is 1–4, and Q is —$N(R^{10})_2$ or —$OR^{10}$.

Another preferred embodiment of this invention is represented by compounds of general structural formula VI:

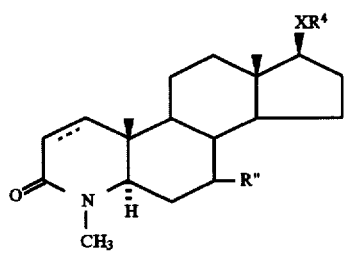

VI wherein $R^4$ is —$C_{1-20}$ alkyl, unsubstituted or substituted with one or more of —OH, halo, —$C_{1-8}$alkoxy, —$C_{1-6}$alkenyl, —$S(O)_p$—$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$ and X, p, $R^5$, $R^7$ and $R^9$ are all defined as in general structural formula I.

Another preferred embodiment of this invention is represented by compounds of general structural formula VI wherein $R^4$ is —$C_{1-20}$ alkyl substituted with —$CONR^5R^5$, —$COOR^6$ or —$CONR^8CONHR^8$, and X, $R^5$, $R^6$ and $R^8$ are defined as in general structural formula I.

Another preferred embodiment of this invention is represented by compounds of general structural formula VI wherein $R^4$ is aryl unsubstituted or substituted with one or more of aryl, $R^7$ or $R^9$; heterocycle unsubstituted or substituted with one or more of $R^7$ or $R^9$; or —$C_{3-10}$ cycloalkyl unsubstituted or substituted with one or more of $R^7$ or $R^9$; and X, $R^7$ and $R^9$ are defined as in general structural formula I.

Another preferred embodiment of this invention is represented by compounds of general structural formula VII:

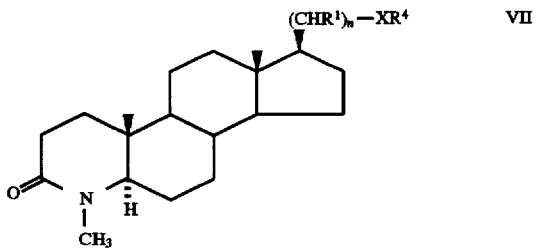

VII wherein $R^4$ is —$C_{1-20}$ alkyl, unsubstituted or substituted with one or more of —OH, halo, —$C_{1-8}$alkoxy, —$C_{1-6}$alkenyl, —$S(O)_p$—$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$, and X, $R^1$, n, p, $R^5$, $R^7$ and $R^9$ are defined as in general structural formula I.

Another preferred embodiment of this invention is represented by compounds of general structural formula VII wherein $R^4$ is —$C_{1-20}$ alkyl substituted with —$CONR^5R^5$, —$COOR^6$ or —$CONR^8CONHR^8$, and X, $R^1$, n, $R^5$, $R^6$ and $R^8$ are defined as in general structural formula I.

Another preferred embodiment of this invention is represented by compounds of formula VII wherein $R^4$ is aryl unsubstituted or substituted with one or more of aryl, $R^7$ or $R^9$; heterocycle unsubstituted or substituted with one or more of $R^7$ or $R^9$; or —$C_{3-10}$ cycloalkyl unsubstituted or substituted with one or more of $R^7$ or $R^9$; and X, $R^1$, n, $R^7$ and $R^9$ are defined as in general structural formula I.

Novel compounds of the present invention include but are not limited to the following compounds:

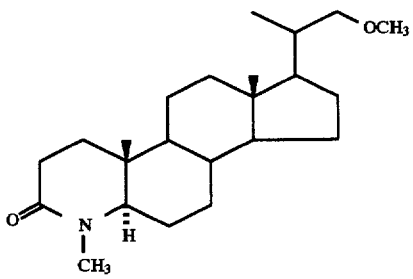

20-(methoxymethyl)-4-methyl-5α-4-azapregnan-3-one,

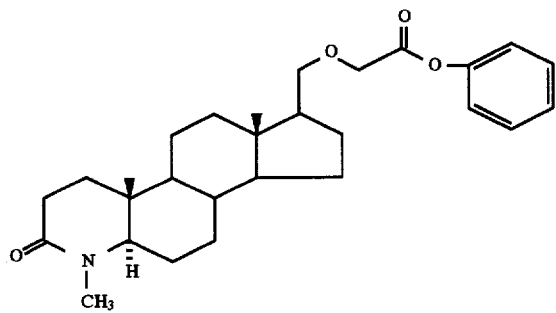

17-(carbobenzyloxymethoxymethyl)-4-methyl-5α-4-azaandrostan-3-one,

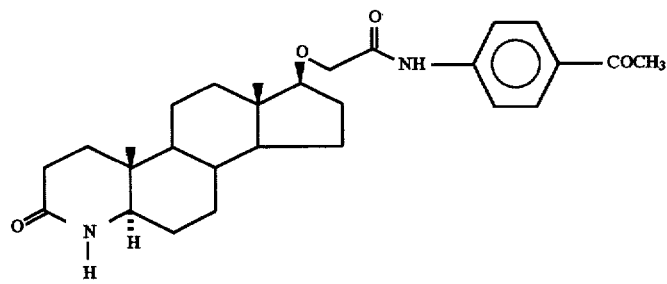

5α-4-azaandrostan-3-on-17β-yloxy-N-(4-acetylphenyl) acetamide,

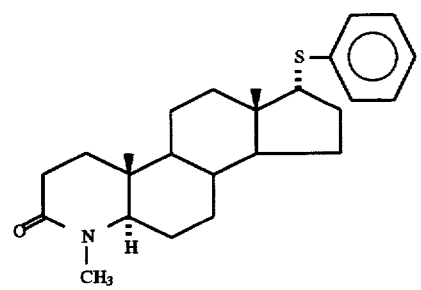

17α-thiophenoxy-4-methyl-5α-4-azaandrostan-3-one,
17-(methoxymethyl)4-methyl-5α-4-azaandrostan-3-one,
17-(ethylthiomethyl)-4-methyl-5α-4-azaandrostan-3-one,
17-(carboxymethoxymethyl)-4-methyl-5α-4-azaandrostan-3-one,
17-(carboethoxymethoxymethyl)-4-methyl-5α-4-azaandrostan-3-one,
17-(carbobenzyloxymethoxymethyl)-4-methyl-5α-4-azaandrostan-3-one,
17-(diphenylmethoxymethyl)-4-methyl-5α-4-azaandrostan-3-one,
20-(diphenylmethoxy)-4-methyl-5α-4-azapregnan-3-one,
20-(methoxy)-4-methyl-5α-4-azapregnan-3-one,
20-(methoxymethyl)-4-methyl-5α-4-azapregnan-3-one,
20-(diphenylmethoxymethyl)-4-methyl-5α-4-azapregnan-3-one,
20-(ethylthiomethyl)-4-methyl-5α-4-azapregnan-3-one,
20-(isopropylthiomethyl)-4-methyl-5α-4-azapregnan-3-one, ethyl 4-methyl-5α-4-azaandrostan-3-on-17β-yloxyacetate,
diphenylmethyl 4-methyl-5α-4-azaandrostan-3-on-17β-yloxyacetate,
4-methyl-5α-4-azaandrostan-3-on-17β-yloxy-N-(3,4-dihlorobenzyl)acetamide,
4-methyl-5α-4-azaandrostan-3-on-17β-yloxy-N-phenylacetamide,
4-methyl-5α-4-azaandrostan-3-on-17β yloxyacetic acid,
4-methyl-5α-4-azaandrostan-3-on-17β-yloxy-N-(4-acetylphenyl)acetamide,
4-methyl-5α-4-azaandrostan-3-on-17β-yloxyacetamide, 17β-(4-biphenyloxy)-4-methyl-5α-4-azaandrostan-3-one,
17β-(2,4-dinitrophenoxy)-4-methyl-5α-4-azaandrostan-3-one,
4-methyl-17α-phenoxy-5α-4-azaandrostan-3-one,
7α-(4-biphenyloxy)-4-methyl-5α-4-azaandrostan-3-one,
17β-diphenylmethoxy-4-methyl-5α-4-azaandrostan-3-one,
4-methyl-17α-thiophenoxy-5α-4-azaandrostan-3-one, 4-methyl-17α-phenylsulfonyl-5α-4-azaandrostan-3-one,
4-methyl-17α-phenylsulfinyl-5α-4-azaandrostan-3-one (isomer a),
4-methyl-17α-phenylsulfinyl-5α-4-azaandrostan-3-one (isomer b),
4-methyl-17β-(4-nitrophenoxy)-5α-4-azaandrostan-3-one,
17β-(4-aminophenoxy)-4-methyl-5α-4-azaandrostan-3-one hydrochloride,
17β-(4-acetamidophenoxy)-4-methyl-5α-4-azaandrostan-3-one,
17β-(4-cyanophenoxy)-4-methyl-5α-4-azaandrostan-3-one,
17β-(4-carboxamidophenoxy)-4-methyl-5α-4-azaandrostan-3-one,
17β-methyleneoxy-[N-cyclohexyl-N-(N-cyclohexylcarbamoyl)-carbamoyl]-4-methyl-5α-4- azaandrostan-3-one,
4-methyl-17β-(3-pyridyl)oxy-5α-4-azaandrostan-3-one,
4-methyl-17β-(2-pyridyl)methoxy-5α-4-azaandrostan-3-one,
17β-benzyloxy-4-methyl-5α-4-azaandrostan-3-one, ethyl 5α-4-azaandrostan-3-on-17β-yloxyacetate,
5α-4-azaandrostan-3-on-17β-yloxyacetic acid,
5α-4-azaandrostan-3-on-17β-yloxy-N-phenylacetamide, 5α-4-azaandrostan-3-on-17β-yloxy-N-(4-acetylphenyl) acetamide, diphenylmethyl 5α-4-azaandrostan-3-on-17β-yloxyacetate, 17β-methyleneoxy-[N-cyclohexyl-N-(N-cyclohexylcarbamoyl)carbamoyl]-5α-4-azaandrostan-3-one, 5α-4-azaandrostan-3-on-17β-yloxy-N-[4-(1(RS)-hydroxyethyl)phenyl]acetamide, 5α-4-azaandrostan-3-on-17β-yloxy-N-(4-t-butyl-phenyl) acetamide, 17β-methyleneoxy-[N-isopropyl-N-(N-isopropyl-carbamoyl)-carbamoyl]-5α-4-azaandrostan-3-one, 17-(4-methylpentyloxy)-4-methyl-5α-4-azaandrostan-3-one, 17-hexyloxy-4-methyl-5α-4-azaandrostan-3-one ,4-methyl-17-propyloxy-5α-4-azaandrostan-3-one, 4-methyl-17-undecyloxy-5α-4-azaandrostan-3-one, 17-allyloxy-4-methyl-5α-4-azaandrostan-3-one, 17-allyloxy-4-methyl-4-azaandrost-5-en-3-one, or 17-hexyloxy-4-methyl-4-azaandrost-5-en-3-one.

Novel compounds of this invention further include, but are not limited to:

17-(4-(isobutyl)benzyloxy)methyl-4-methyl-5α-4-azaandrostan-3-one, 17-(4-acetamidobenzyloxy)methyl-4-methyl-5α-4-azaandrostan-3-one, 4-methyl-17-(3-nitrobenzyloxy)methyl-5α-4-azaandrostan-3-one, 4-methyl-17-(phenoxyethoxymethyl)-5α-4-azaandrostan-3-one, 17-(3-(isopropylthio)propyloxy)methyl-4-methyl-5α-4-azaandrostan-3-one, 17-(2-fluorobenzyloxy)methyl-4-methyl-5α-4-zaandrostan-3-one, 4-methyl-17-(3-(trifluoromethyl)benzyloxy)methyl-5α-4-azaandrostan-3-one, 17-(4-dimethylaminobenzyloxy)methyl-4-methyl-5α-4-azaandrostan-3-one, 17-((N-t-butyl-carboxamido)methoxymethyl)-4-methyl-5α-4-azaandrostan-3-one, 20-(3-(ethylthio)propyl)-4-methyl-5α-4-azapregnan-3-one, 20-(2-(benzyloxy)ethyl)-4-methyl-5α-4-azapregnan-3-one, 20-(3-methoxybenzyloxy)methyl-4-methyl-5α-4-azapregnan-3-one, 17a-(carboethoxymethoxy)benzyl-4-methyl-5α-4-azaandrostan-3-one, 20-(4-(methylthio)benzyloxy)methyl-4-methyl-5α-4-azapregnan-3-one, 4-methyl-17-n-octylthiomethyl-5α-4-azaandrostan-3-one, 20-(t-butylthiomethyl)-4-methyl-5α-4-azapregnan-3-one, 17-(2-furfuryl)thiomethyl-4-methyl-5α-4-azaandrostan-3-one, 17-(geranyloxymethyl)-4-methyl-5α-4-azaandrostan-3-one, 4-methyl-20-(2-(n-nonylthio)ethyl)-5α-4-azapregnan-3-one, 20-(methylthiomethyl)-4-methyl-5α-4-azapregnan-3-one, 17-(4-(benzyloxy)benzyloxy)methyl-4-methyl-5α-4-azaandrostan-3-one, 20-(diphenylmethylthio)methyl-4-methyl-5α-4-azapregnan-3-one, 17-(3-(ethylthio)propyl)-4-methyl-5α-4-azaandrostan-3-one, 4-methyl-20-(phenylthiomethyl)-5α-4-azapregnan-3-one, 17-(ethylsulfonylmethyl)-4-methyl-5α-4-azaandrostan-3-one, or 17-(4-ethoxybenzyloxy)methyl-4-methyl-5α-4-azaandrostan-3-one.

Also included within the scope of this invention are pharmaceutically acceptable salts or esters, where a basic or acidic group is present in a compound of formula I, such as on the substituted alkyl, cycloalkyl, aryl or heterocyclic moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention, may have asymmetric centers and occur as racemates, racemic mixtures and as individual diastereomers, with all isomeric forms being included in the present invention.

When any variable (e.g., aryl, heterocycle, $R^1$, $R^2$, n, X, etc.) occurs more than one time in any constituent or general structural formula its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. "Cycloalkyl" is intended to include saturated mono-, bi- and tricyclic ring groups, such as cyclopropyl, cyclobutyl, cyclopentyl, cyclohexyl (Cyh), cycloheptyl, norbornanyl and adamantyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Halo", as used herein, means fluoro, chloro, bromo and iodo.

As used herein, with exceptions as noted, "aryl" is intended to mean phenyl (Ph) or naphthyl.

The term heterocycle or heterocyclic, as used herein except where noted, represents a stable 5- to 7-membered monocyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl. Preferred heterocycles are piperidinyl, 2-oxopyrrolodinyl, pyrrolyl, pyrazolyl, imidazolyl, pyridyl, pyrazinyl, pyrimidinyl, pyridazinyl, oxazolyl, isoxazolyl, morpholinyl, thiazolyl, isothiazolyl, quinuclidinyl, indolyl, quinolinyl, isoquinolinyl, benzimidazolyl, thiadiazoyl, benzothiazolyl, benzoxazolyl, furyl, tetrahydrofuryl, thienyl, and benzothienyl.

As used herein, "heteroaryl" represents a stable 5- to 7-membered monocyclic unsaturated heterocyclic ring, which consists of carbon atoms and from one to three heteroatoms selected from the group consisting of N, O and S, and wherein the nitrogen and sulfur heteroatoms may optionally be oxidized, and the nitrogen heteroatom may optionally be quaternized.

Further abbreviations that may appear herein are defined as follows:

| DCC | N,N'-dicyclohexylcarbodiimide |
|---|---|
| DIC | 1,3-diisopropylcarbodiimide |
| DEAD | diethyl azodicarboxylate |
| DMAP | 4-dimethylaminopyridine |
| DMF | N,N-dimethylformamide |
| DMSO | dimethyl sulfoxide |
| EtOAc | ethyl acetate |
| Ph₃P | triphenylphosphine |
| m.p (or mp) | melting point |
| THF | tetrahydrofuran |
| m.w. (or mw) | molecular weight |

Additional methods of making the compounds of the present invention are made by methods as described as follows and in general flowsheets IV through VII, below.

The compounds of this invention can be made from a steroid alcohol starting material, represented by general structural formula VIII:

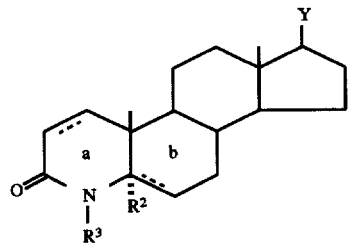

wherein a and b are both single bonds and R² is hydrogen, or a is a double bond, b is a single bond and R² is hydrogen, or a is a single bond, b is a double bond and R² is absent; R³ is —H, methyl or ethyl; Y is —OH or —(CHR¹)ₙ—OH; R¹ is —H, aryl, or C₁₋₃ alkyl unsubstituted or substituted with aryl; and n is 1–10. Methods of making starting alcohols of formula VIII are well known to those skilled in the art, and are described, for example, in the following publications: Rasmusson, G. H., et al., *J. Med. Chem.*, 29, 2298–2315 (1986); Rasmusson, G. H., et al., *J. Med. Chem.*, 27 1690–1701 (1984).

Furthermore, the, starting 4-azasteroid-20-alcohols of formula VIII may be made by several methods well known to those skilled in the art. For example, 4-azasteroids containing a 17-carbonyl group (e.g. carboxaldehyde) may be reacted with the appropriate organo-metallic reagent to yield the corresponding secondary alcohol, while reduction yields the primary alcohol. Also, an appropriate 17-ketone may be reduced (e.g. with sodium borohydride) to the desired alcohol. The above mentioned ketones may be made by several methods well known in the art; one particularly useful method is that of A. Bhattacharya et al., Synthetic Communications 20 (17), 2683–2690 (1990), in which an activated carbonyl compound is reacted with a suitable Grignard reagent to give the desired ketone. Other activated carbonyl compounds (e.g. pyridine thioesters) may also be used. These alcohol functions may be constructed both before and after the formation of the 4-aza moiety.

For purposes of illustration, general flowsheets IV through VII below employ specific steroid alcohol starting materials such as 17-hydroxymethyl-4-methyl-5α-4-azaandrostan-3-one (compound (ii) below) or 17-hydroxy-4-methyl-5α-4-azaandrostan-3-one (compound (v) below) as the starting alcohol. However, the present invention and the synthetic methods described herein are not limited by the use of any particular compounds in any of the schemes or synthetic descriptions presented below, except where otherwise noted, but rather the schemes and synthetic descriptions are presented for illustrative purposes to those skilled in the art. A person skilled in the art would be able to choose the appropriate alcohol starting material to use in the following general synthetic route descriptions to arrive at a target product within the scope of generic formula I.

As depicted in general flowsheet IV below, thioethers (iv) can generally be made by forming the mesylate (iii) of alcohol (ii) by common methods known in the art, e.g. using methanesulfonyl chloride in CH₂Cl₂ with pyridine, and then treating the mesylate with M⁺S⁻—R⁴, wherein M⁺ is a metal ion, e.g. Na⁺ or K⁺, and R⁴ is as defined in formula I. The M⁺S⁻—R⁴ reagents are either commercially available, such as sodium thioethoxide or potassium thiophenoxide, or can be generated by methods well known in the art, e.g., as described in *J.Org. Chem*, 40, p 1181 (1975) or *J. Chem. Soc.*, p 3127 (1928).

FLOWSHEET IV

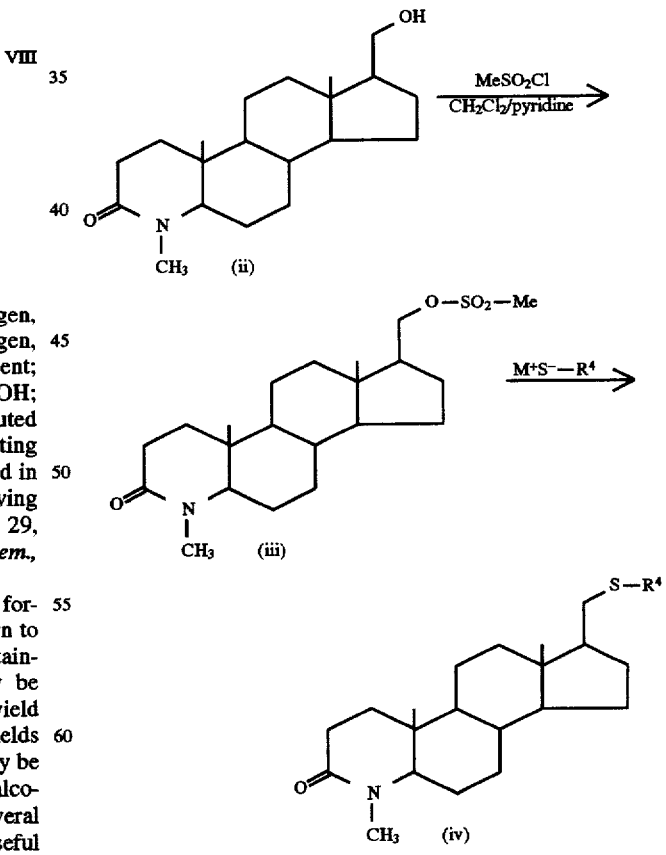

As depicted in general flowsheet V, below, the starting alcohol (v) can be treated with a diazo-reagent (vi) using techniques well known in the art, e.g. using boron trifluoride etherate or $Rh_2(OAc)_4$, to obtain ethers of formula (vii). Diazo-reagents, such as diazomethane, diphenyldiazomethane, benzyldiazo-acetate, etc., are generated by methods well know in the art, such as by the methods described in the following publications: British Patent 1,533,381; British Patent 1,459,285; *J. Chem. Soc.*, Perkins I; p. 2030 (1975); *Organic Synthesis*, Collective Vol. III, p. 351 (1955); *J. Org. Chem.*, 24, p. 560 (1959).

When $R^a$ is —H and $R^b$ is —$COOC_2H_5$ in compound (vii), hydrolysis of the ester with base followed by treatment with acid produces compound (viii). The acid (viii) can be coupled with an amine, e.g. an arylamine such as aniline, 4-t-butyl aniline, or p-amino-acetophenone, by common amide coupling procedures well known in the art, e.g., using the carbodiimide method with reagents such as DCC or DIC in the presence of DMAP, to form an amide exemplified by (x). When DCC is used, the sideproduct (xi) is formed as well; when DIC is used, a sideproduct similar to (xi) is formed except instead of a cyclohexyl urea moiety, it contains an isopropyl urea moiety. Treatment of (viii) with a diazo reagent, such as diphenyl diazomethane, and $Rh_2(Ac)_4$ under conditions well known in the art leads to formation of compounds exemplified by (ix).

The 5α-4-azandrostan-3-on-17-yloxyacetic acid and ethyl 5α-4-azaandrostan-3-on-17β-yloxy-acetate analogs can be prepared according to general scheme 2 but are more preferably prepared according to the routes described in Examples 17 and 21 herein.

GENERAL FLOWSHEET V

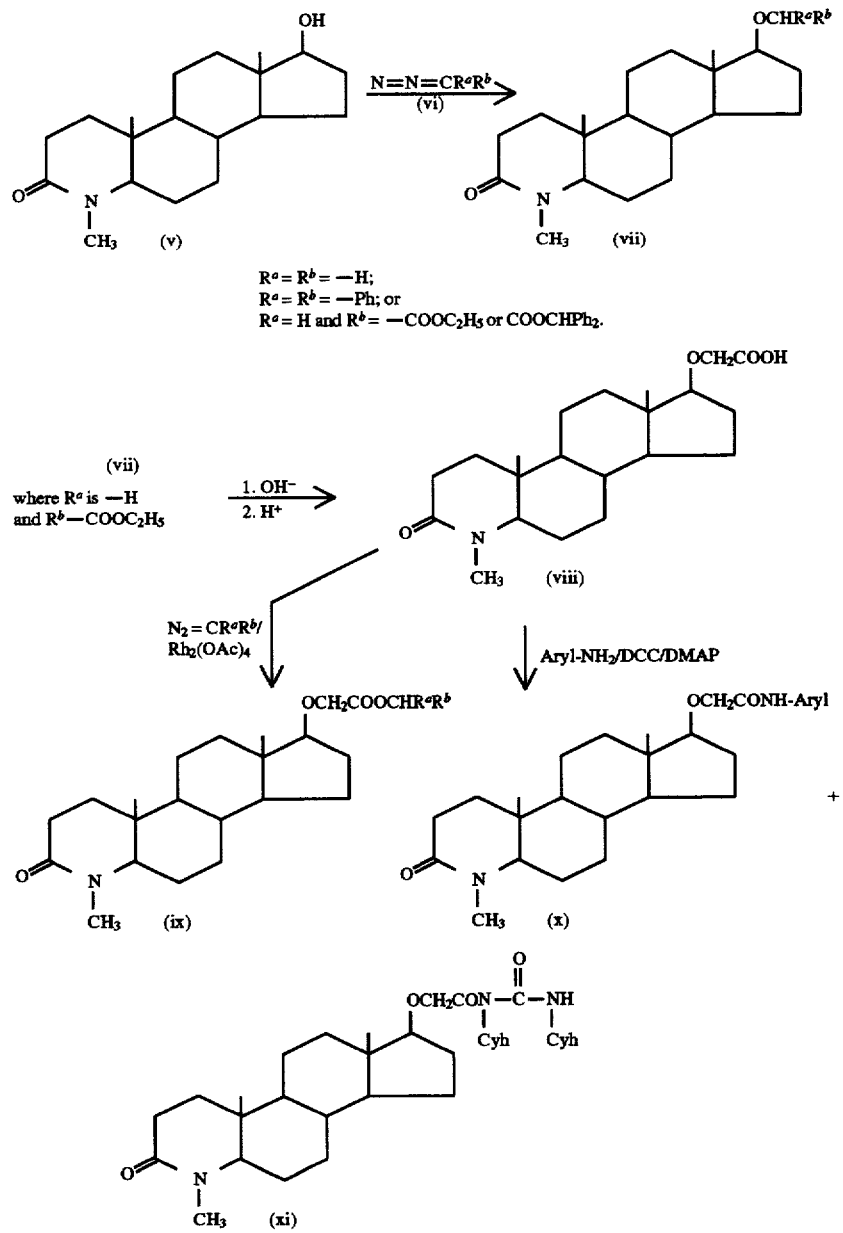

Amide compounds of formula (x) can also be made by alternative methods well known in the art, e.g., by reacting (vii) wherein $R^a$ is —H and $R^b$ is —COOC$_2$H$_5$ directly with an unsubstituted or substituted aryl-NH$_2$ compound and heating the reaction, e.g., to about 170° C.–180° C. Another method, e.g., is to form a mixed anhydride of acid (viii) and react it with the desired primary amine to obtain compounds of formula (x).

As depicted in Scheme 3, below, the starting alcohol (v) can be treated with a strong base, such as NaH or KOH, in an appropriate solvent such as DMF or DMSO, followed by treatment with an alkyl- or alkenyl-halide (xii-a), such as hexyliodide or allylbromide for example, to form the corresponding alkyl- or alkenyl-ether product (xiii-a). Use of KOH in DMSO is preferred.

FLOWSHEET VI

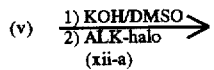

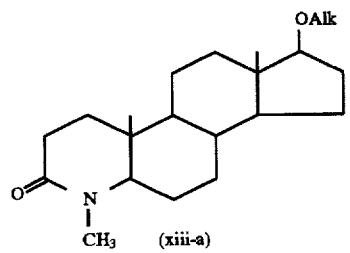

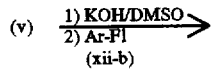

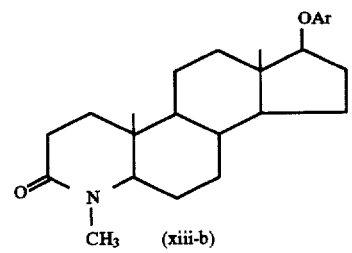

Also as depicted in flowsheet V, aryl ether and heteroaryl ether products (xiii-b) can be prepared by treating the steroid alcohol starting material with a fluoroaryl or fluoroheteroaryl compound (xii-b), such as p-nitrofluorobenzene, p-cyanofluoro-benzene or 3-fluoropyridine for example, and NaH or KOH in an appropriate solvent such as DMF or DMSO, with KOH/DMF and KOH/DMSO being preferred.

Alternatively, aryl ether and heteroaryl ether products of formula (xiii-b) can be prepared by treating the steroid alcohol starting material with an unsubstituted or substituted hydroxy aryl or hydroxy heteroaryl compound such as phenol or 4-hydroxybiphenyl for example, and triphenylphosphine and diethyl azodicarboxylate (DEAD). With this method, the ether product will have stereochemistry at the 17-position that is the opposite of the starting alcohol when Y is —OH in formula (i). For example, using this procedure, 4-methyl-17α-phenoxy-5α-4-azaandrostan-3-one is the product of 17β-hydroxy-4-methyl-5α-4-azaandrostan-3-one and phenol.

Heteroaryl ether products can be reduced by methods well known in the art, e.g., by hydrogenation in an appropriate solvent such as MeOH, in the presence of a catalyst such as palladium or platinum on carbon, to obtain compounds of formula I wherein $R^4$ is a saturated heterocycle.

As depicted in flowsheet VII below, compounds of formula (xvii) can be prepared by treating the amino hydrochloride derivative (xv) with the appropriate anhydride reagent using methods well known to those skilled in the art. "$R^d$" in Scheme 4 can be heterocycle, "A" as defined in the generic description of compounds of formula I, or —(CH$_2$)$_q$—CO-Q, wherein the variables "q" and "Q" are as defined in the generic description of compounds of formula I. Alternatively, compounds of formula (xvii) where $R^d$ is —(CH$_2$)$_q$—CO-Q can be made by treating (xv) with an anhydride of formula

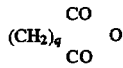

and base, such as pyridine, to make intermediate compounds of formula (xvii) where $R^d$ is —(CH$_2$)$_q$—COOH, and then making amides and esters from the intermediate acid. Compound (xv) is prepared by reduction of the nitro group of compound (xiv) wherein $R^c$ is —NO$_2$, by common techniques well known in the art, e.g., hydrogenation in the presence of a catalyst such as PtO$_2$, and treatment with an acid such as HCl. Compound (xiv) wherein $R^c$ is —NO$_2$ can be prepared by methods decribed above for making aryl ethers.

Also as depicted in scheme 4, below, the cyano group of compound (xiv), wherein $R^c$ is —CN, can be hydrolyzed by methods well known in the art, e.g., by treatment with H$_2$O$_2$ and base such as NaOH, to provide compound (xvi). The primary amide of (xvi) can be alkylated by methods well known in the art, such as with methyl iodide, for example, to make the secondary or tertiary amide derivatives.

FLOWSHEET VII

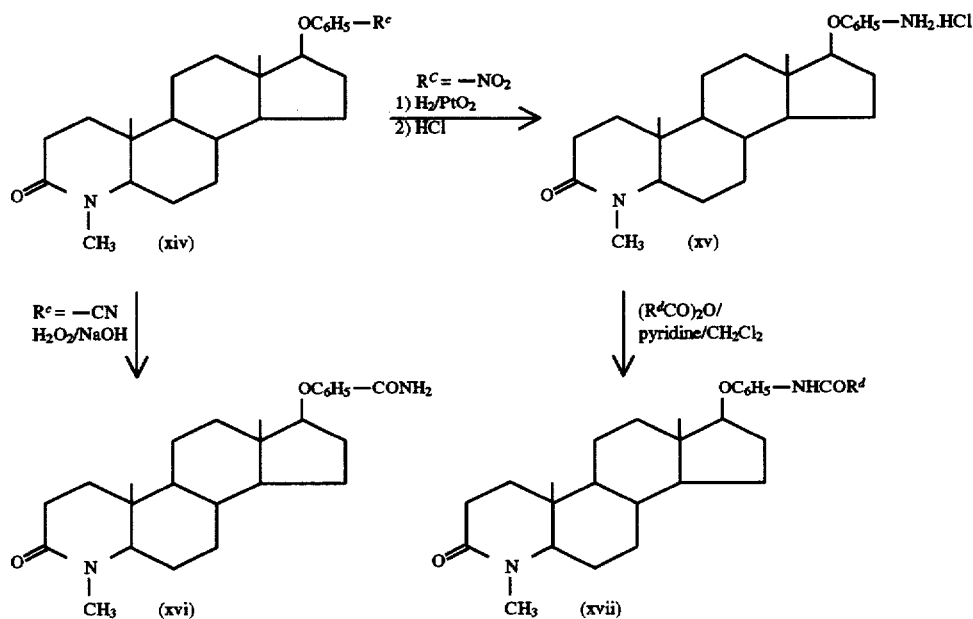

By using methods well known to those skilled in the art, the diazonium salt of compound (xv) can be made by treatment of (xv) with $HNO_2$ or an alkyl nitrite. The resulting diazonium salt can be used as an intermediate in a variety of reactions to replace the diazonium moiety to make other substituted aryl ether derivatives. For example, the diazonium salt moiety can be replaced with a halo, —CN, —OH or alkoxy group by common methods well known to those skilled in the art. Or the diazonium moeity can be replaced with hydrogen to yield the unsubstituted aryl ether derivative.

Alternatively, the ethers of this invention may be obtained by first preparing the desired ether and thioether groups at the desired position in the appropriate non-aza steroid followed by ring opening of the A-ring and subsequent closure to the desired 4-azasteroid. For example, a 20-alkoxy-substituted pregn-4-en-3-one may be oxidized with permanganate periodate to the corresponding seco-acid which is then reacted with an appropriate amine to give, after reduction of the first obtained 4-aza-5-enesteroid, the desired 20-ether-substituted-5α-4-azapregnan-3-one.

EXAMPLES FOR THE CASE WHEN SUBSTITUENT "A" OF GENERAL FORMULA "T" IS AS DEFINED IN GROUP "III(A)" DESCRIPTION WHERE STRUCTURE A IS IIIA

A first preferred embodiment of this class is represented by compounds of formula IX:

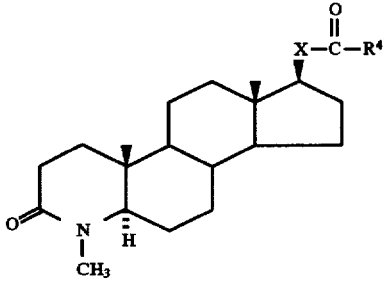

wherein $R^4$ is —$C_{1-20}$alkyl, unsubstituted or substituted with one or more of —OH, halo, —$C_{1-8}$alkoxy, —$C_{1-6}$alkenyl, —$S(O)_p$—$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$, and X, p, $R^5$, $R^7$, and $R^9$ are all as defined in formula I.

Another preferred embodiment of this invention is represented by compounds of general structural formula IX wherein $R^4$ is —$C_{1-20}$ alkyl substituted with —$CONR^5R^5$, —$COOR^6$ or —$CONR^8CONHR^8$, and X, $R^5$, $R^6$, and $R^8$ are all as defined in formula I.

Another preferred embodiment of this invention is represented by compounds of formula IX wherein $R^4$ is aryl unsubstituted or substituted with one or more of aryl, $R^7$ or $R^9$; heterocycle unsubstituted or substituted with one or more of $R^7$ or $R^9$; $C_{3-10}$ cycloalkyl unsubstituted or substituted with one or more of $R^7$ or $R^9$; —$NR^5R^5$; or —$OR^5$;

and X, $R^5$, $R^7$, and $R^9$ are all as defined in formula I.

Another preferred embodiment of this invention is represented by compounds of general structural formula X:

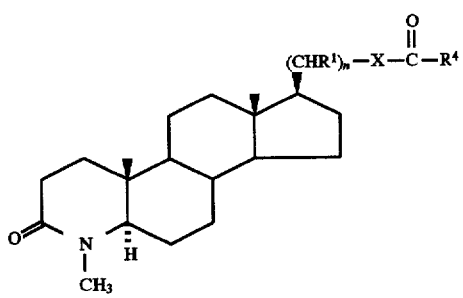

wherein $R^4$ is $—C_{1-20}$ alkyl, unsubstituted or substituted with one or more of —OH, halo, —$C_{1-8}$alkoxy, —$C_{1-6}$alkenyl, —$S(O)_p$—$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$, and X, n, p, $R^1$, $R^5$, $R^7$, and $R^9$ are all as defined in formula I.

Another preferred embodiment of this invention is represented by compounds of general structural formula X wherein $R^4$ is —$C_{1-20}$ alkyl substituted with —$CONR^5R^5$, —$COOR^6$ or —$CONR^8CONHR^8$, and X, n, $R^1$, $R^5$, $R^6$, and $R^8$ are all as defined in formula I.

Another preferred embodiment of this invention is represented by compounds of formula X wherein $R^4$ is aryl unsubstituted or substituted with one or more of aryl, $R^7$ or $R^9$; heterocycle unsubstituted or substituted with one or more of $R^7$ or $R^9$; —$C_{3-10}$ cycloalkyl unsubstituted or substituted with one or more of $R^7$ or $R^9$; —$NR^5R^5$; or —$OR^5$;

and X, n, $R^1$, $R^5$, $R^7$, and $R^9$ are all as defined in formula I.

Novel compounds of the present invention include but are not limited to the following compounds:

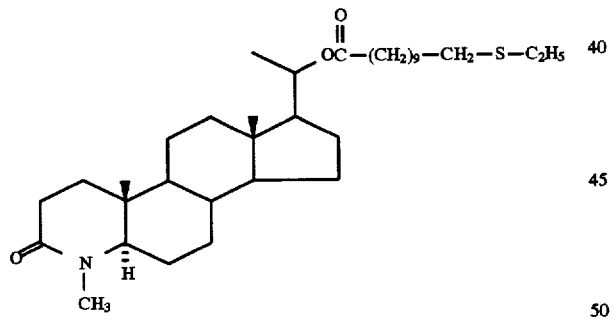

20-(11-(ethylthio)undecanoyloxy)-4-methyl-5α-4-azapregnan-3-one,

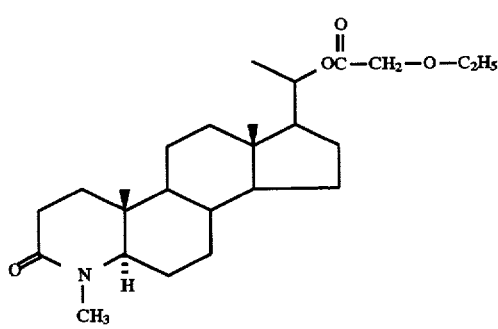

20-ethoxyacetyloxy-4-methyl-5α-4-azapregnan-3-one,

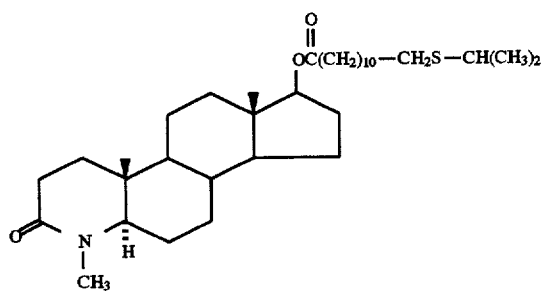

17-(12-(isopropylthio)dodecanoyloxy)-4-methyl-5α-4-azaandrostan-3-one,

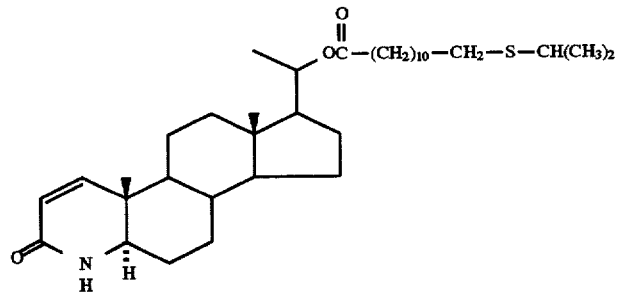

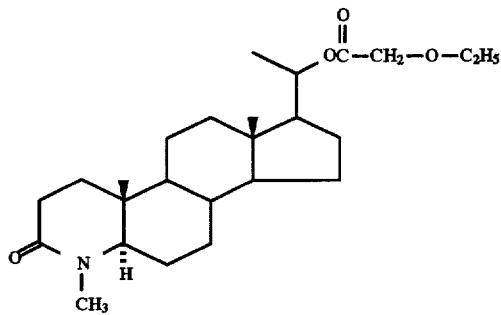

20-ethoxyacetyloxy-4-methyl-5α-4-azapregnan-3-one,

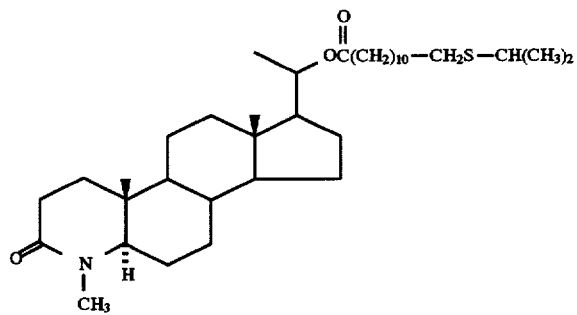

17-(12-(isopropylthio)dodecanoyloxy)-4-methyl-5α-4-azaandrostan-3-one,

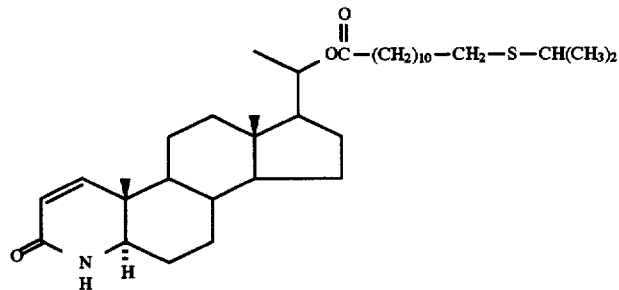

20-(12-(isopropylthio)dodecanoyloxy)-4-methyl-5α-4-azapregnan-3-one,
20-(11-(ethylsulfinyl)undecanoyloxy)-4-methyl-5α-4-azapregnan-3-one,
20-(12-(t-butylthio)dodecanoyloxy)-4-methyl-5α-4-azapregnan-3-one
4-methyl-20-(4-thien-2-yl)butyroyloxy-5α-4-aza-pregnan-3-one,
20-trimethylacetyloxy-5α-4-azapregnan-3-one,
20-(9-(isopropylthio)nonanoyloxy)-5α-4-azapregnan-3-one,
20-(12-(isopropylthio)dodecanoyloxy)-5α-4-azapregnan-3-one,
20-acetoxymethyl-4-methyl-5α-4-azapregnan-3-one,
4-methyl-20-(trimethylacetyloxy)methyl-5α-4-azapregnan-3-one,
20-(12-(isopropylthio)dodecanoyloxy)methyl-4-methyl-5α-4-azapregnan-3-one,
17-acetyloxymethyl-4-methyl-5α-4-azaandrostan-3-one,
4-methyl-17-trimethylacetyloxymethyl-5α-4-azaandrostan-3-one,
17-(2-ethylhexanoyloxy)methyl-4-methyl-5α-4-azaandrostan3-one,
17-(methylaminocarbonyloxymethyl)-4-methyl-5α-4-azaandrostan-3-one,
17-(12-(isopropylthio)dodecanoyloxy)methyl-4-methyl-5α-4-azaandrostan-3-one,
17β-(benzylaminocarbonyloxy)-4-methyl-5α-4-azaandrostan-3-one,
20-trimethylacetyloxy-5α-4-azapregn-1-ene-3-one, or
20-(t-butylaminocarbonyloxy)-4-methyl-5α-4-azapregnan-3-one.

Novel compounds of the present invention further include, but are not limited to the following compounds:

17-(2-furylacetoxymethyl)-4-methyl-5α-4-azaandrostan-3-one,
17-(4-isopropylphenylacetoxymethyl)-4-methyl-5α-4-azaandrostan-3-one,
17-(cyclohexylacetoxymethyl)-4-methyl-5α-4-azaandrostan-3-one,
17-(3-indolylacetoxymethyl)-4-methyl-5α-4-azaandrostan-3-one,
17-(4-methylcyclohexanecarbonyloxymethyl)-4-methyl-5α-4-azaandrostan-3-one,
17-(4-(3-indolyl)-butyroyloxymethyl)-4-methyl-5α-4-azaandrostan-3-one,
17-(4-isobutylbenzoyloxymethyl)-4-methyl-5α-4-azaandrostan-3-one,
17-(acetoxyacetyloxymethyl)-4-methyl-5α-4-azaandrostan-3-one,
17-(6-bromohexanoyloxymethyl)-4-methyl-5α-4-azaandrostan-3-one,
4-methyl-20-(4-nitrobenzoyloxymethyl)-5α-4-azapregnan-3-one,
20-((3-acetamido)benzoyloxy)-4-methyl-5α-4-azapregnan-3-one,
20-(3,4-dimethoxyphenylacetyloxymethyl)-4-methyl-5α-4-azapregnan-3-one,
17-(4-ethoxybenzoyloxymethyl)-4-methyl-5α-4-azaandrostan-3-one,
4-methyl-20-(palmitoyloxymethyl)-5α-4-azapregnan-3-one,
17-(iminodibenzyl-5-carbonyloxymethyl)-4-methyl-5α-4-azaandrostan-3-one,
4-methyl-20-(stearoyloxy)-5α-4-azapregnan-3-one,
17-(3,5-bis-(trifluoromethyl)benzoyloxymethyl)-4-methyl-5α-4-azaandrostan-3-one,
17-(3-cyanobenzoyloxymethyl)-4-methyl-5α-4-azaandrostan-3-one,
20-(heptafluorobutyroyloxymethyl)-4-methyl-5α-4-azapregnan-3-one,
20-(4-benzoylbenzoyloxymethyl)-4-methyl-5α-4-azapregnan-3-one,
17-(benztriazol-5-carbonyloxymethyl)-4-methyl-5α-4-azaandrostan-3-one,
20-(3,5-difluorobenzoyloxy)-4-methyl-5α-4-azapregnan-3-one, 17-(bis-(4-isopropyl)phenyl)acetyloxymethyl-4-methyl-5α-4-azaandrostan-3-one, 4-methyl-20-(salicyloyloxymethyl)-5α-4-azapregnan-3-one, 17-((3-hydroxy-4,4,4-trichlorobutyroyloxy)methyl)-4-methyl-5α-4-azaandrostan-3-one, or 17-(cinnamoyloxymethyl)-4-methyl-5α-4-azaandrostan-3-one.

Also included within the scope of this invention are pharmaceutically acceptable salts or esters, where a basic or acidic group is present in a compound of formula I, such as on the substituted alkyl, cycloalkyl, aryl or heterocyclic moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention, may have asymmetric centers and occur as racemates, racemic mixtures and as individual diastereomers, with all isomeric forms being included in the present invention.

The compounds of this invention can alternatively be made generally from a steroid alcohol starting material, represented by formula XI:

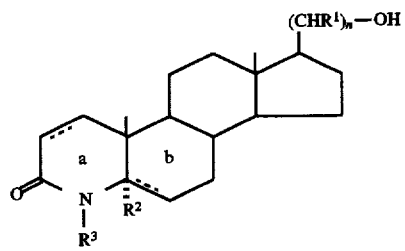

wherein a and b are both single bonds and $R^2$ is hydrogen, or a is a double bond, b is a single bond and $R^2$ is hydrogen, or a is a single bond, b is a double bond and $R^2$ is absent; $R^1$ is —H, aryl, or $C_{1-3}$alkyl unsubstituted or substituted with aryl; $R^3$ is —H, methyl or ethyl; and n is zero through 10.

Methods of making starting alcohols of formula XI are well known to those skilled in the art, and are described, for example, in the following publications: Rasmusson, G. H. et al., *J. Med. Chem.*, 29, 2298–2315 (1986); Rasmusson, G. H. et al., *J. Med. Chem.*, 27, 1690–1701 (1984).

Furthermore, the starting 4-azasteroid-20-alcohols of Formula XI may be made by several methods well known to those skilled in the art. For example, 4-azasteroids containing a 17-carbonyl group (e.g. carboxaldehyde) may be reacted with the appropriate organo-metallic reagent to yield the corresponding secondary alcohol, while reduction yields the primary alcohol. Also, an appropriate 17-ketone may be reduced (e.g. with sodium borohydride) to the desired alcohol. The above mentioned ketones may be made by several methods well known in the art; one particularly useful method is that of A. Bhattacharya et al., Synthetic Communications 20(17), 2683–2690 (1990), in which an activated carbonyl compound is reacted with a suitable Grignard reagent to give the desired ketone. Other activated carbonyl compounds (e.g. pyridine thioesters) may also be used.

These alcohol functions may be constructed both before and after the formation of the 4-aza moiety.

One method of preparing compounds of formula I is to condense the starting steroid alcohol with an acid of formula (ii)

under conditions known to those skilled in the art, e.g., in an appropriate solvent such as $CH_2Cl_2$, in the presence of 4-(dimethylamino)-pyridine (DMAP) and N,N'-dicyclohexylcarbodiimide (DCC). Another method of preparing compounds of formula I is to combine the starting alcohol (i) with an acid chloride of formula (iii) or acid anhydride or mixed anhydride of formula (iv)

under conditions known to those skilled in the art, e.g. under dry conditions using an appropriate solvent such as $CH_2Cl_2$ at a reduced temperature, such as about 0° C., in the presence of a base such as pyridine.

Carbamate derivatives of formula I can be prepared by reacting the starting alcohol XI with an isocyanate compound, such as benzyl isocyanate or t-butylisocyanate for example, under conditions known to those skilled in the art, e.g., under dry conditions in an appropriate solvent such as benzene, in the presence of a base such as 1,8-diazabicyclo[5.4.0]undec-7-ene (DBU), with heating e.g. to 60°–70° C.

The thiol esters may be conveniently prepared from the corresponding alcohol via the literature procedure described in Tetrahedron Letters, 22 (1981) pp. 3119–3122, that is, the alcohol and a thiolacid are reacted together in the presence of the preformed adduct from triphenylphosphine and diisopropyl azodicarboxylate. Alternatively, the free thiol obtained from these thiolesters via standard saponification or reduction methods may then be acylated via standard procedures to obtain other thiolesters.

The variable "$R^4$" used in the above synthetic method descriptions is defined in formula I.

EXAMPLES FOR THE CASE WHEN SUBSTITUENT "A" OF GENERAL FORMULA "I" IS AS DEFINED IN GROUP "IV(A)"

An embodiment of this category is where:

A is:

(a) 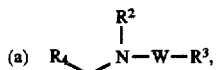

(b) 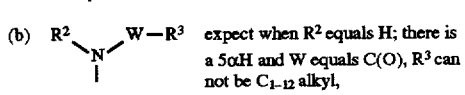 expect when $R^2$ equals H; there is a 5αH and W equals C(O), $R^3$ can not be $C_{1-12}$ alkyl, (c) 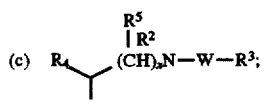;

wherein $R^1$ is:

H, or $C_{1-20}$ alkyl;
R² is:
  H, or
  $C_{1-20}$ alkyl;
R³ is:
  $C_{1-20}$ alkyl,
  $C_{6-14}$ aryl,
  heteroaryl,
  $C_{6-14}$ aryl$C_{1-20}$alkyl,
  heteroaryl$C_{1-20}$alkyl,
  $C_{1-20}$ alkylthio$C_{1-20}$alkyl,
  $C_{1-20}$ alkylsufonyl$C_{1-20}$alkyl,
  $C_{1-20}$ alkylsulfinyl$C_{1-20}$alkyl,
  $C_{1-20}$ alkyloxycarbonyl$C_{1-20}$alkyl,
  $C_{1-20}$ alkyl$C_{6-14}$aryl$C_{1-20}$alkyl,
  carboxy$C_{1-20}$alkyl,
  $C_{1-20}$alkyloxy$C_{1-20}$alkyl,
  $C_{1-20}$alkoxycarbonyl$C_{1-20}$alkyl;
  $C_{1-20}$alkylcarbonyl$C_{1-20}$alkyl,
  $C_{3-20}$cycloalkyl,
  $C_{3-20}$cycloalkyl$C_{1-20}$alkyl,
  $C_{6-14}$ aryl$C_{1-20}$alkyloxycarbonyl$C_{1-20}$alkyl,
  heteroaryl$C_{1-20}$alkyloxycarbonyl$C_{1-20}$ alkyl,
  halo$C_{1-20}$alkyl,
  halohydroxy$C_{1-20}$alkyl,
  hydroxy$C_{1-20}$alkyl,
  thiosulfato$C_{1-20}$alkyl,
  $C_{6-14}$ aryl$C_{1-20}$alkyloxy$C_{1-20}$alkyl,
  diaryl$C_{1-20}$alkyl,
  triaryl$C_{1-20}$alkyl,
  $C_{2-20}$ alkenyl,
  $C_{2-20}$ alkenyl$C_{1-20}$alkyl,
  $C_{6-14}$ aryl$C_{2-20}$alkenyl,
  heteroaryl$C_{2-20}$alkenyl,
  $C_{6-14}$ arylcarbonylaryl$C_{1-20}$alkyl,
  $C_{2-20}$alkynyl$C_{1-20}$alkyl,
  $C_{6-14}$ aryl$C_{2-20}$alkynyl$C_{1-20}$alkyl, or
  heteroaryl $C_{2-20}$alkynyl$C_{1-20}$alkyl;
R⁴ is
  H,
  $C_{1-20}$ alkyl,
  $C_{6-14}$ aryl, or
  heteroaryl;
R⁵ is:
  H, or
  $C_{1-20}$ alkyl;
W is $$\overset{O}{\underset{}{\overset{\|}{-C-}}}, \text{ or } \overset{O}{\underset{\overset{\|}{O}}{\overset{\|}{-S-}}};$$

x is an integer from 1 to 25;
and dashes indicate a double bond is optionally present.

Advantageously, compounds of the following general structural formula XII are disclosed:

XII (structure shown)

and the pharmaceutically acceptable salts thereof, wherein A is:

(a) $R_4 \underset{\underset{R^2}{|}}{\diagup} N-W-R^3$, (b) $R^2 \diagdown N \diagup W-R^3$  expect when R² equals H; there is a 5αH and W equals C(O), R³ can not be $C_{1-12}$ alkyl, (c) $R_4 \diagup \overset{R^5}{\underset{|}{(}}\!\!\diagdown\!\!)_x \underset{\underset{R^2}{|}}{N}-W-R^3$;

wherein
R¹ is:
  H, methyl or ethyl;
R² is:
  H, or
  $C_{1-20}$alkyl;
R³ is:
  H,
  $C_{1-20}$alkyl further comprising a straight or branched chain alkane of up to 20 carbon atoms;
  $C_{6-14}$ aryl wherein aryl comprises a mono or polycyclic system composed of 6-membered aromatic rings either unsubstituted or substituted with R wherein R comprises H, $C_{1-6}$alkyl, aryl$C_{1-20}$alkyl with the alkyl groups unsubstituted or substituted with hydroxyl, $C_{1-8}$alkyloxy, carboxy $C_{0-10}$alkyl, or halogen or aryl is directly substituted independently with hydroxyl, halo$C_{1-20}$alkyl, carboamide, benzoyl, $C_{1-20}$alkyloxy, $C_{1-20}$alkyl, $C_{2-20}$alkenyl, cyano, nitro, acetamide or halogen;
  heteroaryl which comprises a mono or polycyclic system composed of 5 or 6-membered aromatic rings containing 1, 2, 3 or 4 heteroatoms chosen from N, O, or S and either unsubstituted or substituted with R or independently with hydroxyl $C_{1-20}$alkyloxy, $C_{1-20}$alkyl, benzoyl, carboamide, acetamide, halogens, $C_{2-20}$alkenyl, cyano, nitro, or haloalkyl directly bonded to the aromatic carbon atom(s);
  $C_{6-14}$ aryl$C_{1-20}$alkyl of the formula:

(structure shown with R⁵, R⁷, R⁸, -(CH)ₙ)

wherein the aromatic ring is optionally and independently substituted with R⁷ and R⁸ wherein R⁷ and R⁸ comprise:
  H,
  CH₃, $C_2H_5$,
carboxamido,
$OCH_3$,
$C_1C_6$alkylthio,
$C_1C_6$alkylsulfinyl,
$C_1C_6$alkylsulfonyl,
$NH_2$,
$CH_3NH,(CH_3)_2N-$,
$NO_2$,
CN,
OH,
Fl,
acetamido,
Cl,
$OC_2H_5$,
$CF_3$,
isopropyl, or
isobutyl; n equals 1–20 and the $C_{1-20}$alkyl group is optionally substituted with $R^7$;
Heteroaryl$C_{1-20}$alkyl further comprising the formula

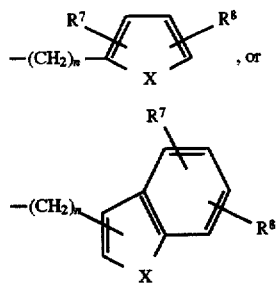

wherein X equals O, S, or NR; and n equals 1–20;
$C_{1-20}$alkylsulfonyl$C_{1-20}$alkyl
$C_{1-20}$alkylthio$C_{1-20}$alkyl
$C_{1-20}$alkylsulfinyl$C_{1-20}$alkyl comprising the formula:
—$(CH_2)_nS(O)_p$—$R^9$ wherein $R^9$ comprises $CH_3$,
$C_2H_5$,
$C_3H_7$,
$C_4H_9$,
isopropyl,
isobutyl,
sec-butyl,
t-butyl,
isopentyl,
neopentyl, or
isohexyl; n equals 1–20, p=0–2;
$C_{1-20}$alkyloxycarbonyl$C_{1-20}$alkyl further comprising the formula:

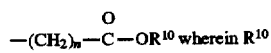

wherein $R^{10}$ comprises:
$CH_3$,
$C_2H_5$,
$C_3H_7$,
$C_4H_9$, or
$C_5H_{11}$; and n equals 1–20;

Carboxyl$C_{1-20}$alkyl further comprising:

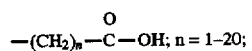

n=1–20;
$C_{1-20}$alkylcarbonyl$C_{1-20}$alkyl further comprising the formula

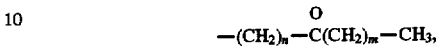

n equals 1–20;
m equals 0–19;
$C_{3-20}$cycloalkyl$C_{1-20}$alkyl of the formula:
—$(CH_2)_n$-(cycloalkyl) wherein the cycloalkyl portion comprises monocyclic, bicyclic, or polycyclic hydrocarbons of up to 20 carbon atoms wherein the rings are optionally substituted with $R^1$; and n=1–20;
Aryl$C_{1-20}$alkyloxycarbonyl$C_{1-20}$alkyl of the formula:

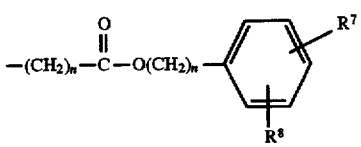

wherein n=1–20;
Heteroaryl$C_{1-20}$alkyloxycarbonyl$C_{1-20}$alkyl of the formula:

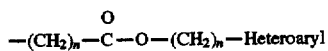

wherein Heteroaryl is as defined and n=1–20;
halo$C_{1-20}$alkyl of the formula:
—$(CH_2)_n$—$CH_2X$ wherein
X equals Br, Cl, F or I; n is 1–19;
hydroxyl$C_{1-20}$alkyl of the formula:
—$(CH_2)_nCH_2OH$; n is 1–19;
halohydroxyl$C_{1-20}$alkyl of the formula:

wherein X equals Br, Cl, F or I; n=0–18, q=0–18 n+q=0–18;
Thiosulfato$C_{1-20}$alkyl of the formula:
—$(CH_2)_nCH_2SSO_3Na$; n is 1–20;
Aryl $C_{1-20}$alkyloxy $C_{1-20}$alkyl of the formula:

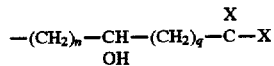

; n is 1–20;

Arylcarbonylaryl$C_{1-20}$alkyl of the formula:

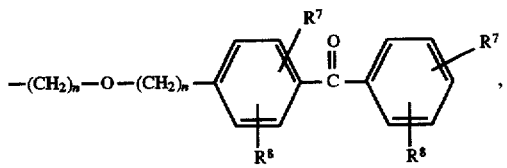

-continued n equals 1–20;

DiarylC$_{1-20}$alkyl of the formula:

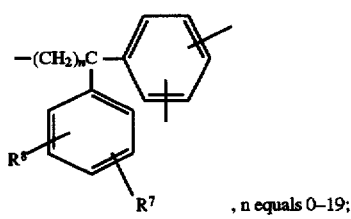

, n equals 0–19;

TriarylC$_{1-20}$alkyl of the formula:

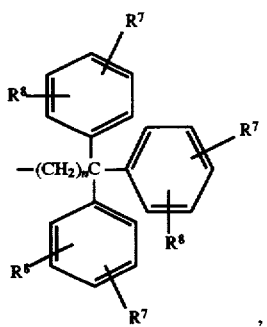

n equals 0–19;
C$_{6-14}$arylC$_{2-20}$alkenyl of the formula:

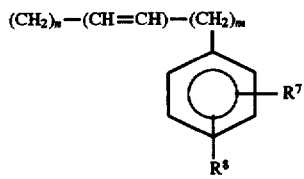

wherein:
n=0–18,
m=0–18,
n+m=0–18;
R$^4$ is
H,
C$_{1-20}$alkyl,
C$_{6-14}$aryl, or
heteroaryl;
R$^5$ is:
H, or
C$_{1-12}$alkyl;
W is:

$$-\overset{O}{\underset{}{C}}-, \text{ or } -\overset{O}{\underset{O}{S}}-,$$

x is an integer from 1–10;

and the dashes indicate a double bond is optionally present.

Compounds of the general structural formula XIII

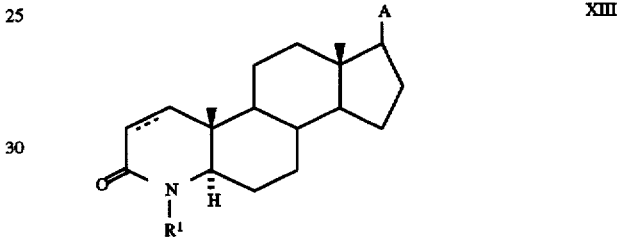

and listed in Table I are representative of the compounds claimed in the instant invention. In a preferred embodiment, R$^1$ may be H or CH$_3$ and A may be as indicated in Table 1. Particular representative chemical names are also listed in Table 1 adjacent to the respective side chain and specifically reflect whether the 1 position is saturated or unsaturated. Advantageously, R$^1$ is CH$_3$, A is as indicated in Table 1 and the 1 position is saturated.

TABLE 1

| | Side Chain A | Compound(s): |
|---|---|---|
| (1) | 21 H O<br>  \\_N—C—⊥<br>  20 | 4-methyl-20(trimethylacetamido)-<br>5α-4-aza-pregnan-3-one<br>4-methyl-20(trimethylacetamido)-<br>5α-4-aza-1-pregnen-3-one |
| (2) | H O<br>  \\_N—C—⊥ | 4-methyl-17β(trimethylacetamidomethyl)-4-aza-<br>5α-androst-1-en-3-one<br>4-methyl-17β(trimethylacetamidomethyl)-4-aza-<br>5α-androstan-3-one |
| (3) | H O<br>  \\_N—C—⊥ | 4-methyl-17β(trimethylacetamido)-4-aza-<br>5α-androst-1-en-3-one<br>4-methyl-17β(trimethylacetamido-4-aza-<br>5α-androstan-3-one |

TABLE 1-continued

| Side Chain A | Compound(s): |
|---|---|
| (4) 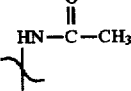 | 17β(acetamido)-4-methyl-4-aza-5α-androst-1-ene-3-one<br>17β(acetamido)-4-methyl-4-aza-5α-androstan-3-one |
| (5) 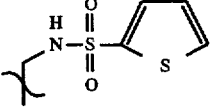 | 4-methyl-17β(2-thiophenesulfonamidomethyl-4-aza-5α-androst-1-en-3-one<br>4-methyl-17β(2-thiophenesulfonamidomethyl)-4-aza-5α-androstan-3-one |
| (6) 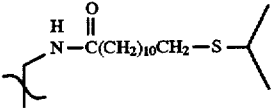 | 17β(isopropylthiododecanoylamidomethyl)-4-methyl-4-aza-5α-androst-1-en-3-one<br>17β(isopropylthiododecanoylamidomethyl)-4-methyl-4-aza-5α-androstan-3-one |
| (7) 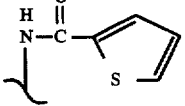 | 4-methyl-17β(2-thiophenecarboxamidomethyl)-4-aza-5α-androst-1-en-3-one<br>4-methyl-17β(2-thiophenecarboxamidomethyl)-4-aza-5α-androstan-3-one |
| (8) 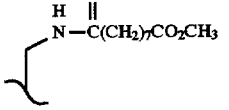 | 17β(carbomethoxyoctanoylamidomethyl)-4-methyl-4-aza-5α-androst-1-en-3-one<br>17β(carbomethoxyoctanoylamidomethyl)-4-methyl-4-aza-5α-androstan-3-one |
| (9) 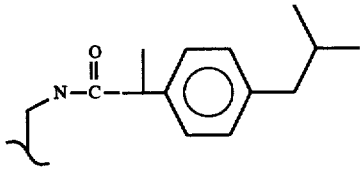 | 17β((2-(4-isobutylphenyl)-propionamidomethyl)-4-methyl-4-aza-5α-androst-1-en-3-one<br>17β((2-(4-isobutylphenyl)-propionamidomethyl)-4-methyl-4-aza-5α-androstan-3-one |
| (10) 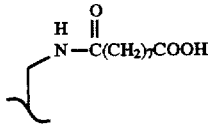 | 17β(8-carboxyoctanoylamidomethyl)-4-methyl-4-aza-5α-androst-1-en-3-one<br>17β(8-carboxyoctanoylamidomethyl)-4-methyl-4-aza-5α-androstan-3-one |
| (11) 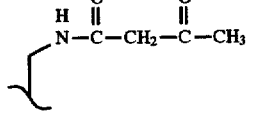 | 17β(acetoacetamidomethyl)-4-methyl-4-aza-5α-androst-1-en-3-one<br>17β(acetoacetamidomethyl)-4-methyl-4-aza-5α-androstan-3-one |
| (12) 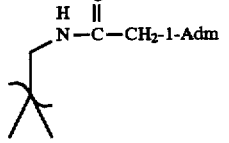 | 17β(1-Adamantylacetamidomethyl)-4-methyl-4-aza-5α-androst-1-en-3-one<br>17β(1-Adamantylacetamidomethyl)-4-methyl-4-aza-5α-androstan-3-one) |
| (13) 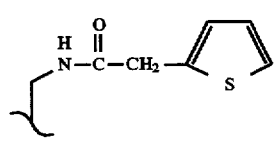 | 4-methyl-17β(2-thiopheneacetamidomethyl)-4-aza-5α-androst-1-en-3-one<br>4-methyl-17β(2-thiopheneacetamidomethyl)-4-aza-5α-androstan-3-one |
| (14) 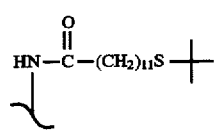 | 17β(12-(t-butylthio)dodecanoylamido)-4-methyl-4-aza-5α-androst-1-en-3-one<br>17β(12-(t-butylthio)dodecanoylamido)-4-methyl-4-aza-5α-androstan-3-one |

TABLE 1-continued

| Side Chain A | Compound(s): |
|---|---|
| (15) [structure: -N(H)-C(=O)-CH₂-CH₂-C(=O)-OCH₂-phenyl] | 17β(3-(carbobenzyloxy)propionamidomethyl)-4-methyl-4-aza-5α-androst-1-en-3-one<br>17β(3-(carbobenzylox)propionamidomethyl)-4-methyl-4-aza-5α-androstan-3-one |
| (16) [structure: -N(H)-C(=O)-(CH₂)-phenyl with 3,4-di-OMe] | 17β(carbomethoxyoctanoylamidomethyl)-4-methyl-4-aza-5α-androst-1-en-3-one<br>17β(carbomethoxyoctanoylamidomethyl)-4-methyl-4-aza-5α-androstan-3-one |
| (17) [structure: HN-C(=O)-(CH₂)₇CO₂CH₃ with isobutyl] | 17β(8-(carbomethoxy)octanoylamido)-4-methyl-4-aza-5α-androst-1-en-3-one<br>17β(8-(carbomethoxy)octanoylamido)-4-methyl-4-aza-5α-androstan-3-one |
| (18) [structure: HN-C(=O)-(CH₂)₁₁-S-isopropyl with isobutyl] | 17β(isopropylthiododecanoylamido)-4-methyl-4-aza-5α-androst-1-en-3-one<br>17β(isoproplthiododecanoylamido)-4-methyl-4-aza-5α-androstan-3-one |
| (19) [structure: -N(H)-S(=O)₂-phenyl] | 17β(benzenesulfonamidomethyl)-4-methyl-4-aza-5α-androst-1-en-3-one<br>17β(benzenesulfonamidomethyl)-4-methyl-4-aza-5α-androstan-3-one |
| (20) [structure: -N(H)-C(=O)-(CH₂)₄CH₂Br] | 17β(6-Bromohexanoylamidomethyl)-4-methyl-4-aza-5α-androst-1-en-3-one<br>17β(6-Bromohexanoylamidomethyl)-4-methyl-4-aza-5α-androstan-3-one |
| (21) [structure: -N(H)-C(=O)-(CH₂)₁₁OH] | 17β(12-hydroxydodecanoylamidomethyl)-4-methyl-4-aza-5α-androst-1-en-3-one<br>17β(12-hydroxydodecanoylamidomethyl)-4-methyl-4-aza-5α-androstan-3-one |
| (22) [structure: -N(H)-C(=O)-CH(CH₃)-phenyl-NO₂] | 4-methyl-17β(2-(4-nitrophenyl)propionamidomethyl)-4-aza-5α-androst-1-en-3-one<br>4-methyl-17β(2-(4-nitrophenyl)propionamidomethyl)-4-aza-5α-androstan-3-one |
| (23) [structure: -N(H)-C(=O)-CH₂-S-isopropyl] | 17β(isopropylthioacetamidomethyl)-4-methyl-4-aza-5α-androst-1-en-3-one<br>17β(isopropylthioacetamidomethyl)-4-methyl-4-aza-5α-androstan-3-one |
| (24) [structure: -N(H)-C(=O)-(CH₂)₄CH₂SSO₃Na] | 4-methyl-17β(thiosulfatohexanoylamidomethyl)-4-aza-5α-androst-1-en-3-one<br>4-methyl-17β(thiosulfatohexanoylamidomethyl)-4-aza-5α-androstan-3-one |

TABLE 1-continued

| Side Chain A | Compound(s): |
|---|---|
| (25) 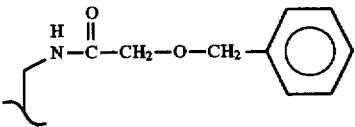 | 17β(benzyloxyacetamidomethyl)-4-methyl-4-aza-5α-androst-1-en-3-one<br>17β(benzyloxyacetamidomethyl)-4-methyl-4-aza-5α-androstan-3-one |
| (26) 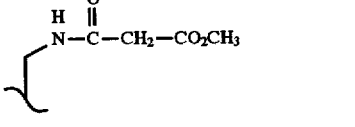 | 17β(carbomethoxyacetamidomethyl)-4-methyl-4-aza-5α-androst-1-en-3-one<br>17β(carbomethoxyacetamidomethyl)-4-methyl-4-aza-5α-androstan-3-one |
| (27) 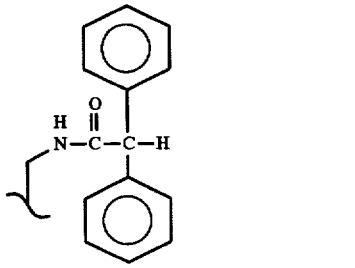 | 17β(diphenylacetamidomethyl-4-methyl-4-aza-5α-androst-1-en-3-one<br>17β(diphenylacetamidomethyl)-4-methyl-4-aza-5α-androstan-3-one |
| (28) 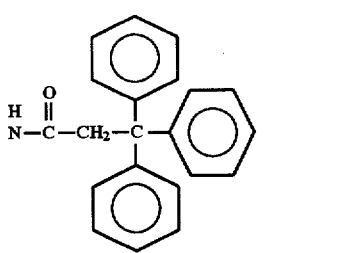 | 4-methyl-17β(3,3,3-triphenylpropionamido-methyl)-4-aza-5α-androst-1-en-3-one<br>4-methyl-17β(3,3,3-triphenylpropionamido-methyl)-4-aza-5α-androstan-3-one |

The following additional compounds may also be prepared according to the procedures described in the instant specification.

17β-(2-Furylacetamidomethyl)-4-Methyl-4-aza-5α-androstan-3-one;
17β-(4-Isopropylphenylacetamidomethyl)-4-Methyl-4-aza-5α-androstan-3-one;
17β-(Cyclohexylacetamidomethyl)-4-Methyl-4-aza-5α-androstan-3-one;
17β-(3-Indolylacetamidomethyl)-4-Methyl-4-aza-5α-androstan-3-one;
4-Methyl-17β-(4-Methylcyclohexanecarboxamidomethyl)-4-aza-5α-androstan-3-one;
17β-(4-(3-Indolyl)-butyramidomethyl)-4-Methyl-4-aza-5α-androstan-3-one;
17β-(4-Isobutylbenzamidomethyl)-4-Methyl-4-aza-5α-androstan-3-one;
17β-(Acetoxyacetamidomethyl)-4-Methyl-4-aza-5α-androstan-3-one;
17β-(6-Bromohexanoylamidomethyl)-4-Methyl-4-aza-5α-androstan-3-one;
4-Methyl-20-(4-Nitrobenzamidomethyl)-4-aza-5α-pregnan-3-one;
20-((3-Acetamido)benzamido)-4-Methyl-4-aza-5α-pregnan-3-one;
20-(3,4-Dimethoxyphenylacetamidomethyl)4-Methyl-4-aza-5α-pregnan-3-one;
17β-(4-Ethoxybenzamidomethyl)-4-Methyl-4-aza-5α-androstan-3-one;
4-Methyl-20-(Palmitoylamidomethyl)-4-aza-5α-pregnan-3-one;
17β-(Iminodibenzyl-5-carboxamidomethyl)-4-Methyl-4-aza-5α-androstan-3-one;
4-Methyl-20-(Stearoylamido)-4-aza-5α-pregnan-3-one;
4-Methyl-17β-(3,5-Bis-(Trifluoromethyl)benzamidomethyl)-4-aza-5α-androstan-3-one;
17β-(3-Cyanobenzamidomethyl)-4-Methyl-4-aza-5α-androstan-3-one;
20-(Heptafluorobutyramidomethyl)-4-Methyl-4-aza-5α-pregnan-3-one;
20-(4-Benzoylbenzamidomethyl)-4-Methyl-4-aza-5α-pregnan-3-one;
17β-(Benztriazol-5-carboxamidomethyl)-4-Methyl-4-aza-5α-androstan-3-one;
20-(3,5-Difluorobenzamido)-4-Methyl-4-aza-5α-pregnan-3-one;
17β-(Bis-(4-Isopropyl)phenyl)acetamidomethyl-4-Methyl-4-aza-5α-androstan-3-one;
4-Methyl-20-(Salicylamidomethyl)-4-aza-5α-pregnan-3-one;
17β-(Cinnamoylamidomethyl)-4-Methyl-4-aza-5α-androstan-3-one;
17β-((3-Hydroxy-4,4,4-trichlorobutyramido)methyl)-4-Methyl-4-aza-5α-androstan-3-one.

Synthesis of Testosterone 5-α Reductase Inhibitors:

General flowsheet VIII illustrates the synthesis of the intermediate oximes and amines used to produce compounds claimed in the instant invention.

FLOWSHEET VIII

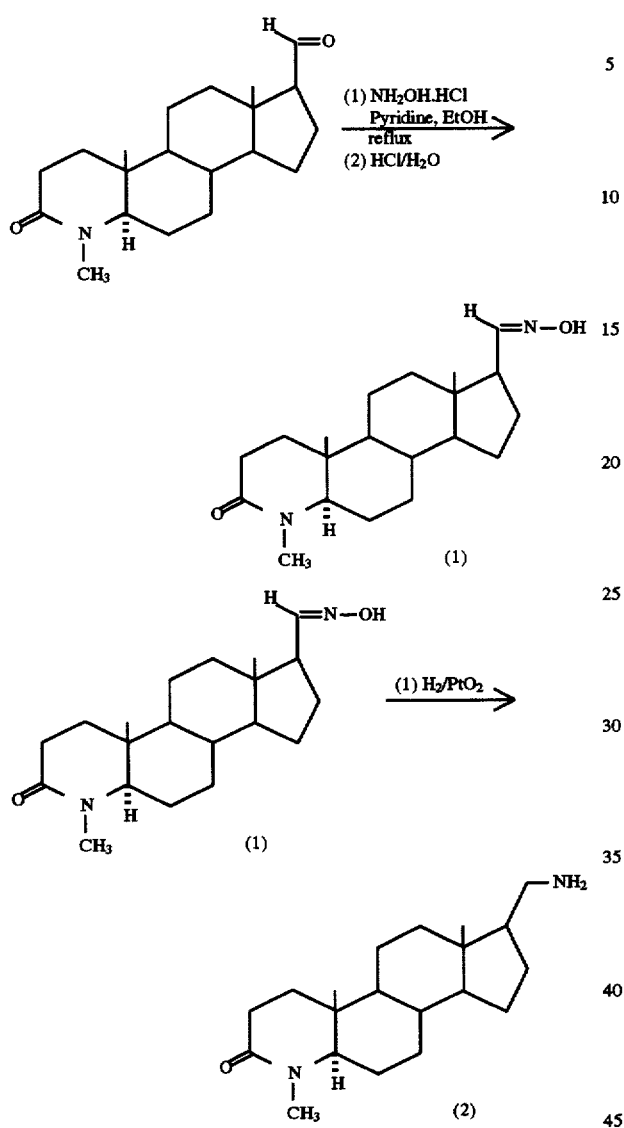

A stirred mixture of 4-methyl-3-oxo-5-α-4-azaandrostan-17-carboxaldehyde, hydroxylamine hydrochloride, anhydrous pyridine, and anhydrous ethanol is refluxed gently under a nitrogen atomosphere for six to seven hours. After cooling, the ice-cooled mixture is diluted, with stirring, with a slight excess of chilled dilute hydrochloric acid. The suspension is then aged for about twenty minutes, filtered, washed with water and dried to give compound 1.

With reference to flowsheet VIII, a mixture of the oxime (1), ethanol, glacial acetic acid and water is reduced in the presence of platinum oxide ($PtO_2$) until chromatographic analysis (TLC) indicates complete reduction to the amine (2). The filtered reaction mixture is concentrated in vacuo; the resultant residue is dissolved in chloroform ($CHCl_3$) and washed with fresh dilute sodium hydrogen carbonate solution. The chloroform phase is then dried with sodium sulfate ($Na_2SO_4$). Concentration of the resultant $CHCl_3$ solution followed by trituration of the residue with hexane/ether will yield 2 as a white solid.

The following amines are representative of those obtained from the corresponding carbonyl compounds utilizing the basic procedures described in flowsheet VIII for preparation of the oximes and amines:

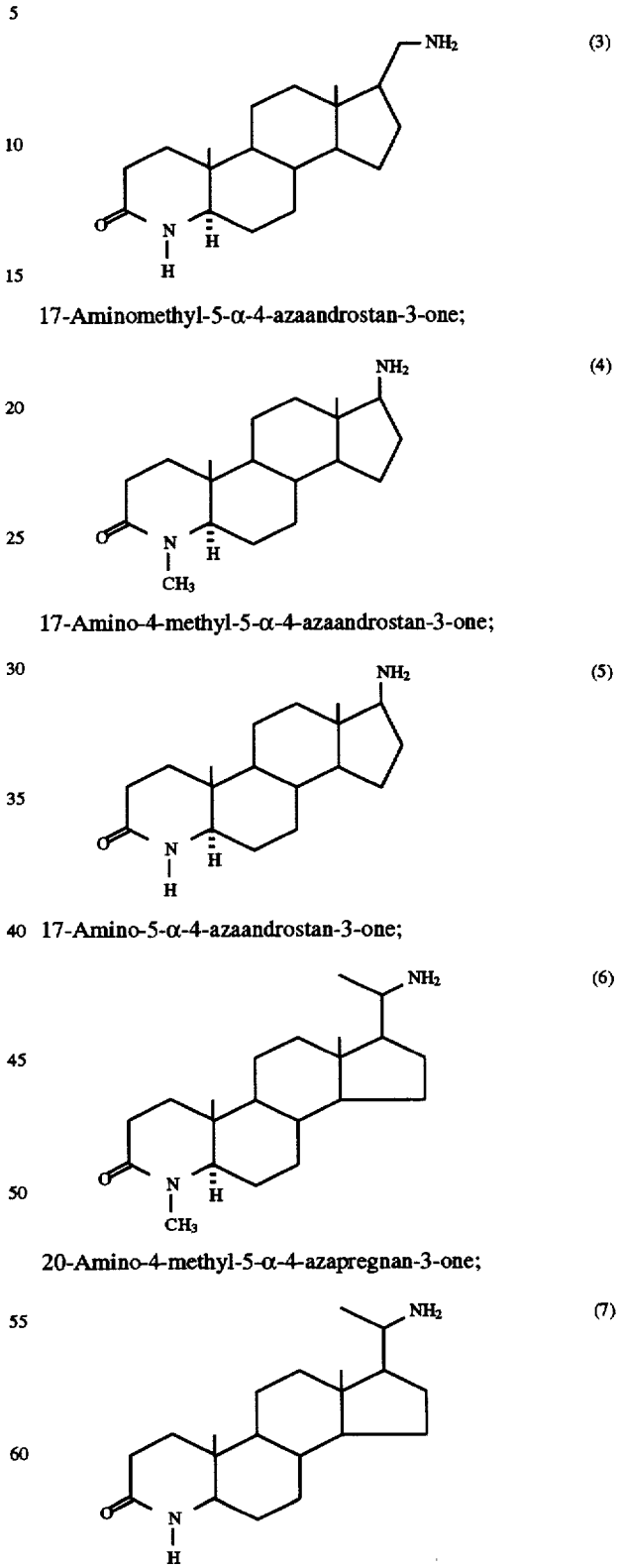

17-Aminomethyl-5-α-4-azaandrostan-3-one;

17-Amino-4-methyl-5-α-4-azaandrostan-3-one;

17-Amino-5-α-4-azaandrostan-3-one;

20-Amino-4-methyl-5-α-4-azapregnan-3-one;

20-Amino-5-α-4-azapregnan-3-one;

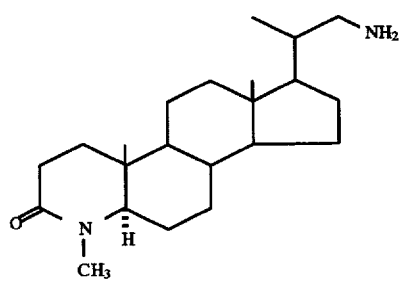

20-(Aminomethyl)-4-methyl-5-α-4-azapregnan-3-one;

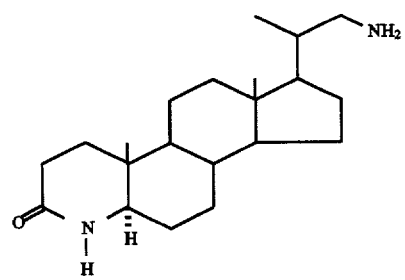

20-(Aminomethyl)-5-α-4-azapregnan-3-one;

As flowsheet VIII indicates, the oximes useful as intermediates may readily be prepared by reacting 4-azasteroidal. aldehyde or ketone with hydroxylamine hydrochloride to form the corresponding oxime. The resultant oximes are subsequently reduced with hydrogen ($H_2$) and platinum oxide ($PtO_2$) or other suitable reducing agent to yield the respective amine. The product amides may be further alkylated with, for example, alkyl halides to give the corresponding $R^2$ alkylated compounds. Alternatively, the primary amines may be alkylated by well known synthetic procedures to the corresponding secondary amines and then acylated to the product amides.

Flowsheet IX illustrates the synthesis of the compound 4-methyl-17(trimethylacetylamido)-5-α-4 azaandrostan-3-one and is representative of a basic synthesis of compounds claimed in the instant invention in which an amine is reacted with an acylating agent (or acid equivalent). These reagents include acyl halides and acid anhydrides.

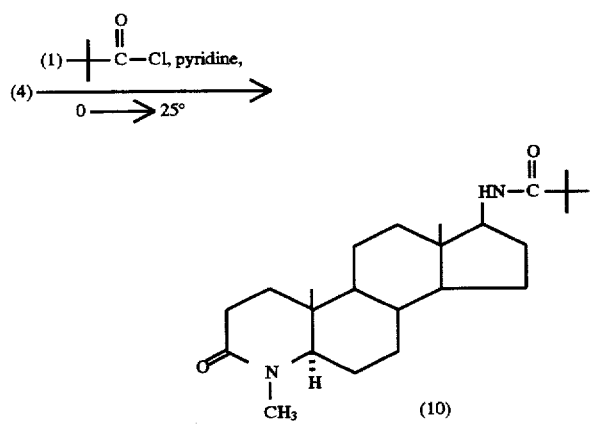

To a stirred, ice-cold solution of (4), anhydrous methylene chloride and pyridine is added trimethylacetylchloride dropwise over approximately one minute under a nitrogen atmosphere. After an additional fifteen minutes at ice-bath temperatures, the mixture is allowed to warm to room temperature (25° C.) and stirred for an additional fourteen hours. The mixture is then transferred to a separatory funnel washed with additional $CH_2Cl_2$, washed with dilute (0.3N) HCl, dried ($Na_2SO_4$), concentrated and recrystallized (ethyl acetate) to yield 10 as a white solid.

As flowsheet IX illustrates, 4-azasteroidal primary or secondary amines described in the instant invention are reacted with the desired activated carbonyl compound, such as trimethylacetyl chloride, to yield the target amide. Representative acyl halides or acid anhydrides of the formula:

$$X-\overset{O}{\underset{\|}{C}}-R^3 \text{ wherein}$$

$R^3$ equals $C_{1-20}$alkyl, aryl, heteroaryl, aryl$C_{1-20}$alkyl, heteroaryl$C_{1-20}$alkyl, $C_{1-20}$alkylaryl$C_{1-20}$alkyl, $C_{1-20}$alkyloxycarbonylalkyl, $C_{1-20}$alkylcarbonyl$C_{1-20}$alkyl, $C_{1-20}$cycloalkyl$C_{1-20}$alkyl, aryl$C_{1-20}$alkyloxycarbonyl$C_{1-20}$alkyl, halo$C_{1-20}$alkyl, aryl$C_{1-20}$alkyloxo$C_{1-20}$alkyl, diaryl$C_{1-20}$alkyl, triaryl$C_{1-20}$alkyl, $C_{2-20}$ alkenyl, $C_{2-20}$ alkenyl$C_{1-20}$alkyl, $C_{2-20}$alkynyl$C_{1-20}$alkyl, aryl$C_{2-20}$alkynyl$C_{1-20}$alkyl, heteroaryl$C_{2-20}$alkylnyl$C_{1-20}$alkyl, or aryl$C_{2-20}$alkenyl may be used in the instant invention.

Acyl halides or activated carbonyl compounds disclosed in this invention are commercially available or may be prepared from the corresponding carboxylic acid and thionyl chloride ($SOCl_2$), phosphorous pentahalide ($PX_5$), or phosphorous trihalide ($PX_3$). See Ansell in Patai, "The Chemistry of Acyl Halides", 35–48, Interscience, New York (1972).

The primary or secondary amines disclosed in the instant invention may also be reacted with alkyl and aryl sulfonyl halides or anhydrides to yield compounds claimed in the instant invention.

If a sulfonylhalide or anhydride of the formula $$X-\overset{O}{\underset{\underset{O}{\|}}{\overset{\|}{S}}}-R^3$$

is used, $R^3$ may equal the groups defined above for the carbonyl species.

Amides or sulfonamides representative of those obtained from the corresponding amines utilizing the basic procedure described in flowsheet IX by substituting either the amine or the activated carbonyl compound may be prepared. For example, compound 6 may be substituted for compound 4 in flowsheet IX and reacted with the indicated acylating agent (trimethylacetyl chloride) to yield compound 11 (4-methyl-20-(trimethylacetamido)-5-α-4-azapregnan-3'-one). If compound 2 is reacted with 8-(carbomethoxy)octanoyl chloride using the procedure described in flowsheet IX, (17-(8-(Carbomethoxy)-octanoylamidomethyl)-4-methyl-5-α-4-aza-androstan-3-one) is produced:

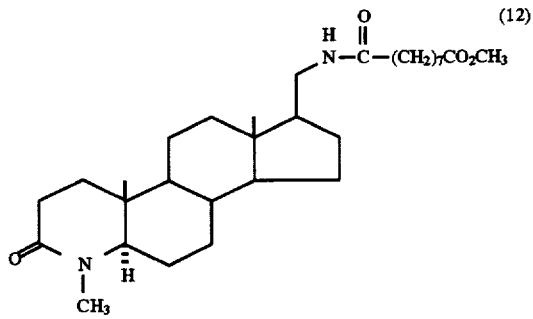

If sulfonyl halide is substituted for an acyl halide and reacted with an amine such as 2, (4-methyl-17-(2-thiophenesulfonylamidomethyl)-5-α-4-azaandrostan-4-one) may be prepared:

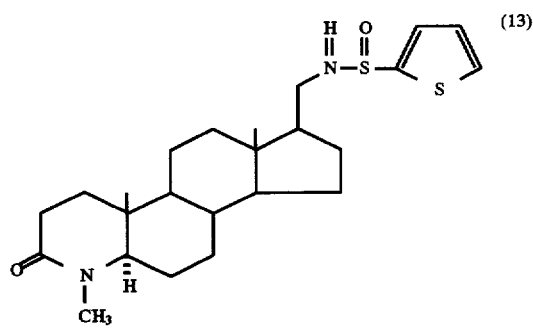

Flowsheet X illustrates the synthesis of 17β-(12-(Isopropyl-thio)dodecanoylamidomethyl)-4-methyl-5α-aza-androstan-3-one (14):

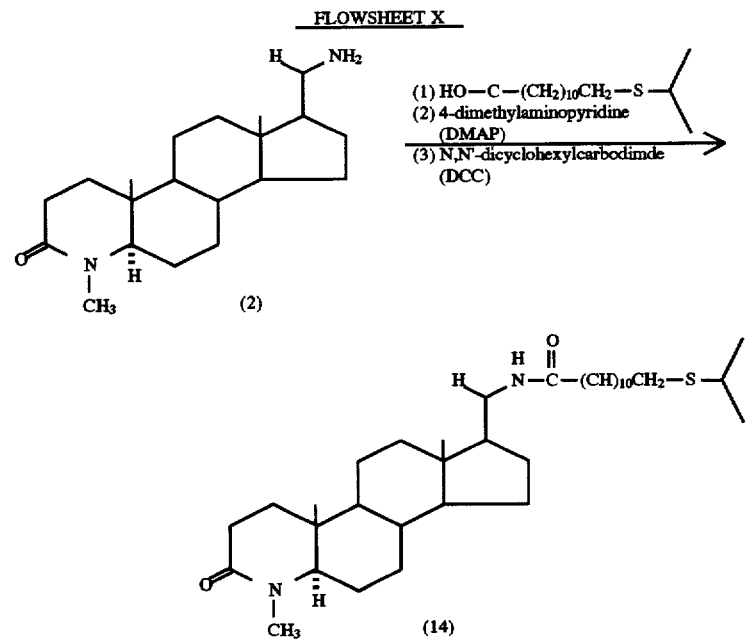

*prepared from 12-bromododecanoic acid and sodium isopropylthiolate

DCC is a well known coupling reagent used in peptide synthesis to generate amide bonds from a free acid and an amine. Coupling reagents may generally be used when the free acid is readily available or when the alternative acid halide is internally labile (e.g., when a thio group is present). An intermediate anhydride of the acid is generated which futher reacts with the amine. In flowsheet X, 12-(isopropylthio)-dodecanoic acid is reacted with 2, DCC, and DMAP to produce the corresponding amide (14). For example, DCC is used when $R^3$ is $C_{1-20}$alkylthio$C_{1-20}$alkyl or hydroxyl$C_{1-20}$alkyl. Additionally, dehydrogenation of the 1,2 position or the 5,6 position may readily be accomplished by known synthetic methodology to produce the claimed 1-en or 5-en derivatives. See U.S. Pat. No. 5,061,802; Dolling et al., JACS, 110, 3318–19 (1988).

General flowsheets XI, XII and XIII further illustrate how compounds claimed in the instant invention may be prepared. In flowsheet XI, the starting 4-azasteroid aldehyde or ketone (XV), obtained by known synthetic methods, is reacted to form the oxime (XVI); reduced to the amine (XVII) and reacted with an activated carbonyl or sulfonyl compound and an alkylhalide (X-$R^2$) to form XVIII.

General Flowsheet XI

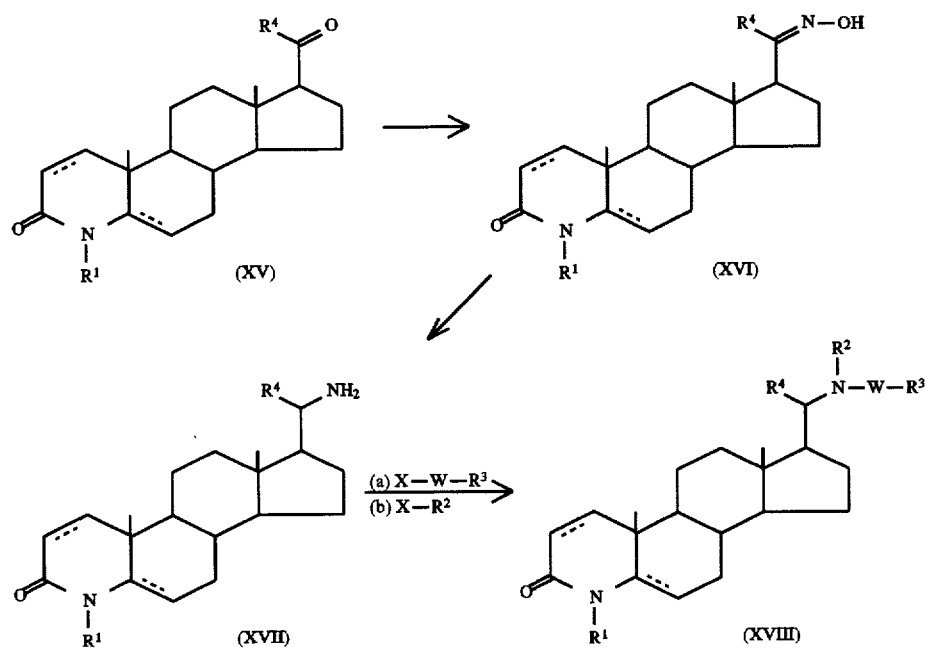

In flowsheet XII, the identical procedure is followed using a generic 4-azasteroid (XIX) prepared by known synthetic methods to produce the oxime (XX) which is reduced to the amine (XXI) and reacted with an activated carbonyl or sulfonyl compound (X-W-R³) to yield (XXII).

In flowsheet XIII, the generic 4-azasteroid XXIII, also obtained from well known synthetic methodology, is reacted to form the oxime XXIV which is further reduced to form XXV and subsequently reacted with an activated carbonyl or sulfonyl compound to form XXVI.

FLOWSHEET XII

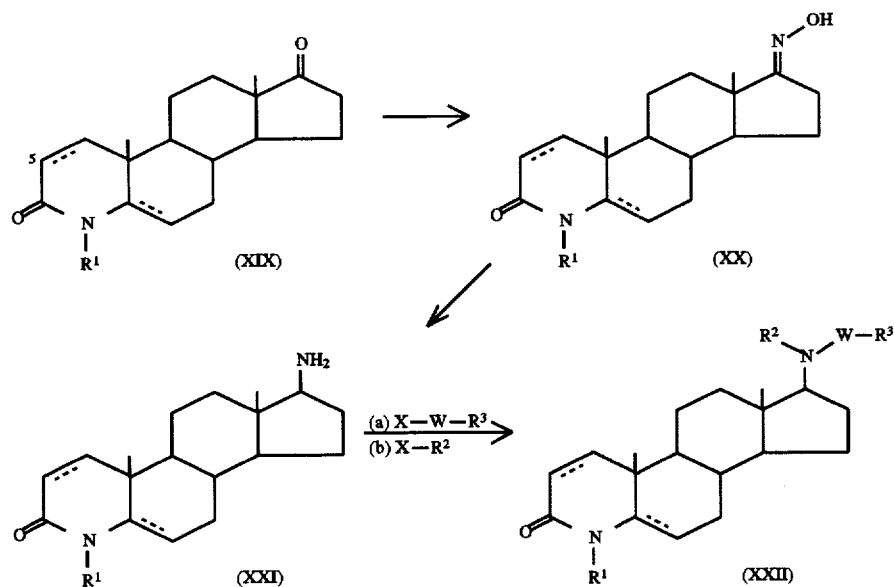

FLOWSHEET XIII
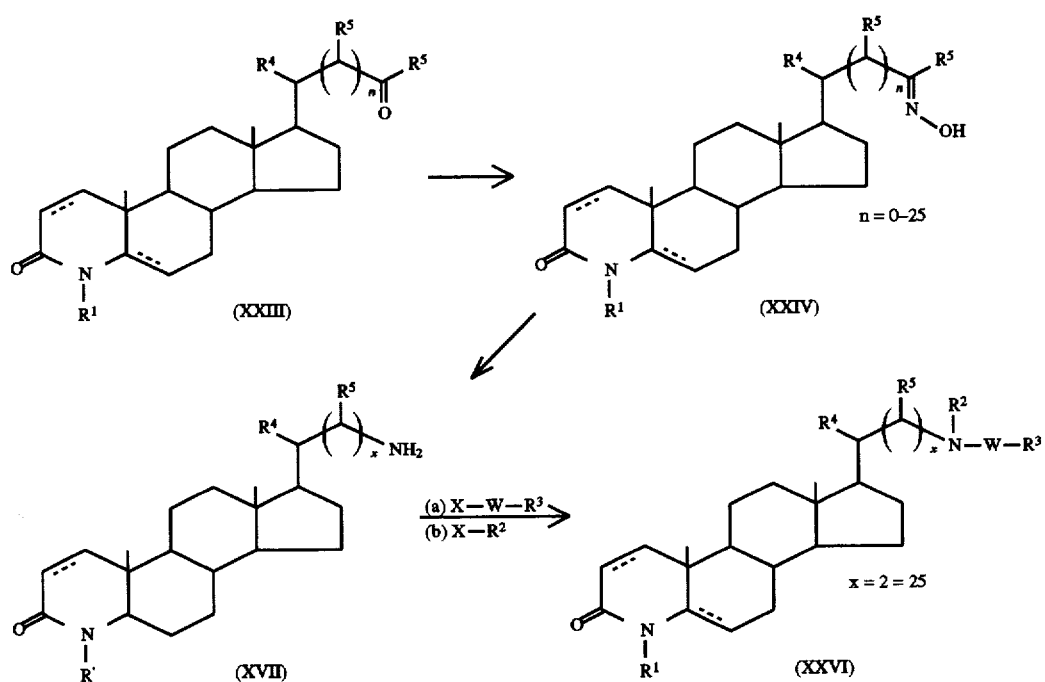
The starting 4-azasteroidal ketones used in the present invention may be prepared according to the well known basic procedures described in flowsheet XIV.
FLOWSHEET XIV
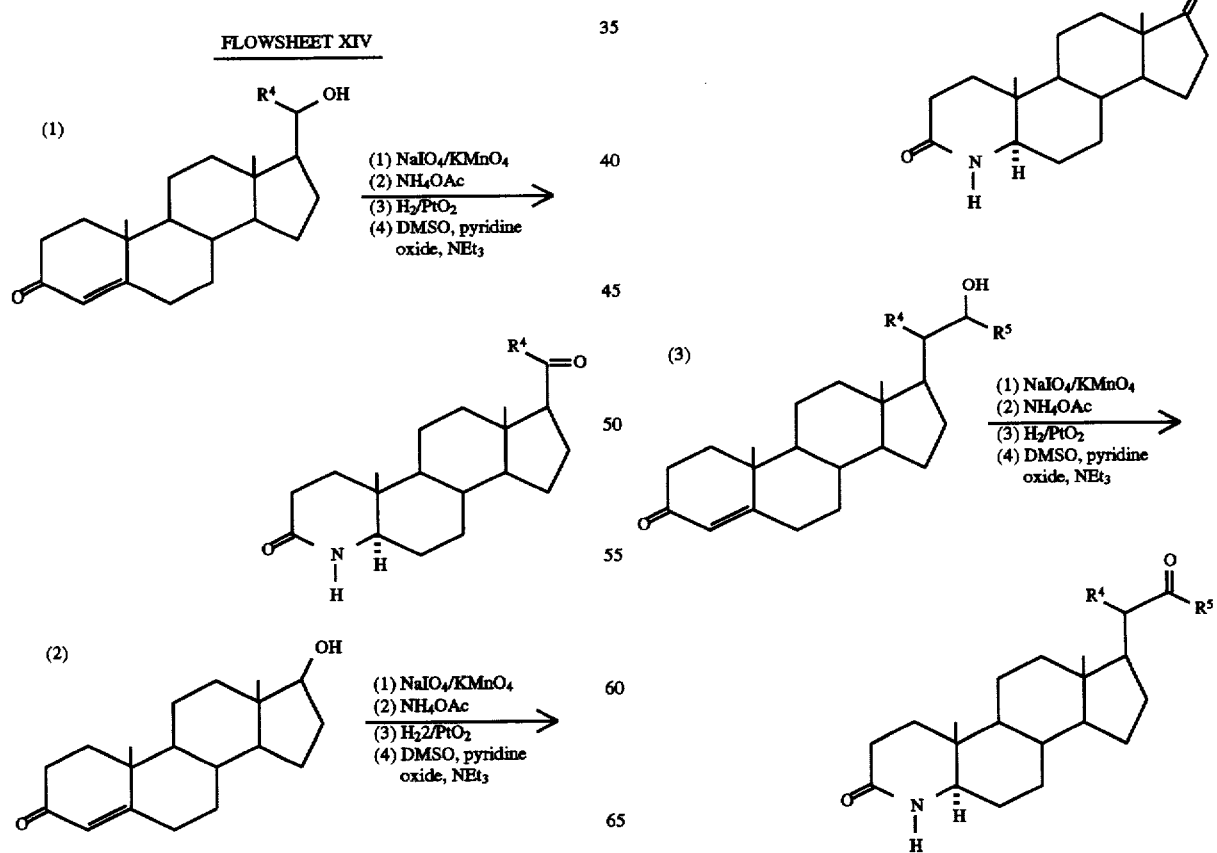

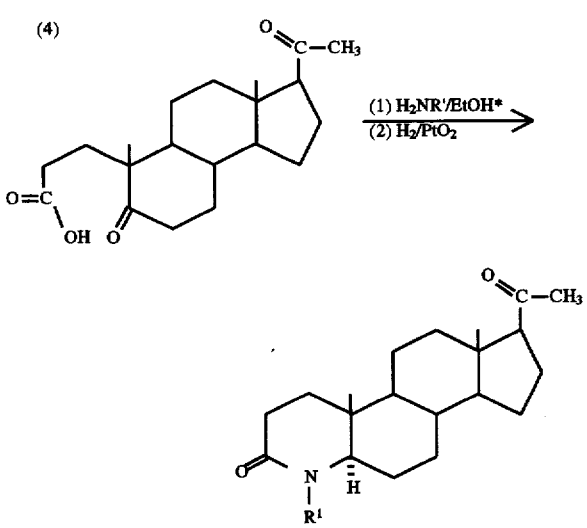

*U.S. PAT. NO. 4,377,584

FLOWSHEET XIV, CONTINUED

The following examples further describe the synthesis of compounds claimed in the instant invention.
Synthesis of Starting -4-azasteroid oximes:

EXAMPLE 9

(9) 4-Methyl-3-oxo-4-α-4-azaandrostan-17-carboxaldehyde oxime

A stirred mixture of 4-methyl-3-oxo-5-α-4-azaandrostan-17-carboxaldehyde (0.952 g, 3.0 mM), hydroxylamine hydrochloride (1.10 g, 15.8 mM), anhydrous pyridine (6 mL), and anhydrous ethanol (12 mL) was refluxed gently under a nitrogen atmosphere for 6.3 hours. After cooling, the ice-cooled mixture was diluted, with stirring, with a slight excess of chilled dilute hydrochloric acid (ca. 0.3N), the suspension was aged for ca. 20 minutes, filtered, washed with water and dried to give (9) 0.855 g. MS M⁺ calcd for $C_{20}H_{32}H_2O_2$ 332.48, observed m/e 332.
Synthesis of Reactant 4-azasteroid Amines:

EXAMPLES 10–17

(10) 17-Aminomethyl-4-methyl-5-α-4-azaandrostan-3-one

A mixture of (9) (0.67 g., 2.0 mM), ethanol (100 mL), glacial acetic acid (8 mL) and water (4 mL) was reduced in a hydrogen atmosphere (40 p.s.i.) at room temperature in the presence of $PtO_2$ until TLC analysis ndicated complete reduction. The filtered reaction mixture was concentrated in vacuo, the residue taken up in chloroform, and the chloroform solution washed with fresh dilute sodium hydrogen carbonate solution and dried ($Na_2SO_4$). Conentration of the filtered chloroform solution followed by trituration of the residue obtained with hexane containing a small amount of ether yielded (10) as an off-white solid. MS MH⁺ calcd for $C_{20}H_{34}N_2O$ 318.49, observed m/e 319.

The following amines are representative of those obtained from the corresponding carbonyl compounds utilizing the above procedures:

(11) 17-Aminomethyl-5-α-4-azaandrostan-3-one.
(12) 17-Amino-4-methyl-5-α-4-azaandrostane-3-one.
(13) 17-Amino-5-α-4-azaandrostan-3-one.
(14) 20-Amino-4-methyl-5-α-4-azapregnan-3-one.
(15) 20-Amino-5-α-4-azapregnan-3-one.

(16) 20-(Aminomethyl)-4-methyl-5-α-4-azapregnan-3-one.
(17) 20-(Aminomethyl)-5-α-4-azapregnan-3-one.

Synthesis of Amino substituted azasteroids:

EXAMPLES 18–22

(18) 4-Methyl-17β-(trimethylacetamido)-5-α-4-azaandrostan-3-one

To a stirred, ice-cold colution of (12) (0.091 g, 0.3 mM), anhydrous methylene chloride (5 mL), and pyridine (0.1 mL, 1.2 mM), was added trimethylacetyl chloride (0.05 mL, 0.4 mm) dropwise over ca. one minute (nitrogen atmosphere). After an additional 15 min. at ice-bath temperatures the mixture was allowed to warm to room temperature and stir at ambient temperature overnight. The mixture was then transferred to a separatory funnel with additional methylene chloride, washed with dilute (ca. 0.3N) hydrochloric acid, and dried ($Na_2SO_4$). Concentration of the filtered solution followed by recrystallization (ethyl acetate) of the residue obtained gave (18) as a white solid. MS M⁺ calcd for $C_{24}H_{40}N_2O_2$ 388.59, observed m/e 388.

(19) 4-Methyl-20-(trimethylacetamido)-4-α-4-azapregnan-3-one

When (12) in the above reaction was replaced by (14), (19) was obtained as a white solid. MS M⁺ calcd for $C_{26}H_{44}H_2O_2$ 416.65, observed m/e 416.

(20) 17β-(8-(Carbomethoxy)octanoylamidomethyl)-4-methyl-5-α-4-azaandrostan-3-one When (10) was reacted with 8-carbomethoxyoctanoyl chloride using the conditions of Example (18), compound (20) was obtained as a thick oil. MS M⁺ calcd for $C_{30}H_{50}N_2O_4$ 502.74, observed m/e 502.

(21) 4-Methyl-17β-(2-thiophenesulfonylamidomethyl)-5-α-4-azaandrostan-3-one

When the 8-carbomethoxyoctanoyl chloride n the above example was replaced with 2-thiophene-sulfonyl chloride, (21) was obtained as a white solid. MS M⁺ calcd for $C_{24}H_{36}N_2O_3S_2$ 464.68, observed m/e 464.

22) 17β-(12-(Isopropylthio)dodecanoylamidomethyl)-4-methyl-5-α-4-aza-androstan-3-one To a stirred solution of (10) (0.028 g, 0.09 mM) and 12-(isopropylthio)dodecanoic acid (0.025 g, 0.09 mM) (prepared from 12-bromododecanoic acid and sodium isopropylthiolate by heating in 1,2-dimethoxyethane) in methylene chloride (3 mL) was added 4-(dimethylamino)-pyridine (0.011 g, 0.09 mM) followed by a solution of N,N'-dicyclohexylcarbodiimide (0.020 g, o.097 mM) in a minimum of the same solvent. After stirring for 12–14 hours, the mixture was filtered and the filtrate concentrated in vacuo. Flash chromatography (silica gel, ethyl acetate as eluant) yielded (22) as a very thick oil. MS MH⁺ calcd for $C_{35}H_{62}N_2O_2S$ 574.95, observed m/e 575.

Examples 23–45 prepared according to the basic procedures described above further exemplify the invention.

23) 4-Methyl-17β(trimethylacetamidomethyl)-4-aza-5α-androstan-3-one;
24) 17β(acetamido)-4-Methyl-4-aza-5α-androstan-3-one;
25) 4-Methyl-17β(2-thiophenecarboxamidomethyl)-4-aza-5α-androstan-3-one;
26) 17β(2-(4-isobutylphenyl)propionamidomethyl)-4-Methyl-4-aza-5α-androstan-3-one;
27) 17β(8-carboxyoctanoylamidomethyl)-4-Methyl-4-aza-5α-androstan-3-one;
28) 17β(acetoacetamidomethyl)-4-Methyl-4-aza-5α-androstan-3-one;
29) 17β(1-Adamantylacetamidomethyl)-4-Methyl-4-aza-5α-androstan-3-one;

30) 4-Methyl-17β(2-thiopheneacetamidomethyl)-4-aza-5α-androstan-3-one;
31) 7β(12-(t-butylthio)dodecanoylamido)-4-Methyl-4-aza-5α-androstan-3-one;
32) 17β(3-(carbobenzyloxy)propionamidomethyl)-4-Methyl-4-aza-5α-androstan-3-one;
33) 17β(3,4-dimethoxyphenylacetamidomethyl)-4-Methyl-4-aza-5α-androstan-3-one;
34) 17β(8-(carbomethoxy)octanoylamido)-4-Methyl-4-aza-5α-androstan-3-one;
35) 17β(isopropylthhiododecanoylamido)-4-Methyl-4-aza-5α-androstan-3-one;
36) 17β(benzenesulfonamidomethyl)-4-Methyl-4-aza-5α-androstan-3-one;
37) 17β(6-Bromohexanoxylamidomethyl)-4-Methyl-4-aza-5α-androstan-3-one;
38) 17β(12-hydroxydodecanoylamidomethyl)-4-Methyl-4-aza-5α-androstan-3-one;
39) 4-Methyl-17β(2-(4-nitrophenyl)propionamido-methyl)-4-aza-5α-androstan-3-one,
40) 17β(isopropylthioacetamidomethyl)-4-Methyl-4- aza-5α-androstan-3-one;
41) 4-Methyl-17β(6-(thiosulfato)hexanoylamidomethyl)-4-aza-5α-androstan-3-one;
42) 17β(benzyloxyacetamidomethyl)-4-Methyl-4-aza-5α-androstan-3-one;
43) 17β(carbomethoxyacetamidomethyl)-4-Methyl-4-aza-5α-androstan-3-one;
44) 17β(diphenylacetamidomethyl)-4-Methyl-4-aza-5α-androstan-3-one;
45) 4-Methyl-17β(3,3,3-triphenylpropionamidomethyl)-4-aza-5α-androstan-3-one;

Table 2 illustrates the NMR data of the above examples.

TABLE 2

| | NMR DATA (PPM) | | |
|---|---|---|---|
| Example | Angular | Methyls | Miscellaneous |
| 18 | 0.68, | 0.88 | 1.20 (—NHCOC(CH₃)₃) |
| 19 | 0.72 | 0.88 | 1.17 (—NHCOC(CH₃)₃) |
| 20 | 0.67, | 0.89 | 3.66 (—CO₂CH₃) |
| 21 | 0.61, | 0.88 | 2.93 (4-NCH₃) |
| 22 | 0.67, | 0.89 1.28 | 1.24 (—SCH(CH₃)₂) |
| 23 | 0.67, | 0.88 | 1.18 (—NHCOC(CH₃)₃) |
| 24 | 0.70, | 0.88 | 1.98 (—NHCOCH₃) |
| 25 | 0.72, | 0.89 | 2.93 (4-NCH₃) |
| 26 | 0.57, (split) | 0.85 | 2.91 (4-NCH₃) |
| 27 | 0.66, | 0.88 | 2.92 (4-NCH₃) |
| 28 | 0.64, | 0.88 | 2.24 (—COCH₃) |
| 29 | 0.66, | 0.88 | 2.93 (4-NCH₃) |
| 30 | 0.61, | 0.87 | 3.78 (—COCH₂—(C₄H₃S)) |
| 31 | 0.70, | 0.89 | 1.33 (—SC(CH₃)₃) |
| 32 | 0.64, | 0.88 | 5.12 (—CO₂CH₂Ph) |
| 33 | 0.60, | 0.88 | 3.52(d) (—Ph—(OCH₃)₂) |
| 34 | 0.70, | 0.89 | 3.66 (—CO₂CH₃) |
| 35 | 0.70, | 0.89 1.28 | 1.24 (—SCH(CH₃)₂) |
| 36 | 0.57, | 0.87 | 2.91 (4-NCH₃) |
| 37 | 0.67, | 0.88 | 2.92 (4-NCH₃) |
| 38 | 0.66, | 0.88 | 2.92 (4-NCH₃) |
| 39 | 0.61, (split) | 0.86 | 2.92 (4-NCH₃) |
| 40 | 0.68, | 0.88 1.28 | 1.24 (—SCH(CH₃)₂) |
| 41 | 0.67, | 0.89 | 2.93 (4-NCH₃) |
| 42 | 0.65, | 0.88 | 4.56 (—OCH₂Ph) |

TABLE 2-continued

| | NMR DATA (PPM) | | |
|---|---|---|---|
| Example | Angular | Methyls | Miscellaneous |
| 43 | 0.68, | 0.89 | 3.75 (—CO₂CH₃) |
| 44 | 0.60, | 0.86 | 4.92 (—COCH(Ph)₂) |

The above examples are non-limiting and suitable acylating agents may readily be substituted according to the methods described in the present invention and reacted with a described amine to form the claimed amides. The following definitions further clarify the present invention.

The term "pharmaceutically acceptable salts" shall mean non-toxic salts of the compounds of this invention which are generally prepared by the free base with a suitable organic or inorganic acid. Representative salts include the following salts: Acetate, adipate, alginate, aspartate benzenesulfonate, benzoate, bicarbonate, bisulfate borate, butyrate, camsylate, carbonate, camphorate, chloride, citrate, digluconate, fumarate, glucoheptanate, gluconate, glutamate, glycerophosphate, hydrobromide, hydrochloride, hydroiodide, lactate, laurate, malate, maleate, mandelate, mesylate, methylbromide, methylnitrate, methylsulfate, mucate, napsylate, nitrate, oleate, oxalate.

The term "pharmaceutically effective amount" shall mean that amount or quantity of a drug or pharmaceutical agent that will elicit the biological or medical response of a tissue, system or animal that is being sought by a reseacher or clinician or physician.

In the schemes and examples described in this disclosure, various reagent symbols have the following meanings:

PtO₂ is platinum oxide
TLC is thin layer chromatography
Na₂SO₄ is sodium sulfate
DMAP is 4-(dimethylaminno)pyridine
DCC is N,N'-dicyclohexylcarbodiimide EXAMPLES FOR THE CASE WHEN SUBSTITUENT "A" OF GENERAL FORMULA "I" IS AS DEFINED IN GROUP "V(A)"

The present invention can utilize compounds of the general structural formula:

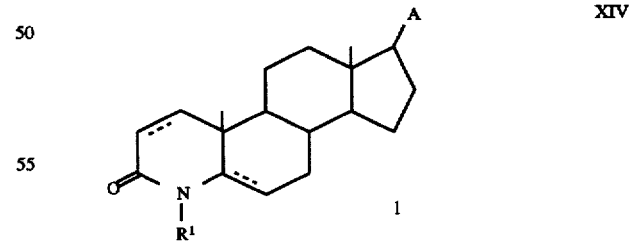

and the pharmaceutically acceptable salts thereof, wherein:
A is:

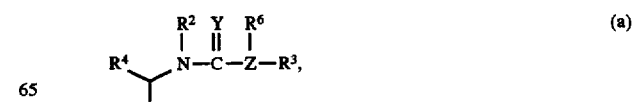

-continued

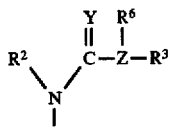
(b)

except when R² equals H, Y equals O, Z equals N, and there is a 5α H, R⁶ and R³ cannot be independently selected from H, $C_{1-8}$ alkyl, $C_{3-6}$ cycloalkyl, phenyl or when R⁶ and R³ are taken together with the adjacent N to form a 5–6 membered ring comprising up to one other heteroatom selected from O or N, or

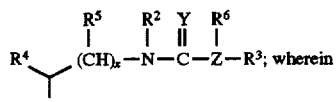

R¹ is:
H,
methyl or ethyl;
R² is:
H, or
$C_{1-20}$ alkyl;
R³ is:
H,
$C_{1-20}$ alkyl,
$C_{6-14}$ aryl,
heteroaryl,
$C_{6-14}$ aryl$C_{1-20}$alkyl,
$C_{3-20}$ cycloalkyl,
$C_{3-20}$ cycloalkyl$C_{1-20}$alkyl,
heteroaryl$C_{1-20}$alkyl,
$C_{6-14}$ arylcarbonyl$C_{6-14}$aryl$C_{1-20}$alkyl,
$C_{2-20}$ alkenyl$C_{1-20}$alkyl,
halo$C_{1-20}$alkyl,
$C_{1-20}$alkyloxycarbonyl$C_{1-20}$alkyl,
$C_{1-20}$ alkyloxy$C_{1-20}$alkyl,
carboxy$C_{1-20}$ alkyl,
$C_{1-20}$ alkylcarbonyl$C_{1-20}$alkyl,
$C_{6-14}$ aryl$C_{1-20}$alkyloxycarbonyl$C_{1-20}$alkyl,
heteroaryl$C_{1-20}$alkyloxycarbonyl$C_{1-20}$alkyl,
hydroxyl$C_{1-20}$alkyl,
halohydroxyl$C_{1-20}$alkyl,
$C_{6-14}$ aryl$C_{1-20}$alkyloxy $C_{1-20}$ alkyl,
heteroaryl$C_{1-20}$alkyloxy $C_{1-20}$alkyl,
diaryl$C_{1-20}$alkyl,
triaryl$C_{1-20}$alkyl,
$C_{2-20}$ alkenyl,
$C_{2-20}$ alkenyl$C_{1-20}$alkyl,
$C_{2-20}$ alkynyl$C_{1-20}$alkyl,
$C_{6-14}$ aryl$C_{2-20}$alkynyl$C_{1-20}$alkyl,
heteroaryl$C_{2-20}$alkynyl$C_{1-20}$alkyl,
$C_{1-20}$ alkylthio$C_{1-20}$alkyl,
$C_{1-20}$ alkylsulfonyl$C_{1-20}$alkyl, or
$C_{1-20}$ alkylsulfinyl$C_{1-20}$alkyl,
R⁴ is:
H,
$C_{1-20}$ alkyl,
heteroaryl, or
$C_{6-14}$ aryl;
R⁵ can be the same or different when x is greater than 1 and is:
H,
$C_{1-20}$ alkyl,
heteroaryl, or
$C_{6-14}$ aryl;
R⁶ is present when Z equals N and is
H, or
$C_{1-20}$ alkyl; or taken together with R³ and the N to which they are attached represent a heteroaryl ring system;
Y is:
O, or
S;
Z is:
N, or
O;
n is an integer from 1–25,
and dashes indicate a double bond is optionally present.
Advantageously, compounds of the following formula are disclosed in the present invention.

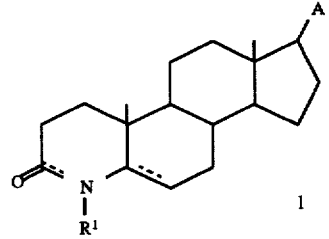

and the pharmaceutically acceptable salts thereof, wherein:
A is:

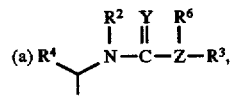

except when R² equals H, Y equals O, Z equals N and there is a 5α H, R⁶ and R³ cannot be independently selected from H, $C_{1-8}$ alkyl, $C_{3-6}$ cycloalkyl, phenyl or when R⁶ and R³ are taken together with the adjacent N to form a 5–6 membered ring comprising up to one other heteroatom selected from O or N, or

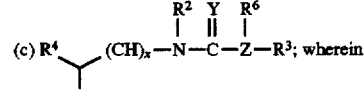

R¹ is:
H, or
methyl or ethyl;
R² is:
H, or
$C_{1-20}$ alkyl;

$R^3$ is:

H, $C_{1-20}$ alkyl further comprising a straight or branched chain alkane of up to 20 carbon atoms;

$C_{6-14}$ aryl wherein aryl comprises a mono or polycyclic system composed of 6-membered aromatic rings either unsubstituted or substituted with R wherein R comprises H, $C_{1-20}$ alkyl, aryl$C_{1-20}$alkyl with the alkyl groups unsubstituted or substituted with hydroxyl, $C_{1-8}$alkyloxy, carboxy $C_{1-10}$alkyl, or halogen; or aryl can be directly substituted or multisubstituted independently with hydroxyl, halo$C_{1-20}$alkyl, benzoyl, $C_{1-20}$alkyloxy, $C_{1-20}$alkyl, $C_{2-20}$alkenyl, cyano, nitro, carboamide, acetamide, or halogen;

heteroaryl which comprises a mono or polycyclic system composed of 5 and 6-membered aromatic rings containing 1, 2, 3 or 4 heteroatoms chosen from N, O, or S and either unsubstituted or substituted with R as defined for aryl or substituted or multisubstituted independently with hydroxyl, $C_{1-20}$ alkyloxy, $C_{1-20}$alkyl, benzyl, carboamide, acetamide, $C_{2-20}$alkenyl, cyano, nitro, halo$C_{1-20}$alkyl, or halogens, directly bonded to the aromatic carbon atom(s);

$C_{6-14}$ aryl$C_{1-20}$alkyl of the formula:

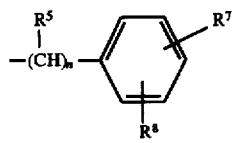

wherein the aromatic ring is optionally and independently substituted with $R^7$ and $R^8$ wherein $R^7$ and $R^8$ comprise

H, $CH_3$, $C_2H_5$, carboamide,

OH, $OCH_3$, $NO_2$,

CN,

RS, RSO, $RSO_2$, $R_2N$, where R can be the same or different and is selected from: H, C1–C4alkyl, C6–C14 aryl;

Cl, acetamido, $OC_2H_5$, $CF_3$, isopropyl, or isobutyl; n equals 1–10 and the $C_{1-20}$alkyl portion is optionally substituted with $R^7$;

Heteroaryl$C_{1-20}$alkyl further comprising the formula:

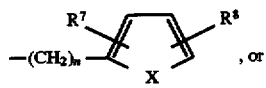, or

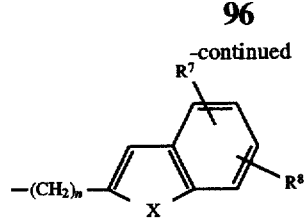

wherein X equals O, S, or NR; and n equals 1–20;

$C_{1-20}$alkylsulfonyl$C_{1-20}$alkyl, $C_{1-20}$alkylthio$C_{1-20}$alkyl, $C_{1-20}$alkylsulfmyl$C_{1-20}$alkyl, comprising the formula:
—$(CH_2)_n S(O)_p$—$R^9$ wherein $R^9$ comprises $CH_3$, $C_2H_5$, $C_3H_7$, $C_4H_9$, isopropyl, isobutyl, sec-butyl, t-butyl, isopentyl, neopentyl, or isohexyl; n equals 1–20; p=0 1, or 2;

$C_{1-20}$ alkyloxycarbonyl$C_{1-20}$alkyl further comprising the formula:

wherein $R^{10}$ comprises:

$CH_3$, $C_2H_5$, $C_3H_7$, $C_4H_9$, or $C_5H_{11}$; n equals 1–20;

carboxyl$C_{1-20}$ alkyl further comprising:

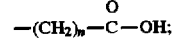

n equals 1–20;

$C_{1-20}$alkylcarbonyl$C_{1-20}$ alkyl further comprising

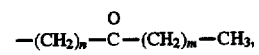

n equals 1–20; m equals 0–19;

$C_{1-20}$ cycloalkyl$C_{1-20}$ alkyl of the formula:
—$(CH_2)_n$-(cycloalkyl) wherein the cycloalkyl portion comprises monocyclic, bicyclic, or polycyclichydrocarbons of up to 20 carbon atoms Wherein the rings are optionally substituted with $R^1$, and n equals 1–20;

$C_{6-14}$ aryl$C_{1-20}$ alkyloxycarbonyl$C_{1-20}$ alkyl of the formula:

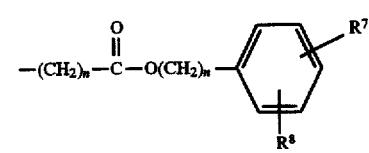

wherein $R^7$ and $R^8$ are as defined; n equals 1–20;

HeteroarylC$_{1-20}$ alkyloxycarbonylC$_{1-20}$alkyl of the formula:

$$-(CH_2)_n-\overset{O}{\underset{\|}{C}}-O-(CH_2)_n-\text{Heteroaryl}$$

wherein Heteroaryl is as defined; n equals 1–20;
haloC$_{1-20}$ alkyl of the formula:

$-(CH_2)_n-CH_2 X$ wherein X equals Br, Cl, F or I; n is 1–9;

hydroxylC$_{1-20}$alkyl of the formula:

$-(CH_2)_n CH_2OH$; n equals 1–19;

halohydroxylC$_{1-20}$alkyl of the formula:

$$-(CH_2)_n-\underset{OH}{CH}-(CH_2)_q-\overset{X}{\underset{X}{C}}-X$$

wherein X equals Br, Cl, F or I; n=0–18, q=0–18; n+q=0–18;
C$_{6-14}$ arylC$_{1-20}$alkyloxyC$_{1-20}$ alkyl of the formula:

$$-(CH_2)_n-O-(CH_2)_n-\underset{R^8}{\overset{R^7}{\text{Ar}}} \quad \text{wherein}$$

R$^7$ and R$^8$ are as defined; n is 1–20;
ArylcarbonylarylC$_{1-20}$alkyl of the formula:

$$-(CH_2)_n-\underset{R^8}{\overset{R^7O}{\text{Ar}}}-\overset{\|}{C}-\underset{R^8}{\overset{R^7}{\text{Ar}}},$$

n equals 1–20;

DiarylC$_{1-20}$alkyl of the formula:

$$-(CH_2)_nC\underset{R^7}{\overset{R^7}{\text{Ar}}}$$

n equals 1–19;
TriarylC$_{1-20}$alkyl of the formula:

$$-(CH_2)_n-C(Ar)_3$$

n equals 1–10;

ArylC$_{2-20}$ alkenyl of the formula:

$$-(CH_2)_n-(CH=CH)-(CH_2)_m-\underset{R^8}{\overset{R^7}{\text{Ar}}},$$

n = 0–18
m = 0–18
n + m = 0–18

R$^4$ is:
H,
C$_{1-20}$alkyl,
C$_{6-14}$ aryl, or
Heteroaryl;

R$^5$ is:
H, or
C$_{1-12}$ alkyl;

R$^6$ is present when Z equals N and is independently
H,
C$_{1-20}$ alkyl,
equivalent to R$^3$; or taken together with R$^3$ and the N to which they are attached represent a heteroaryl ring system;

Y is:
O, or
S;

Z is
N, or
O;

x is an integer from 1–10,
dashes indicate a double bond is optionally present.

The present invention is further concerned with compounds of the formula:

and the pharmaceutically acceptable salts thereof, wherein A is:

(a) $R^4\diagdown\underset{}{\diagup}N-\overset{R^2}{\underset{}{C}}-\overset{Y}{\underset{}{\|}}-\overset{R^6}{\underset{}{Z}}-R^3$, (b) $R^4\diagdown\underset{\underset{|}{N}}{\diagup}C-\overset{Y}{\underset{}{\|}}-\overset{R^6}{\underset{}{Z}}-R^3$ except when R$^2$ equals H, Y equals O, Z equals N, and there is a 5α H, R$^6$ and R$^3$ may not be independently selected from H, C$_{1-8}$ alkyl, C$_{3-6}$ cycloalkyl, phenyl or when R$^6$ and R$^3$ are taken together with the adjacent N to form a 5–6 membered ring comprising up to one other heteroatom selected from O or N, or

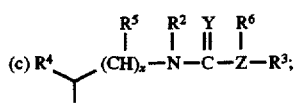

(c) $R^4\underset{}{\diagdown}(CH)_x-\overset{R^5}{\underset{|}{N}}-\overset{R^2}{\underset{|}{C}}-\overset{Y}{\underset{||}{Z}}-R^3$;

wherein
$R^1$ is:
  H,
  methyl or ethyl;
$R^2$ is:
  H, or
  $C_{1-20}$ alkyl;
$R^3$ is:
  H,
  $C_{1-20}$ alkyl,
  $C_{6-12}$ aryl,
  heteroaryl,
  $C_{6-12}$ aryl$C_{1-20}$alkyl,
  heteroaryl$C_{1-20}$alkyl,
  $C_{3-20}$ cycloalkyl,
  $C_{3-20}$ cycloalkyl$C_{1-20}$alkyl,
  $C_{2-20}$ alkenyl$C_{1-20}$alkyl,
  halo$C_{1-20}$alkyl,
  $C_{1-20}$ alkyloxy$C_{1-20}$alkyl,
  $C_{1-20}$alkyloxycarbonyl$C_{1-20}$alkyl,
  $C_{1-20}$ alkylthio$C_{1-20}$alkyl,
  $C_{1-20}$ alkylsulfonyl$C_{1-20}$alkyl,
  $C_{1-20}$alkylsulfinyl$_{1-20}$alkyl,
  carboxy$C_{1-20}$ alkyl,
  $C_{6-12}$ arylcarbonylaryl$C_{1-20}$alkyl
  $C_{1-20}$ alkylcarbonyl$C_{1-20}$alkyl,
  $C_{6-12}$ aryl$C_{1-20}$ alkyloxycarbonyl$C_{1-20}$alkyl,
  heteroaryl$C_{1-20}$alkyloxycarbonyl$C_{1-20}$alkyl,
  halo$C_{1-20}$alkyl,
  hydroxy$C_{1-20}$alkyl,
  halohydroxyl$C_{1-20}$alkyl,
  $C_{6-14}$ aryl$C_{1-20}$alkyloxy $C_{1-20}$alkyl,
  heteroaryl$C_{1-20}$alkyloxy $C_{1-20}$alkyl,
  diaryl$C_{1-20}$alkyl,
  triaryl$C_{1-20}$alkyl,
  $C_{2-20}$ alkenyl,
  $C_{2-20}$ alkenyl$C_{1-20}$alkyl,
  $C_{2-20}$ alkynyl$C_{1-20}$alkyl,
  $C_{6-14}$ aryl$C_{2-20}$alkynyl$C_{1-20}$alkyl, or
  heteroaryl$C_{2-20}$alkynyl$C_{1-20}$alkyl;
$R^4$ is:
  H,
  $C_{1-20}$ alkyl,
  heteroaryl, or
  $C_{6-14}$ aryl;
$R^5$ is:
  H,
  $C_{1-20}$ alkyl,
  heteroaryl, or
  $C_{6-14}$ aryl;
$R^6$ is present when Z equals N and is
  H, or
  $C_{1-20}$ alkyl; or taken together with $R^3$ and the N to which they are attached represent a heteroaryl ring system;
Y is:
  O, or
  S;
Z is:
  N, or
  O;
x is an integer from 1–25, and dashes indicate a double bond is optionally present.

Compounds of the formula

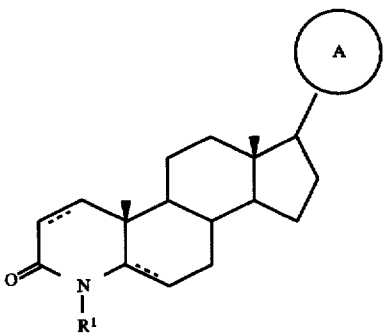

XVIA are likewise representative of preferred embodiment compounds claimed in the instant invention. In a preferred embodiment, $R^1$ may be H or $CH_3$ and A may be as indicated as in Table 3. Particular representative chemical names are also listed in Table 3 adjacent to the respective side chain and specifically reflect whether the 1-position is saturated or unsaturated. Advantageously, $R^1$ is $CH_3$, A is as indicated in Table 3 and the 1 position is saturated.

TABLE 3

| | Side Chain A | Compound(s): |
|---|---|---|
| (1) | $\underset{}{\diagdown}\text{N}-\overset{H}{\underset{}{}}\overset{O}{\underset{||}{C}}-\overset{H}{\underset{}{N}}-CH_3$ | 4-methyl-20-(N'-methyl-ureido)-5α-4-azapregn-1-en-3-one<br>4-Methyl-20-(N'-methyl-uriedo)-5α-4-azapregnane-3-one |
| (2) | $\underset{}{\diagdown}\text{N}-\overset{H}{\underset{}{}}\overset{O}{\underset{||}{C}}-\overset{H}{\underset{}{N}}-\underset{}{\diagup\!\!\!\diagdown}$ | 17-(N'-t-butylureido-methyl)-4-methyl-5α-4-azaandrost-1-en-3-one<br>17-(N'-t-butylureido-methyl)-4-methyl-5α-4-azaandrostan-one |

TABLE 3-continued

| Side Chain A | Compound(s): |
|---|---|
| (3) 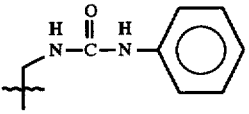 | 4-Methyl-17-(N'-phenyl-ureidomethyl)-5α-4-aza-androst-1-en-3-one<br>4-Methyl-17-(N'-phenyl-ureidomethyl)-5α-4-aza-androstan-3-one |
| (4) 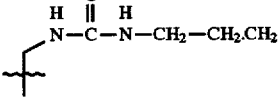 | 4-Methyl-17-(N'-n-propyl-ureidomethyl)-5α-4-aza-androst-1-en-3-one<br>4-Methyl-17-(N'-n-propyl-ureidomethyl)-5α-4-aza-androstan-3-one |
| (5) 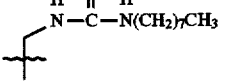 | 4-Methyl-17-(N'-n-octyl-ureidomethyl)-5α-4-aza-androst-1-en-3-one<br>4-Methyl-17-(N'-n-octyl-ureidomethyl)-5α-4-aza-androst-an-3-one |
| (6) 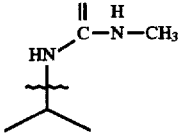 | 4-Methyl-17-(N'-methyl-ureido)-5α-4-azaandrost-1-en-3-one<br>4-Methyl-17-(N'-methyl-ureido)-5α-4-azaandrostan-an-3-one |
| (7) 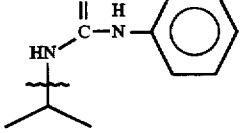 | 4-Methyl-17-(N'-phenyl-ureido)-5α-4-azaandrost-1-en-3-one<br>4-Methyl-17-(N'-phenyl-ureido)-5α-4-aza-androstan-3-one |
| (8) 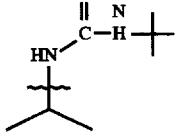 | 17-(N'-t-butylureido)4-methyl-5α-4-azaandrost-1-en-3-one<br>17-(N'-t-butylureido)4-methyl-5α-4-azaandrostan-1-en-3-one |
| (9) 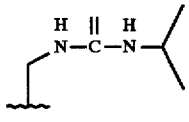 | 17-(N'-t-isopropylureido-methyl)4-methyl-5α-4-aza-androst-1-en-3-one<br>17-(N'-t-isopropylureido-methyl)4-methyl-5α-4-aza-androstan-3-one |
| (10) 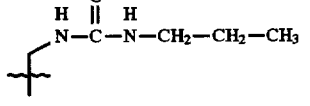 | 4-Methyl-17β(N'-n-propyl-ureidomethyl)5α-4-aza-androstan-3-one<br>4-Methyl-17β(N'-n-propyl-ureidomethyl)5α-4-azaandrost-1-en-3-one |
| (11) 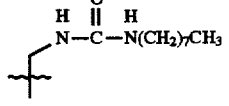 | 4-Methyl-17β(N'-n-octyl-ureidomethyl)5α-4-azaandrostan-3-one |
| (12) 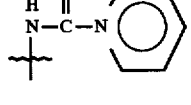 | 4-Methyl-17β-N'-phenyl-ureido)-5α-4-azaandrostan-3-one<br>4-Methyl-17β-(N'-phenyl-ureido)-5α-4-azaandrost-1-en-3-one |
| (13) 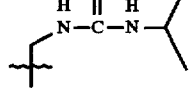 | 17β-(N'-Isopropylureido-methyl)-4-methyl-5α-4-azaandrostan-3-one<br>17β-(N'-Isopropylureido-methyl)-4-methyl-5α-4-azaandrostan-3-one |

TABLE 3-continued

| Side Chain A | Compound(s): |
| --- | --- |
| (14) 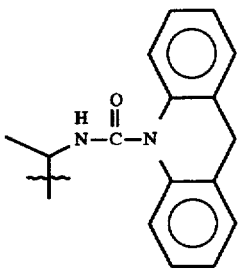 | 20-((Iminodibenz-5-yl)-carbonylaminomethyl)-4-methyl-5α-4-aza-pregan-3-one<br>20-((Iminodibenz-5-yl)-carbonylaminomethyl)-4-methyl-5α-4-aza-pregn-1-en-3-one |
| (15) 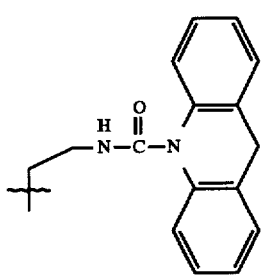 | 17β-((Iminodibenz-5-yl)-carbonylaminomethyl)-4-methyl-5α-4-aza-androstan-3-one<br>17β-((Iminodibenz-5-yl)-carbonylaminomethyl)-4-methyl-5α-4-aza-androstan-3-one |
| (16) 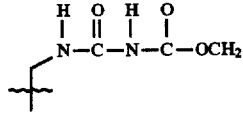 | 17β-(Isobutyloxycarbonyl-aminomethyl)-4-methyl-5α-4-azaandrostan-3-one<br>17β-(Isobutyloxycarbonyl-aminomethyl)-4-methyl-5α-4-azaandrost-1-en-3-one |

The following additional compounds may also be prepared according to the procedures described in the instant specification.

20-(Ethoxycarbonylamino)-4-methyl-5-α-4-azapregnan-3-one,
20-(Benzyloxycarbonylaminomethyl)-5-α-4-azapregnan-3-one,
4-Methyl-17β-(N'-octadecylureidomethyl)-5-α-4-azaandrostan-3-one,
17β-(N'-Benzylureidomethyl)-5-α-4-azaandrostan-3-one,
4-Methyl-17β-(N'-methylureido)-5-α-4-azaandrostan-3-one,
4-Methyl-17β-(Isobutyloxycarbonylamino)-5-α-4-azaandrostan-3-one,
17β-(N'-(2-Ethylphenyl)ureidomethyl)-5-α-4-azaandrostan-3-one,
17β-(N'-Allylureido)-4-methyl-5-α-4-azaandrostan-3-one,
20-(N'-(3-Chlorophenyl)ureido)-5-α-4-azapregnan-3-one,
4-Methyl-20-(N'-phenylureido)-5-α-4-azapregnan-3-one,
20-(N'-p-Tolylureidomethyl)-5-α-4-azapregnan-3-one,
17β-(N'-(2,3,-Dichlorophenyl)ureidomethyl)-4-methyl-5-α-4-azaandrostan-3-one,
17β-(N'-(4-Fluorophenyl)ureido)-5-α-4-azaandrostan-3-one,
20-(N'-(2-Ethoxyphenyl)ureidomethyl)-4-methyl-5-α-4-azapregnan-3-one,
17β-(N'-(3-Methoxyphenylureido)-5-α-4-azaandrostan-3-one,
4-Methyl-17β-(N'-(naphth-2-yl)ureidomethyl)-5-α-4-azaandrostan-3-one,
4-Methyl-17β-(N'-thiazol-2-ylureidomethyl)-5-α-4-azaandrostan-3-one,
4-Methyl-20-(N'-thien-2-ylmethylureido)-5-α-4-azapregnan-3-one.

Synthesis of Testosterone 5α Reductase Inhibitors

Flowsheet XV illustrates the synthesis of intermediate oximes and amines used to produce compounds claimed in the instant invention.

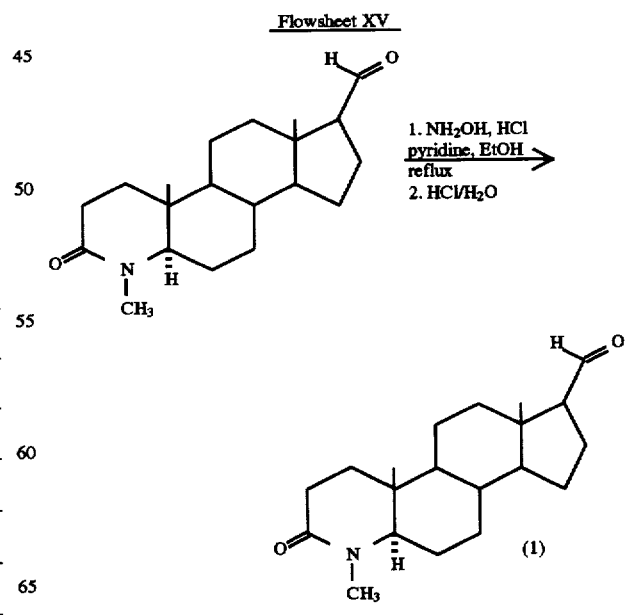

-continued

Flowsheet XV

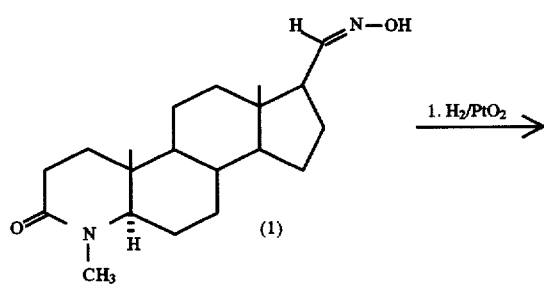
(1)

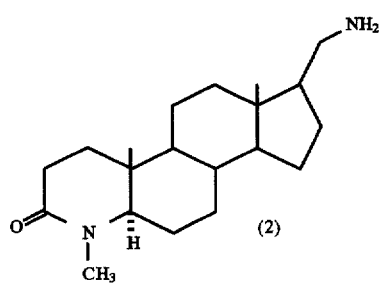
(2)

A stirred mixture of 4-methyl-3-oxo-5α-4-azaandrostan-17 carboxaldehyde, hydroxylamine hydrochloride, anhydrous pyridine, and anhydrous ethanol is refluxed gently under a nitrogen atmosphere for six to seven hours. After cooling, the ice-cooled mixture is diluted, with stirring, with a slight excess of chilled dilute hydrochloric acid. The suspension is then aged for about twenty minutes, filtered, washed with water and dried to give compound 1.

A mixture of the oxime (1), ethanol, glacial acetic acid and water is reduced in the presence of platinum oxide (PtO₂) until chromatographic analysis (TLC) indicates complete reduction to the amine (2). The filtered reaction mixture is concentrated in vacuo; the resultant residue is dissolved in chloroform (CHCl₃) and washed with fresh dilute sodium hydrogen carbonate solution. The chloroform phase is then dried with sodium sulfate (Na₂SO₄). Concentration of the resultant CHCl₃ solution followed by trituration of the residue with hexane/ether will yield 2 as a white solid.

The following amines (3–9) may readily be prepared according to the above process to yield the indicated compounds:

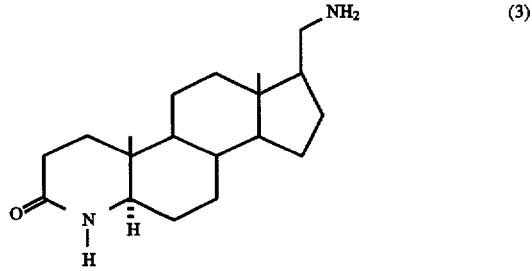
(3)

17-Aminomethyl-5-α-2-4-azaandrostan-3-one;

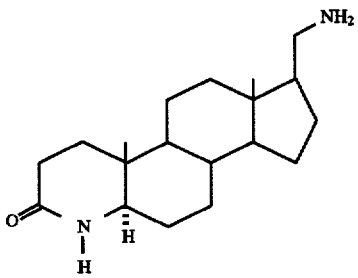
(4)

17-Amino-4-methyl-5-α-2-4-azaandrostan-3-one;

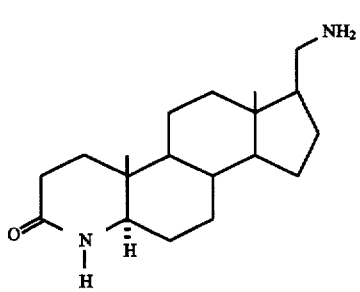
(5)

17-Amino-5-α-2-4-azaandrostan-3-one;

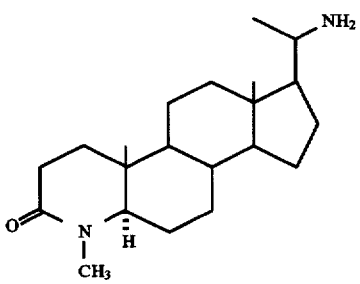
(6)

20-Amino-4-methyl-5-α-4-azapregnan-3-one;

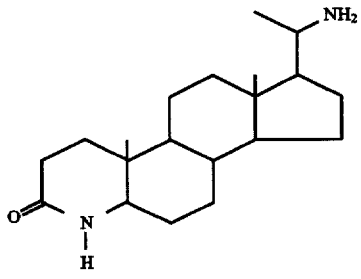
(7)

20-Amino-5-α-4-azapregnan-3-one;

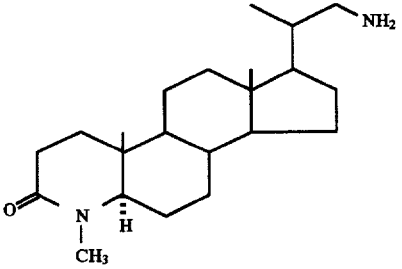
(8)

20-(Aminomethyl)-4-methyl-5-α-4-azapregnan-3-one;

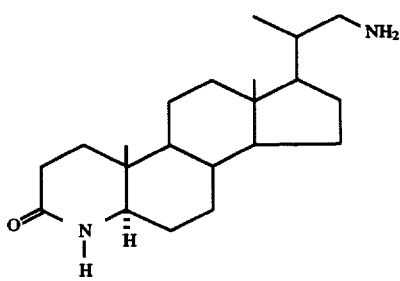

(9)

20-(Aminomethyl)-5-α-4-azapregnan-3-one;

As flowsheet XV indicates, the oximes useful as intermediates may readily be prepared by reacting a 4-azasteroidal aldehyde or ketone with hydroxylamine hydrochloride to form the corresponding oxime. The resultant oximes are subsequently reduced with hydrogen ($H_2$) and platinum oxide ($PtO_2$) or other suitable reducing agent to yield the respective amine. Product ureas or thioureas may be further alkylated with, for example, alkyl halides to give the corresponding $R^2$ alkylated compounds.

Flowsheet XVI illustrates the synthesis of the compound 17-(N'-t-butylureidomethyl)-4-methyl-5α-4-azaandrostan-3-one and is representative of a basic synthesis of compounds claimed in the instant invention in which an amine is reacted with a substituted isocyanate.

FLOWSHEET XVI

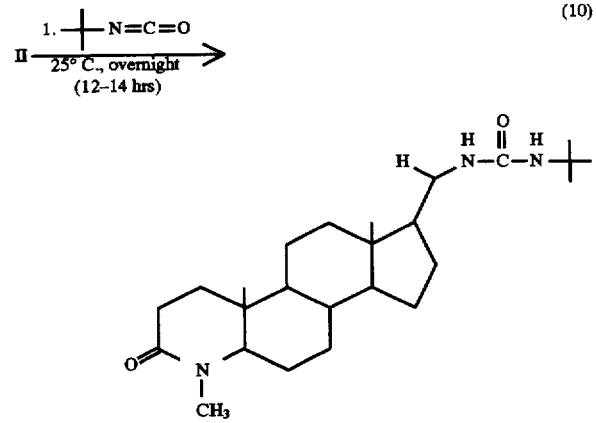

(10)

To a stirred solution of 2 in dry benzene at room temperature (25° C.) is added t-butylisocyanate. After stirring for 12–14 hours, the benzene is removed and purified by flash chromatography (silica gel, EtOAc) to give 10 as a white solid. As flowsheet XVI illustrates, 4-azasteroidal primary or secondary amines described in the instant invention are reacted with the desired substituted isocyanate, such as t-butyl isocyanate, to yield the target ureido derivative.

Representative substituted isocyanates of the formula:

$$R^3—N=C=O$$

wherein $R^3$ equals

H,
$C_{1-20}$ alkyl,
aryl,
heteroaryl,
aryl $C_{1-20}$alkyl,
$C_{3-20}$ cycloalkyl,
$C_{3-20}$ cycloalkyl$C_{1-20}$alkyl,
heteroaryl$C_{1-20}$alkyl,
$C_{2-20}$ alkenyl$C_{1-20}$alkyl,
halo$C_{1-20}$alkyl,
halohydroxyl$C_{1-20}$alkyl,
$C_{1-20}$ alkyloxy$C_{1-20}$alkyl,
$C_{1-20}$ alkylcarbonyl$C_{1-20}$alkyl,
$C_{1-20}$alkyloxycarbonyl$C_{1-20}$alkyl,
aryl$C_{1-20}$alkyloxycarbonyl$C_{1-20}$alkyl,
heteroaryl$C_{1-20}$alkyloxycarbonyl$C_{1-20}$alkyl,
hydroxy$C_{1-20}$alkyl,
aryl$C_{1-20}$alkyloxy$C_{1-20}$alkyl,
heteroaryl$C_{1-20}$alkyloxy$C_{1-20}$alkyl,
arylcarbonylaryl$C_{1-20}$alkyl,
diaryl$C_{1-20}$alkyl,
triaryl$C_{1-20}$alkyl,
$C_{2-20}$ alkenyl,
$C_{2-20}$ alkenyl$C_{1-20}$alkyl,
$C_{2-20}$ alkynyl$C_{1-20}$alkyl,
aryl$C_{2-20}$alkynyl$C_{1-20}$alkyl,
heteroaryl$C_{2-20}$alkynyl$C_{1-20}$alkyl,
$C_{1-20}$ alkylthio$C_{1-20}$alkyl,
$C_{1-20}$ alkylsulfonyl$C_{1-20}$alkyl, or
$C_{1-20}$ alkylsulfonyl$C_{1-20}$alkyl;

The primary or secondary amines disclosed in the instant invention may also be reacted with thioisocyantes of the formula $$R^3—N=C=S$$

to yield compounds claimed in the instant invention. In addition, as flowsheet XVII shows, the described primary or secondary amines disclosed in the invention (such as 2) may be reacted with activated esters or thioesters to yield compounds claimed in the instant invention. $R^3$ is defined as above.

Substituted isocyanates or thioisocynates may readily be prepared by known synthetic methods. For example, phosgene or thiophosgene may be reacted with a suitable primary amine to give a chloroformamide or chloro sulfamide which loses HCl to form the respective substituted isocyanate or thioisocyanate. For reviews of isocyanate and thioisocyanate preparation, see Patai, "The Chemistry of Cyanates and their thio Derivatives," pt 2, Wiley, New York, pp 619–818 and 1003–1221 (1977). In addition, the isocyanates, thioisocyanates, esters or thioesters used to prepare the claimed compounds are commercially available.

FLOWSHEET XVII

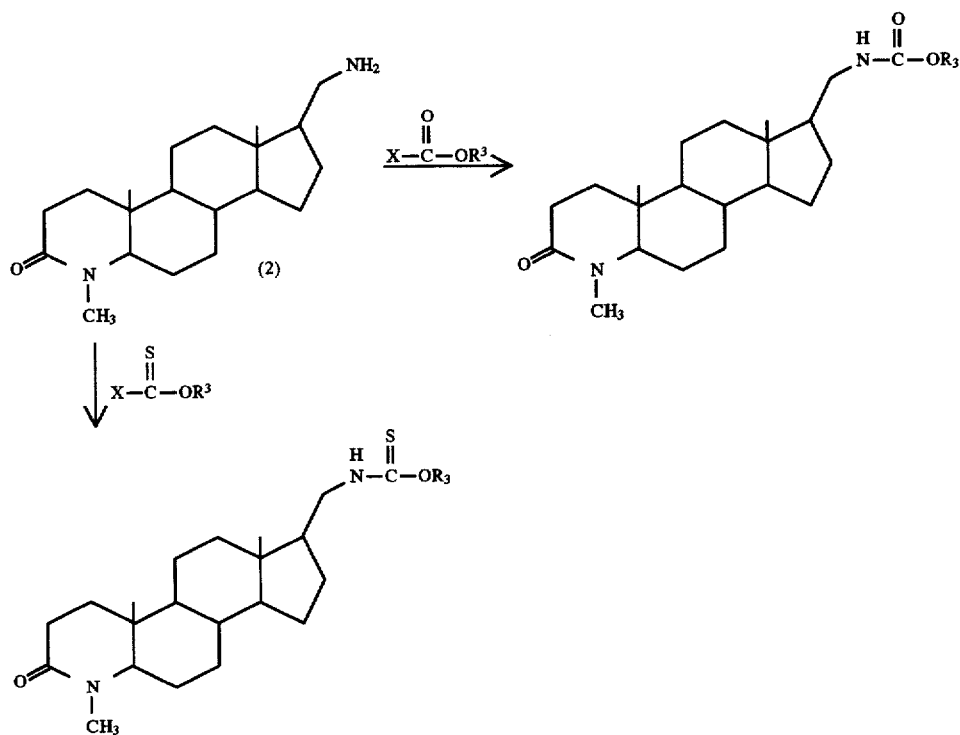

Ureas, thioureas, carbamates, and thiocarbamates claimed in the present invention may readily be obtained by following the basic procedure(s) described in flowsheets XVI and XVII. To further illustrate, compound 2 may be replaced by the amine (4) and reacted with t-butylisocyanate to yield 17-(N'-t-butylureido)-4-methyl-5α-4-azaandrostan-3-one (11) (flowsheet XVIII).

FLOWSHEET XVIII

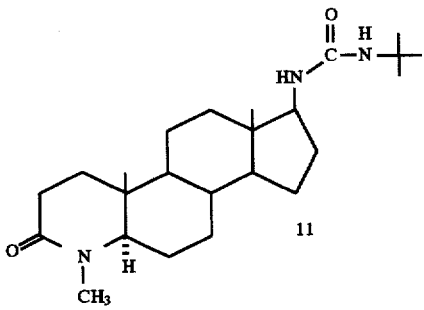

If compound 6 is reacted with methyl isocyante under the conditions described for flowsheet XVI, 4-methyl-20-(N'-methyl-ureido)-5α-4-azapregnan-3-one is obtained (2) (flowsheet XIX)

FLOWSHEET XIX (6) —methyl isocyanate→

-continued
FLOWSHEET XIX

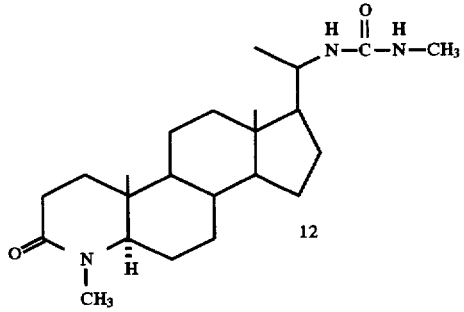

If compound 2 is reacted with phenyl isocyanate under the conditions described in flowsheet 16, 4-methyl-17-(N'-phenyluriedomethyl)-5α-4-azaandrostan-3-one is made (13) (flowsheet XX).

FLOWSHEET XX

2 —phenyl isocyanate→

-continued
FLOWSHEET XX

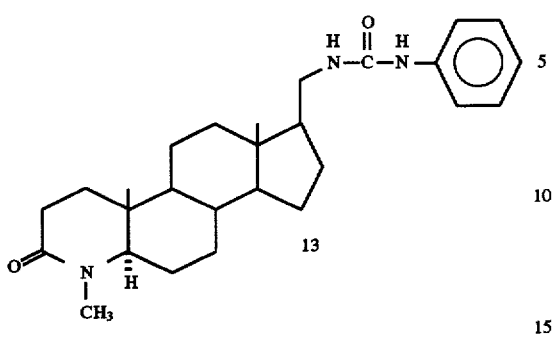

In flowsheet XXII, the identical procedure is followed using a generic 4-azasteroid (XVIII), prepared by known synthetic methods, to produce the oxime (XIX) which is reduced to the amine XX and reacted with a substituted isocyanate, substituted thioisocyante, activated ester or thioester to form XXI.

In addition, dehydrogenation of the 1,2 position may readily be accomplished by known synthetic methodology to produce the claimed 1-en derivatives. See U.S. Pat. No. 5,061,802 and Dolling et al., J. Am. Chem. Soc., 110, 3318–19 (1988).

Flowsheets XXI, XXII and XXIII further illustrate how compounds claimed in the instant invention may be prepared. In flowsheet XXI, the starting 4-azasteroid aldehyde or ketone (XIV), obtained by known synthetic methods, is reacted to form the oxime XV; reduced to the amine XVI and reacted with a substituted isocyanate, substituted thioisocyante, activated ester or thioester to form XVII.

FLOWSHEET XX

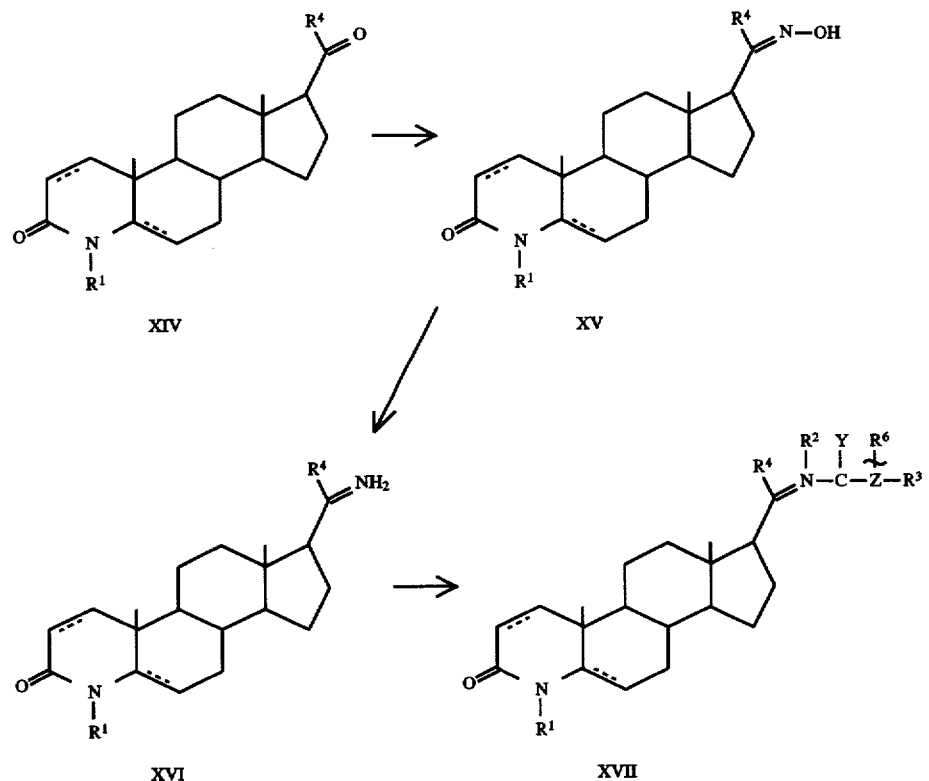

FLOWSHEET XXII
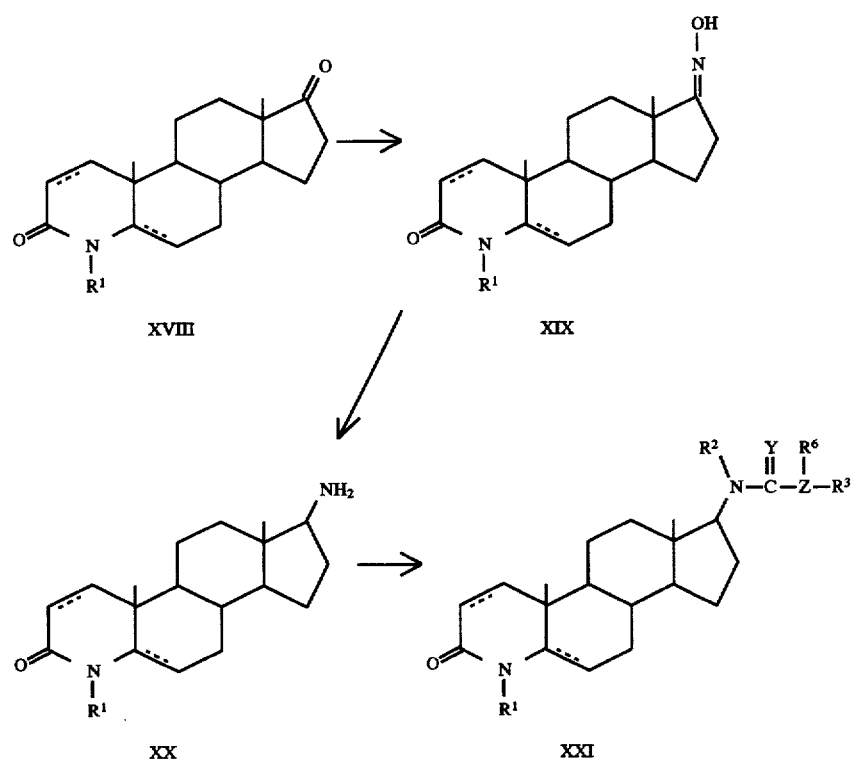
In flowsheet XXIII, the generic 4-azasteroid XXII, also obtained from well known synthetic methodology, is reacted to form the oxime XXIII, which is further reduced to the amine XXIV, and reacted with a substituted isocyante, substituted thioisocyante, activated ester or thioester to form XXV.
FLOWSHEET XXIII
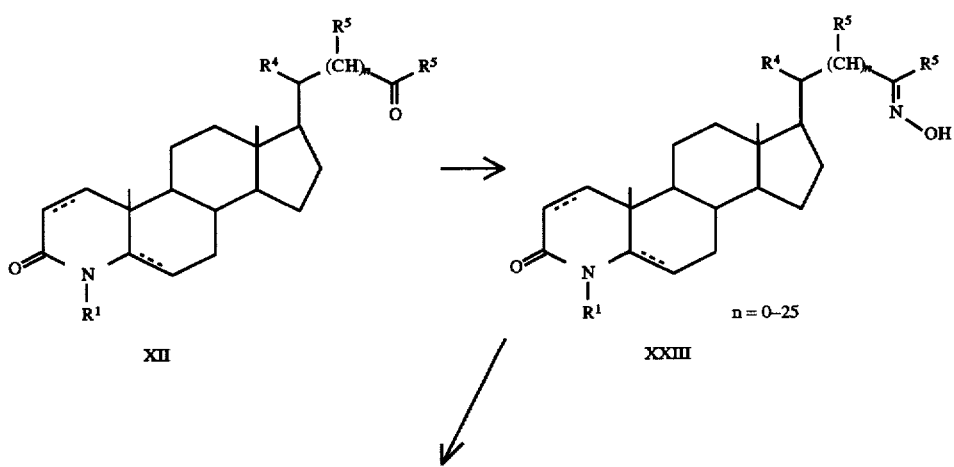

-continued
FLOWSHEET XXIII
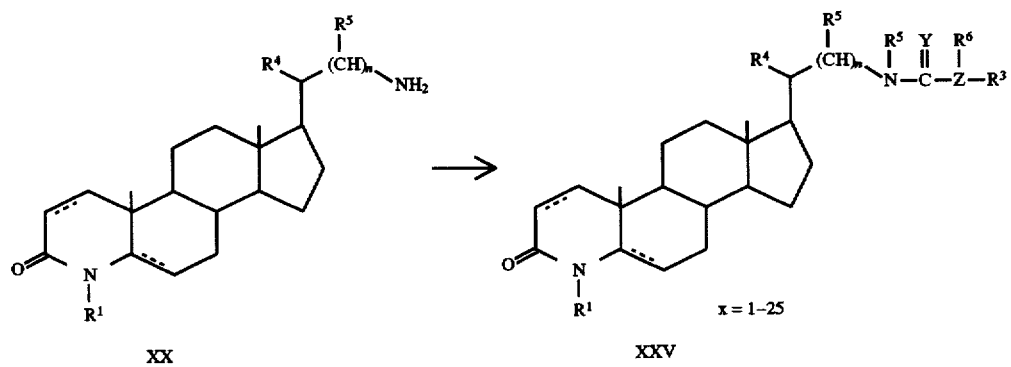
The starting 4-azasteroidal ketones used in the present invention may be prepared according to the basic procedures described in flowsheet XXIV via well known synthetic methodology.
FLOWSHEET XXIV
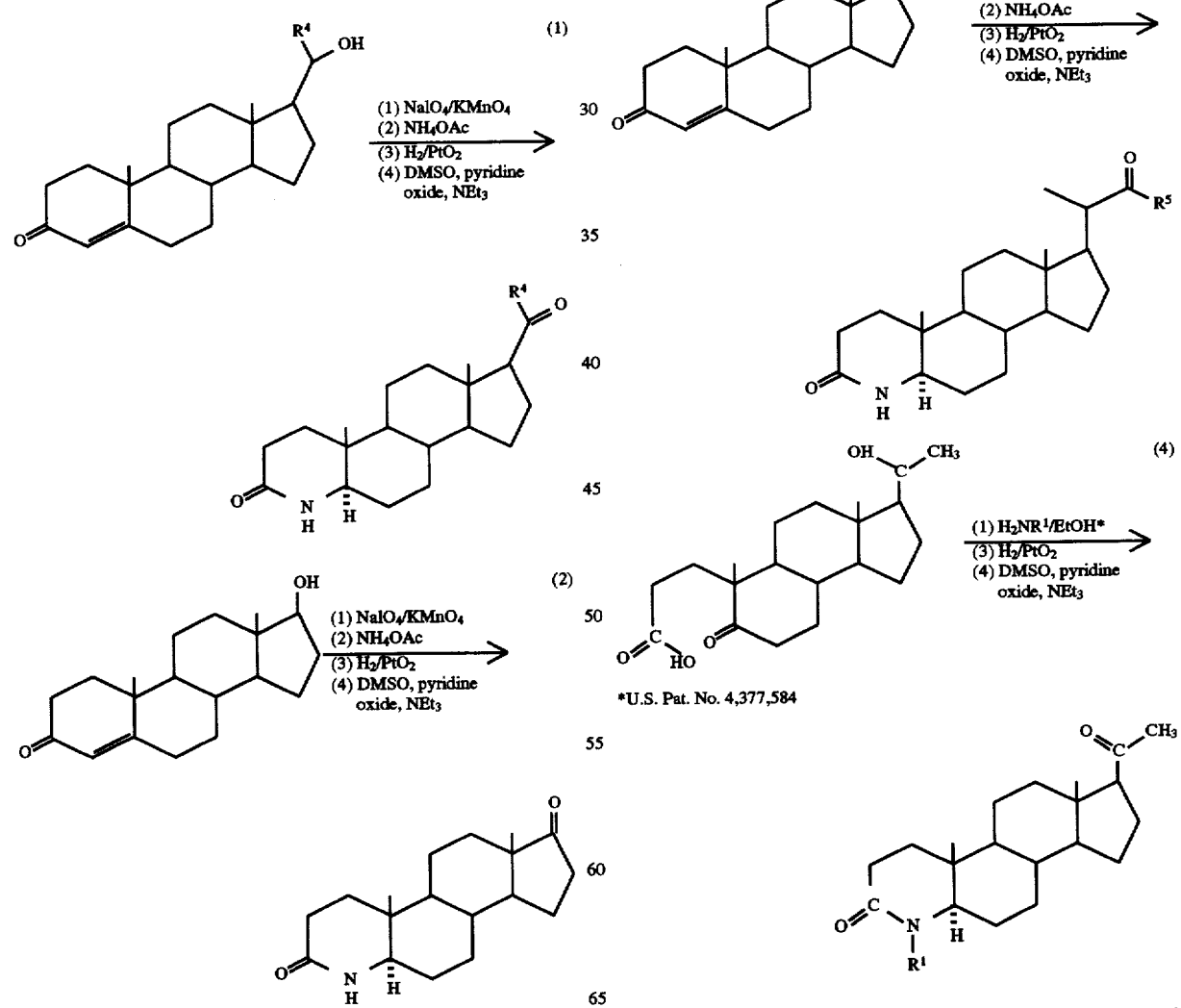
The following examples further describe the synthesis of compounds claimed in the instant invention.

117

Synthesis of Starting 4-Azasteroid Oximes

EXAMPLE 46

46) 4-Methyl-3-oxo-5α-4-azaandrostan-17-carboxaldehyde oxime

A stirred mixture of 4-methyl-3-oxo-5α-4-azaandrostan-17-carboxaldehyde (0.952 g, 3.0 mM), hydroxylamine hydrochloride (1.10 g, 15.8 mM), anhydrous pyridine (6 mL) and anhydrous ethanol (12 mL) was refluxed gently under a nitrogen atmosphere for 6.3 hours. After cooling, the ice-cooled mixture was diluted, with stirring, with a slight excess of chilled dilute hydrochloric acid (ca. 0.3N), the suspension aged for ca. 20 minutes, filtered, washed with water and dried to give (1) 0.855 g. MS M$^+$ calcd for $C_{20}H_{32}N_2O_2$ 332.48, observed m/e 332.

Synthesis of Reactant 4-Azasteroid Amines:

EXAMPLES 47–54

47) 17-Aminomethyl-4-methyl-5α-4-azaandrostan-3-one

A mixture of (46) (0.67 g, 2.0 mM), ethanol (100 mL), glacial acetic acid (8 mL) and water (4 mL) was reduced in a hydrogen atmosphere (40 p.s.i.) at room temperature in the presence of PtO$_2$ until TLC analysis indicated complete reduction. The filtered reaction mixture was concentrated in vacuo, the residue taken up in chloroform, and the chloroform solution washed with fresh dilute sodium hydrogen carbonate solution and dried (Na$_2$SO$_4$). Concentration of the filtered chloroform solution followed by trituration of the residue obtained with hexane containing a small amount of ether yielded (47) as an off-white solid. MS MH$^+$ calcd for $C_{20}H_{34}N_2O$ 318.49, observed m/e 319.

The following amines are representative of those obtained from the corresponding carbonyl compounds utilizing the above procedures:

| 48) | 17-Aminomethyl-5α-4-azaandrostan-3-one. |
| 49) | 17-Amino-4-methyl-5α-4-azaandrostane-3-one. |
| 50) | 17-Amino-5α-4-azaandrostan-3-one. |
| 51) | 20-Amino-4-methyl-5α-4-azapregnan-3-one. |
| 52) | 20-Amino-5α-4-azapregnan-3-one. |
| 53) | 20-(Aminomethyl)-4-methyl-5α-azapregnan-3-one. |
| 54) | 20-(Aminomethyl)-5α-4-azapregnan-3-one. |

Synthesis of Ureido 4-Azasteroid

EXAMPLES 55–58

55) 17-(N'-t-Butylureidomethyl)-4-methyl-5α-4-azaandrostan-3-one

To a stirred solution of (47) (0.064 g, 0.2 mM) in dry benzene (8 mL) at room temperature was added t-butyl isocyanate (0.035 mL, 0.3 mM) dropwise over ca. 0.5 min. After stirring overnight the benzene was removed in vacuo and the residue flash chromatographed (silica gel, ethyl acetate as eluant) to give (55) as a white solid. MS M$^+$ calcd for $C_{25}H_{43}N_3O_2$ 417.64, observed m/e 417.

56) 17-(N'-t-Butylureido)-4-methyl-5α-4-azaandrostan-3-one

When (2) in the above example was replaced by (49), (56) was obtained as a white solid. MS M$^+$ calcd for $C_{24}H_{41}N_3O_2$ 403.61, observed m/e 405.

57) 4-Methyl-20-(N'-methylureido)-5α-4-azapregnan-3-one

When (51) was reacted with methyl isocyanate under the conditions of Example (55), (57) was obtained as a white waxy solid. MS M$^+$ calcd for $C_{23}H_{39}N_3O_2$ 389.58, observed m/e 389.

118

58) 4-Methyl-17-(N'-phenylureidomethyl)-5α-4-azaandrostan-3-one

When (47) was reacted with phenyl isocyanate under the conditions of Example (55), (58) was obtained as a white solid. MS MH$^+$ calcd for $C_{27}H_{39}N_3O_2$ 437.40, observed m/e 438.

Examples 59–66 were prepared according to the basic procedures described above further exemplify the claimed invention.

59) 4-Methyl-17β-(N'-n-propylureidomethyl)-5α-4-azaandro stan-3-one. MS MH$^+$ calc. for $C_{24}H_{41}N_3O_2$ 403.40, observed m/e 404.

60) 4-Methyl-17β-(N'-n-octylureidomethyl)-5α-4- azaandro stan-3-one. MS MH$^+$ calc. for $C_{29}H_{51}N_3O_2$ 473.49, observed m/e 474.

61) 4-Methyl-17β-(N'-phenylureido)-5α-4-azaandro stan-3-one. MS MH$^+$ calc. for $C_{26}H_{37}N_3O_2$ 423.52, observed m/e 424.

62) 17β-(N'-Isopropylureidomethyl)-4-methyl-5α-4- azaandrostan-3-one. MS MH$^+$ calcd for $C_{24}H_{41}N_3O_2$ 403.61 observed m/e 404.

63) 20-(N'-t-Butylureidomethyl)-4-methyl-5α-4-azapregnan-3-one. MS MH$^+$ calcd for $C_{27}H_{47}N_3O_2$ 445.35, observed m/3 446.

64) 20-((Iminodibenz-5-yl)carbonylaminomethyl)-4-methyl-5α-4-azapregnan-3-one. MS MH$_2^{++}$ calcd. for $C_{37}H_{49}N_3O_2$ 567.82, observed m/e 569.

65) 17β-((Iminodibenz-5-yl)carbonylaminomethyl)-4-methyl-5α-4-azaandrostan-3-one. MS MH$_2^{++}$ calcd. for $C_{35}H_{45}N_3O_2$ 539.74, observed m/e 541.

66) 17β-((Isobutyloxycarbonylaminomethyl)-4-methyl-5α-4-azaandrostan-3-one. MS MH$^+$ calcd. for $C_{25}H_{42}N_2O_3$ 418.62, observed m/e 419.

TABLE 4

| | NMR DATA (PPM) | |
|---|---|---|
| Example | Angular Methyls | Miscellaneous |
| 55 | 0.66, 0.86 | 1.33 (—NHCONH—C(CH$_3$)$_3$) |
| 56 | 0.67, 0.88 | 1.33 (—NHCONH—C(CH$_3$)$_3$) |
| 57 | 0.73, 0.88 | 2.92 (-4-NCH$_3$) |
| 58 | 0.64, 0.86 | 2.92 (-4-NCH$_3$) |
| 59 | 0.64, 0.88 | 2.90 (-4-NCH$_3$) |
| 60 | 0.65, 0.88 | 2.92 (-4-NCH$_3$) |
| 61 | 0.63, 0.86 | 2.93 (-4-NCH$_3$) |
| 62 | 0.66, 0.88 | 1.12 (—NH—CH(CH$_3$)$_2$ 1.16 |
| 63 | 0.64, 0.85 | 1.29 (—NHCONH—C(CH$_3$)$_3$) |
| 64 | 0.62, 0.89 | 0.82 —CH(CH$_3$)CH$_2$NHCON— 0.86 |
| 65 | 0.61, 0.88 | 2.92 (-4-NCH$_3$) |
| 66 | 0.66, 0.88 | 2.92 (-4-NCH$_3$) |

The above examples are non-limiting and suitable acylating agents, isocyanates, or thioisocyanates may readily be substituted according to the methods described in the present invention and reacted with a described azasteroidal amine to form the claimed ureas, thioureas, carbamates, and thiocarbamates. The following definitions further clarify the present invention.

EXAMPLES FOR THE CASE WHEN SUBSTITUENT "A" OF GENERAL FORMULA "I" IS AS DEFINED IN GROUP "VII(A)"

Further provided are novel 17β-substituted olefinic and saturated 4-aza-5α-androstan-3-one and related compounds of the general structural formula XVII:

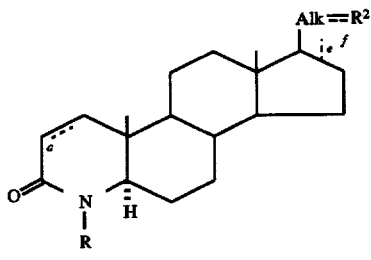

wherein:

Alk is $C_1$–$C_4$ straight or branched chain alkyl or alkenyl;

dashed lines a, e and f each can independently represent a double bond when present, with the proviso that double bonds formed by e and f are not both present concurrently;

R is selected from hydrogen, methyl or ethyl;

$R^2$ is (a) $C_6$–$C_{10}$ aryl, cyano, a 5–6 membered heteroaryl radical, which can contain 1–4 nitrogen atom, one oxygen or sulfur atoms or combinations thereof with 1–2 nitrogen atoms, providing that where $R^2$ is cyano, double bonds e and f are not present;

(b) $COR_1$, where $R_1$ is $C_6$–$C_{10}$ aryl, substituted $C_6$–$C_{10}$ aryl, and heteroaryl;

(c) $CONHR_2$, where $R_2$ is substituted phenyl, heteroaryl, substituted heteroaryl, or $C_7$ to $C_{12}$ cycloalkyl;

(d) $CO_2R_3$, where $R_3$ is $C_1$–$C_{18}$ linear or branded alkyl, $C_6$–$C_{10}$ aryl, substituted $C_6$–$C_{10}$ aryl, or $C_7$–$C_{12}$ cycloalkyl; providing that in (b), (c) or (d), Alk is only alkenyl;

wherein the above aryl or heteroaryl radicals can also be fused with a benzo or another heteroraryl ring and can further be substituted with one or more substitutents; and pharmaceutically acceptable salts and esters thereof.

Further provided is a compound of the general structural formula XVIII:

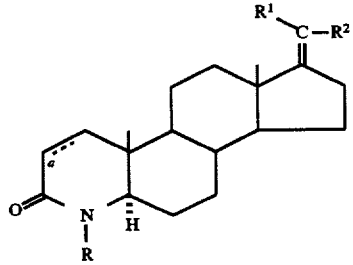

wherein the dashed line a represents a double bond when present, R and $R^1$ are selected from hydrogen, methyl and ethyl; and $R^2$ is as defined above, including both (E) and (Z) forms, and mixtures thereof.

Also provided is a compound of the general structural formula XIX:

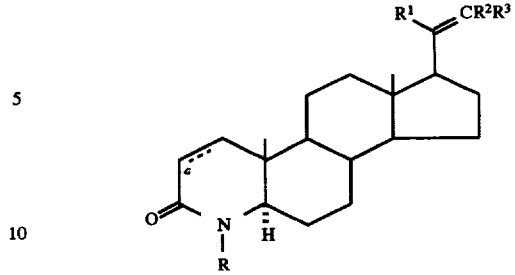

wherein
the dashed line a can represent a double bond when present,
R, $R^1$ and $R^3$ are independently selected from hydrogen, methyl and ethyl, with the proviso that at least one of $R^1$ and $R^3$ is hydrogen,
$R^2$ isis $C_6$–$C_{10}$ aryl or heteroaryl as defined above, and $R^2$ and $R^3$ can be in a E or Z bond configuration, and mixtures thereof.

Additionally, there is provided a compound of the general structural formula XX:

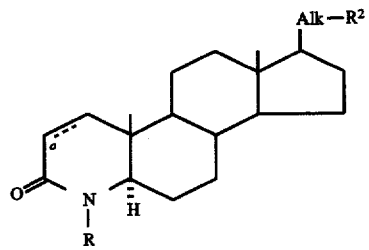

wherein:
Alk is $C_1$–$C_4$ straight or branched chain alkyl; dashed line a can represent a double bond when present;
R is selected from hydrogen, methyl or ethyl; and
$R^2$ is as defined above.

Also specifically provided is a compound of general structural formula XXI:

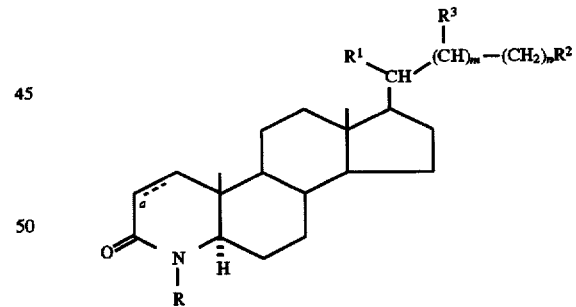

wherein:
the dashed line a can represent a double bond when present, and m is 0–1, n is 0–3; and
R, $R^1$ and $R^3$ are independently selected from hydrogen, methyl and ethyl, with the proviso that at least one of $R^1$ and $R^3$ is hydrogen,
$R^2$ is $C_6$–$C_{10}$ aryl, cyano, or heteroaryl as defined above.

The structures XVII through XXI above encompass starting 5α-reductase inhibitor compounds of this invention.

Where the double bond "e" is present, the compounds are delta-17 olefins and where the double bond "f" is present, the compounds are delta-20 olefins. Note that dashed lines "e" and "f" both cannot be double bonds concurrently.

Dashed line "a" can independently be a double bond and when present, the compound is a delta-1-ene.

$R^2$ is a $C_6–C_{10}$ aryl including phenyl, benzyl, 1- and 2-phenethyl and naphthyl, and also cyano.

Preferred is where $R^2$ aryl is phenyl or cyano.

$R^2$ can also be 5-6 membered heteroaryl radical being fully unsaturated containing 1-4 nitrogen atoms, e.g. pyridyl, pyrryl, imidazolyl, tetrazolyl, pyrazinyl, pyrimidinyl, pyrazolyl, or triazolyl; containing 1-2 oxygen or sulfur atoms, e.g. thienyl, furanyl; or in combination with 1-2 nitrogen atoms, e.g. isothiazolyl, thiazolyl, isoxazolyl, oxazolyl or thiadiazolyl; or fused with a benzo ring, e.g. quinolyl, isoquinolyl, benzothienyl, isobenzofuryl, indolyl, carbazolyl; or fused with another heteroaryl ring, e.g. purinyl, and the like.

Preferred examples are 2-, 3-, and 4-pyridyl, 2-thienyl; 2-pyrazinyl, 2-, 4-, and 5-thiazolyl.

The $R^2$ aryl or heteroaryl ring can be unsubstituted or substituted with one or more of the following substituents providing the substitution leads to a chemically inert, but biologically active 5α reductase inhibitor.

The $R^2$ ring substituents include:

$C_1–C_8$ straight or branched alkyl; e.g. methyl, ethyl, propyl, isopropyl, n-butyl, sec-butyl, isobutyl, t-butyl, n-pentyl, n-hexyl, iso-hexyl, n-butyl, n-octyl, iso-octyl, t-octyl, and the like; $C_2–C_8$ straight or branched alkenyl, e.g. ethenyl, 1-propenyl, 2-propenyl, 1-butenyl, 2-butenyl, 3-butenyl, 1-pentenyl, 1-hexenyl, 1-heptenyl, 1-octenyl, 2-octenyl, and the like;

$C_3–C_8$ cycloalkyl e.g., cyclopropyl, cyclobutyl, cyclopentyl, cyclohexyl, 1-methyl-cyclobutyl, cyclopentyl, cyclohexyl, 1-methyl-cyclohexyl, 2-methylcyclohexyl, 2-ethylcyclohexyl, and the like;

$C_2–C_8$ alkynyl e.g., 1-ethynyl; 1-propynyl, 2-propynyl, 2-butynyl, 2-pentynyl, 1-hexynyl, 1-heptynyl, 1-octynyl;

$CONR^4R^5$ where $R^4$ and $R^5$ independently are H, $C_1–C_8$ alkyl, as defined above, $C_3–C_8$ cycloalkyl as defined above, $C_1–C_4$ perhaloalkyl e.g., trifluoromethyl, perfluoromethyl, trichloromethyl, preferably perfluoroalkyl; phenyl, or substituted phenyl, as described below;

$COR^4$, where $R^4$ is defined above, including acetyl, isobutylcarbonyl, benzoyl and the like;

$S(O)_n R^4$, where n is 0-2 and $R^4$ is defined above, including methylsulfinyl, methylsulfonyl, phenylsulfonyl, 4-chlorophenylsulfinyl and the like;

$OCOR^4$, where $R^4$ is defined above, including acetoxy, propionyloxy, benzoyloxy, 4-chlorobenzoyloxy and the like.

$SO_2NR^4R^5$ where $R^4$ and $R^5$ are described above, including sulfonamido, N-methylsulfonamido, N-phenylsulfonamido, N,N-dimethylsulfonamido and the like;

$NR^4(CO)R^5$, wherein $R^4$ and $R^5$ are defined above, including; acetylamino, benzoylamino, N-methylbenzoylamino and the like;

$NR^4(CO)NHR^5$, wherein $R^4$ and $R^5$ are described above, including; ureido, N-methylureido, N-methyl-$N^1$-phenylureido and the like;

$NHSO_2R^4$, $R^4$ being defined above, including methylsulfonylamino, phenylsulfonylamino and the like;

$OR^4$, where $R^4$ is defined above, including methoxy, phenoxy, 4-chlorophenoxy and the like.

$NR^4R^5$, wherein $R^4$ and $R^5$ are described above, including amino, methylamino, dimethylamino, anilino and the like;

Cyano, nitro, halo, including: fluoro, chloro, bromo and iodo;

Perhalo $C_1–C_4$ alkyl, including: trifluoromethyl, perfluoroethyl, trichloromethyl and the like.

$CO_2R^4$, wherein $R^4$ is defined above, including $CO_2CH_3$, $CO_2Ph$, $CO_2$-(1-adamantyl) and the like; phenyl and substituted phenyl of the formula:

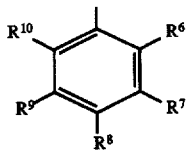

wherein the radicals $R^6–R^{10}$ each can represent one or more of the substituents defined above, including; hydrogen, 4-chlorophenyl, 4-fluorophenyl, 4-methoxyphenyl, 4-phenoxy and the like.

Representative compounds of the present invention include the following:

(17E)-17-[phenyl)methylene]-4-methyl-4-aza-5α-androstan-3-one, (17E)-17-[(4-chlorophenyl)methylene]-4-methyl-4-aza-5α-androstan-3-one, (17E)-17-[(3-chlorophenyl)methylene]-4-methyl-4-aza-5α-androstan-3-one, (17E)-17-[(2-chlorophenyl)methylene]-4-methyl-4-aza-5α-androstan-3-one, (17E)-17-[(4-ethoxycarbonylphenyl)methyl-ene]-4-methyl-4-aza-5α-androstan-one, (17E)-17-[(4-carboxyphenyl)methylene]-4-methyl-4-aza-5α-androstan-3-one, (17E)-17-[4-[[(1,1-dimethylethyl)amino)-carbonyl]phenyl]-methylene]-4-methyl-4-aza-5α-androstan-3-one, (17E)-17-[(3,4,5-trimethoxyphenyl)methyl-ene]-4-aza-5α-androstan-3-one, (17E)-17-[(2-methoxyphenyl)methylene]-4-methyl-4-aza-5α-androstan-3-one, (17E)-17-[(4-methylsulfonylphenyl)methyl-ene]-4-methyl-4-aza-5α-androstan-3-one, (17E)-17-[(4-biphenyl)methylene]-4-aza-5α-androstan-3-one, (17E)-17-[(4-nitrophenyl)methylene]-4-methyl-4-aza-5α-androstan-3-one, (17E)-17-[(4-aminophenyl)methylene]-4-aza-5α-androstan-3-one, (17E)-17-[(4-acetylaminophenyl)methylene]-4-methyl-4-aza-5α-androstan-3-one, (17E)-17-(4-pivaloylaminophenyl)methylene)-4-methyl-4-aza-5α-androstan-3-one, (17E)-17-[(4-phenoxyphenyl)methylene]-4-aza-5α-androstan-3-one, (17E)-17-[(2-imidazolyl)methylene]-4-methyl-4-aza-5α-androst-1-en-3-one, (17E)-17-[(2-thiazolyl)methylene]-4-aza-5α-androst-1-en-3-one, (17E)-17-[(2-pyrazinyl)methylene]-4-methyl-4-aza-5α-androstan-3-one, (17E)-20-phenyl-4-methyl-4-aza-5α-pregn-17-en-3-one, (17E)-20-[(4-chloro)phenyl]-4-aza-5α-pregn-17-en-3-one, (20E)-4-methyl-21-[(4-methoxy)phenyl]-4-aza-5α-pregn-20-en-3-one, (20E)-4-methyl-21-phenyl-4-aza-5α-pregn-20-en-3-one, (20E)-4-methyl-21-[(4-methyl)phenyl]-4-aza-5α-pregn-20-en-3-one, (20E)-4-methyl-21-[(4-chloro)phenyl]-4-aza-5α-pregn-20-en-3-one, (20E)-4-methyl-21-(4-pyridyl)-4-aza-5α-pregn-20-en-3-one, (20E)-4-methyl-21-[(3-chloro)phenyl]-4-aza-5α-pregn-20-en-3-one, (20E)-4-methyl-21-[(2-chloro)phenyl]-4-aza-5α-pregn-20-en-3-one,
(20E)-4-methyl-21-(2-pyridyl)-4-aza-5α-pregn-20-en-3-one,
(20E)-4-methyl-21-(2-thienyl)-4-aza-5α-pregn-20-en-3-one,
(20E)-21-[(4-methoxy)phenyl]-4-aza-5α-pregn-20-en-3-one,
(20E)-4-methyl-21-(3-thienyl)-4-aza-5α-pregn-20-en-3-one,
(20E)-4-methyl-21-(2-furanyl)-4-aza-5α-pregn-20-en-3-one,
(20E)-4-methyl-21-[(2-fluoro)phenyl]-4-aza-5α-pregn-20-en-3-one,
(20E)-21-(4-pyridyl)-4-aza-5α-pregn-1,20-dien-3-one,
(20E)-21-(4-pyridyl)-4-aza-5α-pregn-20-en-3-one,
(20E)-21-[(4-methoxy)phenyl]-4-aza-5α-pregn-1,20-dien-3-one,
(20E)-21-(2-furanyl)-4-aza-5α-pregn-1,20-dien-3-one,
(20E)-21-(2-pyridyl)-4-aza-5α-pregn-1,20-dien-3-one,
(20E)-21-(3-pyridyl)-4-aza-5α-pregn-1,20-dien-3-one
(20E)-21-[(4-ethoxycarbonyl)-phenyl]-4-aza-5α-pregn-1,20-dien-3-one,
(20E)-21-4-[N-phenyl]benzamido-4-aza-5α-pregn-1,20-dien-3-one,
(20E)-21-(2-pyridyl)-4-aza-5α-pregn-20-en-3-one,
(20E)-21-(3-pyridyl)-4-aza-5α-pregn-20-en-3-one,
(20E)-21-(2-thienyl)-4-aza-5α-pregn-20-en-3-one,
(20E)-4,20-dimethyl-21-phenyl-4-aza-5α-pregn-20-en-3-one,
(20E)-4,20-dimethyl-21-(4-chlorophenyl)-4-aza-5α-pregn-20-en-3-one,
(20E)-4,20-dimethyl-21-(2-thienyl)-4-aza-5α-pregn-20-en-3-one,
(20E)-4,20-dimethyl-21-(2-pyridyl)-4-aza-5α-pregn-20-en-3-one,
(20E)-20-methyl-21-(4-pyridyl)-4-aza-5α-pregna-1,20-dien-3-one,
(20E)-4,20-dimethyl-21-(4-pyridyl)-4-aza-5α-pregn-20-en-3-one,
(20E)-20-methyl-21-(2-furyl)-4-aza-5α-pregna-1,20-dien-3-one,
(20E)-20-methyl-21-(2-pyridyl)-4-aza-5α-pregna-1,20-dien-3-one,
(20E)-20-ethyl-21-phenyl-4-aza-5α-pregna-1,20-dien-3-one,
(20E)-20-ethyl-21-(2-pyridyl)-4-aza-5α-pregna-1,20-dien-3-one,
20(E,Z)-4,21-dimethyl-21-phenyl-4-aza-5α-pregn-20-en-3-one,
20(E,Z)-21-methyl-21-(4-chlorophenyl)-4-aza-5α-pregn-20-en-3-one,
20(E,Z)-4,21-dimethyl-21-(2-pyridyl)-4-aza-5α-pregn-1,20-dien-3-one,
17β-[(4-chlorophenyl)methyl]-4-methyl-4-aza-5α-androstan-3-one,
17β-[(phenyl)methyl]-4-aza-5α-androstan-3-one,
17β-[(2-pyridyl)methyl]-4-methyl-4-aza-5α-androst-1-en-3-one,
17β-[(2-thienyl)methyl]-4-aza-5α-androst-1-en-3-one,
20-phenyl-4-methyl-4-aza-5α-pregnan-3-one,
20-(4-chloro)phenyl-4-aza-5α-pregnan-3-one,
20-(2-pyridyl)-4-methyl-4-aza-5α-pregn-1-en-3-one,
20-(2-thienyl)-4-aza-5α-pregn-1-en-3-one,
21-phenyl-4-aza-5α-pregnan-3-one,
21-(2-pyridyl)-4-methyl-4-aza-5α-pregnan-3-one,
21-[(4-methoxy)phenyl]-4-methyl-4-aza-5α-pregnan-3-one,
21-(2-thienyl)-4-methyl-4-aza-5α-pregnan-3-one,
21-[(4-chlorophenyl]-4-aza-5α-pregn-1-en-3-one,
4-methyl-17β-[3-(phenyl)propyl]-4-aza-5α-androstan-3-one,
17β-[3-(2-pyridyl)propyl]-4-aza-5α-androst-1-en-3-one,
17β-[3-(4-chlorophenyl)propyl]-4-aza-5α-androstan-3-one,
4-methyl-17β-[2-(thienyl)propyl]-4-aza-5α-androst-1-en-3-one,
4-methyl-17β-[4-(phenyl)butyl]-4-aza-5α-androstan-3-one,
17β-[3-(2-pyridyl)butyl]-4-aza-5α-androst-1-en-3-one,
17β-[3-(4-chlorophenyl)butyl]-4-aza-5α-androstan-3-one,
4-methyl-17β-[2-(thienyl)butyl]-4-aza-5α-androst-1-en-3-one,
20-ethyl-21-(2-pyridyl)-4-aza-5α-pregnan-3-one,
20-ethyl-21-phenyl-4-aza-5α-pregnan-3-one,
20-ethyl-21-(2-methoxyphenyl)-4-aza-5α-pregnan-3-one,
4,21-dimethyl-21-(2-pyridyl)-4-aza-5α-pregnan-3-one,
4,21-dimethyl-21-[(4-benzoylamino)phenyl]-4-aza-5α-pregnan-3-one,
4,21-dimethyl-21-(2-thiazolyl)-4-aza-5α-preganan-3-one,
21-phenyl-4-aza-5α-pregnan-3-one,
21-(2-pyridyl)-4-aza-5α-pregnan-3-one,
21-(2-thienyl)-4-aza-5α-pregnan-3-one,
21-(2-methoxyphenyl)-4-aza-5α-pregn-1-en-3-one,
21-(3-pyridyl)-4-aza-5α-pregn-1-en-3-one,
21-(2-thiazolyl)-4-aza-5α)-pregn-1-en-3-one,
4-methyl-21-[4-(methylsulfonyl)phenyl]-4-aza-5α-pregn-1-en-3-one,
4-ethyl-21-(4-fluorophenyl)-4-aza-5α-pregn-1-en-3-one,
4-methyl-21-(4-carboxyphenyl)-4-aza-5α-pregn-1,20-dien-3-one,
4-ethyl-21-(4-carbamoylphenyl)-4-aza-5α-pregn-1,20-dien-3-one,
20-(3-pyridyl)-4-aza-5α-pregna-1,17-dien-3-one,
4-methyl-20-(2-pyrazinyl)-4-aza-5α-pregn-1,17-dien-3-one,
20-ethyl-4-methyl-21-phenyl-4-aza-5α-pregn-20-en-3-one,
4,20-dimethyl-21-(2,6-dimethoxyphenyl)-4-aza-5α-pregna-1,20-dien-3-one,
20-ethyl-4-methyl-21-(s-triazinyl)-4-aza-5α-pregna-1,20-dien-3-one,
4-methyl-20-(phenylmethyl)-4-aza-5α-pregnan-3-one,
20-ethyl-4-methyl-21-(2-pyridyl)-4-aza-5α-pregnan-3-one,
20-(2-thiazolyl)-4-aza-5α-pregnan-3-one,
20-ethyl-21-(3-pyridyl)-4-aza-5α-pregnan-3-one,
20-(4-methylsulfonylphenyl)-4-aza-5α-pregn-1-en-3-one,
20-ethyl-21-(4-methoxyphenyl)-4-aza-5α-pregn-1-en-3-one,
4-methyl-20-(3,4-dimethoxyphenyl)-4-aza-5α-pregn-1-en-3-one,
20-ethyl-4-methyl-21-(2-pyrimidinyl)-4-aza-5α-pregn-1-en-3-one,
4,21-dimethyl-21-(4-pyridyl)-4-aza-5α-pregna-1,20-dien-3-one,
21-methyl-21-(2-thienyl)-4-aza-5α-pregn-1-en-3-one,
21-methyl-21-(1-imidazolyl)-4-aza-5α-pregnan-3-one,
4,21-dimethyl-21-(4-carbamoylphenyl)-4-aza-5α-pregn-1-en-3-one,
4-methyl-21-(4-methoxyphenyl)-4-aza-5α-pregnan-3-one,
4-methyl-17-((4-chloro)phenylmethyl)-4-aza-5α-androstan-3-one,
N-(1,1-dimethylethyl)-4-(4-methyl-3-oxo-4-aza-5α-pregn-21-yl)benzamide,
4-methyl-21-(3-pyridyl)-4-aza-5α-pregn-20-en-3-one,
21-(2-pyrazinyl)-4-methyl-4-aza-5α-preg-20-en-3-one,
4-methyl-21-(2-pyrazinyl)-4-aza-5α-pregnan-3-one,
4-methyl-24-nor-4-aza-5α-cholane-23-nitrile, 4-methyl-3-oxo-4-aza-5α-pregnane-21-carbon-nitrile,
24-nor-4-aza-5α-chol-1-ene-23-nitrile,
24-nor-4-aza-5α-cholane-23-nitrile,
4-methyl-24-nor-4-aza-5α-chol-1-ene-23-nitrile,
3-oxo-4-aza-5α-pregn-1-ene-21-carbonitrile,
3-oxo-4-aza-5α-pregnane-21-carbonitrile,
4-methyl-3-oxo-4-aza-5α-pregnane-21-nitrile,
4-methyl-3-oxo-4-aza-5α-cholane-24-nitrile,
3-oxo-4-aza-5α-chol-1-ene-24-nitrile,
4-methyl-3-oxo-21-nor-4-aza-5α-cholane-24-nitrile,
3-oxo-21-nor-4-aza-5α-cholane-24-nitrile,
and also including the corresponding compounds wherein the 4-hydrogen substituent is replaced by a methyl or an ethyl radical, and/or a delta-one double bond is present.

Also included within the scope of this invention are pharmaceutically acceptable salts, i.e. hydrochloride, hydrobromide, acetate, pamoate, and the like, of the compound where a basic heteroaryl radical is present, e.g. 4-pyridyl, which can be used as the dosage form for modifying solubility or hydrolysis characteristics or for use as sustained release or prodrug formulations.

The novel compounds of formula XVII of the present invention are prepared by methods starting with appropriate steroid 17-carboxaldehydes and ketones of the following formulae:

FLOWSHEET XXV

Carboxaldehydes

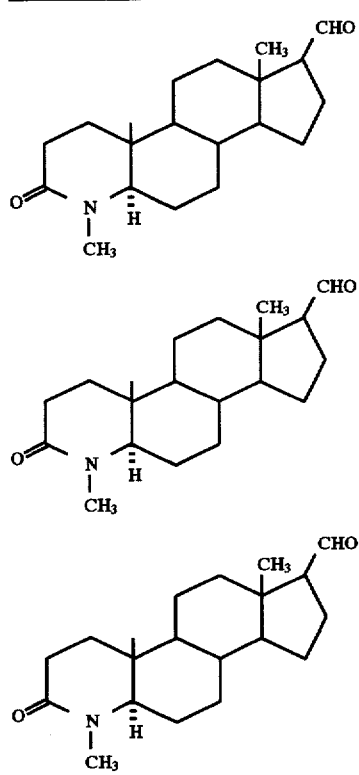

Carboxaldehyde A can be prepared from 17-(2-pyridylthio) carboxylate-4-methyl-5α-androstan-3-one by reaction with Raney nickel to the 17β-carbinol followed by oxidation to the aldehyde with pyridinium chlorochromate. (See J. Med. Chem. 1986, Vol. 29, No. 11, p. 2299, Compound 10bg) The starting 2-pyridylthio ester can be made by hydrolyzing the 17-COOMe derivative to the acid and reacting the acid with 2,2'-dipyridyl disulfide in an inert solvent, e.g. chlorobenzene.

Carboxaldehyde B can be prepared from the lithum aluminum hydride reduction of 17β-(N-methyl-N-methoxy)-carboxamide-5α-4-aza-androst-1-en-3-one (see U.S. Pat. No. 5,061,801 for its preparation, as also described in the following section "Preparation of Starting Materials".

Carboxaldehyde C can be concurrently prepared from the same procedure, as a secondary reaction product, as described above for Carboxaldehyde B (See preparation in "Preparation of Starting Materials").

Note that the corresponding 4-ethyl analogs are also available through conventional alkylation of the 4-NH derivative via, e.g. ethyl iodide, sodium hydride in dry DMF at room temperature.

As seen in Flowsheet XXV, the carboxaldehydes A,B, or C can be reacted with the phosphonate reagent as shown, where $R^2$ is defined above, $R^3$ is hydrogen or methyl and $R_a$ is a conventional ester alkyl radical, e.g. methyl or ethyl, to yield the corresponding D-20 olefins.

In general, the procedure for reacting the carboxaldehyde with the phosphonate ylid reagent is analogous to the conditions as described for the Wadsworth-Emmons modification of the Wittig reaction (See Chem. Rev. 74, p. 87, 1974 and JACS Vol. 83, p. 1733, 1961). The phosphonate ylid is reacted under anhydrous conditions with the carboxaldehyde in about a 1:1 molar ratio together with a hydride reagent, e.g. sodium hydride, also in a 1:1 molar ratio with the phosphonate reagent in a dry solvent, e.g. dimethylformamide, dimethylacetamide, tetrahydrofuran, dioxane, DMSO and the like, under anhydrous conditions, usually a nitrogen atmosphere, at a temperature of about 50°–100° C., preferably 80°–85° C. for about 1–4 hours. Workup is conventional, e.g. organic liquid extraction followed by drying, evaporating off solvent, followed by chromatography, distillation or recrystallization of the crude material to yield the desired product, being a species of Formula XVII.

The starting phosphonates can be prepared by known procedures in the art. One procedure that can be used is the modified Arbuzov reaction in which a chloromethyl-aryl or heteroaryl compound, e.g. thienylmethyl chloride, is reacted with an alkyl phosphite, e.g triethyl phosphite, at 125°–175° C. for 1–10 hours. Conventional workup yields the desired starting phosphonate, e.g. diethyl 2-thienylmethylphosphonate.

FLOWSHEET XXVI
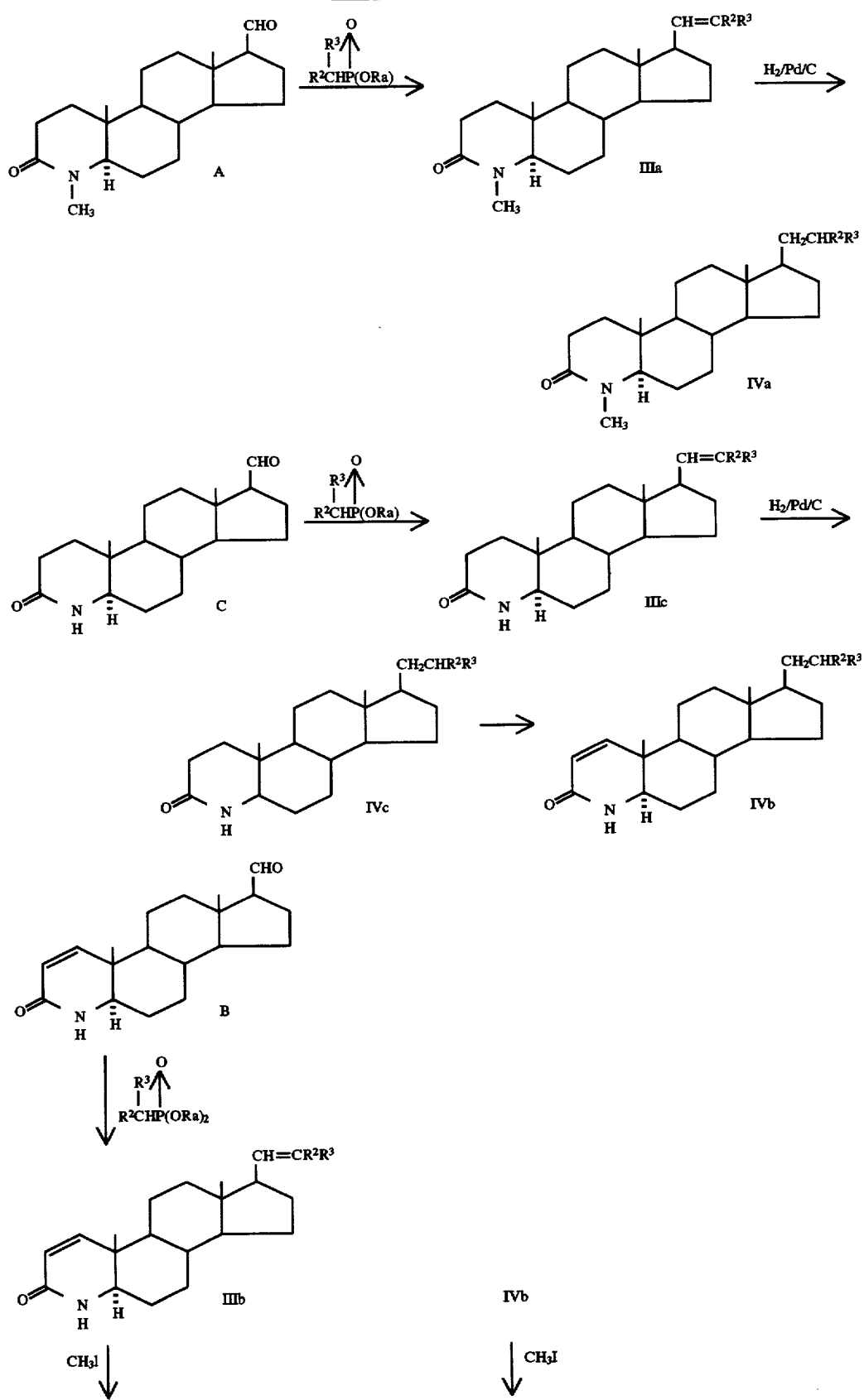

-continued
FLOWSHEET XXVI

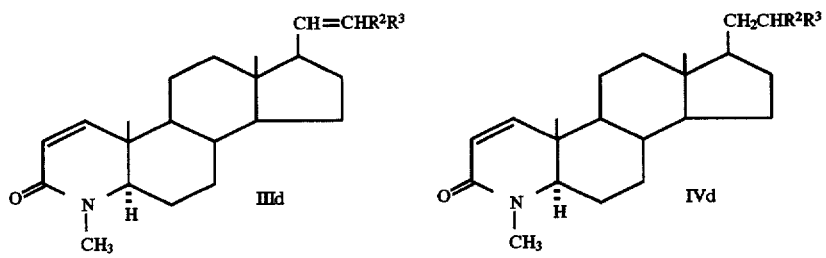

Alternately, the chloromethyl heteroaryl compound, e.g. 4-chloromethylpyridine, can be reacted with diethylphosphite and sodium hydride at about 80°–100° C. for several hours to also produce the desired phosphonate starting materials.

Representative syntheses are given in the "Preparation of Starting Materials" section and representative examples of phosphonate starting materials are:
diethyl 2-thienylmethylphosphonate,
diethyl 4-pyridylmethylphosphonate,
diethyl 4-methylbenzylphosphonate,
diethyl benzylphosphonate,
diethyl 4-chlorobenzylphosphonate,
diethyl 3-chlorobenzylphosphonate,
diethyl 2-chlorobenzylphosphonate,
diethyl 2-pyridylmethylphosphonate,
diethyl 3-thienylmethylphosphonate,
diethyl 2-furanylmethylphosphonate,
diethyl 2-fluorobenzylphosphonate,
diethyl 3-pyridylmethylphosphonate,
diethyl 4-ethoxycarbonylbenzylphosphonate,
diethyl 4-(phenylaminocarbonyl)benzyl phosphonate.

As outlined on Flowsheet XXVI, the $\Delta^{20}$ olefins IIIa and IIIc can be reduced with e.g. 10% palladium on carbon in a suitable solvent, e.g. methanol, ethanol, dioxane, acetic acid and the like, at room temperature under 1–50 psig hydrogen atmosphere to form IVa and IVc. Compound IVc can be further reacted to form the $\Delta^1$ olefin IVb by the procedure of Dolling et al using dichlorodicyanobenzoquinone, see JACS (1988), Vol 110, pp 3318–3319. Alternatively IVb can be formed by reacting IVc with benzeneselenic anhydride in refluxing chlorobenzene. The 4-nitrogen in IIIb and IVb can be alkylated with methyl iodide in the presence of sodium hydride in e.g. dry dimethylformamide solvent to give IIId and IVd.

Note that the 4-methyl group in the appropriate compounds in Flowsheet A can be replaced with a 4-ethyl group to prepare the corresponding 4-ethyl analogs of IIIa, IVa, IIId, and IVd.

The aldehydes A, B and C can be reacted with diethyl a-methyl-benzylphosphonate (U.S. Pat. No. 4,515,883) in the Wadsworth-Emmons modification of the Wittig reaction and the corresponding products hydrogenated, alkylated on the 4-nitrogen and dehydrogenated as outlined in Flowsheet XXVI to give compounds IIIa–d and IVa–d with $R^2$=phenyl and $R^3$=methyl.

Methyl ketone D (see Flowsheet XXVII, below) and its preparation is described in J. Med. Chem., 1984, Vol. 27, p. 1690–1701, by G. H. Rasmusson et. al (see Compound 4d.) These compounds can be prepared by reacting the S-(2-pyridyl)androstan-3-one-17β-thio-carboxylate with methylmagnesium chloride under appropriate Grignard conditions.

Methyl Ketone E can be prepared by reacting N-methoxy-N-methyl-3-oxo-4-aza-5α-androst-1-ene-17β-carboxamide (4) with excess methylmagnesium bromide in tetrahydrofuran.

The above 17-methylketones D and E can be reacted with the phosphonate ylids described above in an analogous manner to achieve the 20-methyl pregn-20-en-3-one compounds IIIi and IIIj as illustrated in the following Flowchart XXVII.

FLOWSHEET XXVII

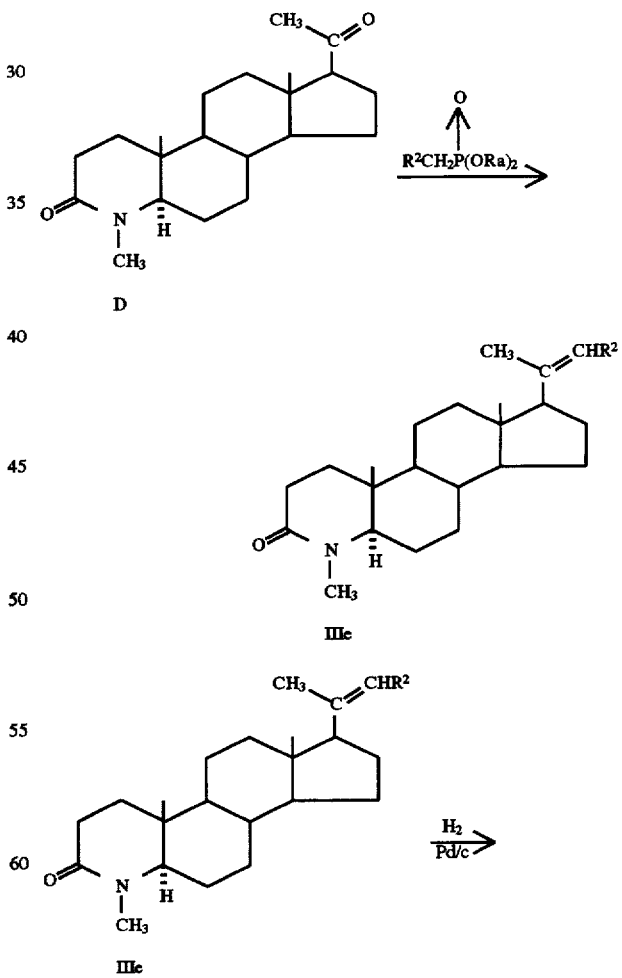

131
-continued
FLOWSHEET XXVII
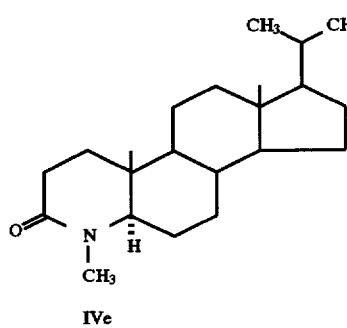
IVe
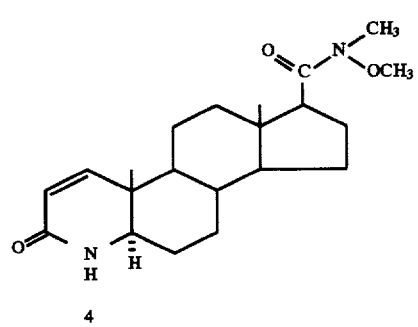
4
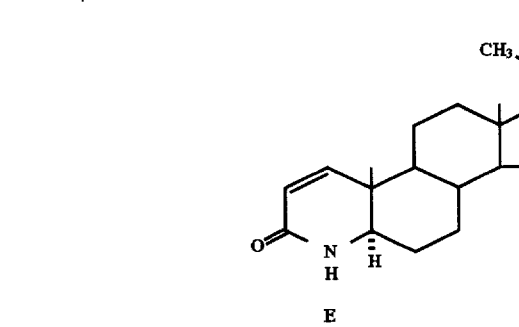
E
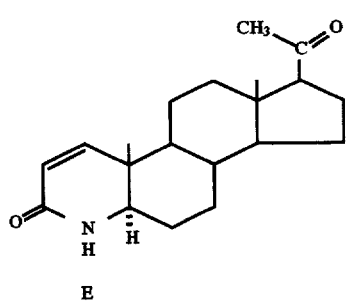
E
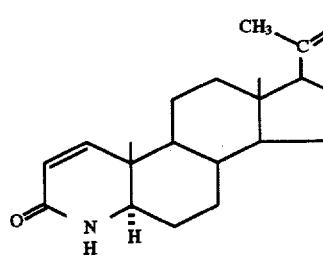
IIIf
132
-continued
FLOWSHEET XXVII
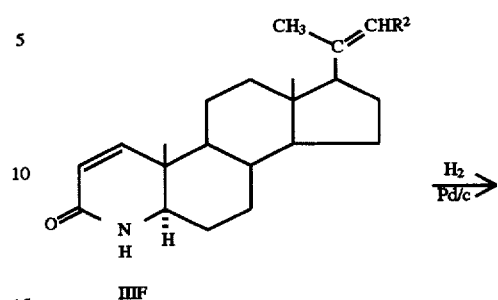
IIIF
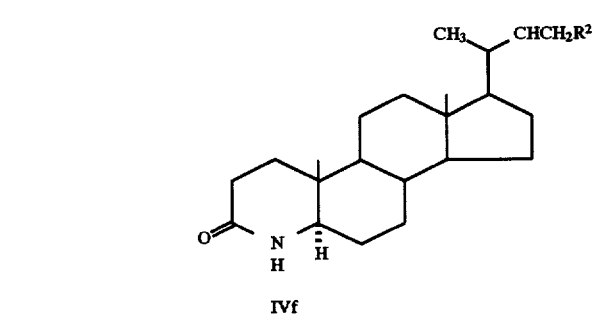
IVf
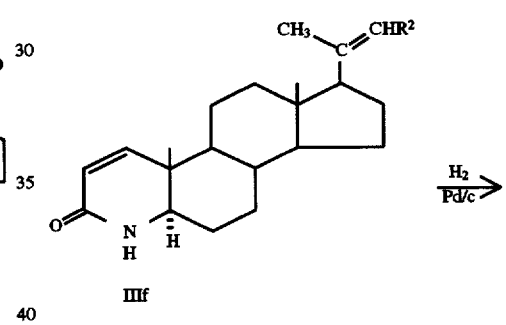
IIIf
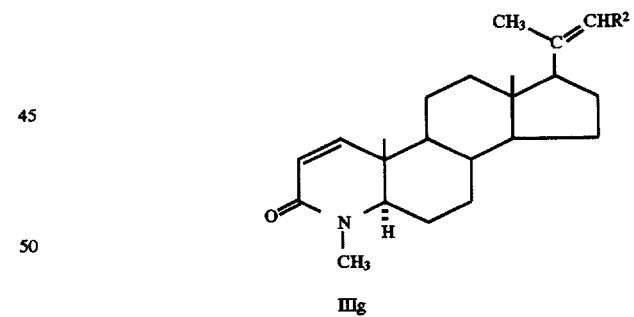
IIIg
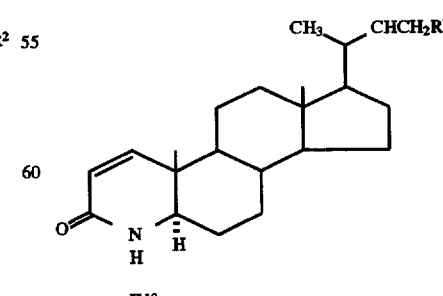
IVf

FLOWSHEET XXVII -continued

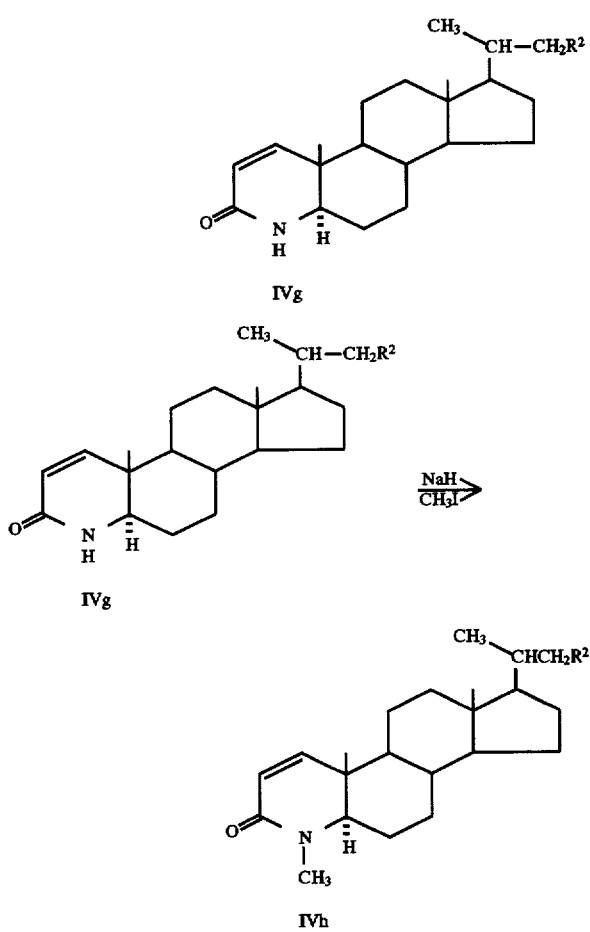

As outlined in Flowsheet XXVII, IIIe and IIIf can be hydrogenated as above to give IVe and IVf. Compound IVf can be dehydrogenated as described above to the Δ'-compound IVg. Compounds IIIf and IVg can be methylated on the 4-nitrogen to give IIIg and IVh.

Also the amide 4 can be reacted with ethylmagnesium bromide to give ethyl ketone versions of D and E. Using the reactions outlined in Flowsheet B compounds IIIe–g and IVe–h with the 20-methyl replaced by a 20-ethyl can be prepared.

Ketone F (Flowsheet XXVIII) can be prepared by conventional techniques, including oxidation of the corresponding 17-β-ol with e.g. Jones reagent, and is known in the art in J. Med. Chem. 1984, Vol. 27, p. 1690–1701 by G. H. Rasmusson et. al., (see Compound 22 on p. 1693).

Ketones G and H can be prepared by Jones reagent oxidation of the corresponding 17β-alcohols described in the above reference. Using the reactions shown in Flowsheet XXVI, the ketones F, G, and H are converted into compounds IIIh–k and IVh–l as seen in Flowsheet C.

As indicated in Example 67, below, the 17β-3-phenylpropyl compound can be prepared from aldehyde A by a phosphonate olefination with diethyl benzoylmethylphosphonate followed by reduction of the ketone and double-bond by hydrogenation with palladium on carbon catalyst in ethanol. Using the reaction sequences outlined in Flowsheet XXVI, the 4-H, Δ'-4-H, and 4—CH₃—Δ' analogs can be prepared starting from aldehydes A or B.

FLOWSHEET XXVIII

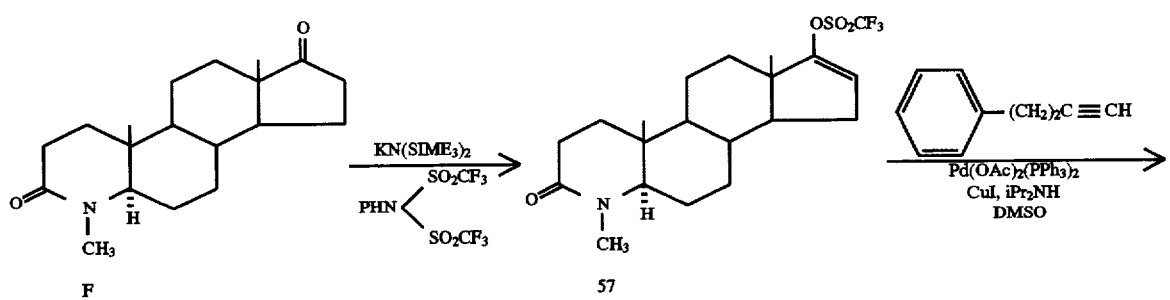

-continued
FLOWSHEET XXVIII

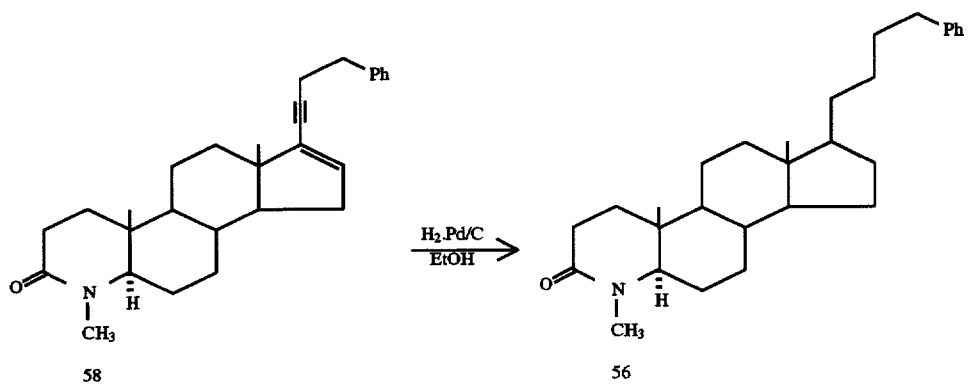

As shown in Flowsheet XXVIII, the 17β-3-phenylbutyl compound 56 can be prepared from the ketone F by conversion of the latter to the $\Delta^{16}$-17-trifluoromethylsulfonate 57 with potassium hexamethyldisilazide and N-phenyltrifluoromethanesulfinimide (Tetrahedron Lett. 24, 979 (1983)). Palladium-catalyzed coupling of 57 with 4-phenyl-1-butyne (Synthesis, 320 (1986)) can give the enyne 58 which can be hydrogenated to the desired 17β-3-phenylbutyl compound 56.

FLOWSHEET XXIX

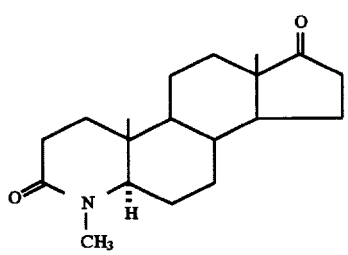
F

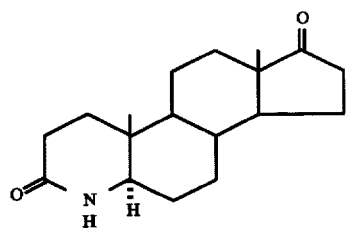
G

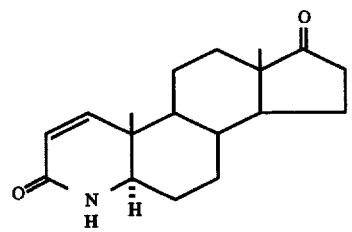
H

-continued
FLOWSHEET XXIX

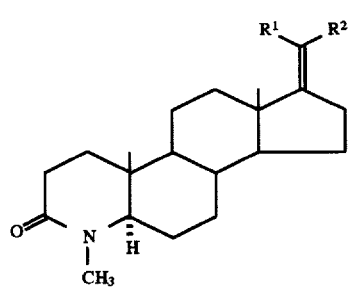
IIa

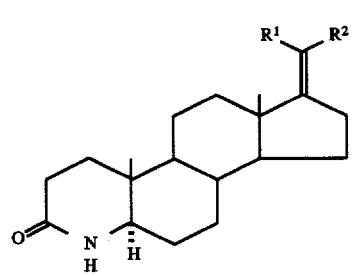
IIb

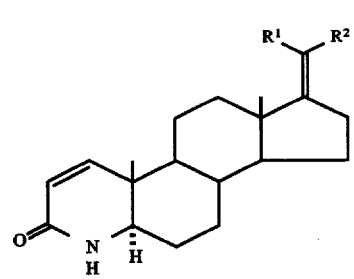
IIc

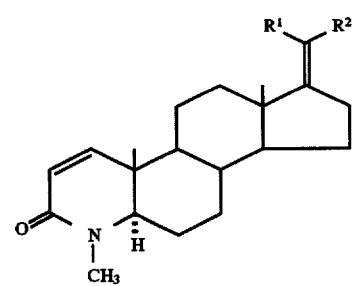
IId

FLOWSHEET XXIX -continued
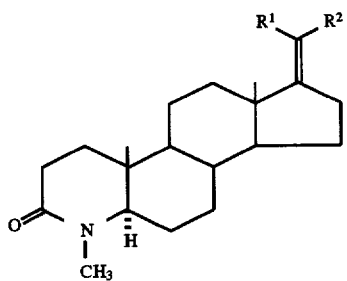 IVi
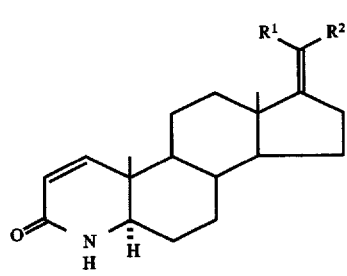 IVj
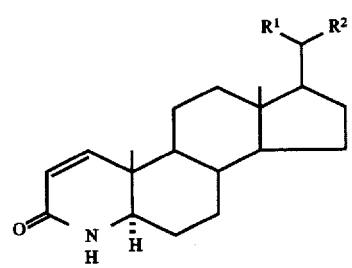 IVk
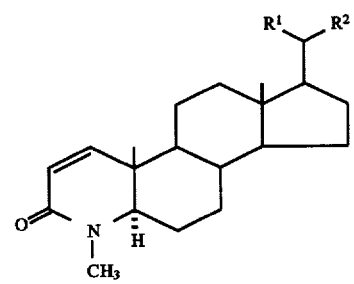 IVl
FLOWSHEET XXX
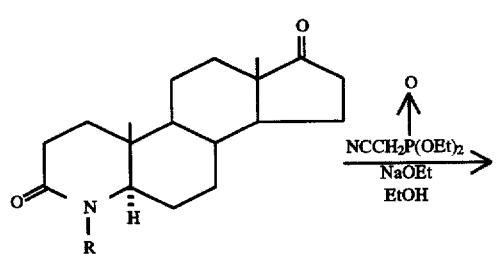
F (R = CH₃)
G (R = H)
FLOWSHEET XXX -continued
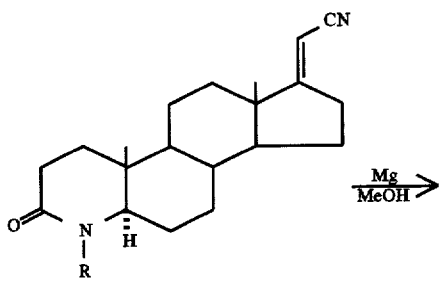
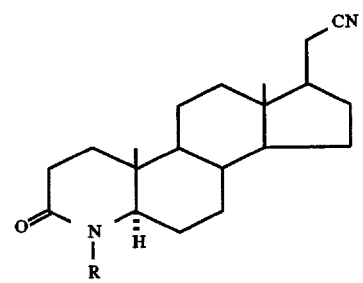
59 (R = CH₃)
60 (R = H)
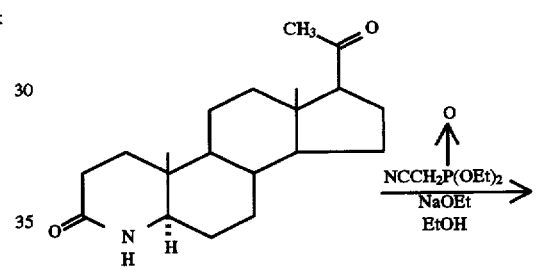
E
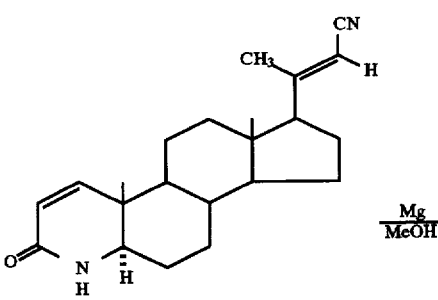
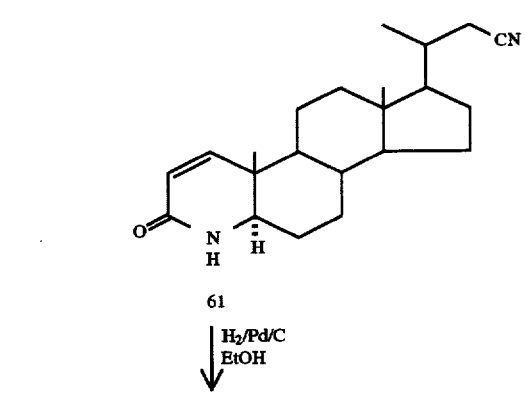
61
$\downarrow$ H₂/Pd/C
    EtOH -continued
FLOWSHEET XXX

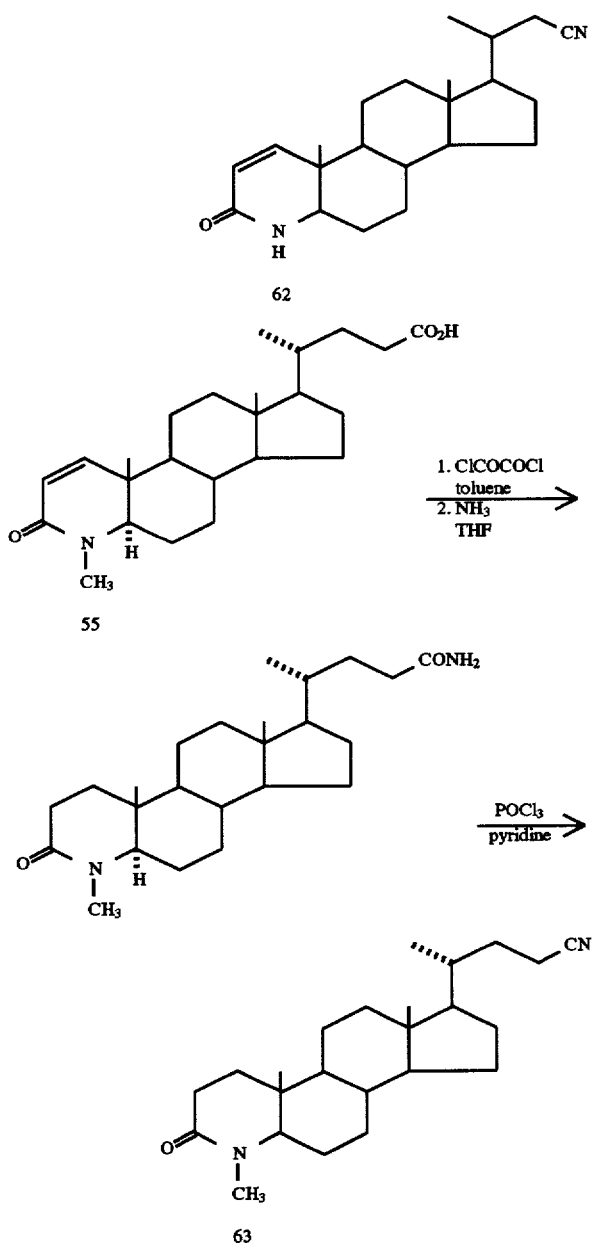

As described in Example 68, the nitriles 54 (R=CH₃, H) were prepared from a "second order" Beckmann rearrangement on the homologous carboxylic acids (55, R=CH₃, H) with sodium nitrite in trifluoroacetic acid and trifluoroacetic arthydride. (J. of Lipid Research 29 1387 (1988)).

The synthesis of other nitriles is outlined in Flowsheet XXX. The pregnane-21-carbonitriles 59 and 60 can be prepared from the ketones F and G by phosphonate olefination with diethyl cyanomethylphosphonate (Steroids 27, 431 (1976)) followed by reduction with magnesium in methanol (J. Org. Chem. 40, 127 (1975)). By the same reaction sequence the ketone E can be converted into the Δ1–4-H-24-nor cholane-23-nitrile 61 and its reduction product 62. The 24-cholane-24-carbonitrile 63 can be prepared from the cholanic acid 55 by conversion to the primary amide with oxalyl chloride and ammonia followed by dehydration with POCl₃ in pyridine (J. Med. Chem. 29, 2298 (1986)). Similarly the 17-butyric (64, n=1) and valeric (n=2) acids, prepared by palladium-catalyzed coupling of 57 with 3-butynoic and 4-pentynoic acids followed by hydrogenation, can converted into the nitriles 66 (n=1,2).

EXAMPLE 67

Synthesis of 4,7β-Dimethyl-4-aza-Androst-5-en-3-one-17β-ol, t-butyldimethylsilyl ether, (68)

To a solution of the product of Example 8 (17β-(t-butyldimethylsilyloxy)-7β-methyl-5-oxo-A-nor-3,5-secoandrostan-3-oic acid), 840 mg in 5 ml ethylene glycol was added 1.5 g sodium acetate and 737 mg. methylamine hydrochloride. After stirring the reaction mixture 4 hours at 180° C., the mixture was cooled, diluted with water, extracted with ethyl acetate, dried and concentrated to afford crude title compound 68. Proton NMR confirmed the assigned structure.

EXAMPLE 68

Synthesis of 4,7β-Dimethyl-4-aza-Androst-5-en-3-one-17β-ol, (69)

To a solution of 700 mg of 68 from Example 67, in 20 ml of acetonitrile at 0° C. was added 500 microliters. aqueous HF. After stirring the reaction mixture for one hour, the HF was neutralized with aqueous sodium carbonate, diluted with water, acetonitrile removed under vacuum, and the residue extracted with ethyl acetate. The organic layer was dried, concentrated to give crude title compound 69 which was further purified by preparative chromatography on silica gel using 3:1 chloroform/acetone.

EXAMPLE 69

Synthesis of 4,7β-dimethyl-4-aza-androstan-3-one-17β-ol, (70)

To a solution of 69 from Example 68, being 350 mg in 10 ml acetic acid was added 100 mg platinum dioxide and the resulting mixture was evacuated and flushed with hydrogen. The reaction was shaken overnight at room temperature under 40 Psig hydrogen pressure. The solution was filtered concentrated. The residue was worked up with ethyl acetate, the organic layer was then concentrated under vacuum, diluted with ethyl acetate, washed with aqueous NaHCO₃, brine, dried, concentrated to yield the title compound 12. Mass Spec: 320 (M+1).

EXAMPLE 70

Synthesis of 17β-pivaloyloxy-4,7β-Dimethyl-4-Aza-Androstan-3-one, (71)

To a solution of 70 from Example 69, being 60.2 mg in 4 ml methylene chloride and 200 ml pyridine was added 15 mg DMAP (4-dimethylaminopyridine) followed by 68.66 mg pivaloyl chloride, i.e., trimethyl acetyl chloride. After stirring for 24 hours, the reaction mixture was diluted with ethyl acetate, washed with water, then aqueous sodium carbonate and brine. The organic layer was dried, concentrated to a residue, which was purified by preparative chromatography on silica gel using 3:1 chloroform/acetone as eluant to yield pure title compound 71 Proton NMR confirmed the assigned structure.

EXAMPLE 71

Synthesis of 17β-(t-Butylaminocarbonyloxy)-4,7-dimethyl-5α-4-aza-Androstan-3-one, (72)

To a solution of 70, 51 mg in 4 ml methylene chloride was added DBU (200 microliters) followed by 63.65 mg.

t-butylisocyanate. After stirring the mixture for 48 hours at room temperature, the reaction mixture was diluted with ethyl acetate, the organic layer washed with water, brine, dried and concentrated to a residue which was purified by preparative chromatography over silica gel using 3:1 CHCl₃/acetone to yield pure title compound 72.

EXAMPLE 72

Synthesis of 17β-Methoxycarbonyl-4-methyl-4-aza-androst-5-en-3,7-dione

Following the analogous oxidation procedure of Example 3, 17β-methoxycarbonyl-4-methyl-4-aza-5α-androsten-3-one, known in the art, was analogously treated to yield the title compound.

The following Table 5 lists the unique proton NMR values (400 MHz in CDCl₃) for several of the above-described compounds. The data are reported as: s=singlet, d=doublet, m=multiplet, J=coupling constant. The absorption values are given del (d) units and are illustrated for the C-18, C-19 and methyl protons and protons associated with unique portions of the molecule.

The numbering of the steroid is given by the following structure:

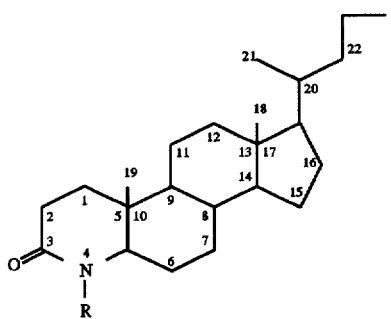

NMR DATA

| Compound No | C-18 CH₃ | C-19 CH₃ | Others |
|---|---|---|---|
| 68 | 0.72 | 1.02 | 7Me, 3H, d, 1.04 J=6.5 |
|  |  |  | 6H, 1H, d, 4.78 J=3 |
| 69 | 0.78 | 1.02 | 7Me, 3H, d, 1.06, J=6.5 |
|  |  |  | 6H, 1H, d, 4.79, J=3 |
| 70 | 0.74 | 0.86 | 7Me, 3H, d, 1.02, J=6.5 |
|  |  |  | 5H, 1H, dd, 3.10 J=4.5 J=13.5 |
| 71 | 0.82 | 0.85 | N—CH₃, 3H, S, 2.90 |
|  |  |  | C-5, 1H, dd, 3.01 J=12.6 J=3.7 |
|  |  |  | C-7β-CH₃, 3H, d, 1.02, J=6.5 |
| 72 | 0.76 | 0.82 | N—CH₃, 3H, S, 2.89 |
|  |  |  | C-5, 1H, dd, 3.01 J=3.7 J=12.6 |
|  |  |  | C-7β-CH₃, 3H; d, 1.02, J=6.5 |

Also included in the invention are the following compounds:
4, 7β-dimethyl-4-aza-5α-androstan-3, 17-dione,
17-oximino-4, 7β-dimethyl-4-aza-5a-androstan-3-one.

The compounds can be by analogous procedures described in J. Med. Chem. 29, 2998–2315 (1986) by Rasmusson et al. for preparing the 17-one. The 17-one can then be reacted with ammonia, substituted amines, hydrazine, substituted hydrazine, by known analogous procedures to produce the above described compounds.

Also included with the scope of this invention are 4-N-X analogs where X is OH, NH₂ or SCH₃. The 4-N—OH and 4-N—NH₂ derivatives can be made with incorporating hydroxylamine or hydrazine, respectively, in place of methylamine in the seco acid ring A closure for the starting androstanes as described in J. Med. Chem. 29, 2998–2315 (1986) by Rasmusson et al. Further, reaction of the anion of the saturated 4-N—H androstanes, wherein the anion is generated from the N—NH precursor by sodium hydride, and methylsulfenyl chloride can produce the corresponding 4-N—S—CH₃ derivatives. Thus, substituent on the 4-N position also includes OH, NH₂ and S—CH₃.

The present invention also discloses novel 17β-ester, amide, and ketone derivatives of 4-aza-5β-androstan-3-one compounds of the general structural formula XXII:

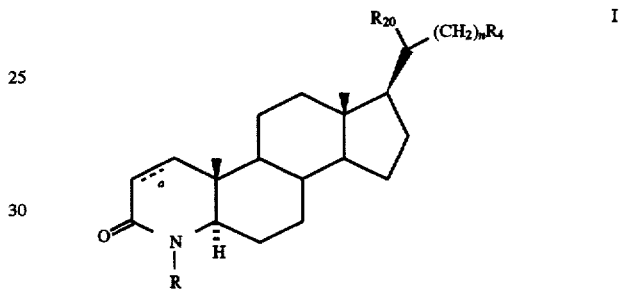

wherein:
dashed line a can represent a double bond when present;
R is selected from hydrogen, methyl, ethyl, hydroxyl, amino, and methylthio;
R₂₀ is selected from hydrogen or methyl;
n is an integer from 0 to 10;
R₄ is selected from:

(a) COR₁, where R₁ is C₆–C₁₀ aryl, substituted C₆–C₁₀ aryl, and heteroaryl;

(b) CONHR₂, where R₂ is substituted phenyl, heteroaryl, substituted heteroaryl, or C₇ to C₁₂ cycloalkyl;

(c) CO₂R₃, where R₃ is C₆–C₁₀ aryl, substituted C₆–C₁₀ aryl, or C₇–C₁₂ cycloalkyl;

where the above aryl and heteraryl radicals can also be fused with a benzo or another heteroaryl ring and can further be substituted with one or more substituents; and pharmaceutically acceptable salts and esters thereof.

Dashed line "a" can independently be a double bond and when present, the compound is a delta-1-ene.

R₁ and R₃ can be a a C₆–C₁₀ aryl including phenyl, benzyl, 1- and 2-phenethyl and naphthyl.

R₂ can be a phenyl group.

R₁ and R₂ can also be 5–6 membered heteroaryl radicals being fully unsaturated containing 1–4 nitrogen atoms, e.g. pyridyl, pyrryl, imidazolyl, tetrazolyl, pyrazinyl, pyrimidinyl, pyrazolyl, or triazolyl; containing 1–2 oxygen or sulfur atoms, e.g. thienyl, furanyl; or in combination with 1–2 nitrogen atoms, e.g. isothiazolyl, thiazolyl, isoxazolyl, oxazolyl or thiadiazolyl; or fused with a benzo ring, e.g. quinolyl, isoquinolyl, benzothienyl, isobenzofuryl, indolyl, carbazolyl; or fused with another heteroaryl ring, e.g. purinyl, and the like.

The C₇–C₁₂ cycloalkyl in R₂ and R₃ can be 1-, 2-adamantyl, norbornyl, and bicyclo[2.2.2.]octyl.

The aryl or heteroaryl ring in $R_1$ and $R_3$ as well as the phenyl group in $R_2$ can be unsubstituted or substituted with one or more of the following substituents providing the substitution leads to a chemically inert, but biologically active 5α reductase inhibitor:

The ring substituents include:

$C_1$–$C_8$ straight or branched alkyl; e.g. methyl, ethyl, propyl, isopropyl, n-butyl, sec-butyl, isobutyl, t-butyl, n-pentyl, n-hexyl, iso-hexyl, n-butyl, n-octyl, iso-octyl, t-octyl, and the like; $C_2$–$C_8$ straight or branched alkenyl, e.g. ethenyl, 1-propenyl, 2-propenyl, 1-butenyl, 2-butenyl, 3-butenyl, 1-pentenyl, 1-hexenyl, 1-heptenyl, 1-octenyl, 2-octenyl, and the like;

$C_3$–$C_8$ cycloalkyl e.g., cyclopropyl, cyclobutyl, cyclopentyl, cyclohexyl, 1-methyl-cyclobutyl, cyclopentyl, cyclohexyl, 1-methyl-cyclohexyl, 2-methylcyclohexyl, 2-ethylcyclohexyl, and the like;

$C_2$–$C_8$ alkynyl e.g., 1-ethynyl; 1-propynyl, 2-propynyl, 2-butynyl, 2-pentynyl, 1-hexynyl, 1-heptynyl, 1-octynyl;

$CONR^4R^5$ where $R^4$ and $R^5$ independently are H, $C_1$–$C_8$ alkyl, as defined above, $C_3$–$C_8$ cycloalkyl as defined above, $C_1$–$C_4$ perhaloalkyl e.g., trifluoromethyl, perfluoromethyl, trichloromethyl, preferably perfluoroalkyl; phenyl, or substituted phenyl, as described below;

$COR^4$, where $R^4$ is defined above, including acetyl, isobutylcarbonyl, benzoyl and the like;

$S(O)_n$ $R^4$, where n is 0–2 and $R^4$ is defined above, including methylsulfinyl, methylsulfonyl, phenylsulfonyl, 4-chlorophenylsulfinyl and the like;

$OCOR^4$, where $R^4$ is defined above, including acetoxy, propionyloxy, benzoyloxy, 4-chlorobenzoyloxy and the like.

$SO_2NR^4R^5$ where $R^4$ and $R^5$ are described above, including sulfonamido, N-methylsulfonamido, N-phenylsulfonamido, N,N-dimethylsulfonamido and the like;

$NR^4(CO)R^5$, wherein $R^4$ and $R^5$ are defined above, including; acetylamino, benzoylamino, N-methylbenzoylamino and the like;

$NR^4(CO)NHR^5$, wherein $R^4$ and $R^5$ are described above, including; ureido, N-methylureido, N-methyl-$N^1$-phenylureido and the like;

$NHSO_2R^4$, $R^4$ being defined above, including methylsulfonylamino, phenylsulfonylamino and the like;

$OR^4$, where $R^4$ is defined above, including methoxy, phenoxy, 4-chlorophenoxy and the like.

$NR^4R^5$, wherein $R^4$ and $R^5$ are described above, including amino, methylamino, dimethylamino, anilino and the like;

Cyano, nitro, halo, including: fluoro, chloro, bromo and iodo;

Perhalo $C_1$–$C_4$ alkyl, including: trifluoromethyl, perfluoroethyl, trichloromethyl and the like.

$CO_2R^4$, wherein $R^4$ is defined above, including $CO_2CH_3$, $CO_2Ph$, $CO_2$-(1-adamantyl) and the like; phenyl and substituted phenyl of the formula:

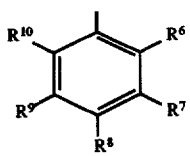

wherein the radicals $R^6$–$R^{10}$ each can represent one or more of the substituents defined above, including; hydrogen, 4-chlorophenyl, 4-fluorophenyl, 4-methoxyphenyl, 4-phenoxy and the like.

Unless otherwise indicated the 17-substituents herein described are assumed to be in the β configuration Representatives of this group of compounds of the present invention include the following:
21-benzoyl-4-aza-5α-pregnan-3-one,
21-benzoyl-4-methyl-4-aza-5α-pregnan-3-one,
21-(2-methoxybenzoyl)-4-aza-5α-pregn-1-ene-3-one,
4-methyl-21-(2-trifluoromethylbenzoyl)-4-aza-5α-pregn-1-en-3-one,
20-benzoyl-4-methyl-4-aza-5α-pregnan-3-one,
23-(2-fluorobenzoyl)-4-methyl-24-nor-4-aza-5α-cholane-3,23-dione,
23-(3-pyridyl)-24-nor-4-aza-5α-chol-1-ene-3,23-dione,
4-methyl-24-(2-pyridyl)-21-nor-4-aza-5α-cholane-3,24-dione,
17β-[5-(3-chlorobenzoyl)pentyl]-4-aza-5α-androstan-3-one,
17β-(6-benzoylhexyl)-4-methyl-4-aza-5α-androstan-3-one,
17β-(10-benzoyldecyl)-4-aza-5α-androst-1-en-3-one,
4-methyl-21-(2-thienyl)-4-aza-5α-pregnane-3,21 -dione,
24-(2-pyrazinyl)-4-aza-5α-chol-1-ene-3,24-dione,
4-ethyl-(2,6-dimethoxybenzoyl)-4-aza-5α-pregnan-3-one,
N-(4-acetylphenyl)-4-methyl-3-oxo -4-aza-5α-pregnane-21-carboxamide,
N-(4-acetylphenyl)-3-oxo-4-aza-5α-pregnane-21-carboxamide,
4-methyl-3-oxo-N-(4-pyridyl)-4-aza-5α-pregnane-21-carboxamide,
3-oxo-N-(4-pyridyl)-4-aza-5α-pregnane-21-carboxamide,
N-(2-adamantyl)-3-oxo-4-aza-5α-pregnane-21-carboxamide,
N-(2-adamantyl)-4-methyl-3-oxo4-aza-5α-pregnane-21-carboxamide,
3-oxo-N-(4-pyridyl)-4-aza-5α-pregnan-21-amide,
4-methyl-3-oxo-4-(4-pyridyl)-4-aza-21-nor-5α-cholan-24-amide,
4-methyl-3-oxo-N-(3-pyridyl)-4-aza-5α-pregnane-21-carboxamide,
4-methyl-3-oxo-N-(2-pyridyl)-4-aza-5α-pregnane-21-carboxamide,
N-(1-adamantyl)-4-methyl-3-oxo-4-aza-5α-pregnane-20(S)-carboxamide,
N-(4-acetylphenyl)-4-methyl-3-oxo-4-aza-5α-pregnane-20 (S)-carboxamide,
N-(4-chlorophenyl)-4-methyl-3-oxo-4-aza-5α-cholan-24-amide,
N-(4-acetylphenyl)-4-methyl-3-oxo-4-aza-5α-cholan-24-amide,
3-oxo-N-(4-trifluoromethylphenyl)-4-aza-5α-cholan-24-amide,
4-methyl-3-oxo-N-(4-pyridyl)-24-nor-4-aza-5α-cholan-24-amide,
N-(1-adamantyl)-11-(4-methyl-3-oxo-4-aza-5α-androstan-17β-yl)undecanamide,
N-(2-pyridyl)-6-(4-methyl-3-oxo-4-aza-5α-androstan-17β-yl)hexanamide,
N-(3-pyridyl)-5-(3-oxo-4-aza-5α-androst-1-en-17β-yl)pentanamide,
N-(2-thienyl)-7-(4-methyl-3-oxo-4-aza-5α-androstan-17β-yl)heptanamide,
3-oxo-N-(2-pyrazinyl)-4-aza-5α-pregnan-21-amide,4-methyl-3-oxo-N-(2-t-butylphenyl)-4-aza-5α-cholane-24-carboxamide,
4-methyl-3-oxo-N-(2-cyanophenyl)-4-aza-chol-1-ene-24-carboxamide,
N-(2-bicyclo[2.2.2]octyl)-9-(3-oxo-4-aza-5α-androstan-17β-yl)nonanamide,
1-adamantyl 4-methyl-3-oxo-4-aza-5α-pregnane-20(S)-carboxylate,
phenyl 4-methyl-3-oxo-4-oxo-4-aza-5α-pregnane-20(S)-carboxylate, 2-(t-butyl)phenyl 4-methyl-3-oxo-4-aza-5α-pregnane-21-carboxylate,
2-methoxyphenyl 4-methyl-3-oxo-4-aza-5α-pregnane-21-carboxylate,
phenyl 3-oxo-4-aza-5α-pregnane-21-carboxylate,
phenyl 4-methyl-3-oxo-4-aza-5α-pregnane-21-carboxylate,
phenyl 5-(4-methyl-3-oxo-4-aza-5α-androstan-17β-yl) pentanoate,
2-(t-butyl)phenyl 3-oxo-4-aza-5α-pregnan-21-oate,
2,6-dimethoxyphenyl 3-oxo-4-aza-5α-pregn-1-en-21-oate,
2-adamantyl 8-(4-methyl-3-oxo-4-aza-5α-androstan-17β-yl)octanoate,
2,6-dimethylphenyl 3-oxo-4-aza-5α-pregn-1-en-21-oate,
2,6-dichlorophenyl 4-methyl-3-oxo-4-aza-5α-pregn-1-en-21-ate,
phenyl 10-(4-methyl-3-oxo-4-aza-5α-androstan-17β-yl) decanoate,
N,4-dimethyl-3-oxo-N-(4-pyridyl)-4-aza-5α-pregnan-21-amide,
N-methyl-3-oxo-N-(4-pyridyl)-4-aza-5α-pregnan-21-amide,
4-methyl-3-oxo-N-(4-pyridyl)-4-aza-5α-pregnane-20-carboxamide,
4-methyl-3-oxo-N-(3-pyridyl)-4-aza-5α-pregnane-20-carboxamide,
4-methyl-3-oxo-N-(2-pyridyl)-4-aza-5α-pregnane-20-carboxamide,
4-methyl-3-oxo-N-(4-pyridyl)-4-aza-5α-cholan-24-amide,
4-methyl-3-oxo-N-(3-pyridyl)-4-aza-5α-cholan-24-amide,
4-methyl-3-oxo-N-(2-pyridyl)-4-aza-5α-cholan-24-amide,
3-oxo-N-(4-pyridyl)-4-aza-5α-pregn-1-ene-20-carboxamide,
3-oxo-N-phenyl-4-aza-5α-pregn-1-ene-21-carboxamide,
N-(4-methoxyphenyl)-3-oxo-4-aza-5α-pregn-1-ene-21-carboxamide,
N-(2-imidazolyl)-3-oxo-4-aza-5α-pregn-1-ene-21-carboxamide,
3-oxo-N-(4-pyridyl)-4-aza-5α-pregn-1-ene-21-carboxamide,
3-oxo-N-(3-pyridyl)-4-aza-5α-pregn-1-ene-21-carboxamide,
3-oxo-N-(2-pyridyl)-4-aza-5α-pregn-1-ene-21-carboxamide,
3-oxo-N-(1,2,4-triazin-3-yl)-4-aza-5α-pregn-1-ene-21-carboxamide,
3-oxo-N-(3-quinolinyl)4-aza-5α-pregn-1-ene-21-carboxamide,
3-oxo-N-(4-pyridyl)-4-aza-5α-chol-1-en-24-amide,
3-oxo-N-(3-pyridyl)-4-aza-5α-chol-1-en-24-amide,
3-oxo-N-(2-pyridyl)-4-aza-5α-chol-1-en-24-amide,
and also including the corresponding compounds wherein the 4-hydrogen substituent is replaced by a methyl or an ethyl radical, and/or a delta-one double bond is present.

The starting materials for these preparations are the appropriate carboxylic acids 1, 2, 9, 16, 17, 34, 37, 40, 45, 63, 64, 68 and 78 (these numbers are with reference to examples 73 through 84). The source of these carboxylic acids is as follows:

The synthesis of acid 1 is published in J. Med. Chem. 1984, Vol. 27, p 1690.

Acid 2 was prepared by the same procedure as acid 1.

The preparation of acid 9 is published in J. Med. Chem. 1984 Vol. 27, p.1690.

The syntheses of acids 16 and 17 are detailed in Example 73, below. The aldehyde 50 was reacted with the methyl (diethylphosphono)acetate anion to give the olefinic Horner-Wadsworth reaction product 51. Hydrogenation to the saturated ester 52 and saponification with aqueous KOH in methanol gave 17. The same sequence of reactions starting with the corresponding 4-methyl aldehyde (J. Med. Chem. 1986 Vol. 29, p. 2304, compound 10bg) produced the acid 16.

Acid 34 was prepared as outlined in Example 82, below. The nitrile 58 was transformed into the methyl ester 59 by conversion to the iminoester with anhydrous HCl in methanol followed by treatment with water. KOH saponification produced the acid 34.

The acid 37 was synthesized by the Arndt-Eistert homologation of 16. Activation of 16 as the mixed anhydride with isobutyl chloroformate and N-methyl morpholine and reaction with diazomethane gave the diazoketone 53. Silver benzoate catalyzed decomposition of 53 in methanol gave the homologous methyl ester 54. Saponification have the corresponding acid 37.

The synthesis of the acids 41 and 65 is published in J. Med. Chem. 1986 Vol. 29, p. 2300. The acids 45, 63, and 64 were prepared by the reaction sequence detailed in Example 83, below. Palladium catalyzed coupling of the $\Delta^{16}$-17-triflate 60 with methyl 4-pentynoate using the procedures published in Synlett. 1991 p. 409; J. Org. Chem. 1992 Vol. 57, p. 973. gave the enyne 61. Hydrogenation catalyzed with palladium on carbon formed the saturated ester 62 and KOH saponification gave 45. Similar reaction sequences using methyl 5-hexynoate and 10-undecynoic acid gave the acids 63 and 64.

Starting with the above acids, the novel ketones, amides, and esters listed in Table 5 were prepared using the procedures discussed below and detailed in the Examples.

The synthesis of the ketones 32 and 33 are given in Examples 5 and 6. Using the procedures published in J. Med. Chem. 1986 Vol. 29, p. 2310, the acids 16 and 17 were converted into the 2-thiopyridyl esters 55 and 56 by reaction with triphenylphosphine and 2,2'-dithiodipyridine.(Example 77). Low temperature reaction of these 2-thiopyridyl esters with phenyl-magnesium chloride produced the phenyl ketones 32 and 33 (Example 78).

The amides listed in Table 5 were prepared by a variety of procedures:

For the unhindered acids 16, 17, 34, 37, 41, 62, 63, 64, 68 and 78, 4-dimethylaminopyridine (DMAP) catalyzed carbodiimide mediated condenstion with the appropriate amine or aniline was used. Either dicyclohexylcarbodiimide (Example 3) or the water soluble 1-(3-dimethylaminopropyl)-3-ethylcarbodiimide hydrochloride (Example 80) could be used.

For the more hindered acids 1 and 2, formation of the mixed anhydride with isobutyl chloroformate and N-methylmorpholine followed by reaction with the appropriate amine (Example 76) proved to be the best procedure.

For the most hindered acid (9), it was necessary to activate the acid for reaction with an amine by either forming the acid chloride with oxalyl chloride (Example 81) or converting it into the 2-thiopyridyl ester (Example 77).

With hindered or unreactive amines such as 1-adamantamine or 4-acetylaniline, reaction of the 2-thiopyridyl ester alone (Example 77) or with silver trifluoromethylsulfonate catalysis (Example79) was used to form the amide derivatives.

The ester derivatives in Table 5 were formed from the appropriate acid and alcohol or phenol using the same procedures (Examples 75, 79, and 80) used for the formation of the corresponding amide derivatives As outlined in Flowsheet XXXII and detailed in Example 84, the 4-H esters II can be converted into the corresponding Δ¹-4-H esters (III) by the procedure of Dolling, et al using dichlorodicyanobenzoquinone (J. Amer. Chem. Soc. 1988, Vol. 110, p. 3318–3319) Using this procedure the 4-H esters 52 and 59a were converted into the Δ¹-4-H esters 69 and 79. The latter esters could be saponified with lithium hydroxide in aqueous t-butanol to the acids 68 and 78. The same conversion of II into III can also be carded out using benzeneselenic anhydride (J. Med. Chem. 1986 Vol. 29, p.2298–2315). Furthermore II and III can be alkylated on the 4-N with methyl or ethyl iodide using sodium hydride in DMF or DMSO to give the 4-methyl- or 4-ethyl-4H esters (IV) or the 4-methyl- or 4-ethyl-Δ¹esters (V). Also II and III can be converted to the 4-SMe esters IV and V by reaction with sodium hydride and methane-sulfenyl chloride (MeSCl). II and III can also be aminated with hydroxylamine-O-sulfonic acid and oxidized with Oxone-acetone reagent to give the 4-$NH_2$ and 4—OH esters IV and V, respectively. After saponification of the esters (II–V), the starting acids containing a 4-hydrogen, methyl, ethyl, hydroxy, amino, or methylthio substituent and either with or without a Δ¹ can be prepared, Using the procedures in Examples 73 through 83, these acids can be converted into the corresponding ketone, amide, and ester derivatives.

FLOWSHEET XXXII

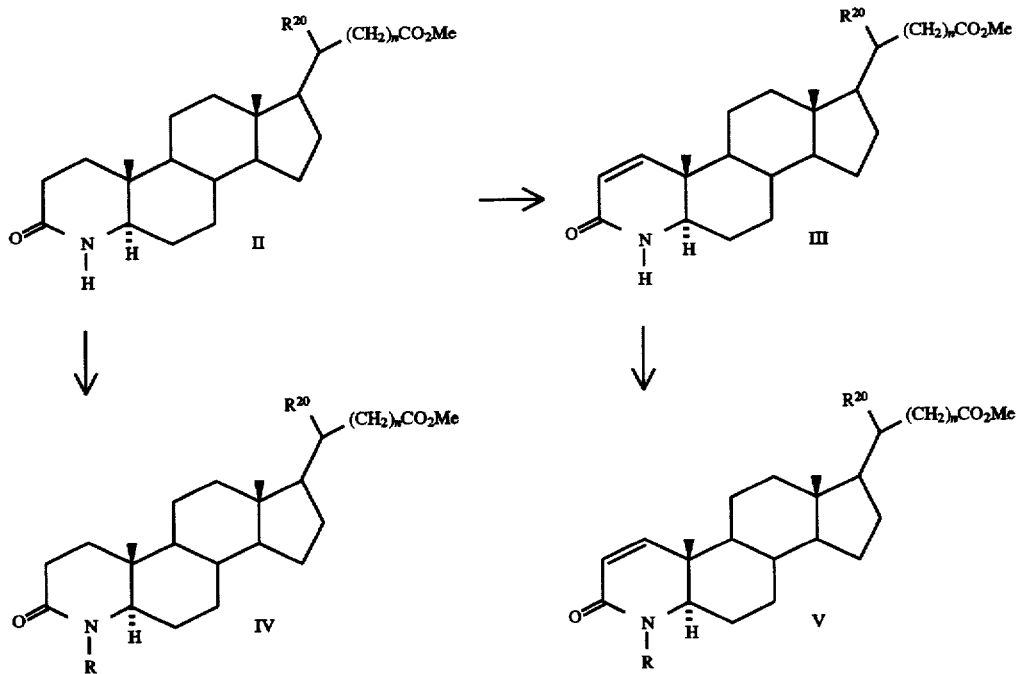

R = Me, Et, OH, $NH_2$, SMe

EXAMPLE 73

3-Oxo-4-aza-5α-pregnan-21-carboxylic acid (17)

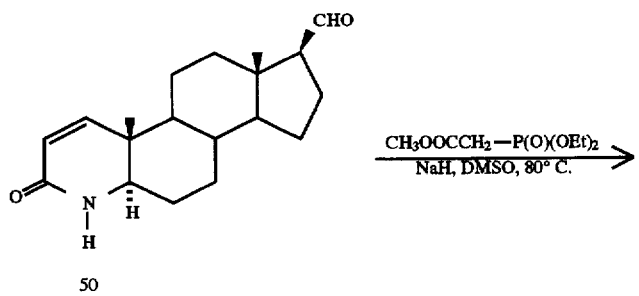

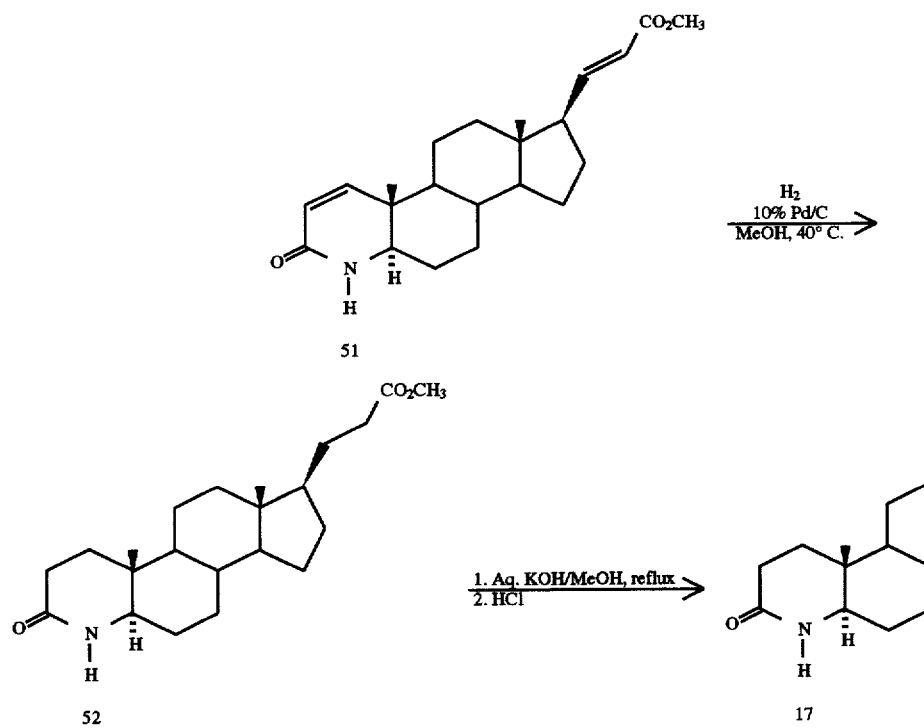

To a suspension of the aldehyde, (1.0 g, 3.32 mmole) in 12 ml DMSO was added 14.6 mg (3.65 mmole) sodium hydride (60% in mineral oil) and 698 μl (3.65 mmole) methyl diethylphosphonoacetate. The mixture was heated under $N_2$ atmosphere at 80° C. for 1 hr. The clear solution was cooled and partitioned between dilute HCl and methylene chloride. The organic phase was washed with water, brine, dried over magnesium sulfate and concentrated in vacuo to give 1.2 g crudeproduct. Purification by flash chromatography on silica gel in 4:1 methylene chloride:acetone gave 956 mg of the unsaturated ester [51, NMR, d=0.66 (s, 3H, 18-Me), 0.97 (s, 3H, 19-Me), 3.72 (s, 3H, OMe), 5.7(d, 1H, $\Delta^1$), 5.82(s, 1H, $\Delta^{20}$), 5.96(bs, 1H, NH), 6.79(d, 1H, $\Delta^1$), 6.92 (dd, 1H, $\Delta^{20}$)].

The unsaturated ester (51) (956 mg, 2.67 mmole) was dissolved in 80 ml warm methanol and hydrogenated with 300 mg 10% Pd/C at 40 psi at a temperature of 40° C. for 3 hrs. The mixture was filtered through a pad of Celite, washing with warm methanol. The filtrate was concentrated in vacuo to give 938 mg of the saturated ester (52).

The saturated ester (52) (938 mg, 2.59 mmole) was dissolved in 9 ml methanol containing 863 μl 9M KOH and refluxed for 1 hr. The mixture was concentrated to a small volume and 100 ml water added. The mixture was cooled to 10° C. and brought to pH 1 with concentrated HCl. The resulting precipitate was filtered, washed with water, sucked dry and dried in a vacuum oven at 60° C., 25 in. for 18 hrs, giving 830 mg of the acid (17).

EXAMPLE 74

3-Oxo-4-methyl-4-aza-5α-21-norcholanic acid (37)

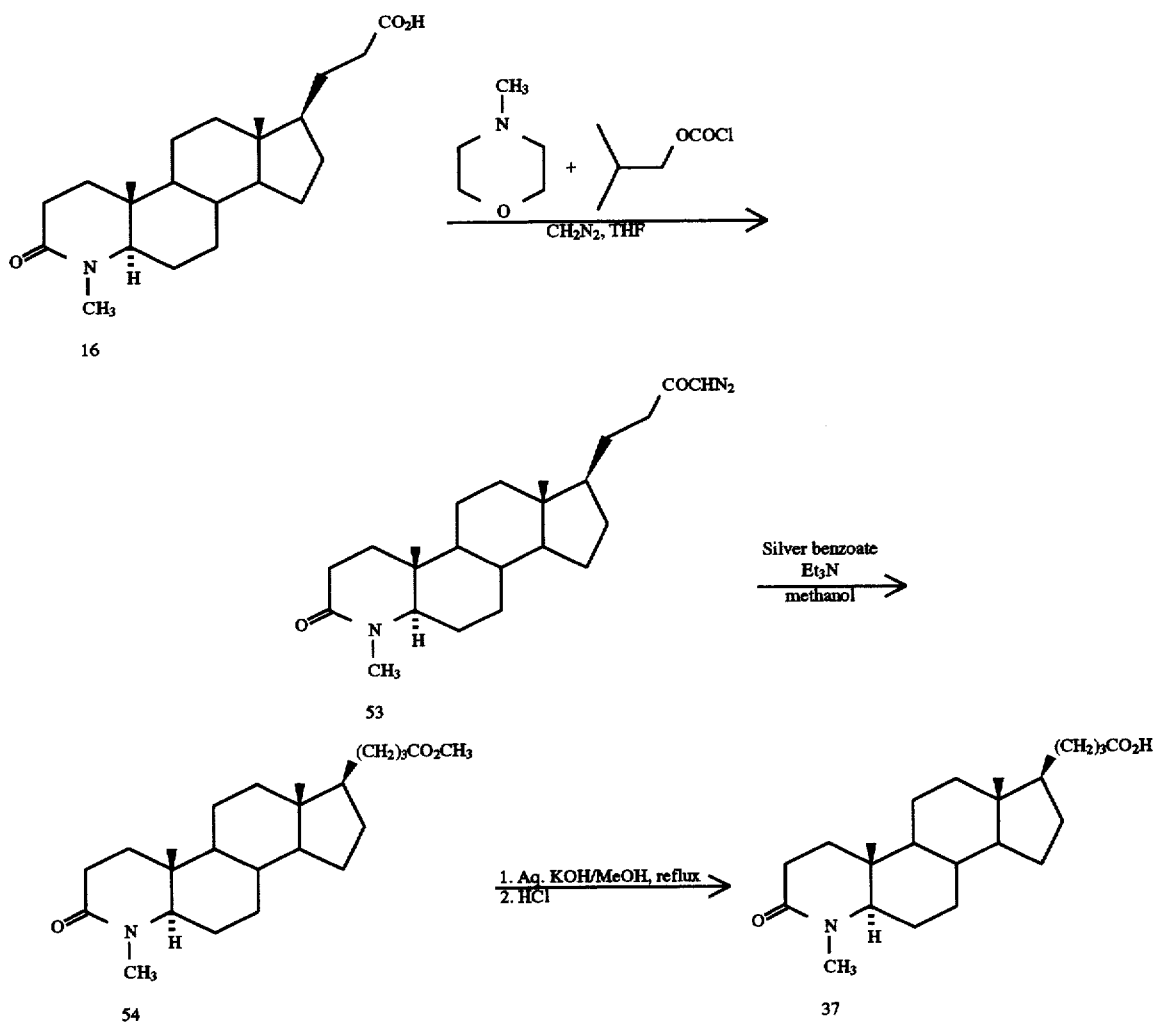

To a solution of the acid (16), (763 mg, 2.66 mmole) and N-methyl morpholine (296 ml, 2.66 mmole) in 60 ml THF at −20° C. under $N_2$ atmosphere was added dropwise isobutyl chloroformate (352 μl, 2.66 mmole). The mixture was stirred at −20° C. for 40 minutes, filtered and concentrated in vacuo to about ¼ its volume on a rotary evaporator using no heat. The mixture was cooled to −10° C. under $N_2$ and a freshly prepared ether solution of excess (12 mmole) diazomethane added. After stirring for 18 hours at room temperature, nitrogen was bubbled through the solution for 20 minutes (to remove excess diazomethane) and the mixture concentrated in vacuo. The residue was partitioned with methylene chloride-water and the organic phase washed with 5% acetic acid, water, brine, dried over magnesium sulfate and concentrated in vacuo to give 1.1 g crude product (oil). Purification by flash chromatography on silica gel in 4:1 methylene chloride:acetone gave 350 mg of the diazoketone (53).

The diazoketone (53), (224 mg, 0.681 mmole) was dissolved in 1 ml of methanol and 266 μl of a 0.218M solution of silver benzoate in triethyl amine (50 mg/ml) was added. The mixture was stirred at room temperature for 2 hours and the dark solution concentrated in vacuo. Methylene chloride was added and the mixture filtered. The filtrate was washed with dilute HCl, water, saturated $NaHCO_3$, brine, dried over magnesium sulfate and concentrated in vacuo to give 212 mg crude product (oil). Purification by flash chromatography on silica gel in 4:1 methylene chloride:acetone gave 153 mg of the methyl butyrate (54).

The methyl ester (54) was converted to the free acid (37) using the same conditions as was used in the previous case (52 converted to 17) except that the reflux time was 2 hours.

EXAMPLE 75

3-oxo-4-methyl-N-phenyl-4-aza-5α-pregnan-21-carboxamide (23)

153

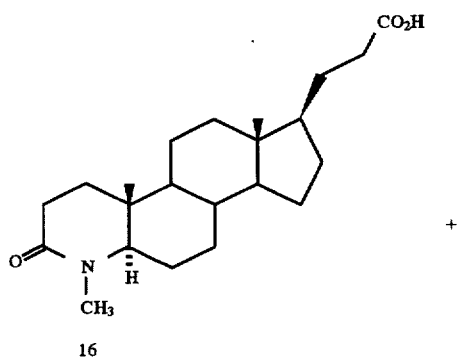

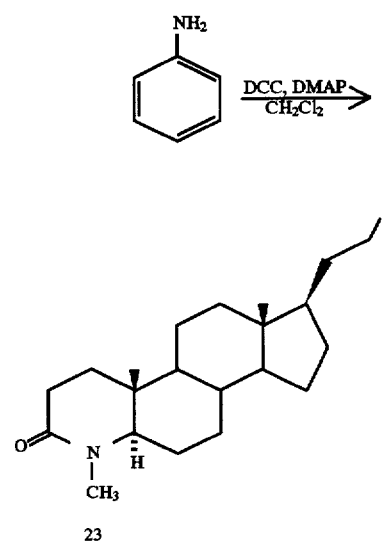

To a solution of the acid (16), (57 mg, 0.158 mmole) in 2 ml methylene chloride was added 17 μl (0.190 mmole) aniline, 45 mg (0.220 mmole) dicyclohexylcarbodiimide (DCC) and 1 mg 4-dimethyl-aminopyridine (DMAP). The mixture was stirred at room temperature for 5 hours, filtered and concentrated in vacuo to give 96 mg crude mixture. Purification by preparative thin layer chromatography on a 1500 g silica gel plate in 5% methanol/methylene chloride and trituration with hexane gave 26 mg of the anilide (23).

Compounds 18–20, 24–28, 30, 38–39, 42 and 44 were prepared by the above procedure.

EXAMPLE 76

3-Oxo-4-methyl-N-phenyl-4-aza-5α-pregnan-21-amide (3)

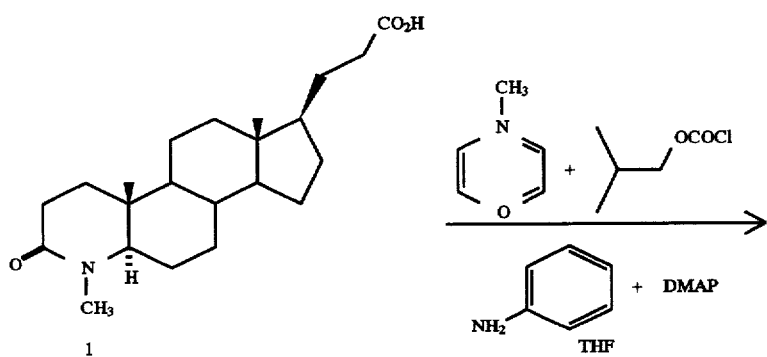

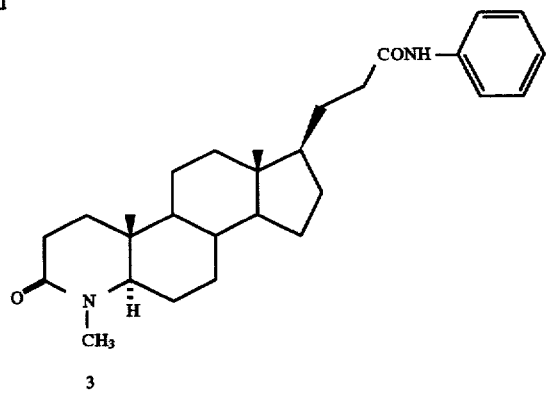

3

To a solution of the acid (1) (174 mg, 0.50 mmole) and N-methyl morpholine (61 µl, 0.55 mmole) in 10 ml THF at −20° C. under a $N_2$ atmosphere was added dropwise isobutyl chloroformate (66 µl, 0.50 mmole). The mixture was stirred at −20° C. for 20 minutes and aniline (64 µl, 0.70 mmoles) plus 4-dimethylaminopyridine (DMAP, 3 mg) was added. The mixture was stirred at −20° C. for 30 minutes and then at room temperature for 18 hours. The mixture was concentrated in vacuo and the residue partitioned with methylene chloride-water. The organic phase was washed with dilute HCl, water, brine, dried over magnesium sulfate and concentrated in vacuo to give 224 mg crude product. Purification by flash chromatography on silica gel in 4:1 methylene chloride:acetone gave 184 mg of the anilide (3).

Compounds 4–8, 29 and 31 were prepared by the above procedure.

EXAMPLE 77

N-2-adamantyl-3-oxo-4-methyl-4-aza-5α-pregnan-21-carboxamide (21)

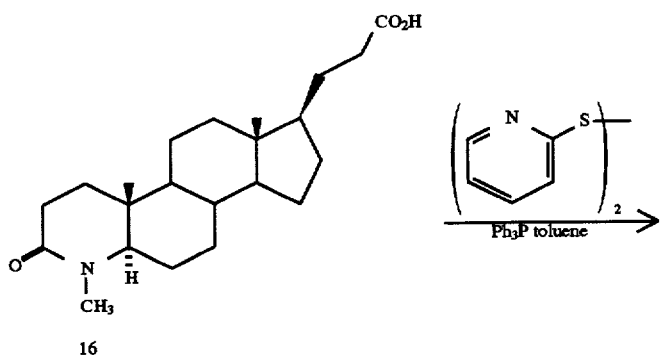

16

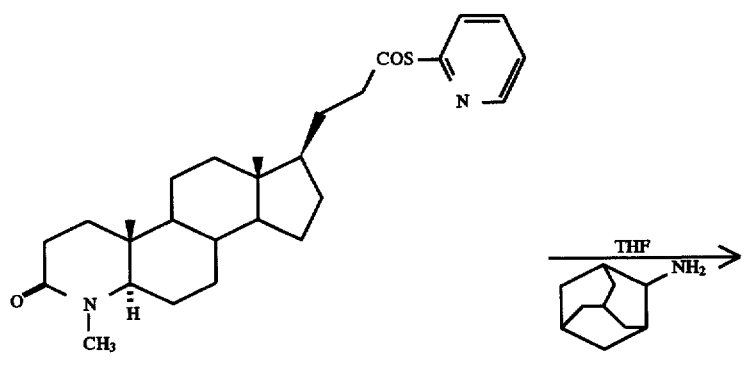

3

-continued

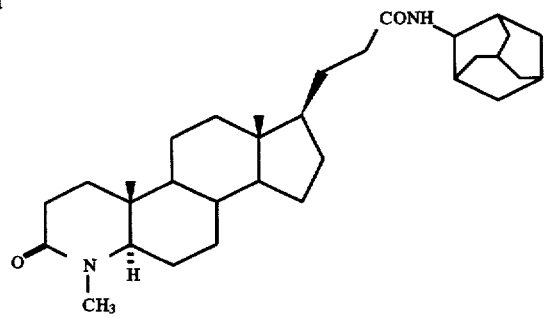

21

To a suspension of the acid (16), (391 mg, 1.08 mmole) in 3 ml toluene was added 487 mg (2.16 mmole) 2,2'-dithiodipyridine followed by 567 mg (2:16 mmole) triphenylphosphine. The mixture was stirred at room temperature for 18 hours, concentrated in vacuo and the residue flash chromatographed on silica gel in 4:1 methylene chloride-:acetone to give a yellow solid. The solid was washed with ether to give 326 mg of the thiopyridyl ester (55).

was flash chromatographed on silica gel in 4:1 methylene chloride:acetone to give 83 mg of the amide (21).

Using the above procedure compounds 14 and 22 were prepared from the thiopyridyl esters 57 and 56 respectively.

EXAMPLE 78

21-Benzoyl-4-aza-5α-pregnan-3-one (33)

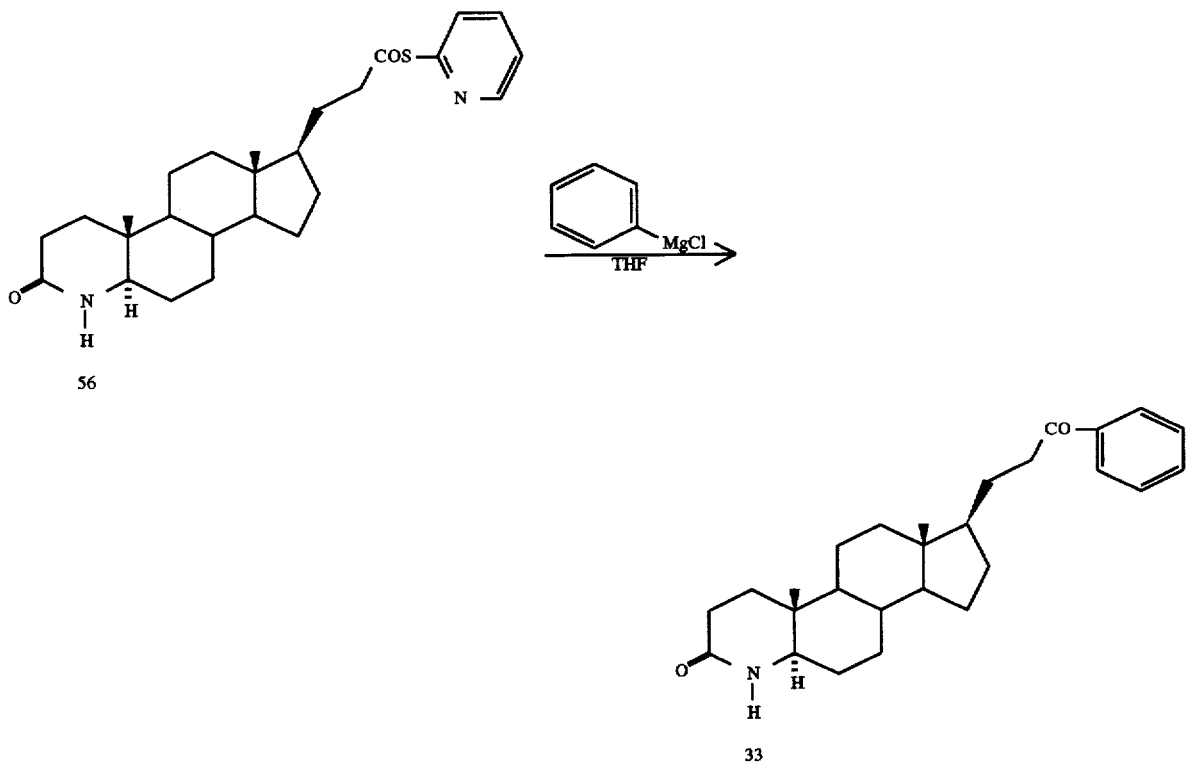

Using the same procedure, the thiopyridyl esters 56, 57, 66 and 83 were prepared from the carboxylic acids 17, 9, 65 and 68 respectively.

To a solution of the thiopyridyl ester (55), (105 mg, 0.231 mmole) in 2.5 ml THF was added 262 mg(1.73 mmole) 2-adamantane amine. The mixture was stirred at room temperature for 18 hours, concentrated in vacuo and the residue partitioned with methylene chloride-2N HCl. The organic phase was washed with water, brine, dried over magnesium sulfate and concentrated in vacuo. The residue To a suspension of the thiopyridyl ester (56), (100 mg, 0.227 mmole) in 4 ml THF at −78° C. under a $N_2$ atmosphere was added phenyl magnesium chloride (250 μl, 0.499 mmole, 2M in THF). The mixture was stirred at −78° C. for 45 minutes and allowed to warm to 0° C. The reaction was quenched by the careful addition of 5 drops of brine. The mixture filtered and washed with THF and methylene chloride. The filtrate was concentrated in vacuo and the residue dissolved in methylene chloride, washed with 2N NaOH, water, brine, dried over magnesium sulfate and concentrated in vacuo to give 84 mg crude mixture. Purification by preparative thin layer chromatography on a 2000μ silica gel plate in 4:1 methylene chloride:acetone (run up the plate 4 times) gave 20 mg of the phenyl ketone (33).

Compound 32 was prepared by the above procedure.

EXAMPLE 79

N-(4-Acetylphenyl)-4-methyl-3-oxo-4-aza-5α-pregnane-20(S)-carboxamide (15)

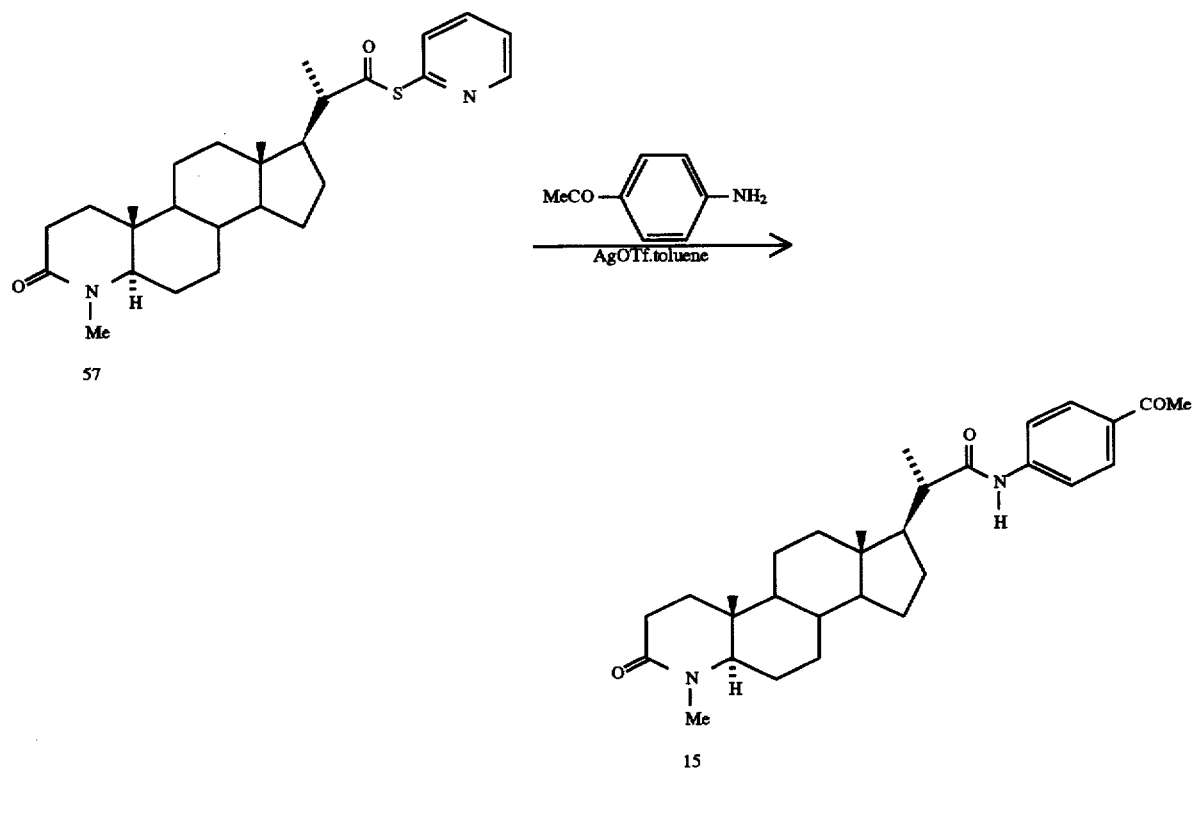

To a suspension of the thiopyridyl ester (57) (136 mg, 0.3 mmoles) and 4-acetylaniline (81 mg, 0.6 mmoles) in 1.5 ml of toluene was added all at once a warm solution of 93 mg (0.36 mmoles) of silver trifluoromethysulfonate in 0.6 ml of toluene. The suspension was stirred at room temperature for 24 hrs. Periodically the gummy precipitate was dispersed with a glass rod. The suspension was diluted with 30 ml of $CH_2Cl_2$ and washed with water, 5% ammonium hydroxide, water, and saturated brine and dried ($MgSO_4$). Evaporation in vacuo gave 117 mg of a pale yellow solid. Preparative TLC on two 20×20 cm, 1000μ, silica gel plates with 4:1 $CH_2Cl_2$-acetone and elution of the strongly UV-active band with 4:1 $CH_2Cl_2$—MeOH gave 32 mg of pure amide 15.

Compounds 10 and 11 were prepared by the above procedure. Compounds 15a, 15b, 15c, 67, 71, 72, and 77 were prepared by the above procedure except that THF was used instead of toluene.

EXAMPLE 80

4-Methyl-3-oxo-N-(4-pyridyl)-24-nor-4-aza-5α-cholan-23-amide (36)

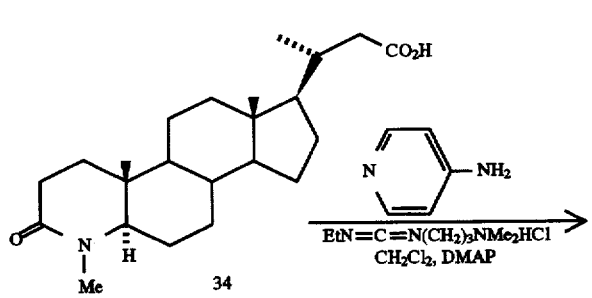

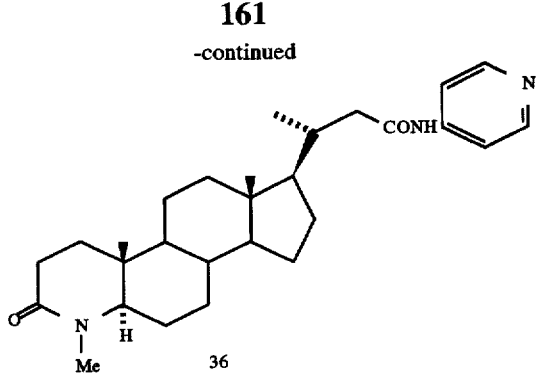

To a solution of 38 mg (0.1 mmole) of the acid 34, 19 mg (0.2 mmoles) of 4-aminopyridine, and 1 mg of 4-dimethylyl-amino-pyridine in 0.3 ml of CH$_2$Cl$_2$ was added 38 mg (0.2 mmoles) of 1-(3-dimethylaminopropyl)-3-ethylcarbodiimide hydrochloride. The solution was kept at room temperature for 24 hrs, diluted with CH$_2$Cl$_2$, washed with water, dilute K$_2$CO$_3$, water, and saturated brine and dried (MgSO$_4$). Evaporation in vacuo gave 45 mg of a gum. Preparative TLC on a 20×20 cm, 1000µ silica gel plate with 7% MeOH in CH$_2$Cl2 and elution of the strongly UV-active band with 2:1 CH$_2$Cl$_2$—MeOH gave 23 mg of pure amide 36.

Compounds 7a, 8a,35, 43, 44a, 44b, 44c, 46, 47, 48, 49, 73, 74, 75, 76, 80, 81 and 82 were prepared from the appropriate acids by the above procedure.

EXAMPLE 81

N-(1-Adamantyl)-4-methyl-3-oxo-4-aza-5α-pregnane-20(S)-carboxamide (13)

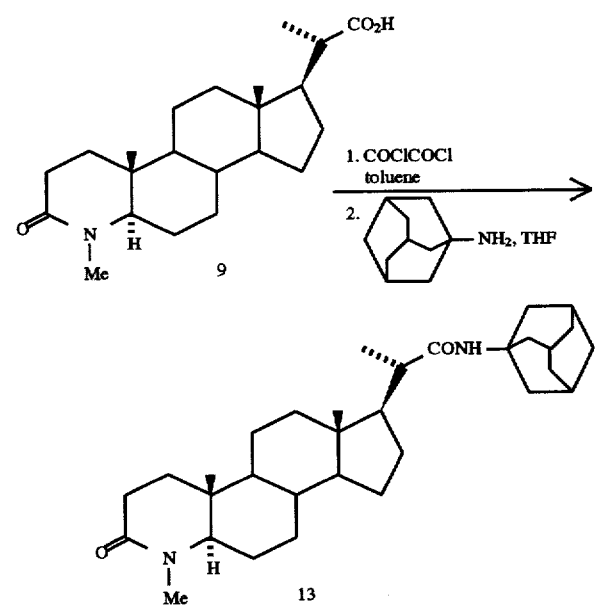

To a suspension of 108 mg (0.3 mmoles) of the acid 9 in 1.3 ml of toluene was added 0.24 ml (2.75 mmoles) of oxalyl chloride at room temperature. After 30 min the volatiles were removed in vacuo, and the residue was dissolved in 1.5 ml of THF. A solution of 181 mg (1.2 mmoles) of 1-adamantanamine and 3 mg of 4-dimethyl-aminopyridine in 1 ml of THF was added, and the mixture allowed to stir at room temperature for 20 hrs. Most of the THF was removed in vacuo, and the residue partitioned between ice water and CH$_2$Cl$_2$. The aqueous phase was extracted with CH$_2$Cl$_2$ (2×). The combined organic extracts were washed with 0.5N HCl, water, and dried (MgSO$_4$). Evaporation in vacuo and flash chromatography of the residue on a 10 mm×18 cm column of silica gel with 1:1 ethyl acetate-acetone gave 47 mg of pure amide 13.

EXAMPLE 82

4-Methyl-3-oxo-24-nor-4-aza-5α-cholan-23-oic acid (34)

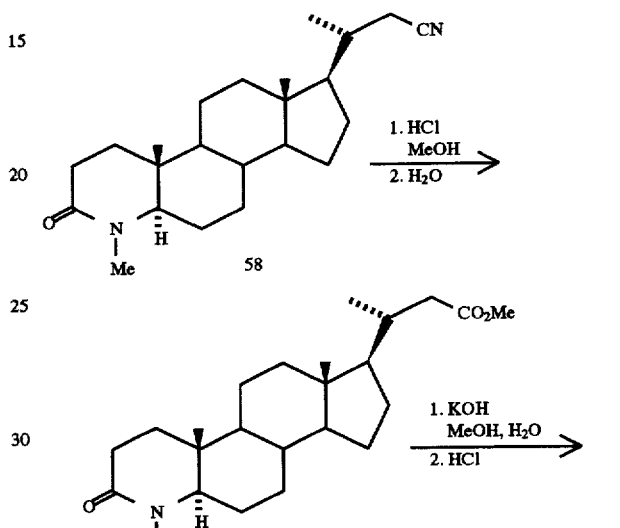

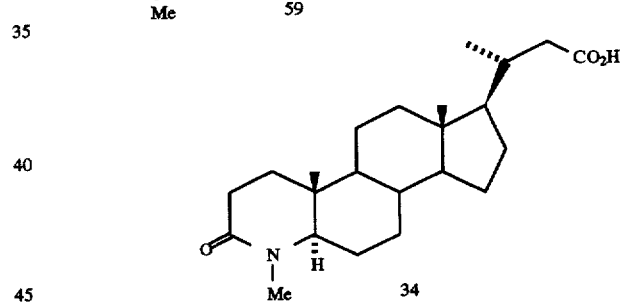

A solution of 144 mg of 4-methyl-3-oxo-24-nor-4-aza-5α-cholano-23-nitrile (58, Case 18671) in 5 ml of methanol saturated with anhydrous HCl was allowed to stand at room temperature for 6 hrs. The residue after evaporation in vacuo was stirred in 10 ml of water for 3 hrs and extracted with CH$_2$Cl$_2$ (3×). The extracts were washed with water and dried (MgSO$_4$). Evaporation in vacuo and flash chromatography of the residue on silica gel with 4:1 CH$_2$Cl$_2$-acetone gave 112 mg of methyl 4-methyl-3-oxo-24-nor-4-aza-5α-cholan-23-oate (59).

The methyl ester 59 (101 mg) was saponified to 90 mg of the acid 34 using the procedure in Example 1.

EXAMPLE 83

4-Methyl-3-oxo-21-nor-4-aza-5α-cholane-24-carboxylic acid (45)

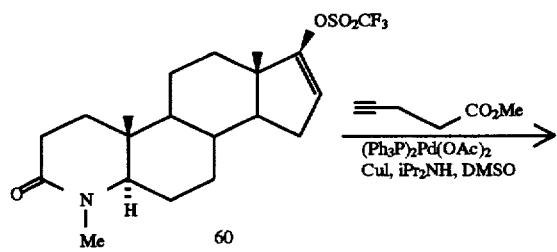

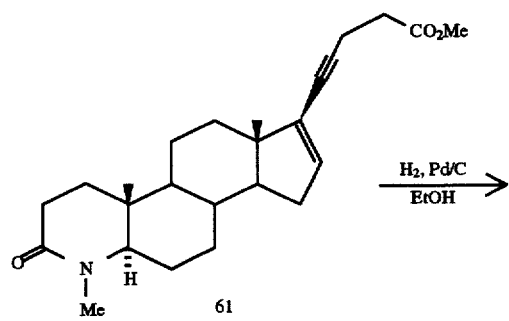

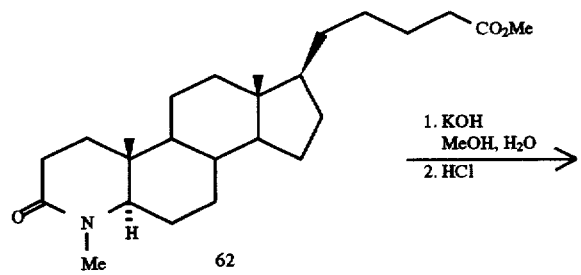

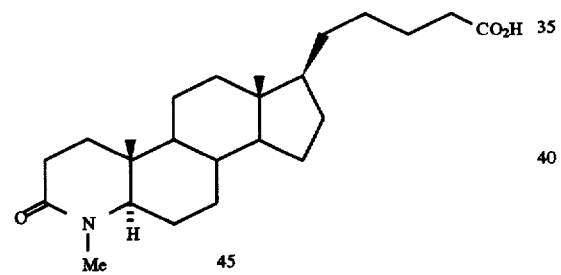

A mixture of 436 mg (1.0 mmole) of 4-methyl-17-triflluoromethylsulfonyloxy-4-aza-5α-androst-16-en-3-one (60) (Case 18730), 168 mg (1.5 mmoles) of methyl 4-pentynoate, 40 mg of bis(triphenylphosphine)palladium (II) acetate, 5 mg of cuprous iodide in 3.0 ml of DMSO and 3.0 ml of N,N-diisopropylamine was stirred at room temperature for 17 hrs. The dark reaction mixture was poured into 50 ml of 0.5M HCl and extracted with $CH_2Cl_2$ (3×). The combined extracts were washed with water (4×) and dried ($MgSO_4$). Evaporation in vacuo and flash chromatography of the residue on silica gel with 6:1 $CH_2Cl_2$-acetone gave 400 mg of enyne 61. The enyne was immediately hydrogenated in 20 ml of EtOH with 150 mg of 10% palladium on carbon catalyst under a hydrogen-filled balloon. After stirring at room temperature for 24 hrs, the reaction mixture was filtered through a bed of Celite., which was washed with EtOH (4×). The filtrate and washes were evaporatated in vacuo and the residue flash chromatographed on silica gel with 5:1 $CH_2Cl_2$ to give 345 mg of methyl 4-methyl-3-oxo-21-nor-4-aza-5α-cholane-24-carboxylate (62).

The methyl ester 62 (300 mg) was saponified to 275 mg of the acid 45 using the procedure in Example 1.

The acids 6-(4-methyl-3-oxo-4-aza-5α-androstan-17β-yl) hexanoic acid (63) and 11-(4-methyl-3-oxo-4-aza-5α-androstan-17β-yl)-undecanoic acid (64) used for the preparation of the anilides 48 and 49 respectively were prepared by the above procedure.

EXAMPLE 84

3-Oxo-4-aza-5α-pregn-1-ene-21-carboxylic acid

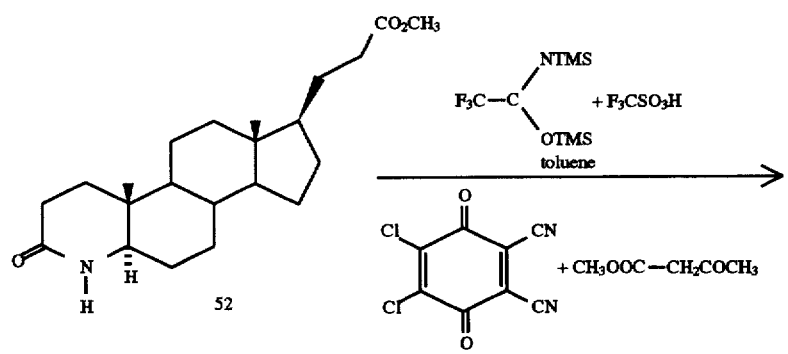

165 166

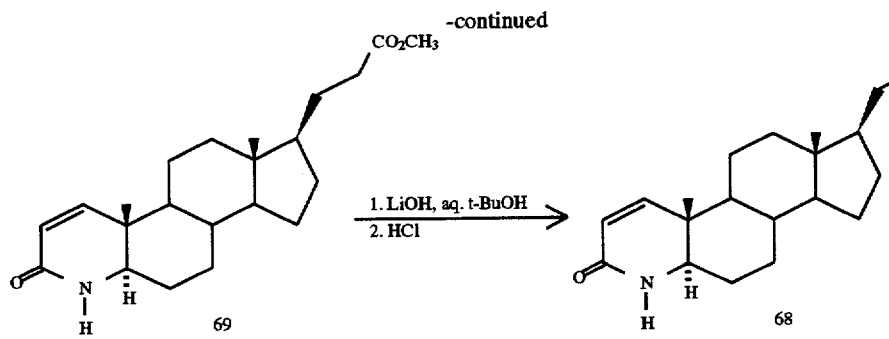

To a dry toluene solution of the ester 52 (361 mg, 1.0 mmole) under $N_2$ was added 2,3-dichloro-5,6-dicyano-1,4-benzoquinone (266 mg, 1.13 mmole), bis(trimethylsilyl)trifluoroacetamide (1.07 ml, 4 mmole) and trifluoromethanesulfonic acid (7 ml, 0.077 mmole) and the clear red solution stirred at room temperature for 24 hours. Methylacetoacetate (11 ml, 0.1 mmole) was added and after stirring for 1 hour at room temperature the solution was refluxed for 24 hours. The reaction mix was concentrated in vacuo to a small volume and the residue dissolved in methylene chloride and extracted with an aqueous solution of 1.5% sodium carbonate plus 0.5% sodium sulfite, 5% sodium bicarbonate, dried over magnesium sulfate and concentrated in vacuo to give 328 mg crude product. Purificaton by flash chromatography on silica gel in 9:1 methylene chloride:acetone gave 229 mg of the unsaturated ester 69.

The unsaturated ester 69 (215 mg, 0.598 mmole) was dissolved in 2 ml tert-butanol containing lithium hydroxide monohydrate (75 mg, 1.79 mmole) and 200 ml water and refluxed for 1.5 hours. The mixture was concentrated in vacuo to a small volume and 20 ml water added. The mixture was cooled to 10° C. and brought to pH 1 with concentrated HCl. The resulting precipitate was filtered, washed with water, sucked dry and dried in a vacuum oven at 60° C., 25 in. for 18 hours giving 174 mg of the unsaturated acid 68.

Using the above procedures the ester 59a was converted into the ester 79 and the acid 78.

The following tables 6 and 7 list some of the compounds made in this invention and their physical properties. The compound numbers in these two tables are with reference to compounds described in Examples 73 through 84.

TABLE 6

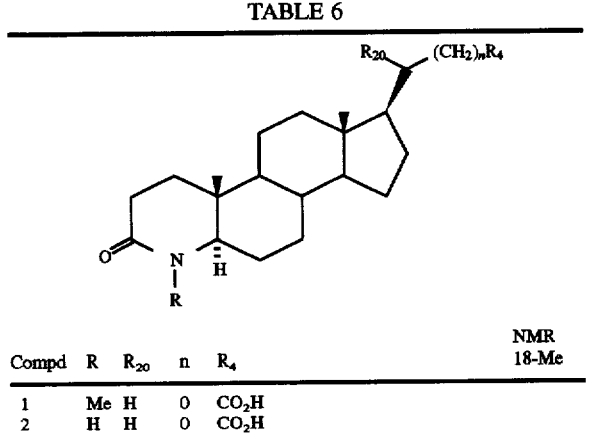

| Compd | R  | $R_{20}$ | n | $R_4$   | NMR 18-Me |
|-------|----|----------|---|---------|-----------|
| 1     | Me | H        | 0 | $CO_2H$ |           |
| 2     | H  | H        | 0 | $CO_2H$ |           |

TABLE 6-continued

| Compd | R | $R_{20}$ | n | $R_4$ | NMR 18-Me |
|-------|----|----|---|----|------|
| 3 | Me | H | 0 | CONH—(phenyl) | 0.62 |
| 4 | H | H | 0 | CONH—(phenyl) | 0.65 |
| 5 | H | H | 0 | CONH—(phenyl)—COMe | 0.66 |
| 6 | H | H | 0 | CONH—(phenyl)—COMe | 0.66 |
| 7 | Me | H | 0 | CONH—(pyridyl) | 0.64 |
| 7a | Me | H | 0 | CONH(Me)—(pyridyl) | 0.44 |
| 8 | H | H | 0 | CONH—(pyridyl) | 0.62 |
| 8a | H | H | 0 | CONH(Me)—(pyridyl) | 0.45 |
| 9 | Me | Me | 0 | $CO_2H$ | |
| 10 | Me | Me | 0 | $CO_2$—(phenyl) | 0.76 |
| 11 | Me | Me | 0 | $CO_2$—(adamantyl) | 0.67 |
| 12 | Me | Me | 0 | CONH—(t-Bu group) | 0.68 |

TABLE 6-continued

| | | | | | |
|---|---|---|---|---|---|
| 13 | Me | Me | 0 | 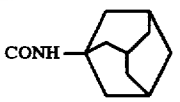 CONH- | 0.68 |
| 14 | Me | Me | 0 | 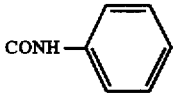 CONH- | 0.74 |
| 15 | Me | Me | 0 | 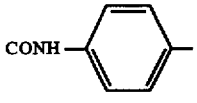 CONH-⌬-COMe | 0.72 |
| 15a | Me | Me | 0 | 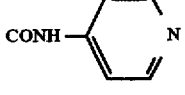 CONH-(pyridyl) | 0.71 |
| 15b | Me | Me | 0 | 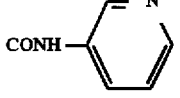 CONH-(pyridyl) | 0.72 |
| 15c | Me | Me | 0 | 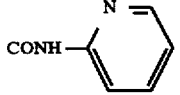 CONH-(pyridyl) | 0.71 |
| 16 | Me | H | 1 | CO$_2$H | 0.60 |
| 17 | H | H | 1 | CO$_2$H | |
| 18 | Me | H | 1 | 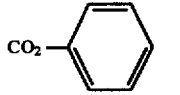 CO$_2$-⌬ | 0.65 |
| 19 | Me | H | 1 | 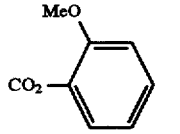 MeO, CO$_2$-⌬ | 0.64 |
| 20 | Me | H | 1 | 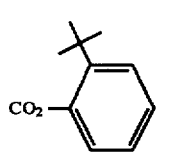 tBu, CO$_2$-⌬ | 0.65 |
| 21 | Me | H | 1 | 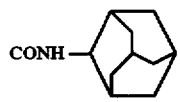 CONH- | 0.62 |
| 22 | H | H | 1 | 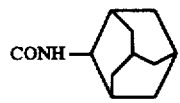 CONH- | 0.62 |
| 23 | Me | H | 1 | 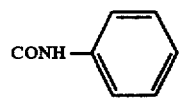 CONH-⌬ | 0.63 |
| 24 | H | H | 1 | 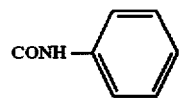 CONH-⌬ | 0.63 |

TABLE 6-continued

| | | | | | |
|---|---|---|---|---|---|
| 25 | Me | H | 1 | 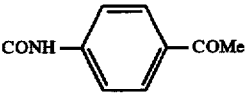 CONH-⌬-COMe | 0.63 |
| 26 | H | H | 1 | 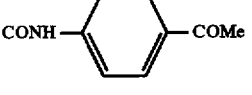 CONH-⌬-COMe | 0.63 |
| 27 | Me | H | 1 | 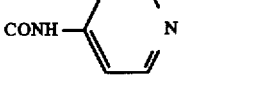 CONH-(pyridyl) | 0.64 |
| 28 | H | H | 1 | 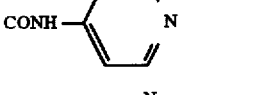 CONH-(pyridyl) | 0.63 |
| 29 | Me | H | 1 | 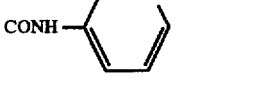 CONH-(pyridyl) | 0.63 |
| 30 | H | H | 1 | 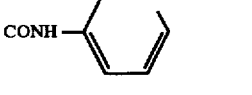 CONH-(pyridyl) | 0.62 |
| 31 | Me | H | 1 | 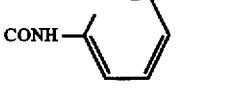 CONH-(pyridyl) | 0.62 |
| 32 | Me | H | 1 | 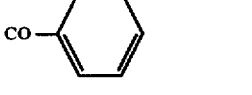 CO-⌬ | 0.64 |
| 33 | H | H | 1 | 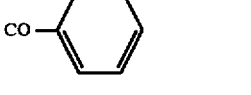 CO-⌬ | 0.63 |
| 34 | Me | Me | 1 | CO$_2$H | 0.69 |
| 35 | Me | Me | 1 | 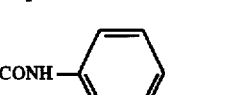 CONH-⌬ | 0.73 |
| 36 | Me | Me | 1 | 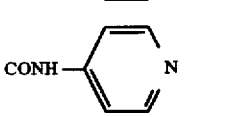 CONH-(pyridyl) | 0.71 |
| 37 | Me | H | 2 | CO$_2$H | 0.58 |
| 38 | Me | H | 2 |  CONH-⌬ | |
| 39 | Me | H | 2 |  CONH-(pyridyl) | 0.59 |
| 40 | Me | Me | 2 | CO$_2$H | |
| 41 | H | Me | 2 | CO$_2$H | 0.65 |

TABLE 6-continued

| Compd | | | | | |
|---|---|---|---|---|---|
| 42 | Me | Me | 2 | CONH—C6H5 | 0.68 |
| 43 | H | Me | 2 | CONH—C6H5 | 0.69 |
| 44 | Me | Me | 2 | CONH—C6H4—COMe | 0.68 |
| 44a | Me | Me | 2 | CONH—(3-pyridyl) | 0.66 |
| 44b | Me | Me | 2 | CONH—(2-pyridyl) | 0.66 |
| 44c | Me | Me | 2 | CONH—(4-pyridyl) | 0.67 |
| 45 | Me | H | 3 | $CO_2H$ | 0.55 |
| 46 | Me | H | 3 | $CO_2$—C6H5 | 0.57 |
| 47 | Me | H | 3 | CONH—C6H5 | 0.56 |
| 48 | Me | H | 4 | CONH—C6H5 | 0.55 |
| 49 | Me | H | 9 | CONH—C6H5 | 0.56 |
| 52 | H | H | 1 | $CO_2Me$ | 0.61 |
| 53 | Me | H | 1 | $COCHN_2$ | 0.58 |
| 54 | Me | H | 2 | $CO_2Me$ | 0.58 |
| 55 | Me | H | 1 | COS—(pyridyl) | 0.62 |
| 56 | H | H | 1 | COS—(pyridyl) | 0.64 |
| 57 | Me | Me | 0 | COS—(pyridyl) | 0.74 |
| 58 | Me | Me | 1 | CN | |
| 59 | Me | Me | 1 | $CO_2Me$ | 0.70 |
| 59a | H | Me | 2 | $CO_2Me$ | 0.64 |
| 62 | Me | H | 3 | $CO_2Me$ | 0.56 |
| 64 | Me | H | 9 | $CO_2H$ | 0.56 |

| Compd | NMR 19-Me | Other | Mass Spectrum |
|---|---|---|---|
| 1 | | J. Med. Chem. 1984, 27, 1690–1701. | |
| 2 | | | m/e334 (M + 1) FAB |
| 3 | 0.84 | 7.04–7.52(m, 5H, ArH) | m/e423 (M + 1) FAB |
| 4 | 0.91 | 7.07–7.53(m, 5H, ArH) | m/e409 (M + 1) FAB |
| 5 | 0.90 | 2.58(s, 3H, COMe); 7.61(d, 2H, ArH); 7.94(d, 2H, ArH) | m/e466 (M + 2) FAB |
| 6 | 0.90 | 2.57(s, 3H, COMe); 7.62(d, 2H, ArH); 7.93(d, 2H, ArH) | m/e451 (M + 1) FAB |
| 7 | 0.90 | 7.56(d, 2H, ArH); 8.46(d, 2H, ArH) | m/e424 (M + 1) FAB |
| 7a | 0.85 | 3.30(s, 3H, NMe); 7.13(d, 2H, ArH); 8.65(d, 2H, ArH) | |
| 8 | 0.88 | 7.58(d, 2H, ArH); 8.44(d, 2H, ArH) | m/e410 (M + 1) FAB |
| 8a | 0.87 | 3.27(s, 3H, NMe); 7.15(d, 2H, ArH); 8.66(d, 2H, ArH) | m/e423 (M) EI |
| 9 | | J. Med. Chem. 1984, 27 1690-1701 | |
| 10 | 0.91 | 1.36(s, 3H, 21-Me); 7.0–7.5(m, 5H, ArH) | |
| 11 | 0.88 | 1.13(d, 3H, 21-Me); 1.64, 2.09, 2.14(bs, 15H, adamantylH); | |
| 12 | 0.90 | 1.03(s, 9H, CMe3); 1.12(d, 3H, 21-Me); 1.40, 1.42(s, 6H, NCMe2); 5.20(s, 1H, NH) | |
| 13 | 0.89 | 1.14(d, 3H, 21-Me); 1.67, 1.99, 2.06(bs, 15H, adamantylH); 5.03(bs, 1H, NH) | |
| 14 | 0.90 | 1.28(d, 3H, 21-Me); 7.06–7.70(m, 5H, ArH) | |
| 15 | 0.89 | 1.28(d, 3H, 21-Me); 2.58(s, 3H, COMe); 7.68(d, 2H, ArH); 7.92(d, 2H, ArH); 8.00(bs, 1H, NH) | |
| 15a | 0.89 | 1.27(d, 3H. 21-Me); 7.64(d, 2H, ArH); 8.44(d, 2H, ArH); 8.50(s, 1H, NH) | |
| 15b | 0.89 | 1.29(d, 3H, 21-Me); 7.28(m, 1H, ArH); 7.92(s, 1H, ArH); 8.30(m, 2H, ArH); 8.61(bs, 1H, NH) | |
| 15c | 0.88 | 1.28(d, 3H, 21-Me); 7.04(m. 1H, ArH); 7.78(m, 1H, ArH); 8.13(m, 3H, ArH+NH) | |
| 16 | 0.90 | | m/e361 (M) EI |
| 17 | | | m/e347 (M) EI |
| 18 | 0.90 | 7.05–7.41(m, 5H, ArH) | m/e437 (M) EI |
| 19 | 0.89 | 3.81(s, 3H, OMe); 6.90–7.29(m, 4H, ArH) | |
| 20 | 0.90 | 1.35(s, 9H, CMe3); 6.95–7.43(m, 4H, ArH) | |
| 21 | 0.90 | | m/e495 (M + 1) FAB |
| 22 | 0.91 | | m/e481 (M + 1) FAB |
| 23 | 0.89 | 7.05–7.54(m, 5H, ArH) | m/e436 (M) EI |
| 24 | 0.91 | 7.06–7.55(m, 5H, ArH) | m/e422 (M) EI |
| 25 | 0.89 | 2.56(s, 3H, COMe); 7.64(d, 2H, ArH); 7.93(d, 2H, ArH) | m/e478 (M) EI |
| 26 | 0.91 | 2.57(s, 3H, COMe); 7.63(d, 2H, ArH); 7.91(d, 2H, ArH) | m/e464 (M) EI |
| 27 | 0.90 | 7.84(d, 2H, ArH); 8.43(d, 2H, ArH) | m/e437 (M) EI |

TABLE 6-continued

| | | | |
|---|---|---|---|
| 28 | 0.91 | 7.58(d, 2H, ArH); 8.46(d, 2H, ArH) | m/e424 (M + 1) FAB |
| 29 | 0.89 | 7.30(m, 1H, ArH); 8.28(m, 2H, ArH); 8.60(s, 1H, ArH) | |
| 30 | 0.90 | 7.33(m, 1H, ArH); 8.32(m, 2H, ArH); 8.62(s, 1H, ArH) | m/e424 (M + 1) FAB |
| 31 | 0.89 | 7.05(m, 1H, ArH); 7.31(m, 1H, ArH); 8.24(m, 2H, ArH) | |
| 32 | 0.91 | 7.38–7.62(m, 3H, ArH); 7.95(d, 2H, ArH) | |
| 33 | 0.90 | 7.05–7.54(m, 5H, ArH) | m/e408 (M + 1) FAB |
| 34 | 0.86 | 1.01(d, 2H, 21-Me) | |
| 35 | 0.89 | 1.04(d, 3H, 21-Me); 7.03–7.62(m, 5H, ArH); 7.21(bs, 1H, NH) | |
| 36 | 0.87 | 1.01(d, 3H, 21-Me); 7.60(bs, 2H, ArH); 8.40(s, 1H, NH); 8.44(bs, 2H, ArH) | |
| 37 | 0.90 | | m/e376 (M + 1) FAB |
| 38 | 0.87 | 7.07–7.49(m, 5H, ArH) | m/e451 (M + 1) FAB |
| 39 | 0.89 | 7.58(d, 2H, ArH); 8.46(d, 2H, ArH) | m/e451 (M + 1) FAB |
| 40 | | J. Med. Chem. 1986, 29 2298–2315 | |
| 41 | 0.88 | 0.91(d, 3H, 21-Me) | |
| 42 | 0.89 | 0.96(d, 3H, 21-Me); 7.03–7.56(m, 5H, ArH); 7.48(bs, 1H, NH) | |
| 43 | 0.91 | 0.96(d, 3H, 21-Me); 5.92(bs, 1H, NH); 7.04–7.64(m, 5H, ArH) | |
| 44 | 0.89 | 0.96(d, 3H, 21-Me); 2.57(s, 3H, COMe); 7.66(d, 2H, ArH); 7.90(d, 2H, ArH); 8.16(bs, 1H, NH) | |
| 44a | 0.88 | 0.94(d, 3H, 21-Me); 7.60(d, 2H, ArH); 8.37(s, 1H, NH); 8.44(d, 2H, ArH) | |
| 44b | 0.88 | 0.96(d, 3H, 21-Me); 7.33(m, 1H, ArH); 8.02(bs, 1H, ArH); 8.33(m, 2H, ArH); 8.64(s, 1H, NH) | |
| 44c | 0.87 | 0.95(d, 3H, 21-Me); 7.08(m, 1H, ArH); 7.78(m, 1H, ArH); 8.25(m, 2H, ArH); 8.68(bs, 1H, NH) | |
| 45 | 0.87 | 2.31(t, 2H, CH2CO2) | |
| 46 | 0.88 | 2.53(t, 2H, CH2CO2); 7.02–7.38(m, 5H, ArH) | |
| 47 | 0.87 | 2.33(t, 2H, CH2CO2); 7.05–7.52(m, 5H, ArH); 7.21(s, 1H, NH) | |
| 48 | 0.87 | 2.33(t, 2H, CH2CO2); 7.05–7.52(m, 5H, ArH); 7.23(s, 1H, NH) | |
| 49 | 0.88 | 2.33(t, 2H, CH2CO2); 7.05–7.54(m, 5H, ArH) | |
| 52 | 0.90 | 3.66(s, 3H, OMe); 5.83(bs, 1H, NH) | |
| 53 | | IR, 2140 cm-1 N2 | |
| 54 | 0.90 | 2.30(t, 2H, CH2CO2); 3.69(s, 3H, OMe) | |
| 55 | 0.90 | 7.30(m, 1H, ArH); 7.70(m, 2H, ArH); 8.62(m, 1H, ArH) | |
| 56 | 0.92 | 5.7(bs, 1H, NH); 7.31(m, 1H, ArH); 7.71(m, 2H, ArH); 8.63(m, 1H, ArH) | |
| 57 | 0.90 | 1.32(d, 3H, 21-Me); 7.32(m, 1H, ArH); 7.72(m, 2H, ArH); 8.63(m, 1H, ArH) | |
| 59 | 0.88 | 0.97(d, 3H, 21-Me); 3.65(s, 3H, OMe) | |
| 59a | 0.88 | 0.91(d, 3H, 21-Me); 3.65(s, 3H, OMe); 5.77(s, 1H, NH) | |
| 62 | 0.88 | 2.29(t, 2H, CH2CO2); 3.66(s, 3H, OMe) | |
| 64 | 0.86 | 2.33(t, 2H, CH2CO2) | |

TABLE 7

| Compd | R20 | n | R4 | NMR 18-Me | NMR 19-Me | Other |
|---|---|---|---|---|---|---|
| 65 | Me | 0 | CO2H | | | |
| 66 | Me | 0 | COS—(pyridyl) | 0.63 | 0.95 | 1.33(d, 3H, 21-Me); 5.81(d, 1H, 1-H); 6.03(bs, 1H, NH); 6.79(d, 1H, 2-H); 7.34, 7.63, 7.79, 8.64(m, 1H ea, ArH) |
| 67 | Me | 0 | CONH—(pyridyl) | 0.72 | 0.94 | 1.25(d, 3H, 21-Me); 5.78(d, 1H, 1-H); 6.79(d, 1H, 2-H); 7.62(d, 2H, ArH); 8.39(d, 2H, ArH) |
| 68 | H | 1 | CO2H | 0.57 | 0.87 | 5.59(d, 1H, 1-H); 6.82(d, 1H, 2-H) |
| 69 | H | 1 | CO2Me | 0.62 | 0.98 | 3.66(s, 3H, OMe); 5.82(d, 1H, 1-H); 6.82(d, 1H, 2-H); |

TABLE 7-continued

| | | | | | | |
|---|---|---|---|---|---|---|
| 70 | H | 1 | CONH—C6H5 (phenyl) | 0.64 | 0.98 | 5.81(d, 1H, 1-H); 6.82(d, 1H, 2-H); 7.05–7.54(m, 5H, ArH) |
| 71 | H | 1 | CONH—C6H4—OMe (4-methoxyphenyl) | 0.64 | 0.97 | 3.79(s, 3H, OMe); 5.82(d, 1H, 1-H); 6.82(d, 1H, 2-H); 6.86(d, 2H, ArH); 7.42(d, 2H, ArH) |
| 72 | H | 1 | CONH—(imidazol-2-yl) | 0.62 | 0.97 | 5.81(d, 1H, 1-H); 6.81(d, 1H, 2-H); 6.78(s, 2H, ArH) |
| 73 | H | 1 | CONH—(pyridin-4-yl) | 0.64 | 0.97 | 5.78(d, 1H, 1-H); 6.83(d, 1H, 2-H); 7.58(d, 2H, ArH); 8.39(d, 2H, ArH) |
| 74 | H | 1 | CONH—(pyridin-3-yl) | 0.63 | 0.96 | 5.79(d, 1H, 1-H); 6.79(d, 1H, 2-H); 7.28(m, 1H, ArH); 8.27(m, 2H, ArH); 8.58(s, 1H, ArH) |
| 75 | H | 1 | CONH—(pyridin-2-yl) | 0.64 | 0.98 | 5.81(d, 1H, 1-H); 6.81(d, 1H, 2H); 7.04(m, 1H, ArH); 7.96(m, 1H, ArH); 8.24(m, 2H, ArH) |
| 76 | H | 1 | CONH—(pyrazin-2-yl) | 0.64 | 0.97 | 5.81(d, 1H, 1-H); 6.80(d, 1H, 2-H); 8.51(d, 1H, ArH); 8.96(d, 1H, ArH) |
| 77 | H | 1 | CONH—(quinolin-3-yl) | 0.64 | 0.95 | 5.82(d, 1H, 1-H); 6.86(d, 1H, 2-H); 7.52–8.06(m, 4H, ArH); 8.71–8.95(m, 2H, ArH) |
| 78 | Me | 2 | CO2H | 0.63 | 0.83 | 0.87(d, 3H, 21-Me); 5.59(d, 1H, 1-H); 6.78(d, 1H, 2-H); |
| 79 | Me | 2 | CO2Me | 0.66 | 0.95 | 0.91(s, 3H, 21-Me); 3.64(s, 3H, OMe); 5.41(s, 1H, 4-NH); 5.78(d, 1H, 1-H); 6.77(d, 1H, 2-H) |
| 80 | Me | 2 | CONH—(pyridin-4-yl) | 0.68 | 0.97 | 0.95(d, 3H, 21-Me); 5.46(s, 1H, 4-NH); 5.81(d, 1H, 1-H); 6.80(d, 1H, 2-H); 7.56(d, 2H, ArH); 8.13(bs, 1H, CONH); 8.46(d, 2H, ArH) |
| 81 | Me | 2 | CONH—(pyridin-3-yl) | 0.68 | 0.96 | 0.94(d, 3H, 21-Me); 5.58(bs, 1H, 4-NH); 5.81(d, 1H, 1-H); 6.80(d, 1H, 2-H); 7.24(m, 1H, ArH); 8.03(m, 1H, ArH); 8.22(d, 1H, ArH); 8.32(bs, 1H, ArH); 8.58(bs, 1H, CONH) |
| 82 | Me | 2 | CONH—(pyridin-2-yl) | 0.69 | 0.96 | 0.97(d, 3H, 21-Me); 5.54(bs, 1H, 4-NH); 5.81(d, 1H, 1-H); 6.79(d, 1H, 2-H); 7.08(m, 1H, ArH); 7.76(m, 1H, ArH); 8.26(m, 2H, ArH); 8.71(bs, 1H, CONH) |

TABLE 7-continued

| 83 | H | 1 | ![COS-pyridyl] | 0.62 | 0.97 | 5.80(d, 1H, 1-H); 6.80(d, 1H, 2-H); 7.18–7.78(m, 3H, ArH); 8.60(d, 1H, ArH) |

| Compd | Mass Spectrum |
|---|---|
| 69 | m/e359 (M+) EI |
| 70 | m/e420 (M+) EI |
| 71 | m/e451 (M + 1) FAB |
| 72 | m/e410 (M+) EI |
| 73 | m/e421 (M+) EI |
| 74 | m/e422 (M + 1) FAB |
| 75 | m/e422 (M + 1) FAB |
| 76 | m/e423 (M+) EI |
| 77 | m/e472 (M + 1) FAB |

Another preferred embodiment of this invention is a series of compounds characterized in having ether moieties at the 17 position, and which can be synthesized according to the following flowsheet:

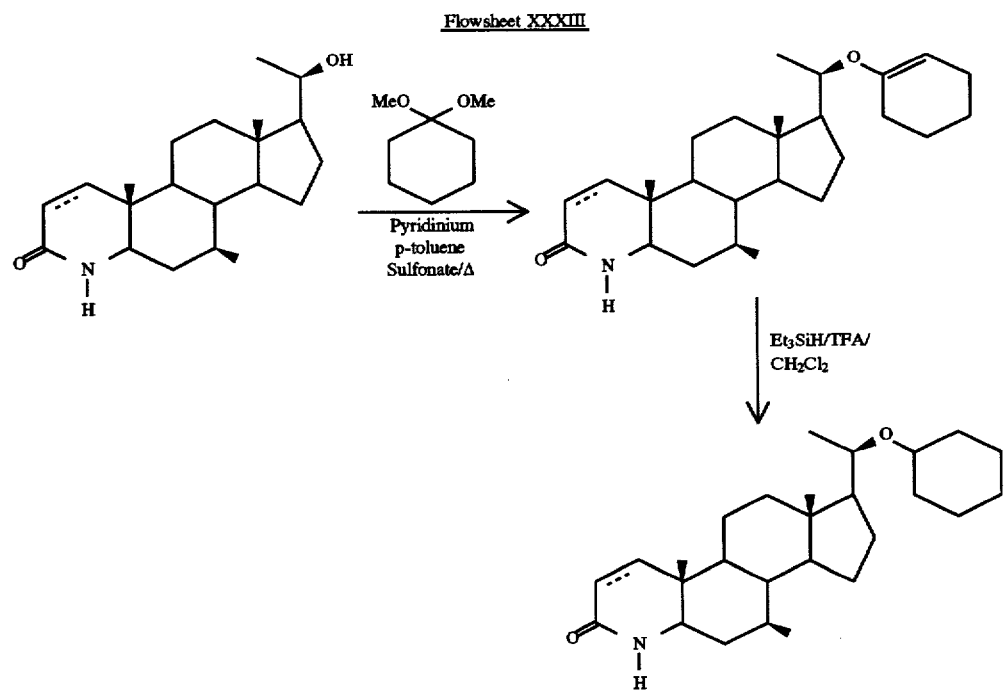

Flowsheet XXXIII

EXAMPLE 85

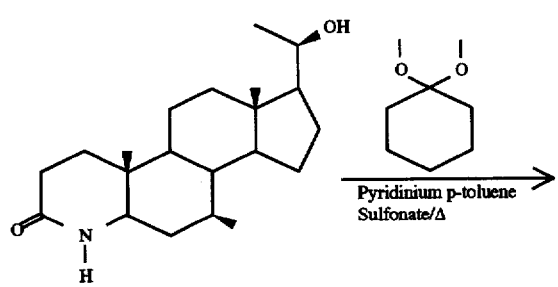

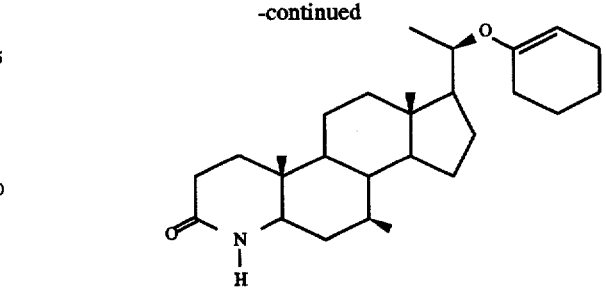

-continued

To a solution of Azasteroid (250 mg) in dimethoxycyclohexane (10 ml) was added pyridinum p-toluenesulfonate and reaction mixture was heated at 140° for 2 hrs. The temperature of reaction was increased and dimethoxycyclohexane was removed slowly by distillation over 4 hrs. Finally all the dimethoxycyclohexane was distilled off and residue taken in ethyl acetate, washed with aqueous sodium bicarbonate, brine, dried and concentrated to give 2. MS calculated for $C_{27}H_{43}NO_2$, 413.65. Observed 413 (EI).

EXAMPLE 86

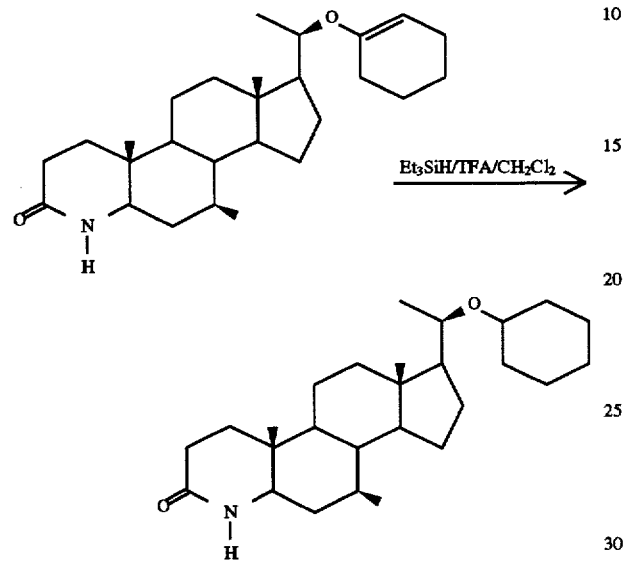

To a solution of Enol Ether (150 mg) in $CH_2Cl_2$ (2 ml) was added triethylsilane (418.6 mg, 10 eq.) followed by slow dropwise addition of TFA (2.07 g). After stirring the reaction for overnight at room temperature, the reaction mixture was diluted with $CH_2Cl_2$, washed with aq. $NaHCO_3$, brine, dried and concentrated. The residue was purified by prep. tlc over sliica gel using 30% acetone/ $CH_2Cl_2$ as solvent. MS calculated for $C_{27}H_{45}NO_2$, 415.66. Observed 415(EI).

An additional preferred embodiment of the invention is presented in the following Table 8, in which compounds are presented that are readily synthesizeable by one of ordinary skill in this art by following the procedures previously presented and exemplified:

TABLE 8

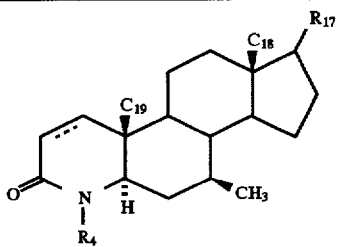

| Example No. | $R_4$ | $R_{17}$ |
|---|---|---|
| 87 | $CH_3$ | β-(R)—CH($CH_3$)($CH_2$)$_3$CH($CH_3$)$_2$ |
| 88 | $CH_3$ | β-COCH$_3$ |
| 89 | $CH_3$ | β-(E)—C($CH_3$)=CH(4-Pyridyl) |
| 90 | $CH_3$ | β-(S)—CH($CH_3$)$CH_2$CN |
| 91 | $CH_3$ | β-(R))CH($CH_3$)$CH_2$CN |
| 92 | $CH_3$ | β-($CH_2$)$_2$CF$_3$ |
| 93 | $CH_3$ | β-OCONHCH($CH_3$)$_2$ |
| 94 | $CH_3$ | β-($CH_2$)$_2$CO$_2$—Ph |
| 95 | $CH_3$ | β-($CH_2$)$_2$-(1-Phenyltetrazol-5-yl) |
| 96 | $CH_3$ | β-($CH_2$)$_2$-(2-Methyl-1,3,4-oxadiazol-5-yl) |
| 97 | $CH_3$ | β-$CH_2$CONH-(4-Pyridyl) |
| 98 | $CH_3$ | β-$CH_2$CH$_3$ |
| 99 | $CH_3$ | $\Delta^{16}$ |
| 100 | $CH_3$ | 17-H |
| 101 | Me | 3-thiophenecarboxamido |
| 102 | Me | 2-methyl-3-fluorobenzamido |
| 103 | Me | phenylthioacetamido |
| 104 | Me | t-butylthioacetamido |
| 105 | Me | phenylthioacetamido |
| 106 | Me | 2-fluorobenzamido |

TABLE 8-continued

| | | |
|---|---|---|
| 107 | Me | 2-thiophenesulfonamido |
| 108 | Me | 2,3-difluorobenzamido |
| 109 | Me | isopropylthioacetamido |
| 110 | Me | O-((isopropylthio)acetyl)oximino |
| 111 | Me | 9-(isopropylthio)nonanoylamino |
| 112 | Me | β-O—phenyl-p-cyano |
| 113 | Me | β-O—CH$_2$COOEt |
| 114 | Me | β-O—CH$_2$COOH |
| 115 | Me | β-O—CH$_2$CONHPh |
| 116 | Me | β-O—CH$_2$CONHPh-p-COMe |
| 117 | Me | exo-methylene |
| 118 | Me | 17α-OH, 17β-CH$_2$N$_3$ |
| 119 | Me | β-Me |
| 120 | Me | α-OH, β-CH$_2$NHCMe$_3$ |
| 121 | Me | α-OH, β-CH$_2$NH$_2$ |
| 122 | Me | cyclopropyl 16-ene |

| | C$_{18}$ | C$_{19}$ | 7β-CH$_3$ | other | °C. | M$^+$ or M + 1$^+$ |
|---|---|---|---|---|---|---|
| 87 | 0.93 | 0.89 | 1.15 d | 1.2 d | 63–65 | 415 (M+) |
| 88 | 0.63 | 0.85 | 1.06 d | 2.13(s, 3H, COMe) | | |
| 89 | 0.64 | 0.84 | 1.09 d | 1.91(s, 3H, C=CMe); 6.23(s, 1H, C=CH); 7.17(bs, 2H, ArH); 8.55(bs, 2H, ArH) | | |
| 90 | 0.71 | 0.85 | 1.05 d | 1.19(d, 3H, 21-Me) | | |
| 91 | 0.70 | 0.84 | 1.05 d | 1.08(d, 3H, 21-Me) | | |
| 92 | 0.62 | 0.85 | 1.06 d | | | |
| 93 | 0.76 | 0.84 | 1.04 d | 1.15(d, 6H, CHMe$_2$); 4.49(t. 1H. 17-H) | | |
| 94 | 0.64 | 0.84 | 1.05 d | 7.04–7.39(m, 5H, Ar) | | 451(M$^+$) |
| 95 | 0.56 | 0.85 | 1.04 d | 7.43–7.63(m, 5H, Ar) | | 476(M + 1)$^+$ |
| 96 | 0.63 | 0.85 | 1.05 d | 2.49(s, 3H, C(CH$_3$))=N | | 413(M$^+$) |
| 97 | 0.64 | 0.86 | 1.06 d | 7.54(d, 2H, Ar); 8.48(d, 2H, Ar) | | 437(M$^+$) |
| 98 | 0.55 | 0.83 | 1.02 d | 0.84(t, 3H, CH$_3$) | | 332(M$^+$) |
| 99 | 0.74 | 0.85 | 1.04 d | 5.65(m, 1H, 16-H); 5.78(m, 1H, 17H) | | |
| 100 | 0.70 | 0.83 | 1.05 d | 2.92(s, 3H, N—Me) | | 304(M$^+$) |
| 101 | 0.755 | 0.833 | 1.033 | 2.904(N—Me) | | M+ = 428 |
| 102 | 0.76 | 0.85 | 1.04 | 2.82(N—Me) | | M+ = 454 |
| 103 | 0.441 | 0.784 | 0.975 | 2.879(N—Me) | | M+ = 468 |
| 104 | 0.719 | 0.820 | 1.011 | 2.891(N—Me) | | M+ = 448 |
| 105 | 0.446 | 0.784 | | 2.879(N—Me) | | M+ = 524 |
| 106 | 0.777 | 0.839 | 1.037 | 2.907(N—Me) | | M + 1 = 440 |
| 107 | 0.688 | 0.812 | 0.975 | 2.884(N—Me) | | M+ = 464 |
| 108 | 0.799 | 0.858 | 1.048 | 2.923(N—Me) | | M+ = 458 |
| 112 | 0.88 | 0.94 | 1.07 | 2.93(N—Me), 4.14(t, 17α) | 200–202 | M$^+$ = 420 |
| 113 | 0.82 | 0.86 | 1.05 | 2.92, 3.38(t, 17α), 4.09(OCH$_2$) | | M$^+$ = 405 |
| 114 | 0.84 | 0.86 | 1.05 | 2.92, 3.42(t, 17α), 4.10(OCH$_2$) | 163–166 | M + 1$^+$ = 378 |
| 115 | 0.88 | 0.89 | 1.06 | 2.92, 3.42(t, 17α), 4.06(OCH$_2$) | 175.5–178.5 | M + 1$^+$ = 453 |
| 116 | 0.89 | 0.90 | 1.07 | 2.58(MeCO), 2.93, 3.44(t, 17α), 4.07 (OCH$_2$) | 212–216 | M + 1$^+$ = 495 |
| 117 | 0.82 | 0.88 | 1.10 | 2.92, 4.67(m, =CH$_2$) | 85–87.5 | M$^+$ = 315 |
| 118 | 0.78 | 0.88 | 1.07 | 2.93, 3.49(ABq, CH$_2$N) | 243.5–246 | M + 1$^+$ = 375 |
| 119 | 0.57 | 0.87 | 1.06 | 0.83(d, 17β-Me) | 98–100 | M$^+$ = 318 |
| 120 | 0.75 | 0.89 | 1.07 | 1.28(CMe$_3$), 2.76 (ABq, CH$_2$N) | | M$^+$ = 404 |
| 121 | 0.76 | 0.87 | 1.09 | | 272–277 | M$^+$ = 348 |
| 122 | 0.83 | 0.89 | 1.06 | 0.39(m, 2H, cyclopropyl), 0.64(m, 2H, cyclopropyl), 5.11 (m, =CH—) | | M$^+$ = 341 |

In this specifications, Rf values cited were carried out on standard thin layer chromatographic Silica gel plates. The elution solvent system used is given in the parentheses following the Rf value.

The mass spectral values cited are given as FAB, i.e., fast atom bombardment, and are reported as (M+1) molecular ion peaks, being the molecular weight plus one atomic mass unit. The electron impact (EI) mass spectrum values cited are reported as molecular ion peaks and are indicated in parentheses, either being (M) or (M+2), the molecular weight, MW, or the MW plus two atomic units.

The nuclear magnetic resonance data was taken at 400 MHz in CDCl$_3$ and is tabulated for representative unique proton values. The coupling constant J is given in Hertz, Hz.

The present invention has the objective of providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and treatment [and prevention] of prostatic carcinoma, hyperandrogenic conditions, can be administered in a wide variety of therapeutic dosage forms in conventional vehicles for systemic administration, as, for example, by oral administration in the form of tablets, capsules, solutions, or suspensions, or by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. For the treatment of androgenic alopecia, acne vulgaris, seborrhea, female hirsutism, the compounds of the present invention are administered in a pharmaceutical composition comprising the active compound in combination with a pharmacologically acceptable carrier adapted for topical, oral or parenteral administration.

These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a 5 α-reductase agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to [prevent,] counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

Oral dosages of the present invention, when used for the indicated effects, will range between about Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carders (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl- methacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

BIOLOGICAL ASSAYS

Preparation of Human Prostatic and Scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethyl-sulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase Assay.

The reaction mixture contained in a final volume of 100 μl is: 40 mM buffer (human scalp, potassium phosphate, pH 6.5; human prostatic 5α-reductase, sodium citrate, pH 5.5), 0.3–10 μM $^{14}$C-T (or $^3$H-T), 1 mM DTT, and 500 μM NADPH. Typically, the assay was initiated by the addition of 50–100 μg prostatic homogenate or 75–200 μg scalp homogenate and incubated at 37° C. After 10–50 min the reaction was quenched by extraction with 250 gl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times DHT, 6.8–7.2 min; androstanediol, 7.6–8.0; T, 9.1–9.7 min). The HPLC system consisted of a Waters Model 680 Gradient System equipped with a Hitachi Model 655A autosampler, Applied Biosystems Model 757 variable UV detector, and a Radiomatic Model A 120 radio-activity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Stumptail Macaque Protocol

The following protocol is utilized with the stumptail macaque monkey to demonstrate the effect of compounds of the present invention for promoting hair growth.

Twenty-one male stumptail macaque monkeys of species *Macaca speciosa* are assigned to vehicle control and drug treatment groups on the basis of baseline hair weight data. This assignment procedure is necessary to insure that the average baseline hair growth for each control and experimental group is comparable. The control and drug treatment groups are as follows:

1. Topical 50:30:20 vehicle (N=6)
2. Oral 5α-reductase and topical 50:30:20 vehicle (N=5)
3. Oral placebo (N=5)
4. 5α-reductase in vehicle (N=5)

The vehicle consists of 50% propylene glycol, 30% ethanol and 20% water. A 100 mM concentration of topical 5α-reductase is formulated in this vehicle. The same 5α-reductase is administered as an oral dose of 0.5 mg per monkey. Immediately prior to the dosing phase of the study, hair is removed from a 1 inch square area (identified by four tatoos) in the center of the balding scalp. This hair collection is the baseline hair growth determination prior to the beginning of treatment. Approximatly 250 μL of vehicle and 5α-reductase in vehicle is prepared and topically administered to the tatooed area of the scelp. The selected 5α-reductase and placebo is ingested by the monekys at the same time as the topical doses are administered. The monkeys are dosed once per day, seven days per week for twenty weeks.

At four week intervals throughout the dosing phase of the study, each monkey is shaved and the hair is collected and weighed. The body weight data (at baseline and during assay) is analyzed by the nonparametric Wilcoxon rank-sum test. Differences are significant at p<0.05. Hair weight data at each week collection for vehicle, placebo and treatment groups are expressed as the change from baseline. Statistical analysis is performed on the rank of the data to show overall differences among groups at each four week collection.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula

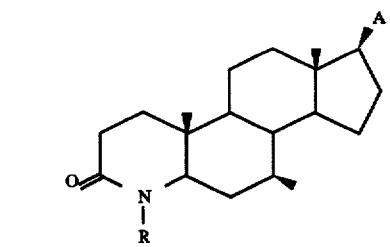

selected from the group consisting of those in the following table:

| R | A |
|---|---|
| H | |
| —CH₃ | CH₂CH₂CO₂—phenyl |
| —CH₃ | O—phenyl—CN |
| —CH₃ | O—CH₂—CO₂C₂H₅ |
| —CH₃ | O—CH₂CO₂H |
| —CH₃ | O—CH₂CONHPh |
| —CH₃ | O—CH₂CONH—phenyl—COCH₃ |

2. A compound of structural formula:
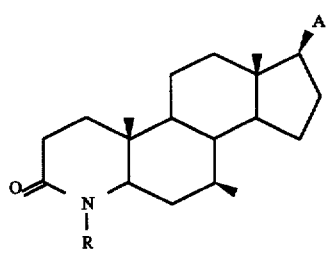
selected from the group consisting of those in the following table:
| R | A |
|---|---|
| —CH₃ |  |
| —CH₃ | N—C(=O)-phenyl-2-F |
| —CH₃ | N—C(=O)-phenyl-2,3-F₂ |
* * * * *